US011607451B2

(12) United States Patent
Gokarn et al.

(10) Patent No.: US 11,607,451 B2
(45) Date of Patent: *Mar. 21, 2023

(54) SELF-BUFFERING ANTIBODY FORMULATIONS

(71) Applicant: Amgen Inc., Thousand Oaks, CA (US)

(72) Inventors: Yatin R. Gokarn, Foster City, CA (US); Eva Kras, Redmond, WA (US); Richard Louis Remmele, Jr., Mountain View, CA (US); David Brems, Newbury Park, CA (US); Susan Irene Hershenson, Newbury Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 809 days.

This patent is subject to a terminal disclaimer.

(21) Appl. No.: 13/797,622

(22) Filed: Mar. 12, 2013

(65) Prior Publication Data

US 2013/0273066 A1 Oct. 17, 2013

Related U.S. Application Data

(60) Continuation of application No. 13/188,329, filed on Jul. 21, 2011, which is a division of application No. 11/917,188, filed as application No. PCT/US2006/022509 on Jun. 8, 2006, now abandoned.

(60) Provisional application No. 60/690,582, filed on Jun. 14, 2005.

(51) Int. Cl.
| | | |
|---|---|---|
| A61K 51/00 | (2006.01) |
| A61K 39/395 | (2006.01) |
| A61K 9/08 | (2006.01) |
| C07K 16/00 | (2006.01) |
| A61K 47/02 | (2006.01) |
| C07K 16/24 | (2006.01) |
| C07K 16/28 | (2006.01) |
| A61K 47/10 | (2017.01) |
| A61K 47/26 | (2006.01) |

(52) U.S. Cl.
CPC ............ *A61K 39/3955* (2013.01); *A61K 9/08* (2013.01); *A61K 39/39591* (2013.01); *A61K 47/02* (2013.01); *A61K 47/10* (2013.01); *A61K 47/26* (2013.01); *C07K 16/00* (2013.01); *C07K 16/241* (2013.01); *C07K 16/2803* (2013.01); *C07K 16/2827* (2013.01); *C07K 16/2851* (2013.01); *C07K 16/2866* (2013.01); *C07K 16/2875* (2013.01); *C07K 2317/21* (2013.01); *C07K 2317/565* (2013.01); *C07K 2317/94* (2013.01)

(58) Field of Classification Search
CPC ........ A61K 9/00; A61K 9/08; A61K 39/3955; A61K 39/39591; A61K 2123/00; A61K 2121/00; A61K 51/00; A61K 51/04; A61K 51/10; A61K 51/1093; A61K 39/00; A61K 47/00; A61K 47/02; A61K 47/10; A61K 47/26; C07K 16/00; C07K 16/2851; C07K 16/2866; C07K 16/2875; C07K 16/2827; C07K 16/241; C07K 16/2803; C07K 2317/21; C07K 2317/94; C07K 2317/565
USPC ........ 424/1.11, 1.65, 1.69, 85.6, 85.7, 130.1, 424/172.1, 1.49; 514/1, 1.1, 8.4, 8.6; 530/300
See application file for complete search history.

(56) References Cited

U.S. PATENT DOCUMENTS

| | | |
|---|---|---|
| 4,322,403 A | 3/1982 | Bunnig |
| 4,396,608 A | 8/1983 | Tenold |
| 4,597,966 A | 7/1986 | Zolton et al. |
| 4,681,713 A | 7/1987 | Miyagi et al. |
| 4,849,508 A | 7/1989 | Magnin et al. |
| 4,876,088 A | 10/1989 | Hirao et al. |

(Continued)

FOREIGN PATENT DOCUMENTS

| | | |
|---|---|---|
| CA | 2 474 943 A1 | 8/2003 |
| EP | 0 025 275 | 3/1981 |

(Continued)

OTHER PUBLICATIONS

Kurnik et al, Biotechnology and Bioengineering, 1995, vol. 45, pp. 149-157.*

(Continued)

*Primary Examiner* — Sean E Aeder
(74) *Attorney, Agent, or Firm* — Knobbe, Martens, Olson & Bear, LLP

(57) ABSTRACT

The invention herein described, provides, among other things, self-buffering protein formulations. Particularly, the invention provides self-buffering pharmaceutical protein formulations that are suitable for veterinary and human medical use. The self-buffering protein formulations are substantially free of other buffering agents, stably maintain pH for the extended time periods involved in the distribution and storage of pharmaceutical proteins for veterinary and human medical use. The invention further provides methods for designing, making, and using the formulation. In addition to other advantages, the formulations avoid the disadvantages associated with the buffering agents conventionally used in current formulations of proteins for pharmaceutical use. The invention in these and other respects can be productively applied to a wide variety of proteins and is particularly useful for making and using self-buffering formulations of pharmaceutical proteins for veterinary and medical use, especially, in particular, for the treatment of diseases in human subjects.

96 Claims, 16 Drawing Sheets

Specification includes a Sequence Listing.

(56) References Cited

U.S. PATENT DOCUMENTS

| | | | |
|---|---|---|---|
| 4,877,866 A | 10/1989 | Rudnick et al. | |
| 5,110,910 A | 5/1992 | Tsav | |
| 5,177,194 A | 1/1993 | Sarno et al. | |
| 5,256,571 A | 10/1993 | Hurley et al. | |
| 5,298,410 A | 3/1994 | Phillips et al. | |
| 5,484,892 A * | 1/1996 | Tedder | C07K 14/70503 435/328 |
| 5,580,856 A | 12/1996 | Pestrelski et al. | |
| 5,608,038 A | 3/1997 | Eibl et al. | |
| 5,691,312 A | 11/1997 | Paques | |
| 5,702,699 A | 12/1997 | Hanisch et al. | |
| 5,717,072 A * | 2/1998 | Mosley | C07K 14/7155 530/388.22 |
| 5,789,554 A | 8/1998 | Leung et al. | |
| 5,945,098 A | 8/1999 | Sarno et al. | |
| 6,004,555 A | 12/1999 | Thorpe et al. | |
| RE36,755 E | 6/2000 | Smith et al. | |
| 6,090,382 A | 7/2000 | Salfeld et al. | |
| 6,093,324 A | 7/2000 | Bertolini | |
| 6,171,586 B1 | 1/2001 | Lam et al. | |
| 6,252,055 B1 | 6/2001 | Relton | |
| 6,281,336 B1 | 8/2001 | Laursen et al. | |
| 6,436,897 B2 | 8/2002 | Danko et al. | |
| 6,610,206 B1 | 8/2003 | Callan et al. | |
| 6,673,347 B1 * | 1/2004 | Offord et al. | 424/178.1 |
| 6,696,056 B1 | 2/2004 | Cheung et al. | |
| 6,875,848 B2 | 4/2005 | Ristol Debart et al. | |
| 7,122,641 B2 | 10/2006 | Vendantham et al. | |
| 7,157,557 B2 | 1/2007 | Sassenfeld et al. | |
| 7,294,481 B1 | 11/2007 | Fung | |
| 7,300,773 B2 | 11/2007 | Drapeau et al. | |
| 7,364,736 B2 | 4/2008 | Boyle et al. | |
| 7,452,695 B2 | 11/2008 | Van Ness et al. | |
| 7,648,702 B2 | 1/2010 | Gombotz et al. | |
| 7,666,413 B2 | 2/2010 | Liu et al. | |
| 7,718,776 B2 | 5/2010 | Boyle et al. | |
| 7,879,331 B2 | 2/2011 | Zurlo et al. | |
| 7,915,225 B2 | 3/2011 | Finck | |
| 8,034,906 B2 | 10/2011 | Borhani et al. | |
| 8,052,645 B2 | 11/2011 | Slate et al. | |
| 8,063,182 B1 | 11/2011 | Brockhaus et al. | |
| 8,119,604 B2 | 2/2012 | Gombotz et al. | |
| 8,119,605 B2 | 2/2012 | Finck | |
| 8,163,522 B1 | 4/2012 | Brockhaus et al. | |
| 8,177,749 B2 | 5/2012 | Slate et al. | |
| 8,410,060 B2 | 4/2013 | Kazama et al. | |
| 8,420,081 B2 | 4/2013 | Fraunhofer et al. | |
| 8,597,709 B2 | 12/2013 | Gahler et al. | |
| 8,722,631 B2 | 5/2014 | Finck | |
| 8,821,865 B2 | 9/2014 | Neu et al. | |
| 8,828,947 B2 | 9/2014 | Gombotz et al. | |
| 8,871,201 B2 | 10/2014 | Li et al. | |
| 8,883,146 B2 | 11/2014 | Fraunhofer et al. | |
| 8,920,374 B2 | 12/2014 | Bokelman et al. | |
| 8,945,564 B2 | 2/2015 | Lu et al. | |
| 9,085,619 B2 | 7/2015 | Fraunhofer et al. | |
| 9,114,166 B2 | 8/2015 | Krause et al. | |
| 9,182,410 B1 | 11/2015 | Rupprechter et al. | |
| 9,302,002 B2 | 4/2016 | Manning et al. | |
| 9,452,138 B2 | 9/2016 | Trollsas et al. | |
| 9,453,067 B2 | 9/2016 | Deutel et al. | |
| 9,518,111 B2 | 12/2016 | Gombotz et al. | |
| 9,616,173 B2 | 4/2017 | Slate et al. | |
| 9,649,383 B2 | 5/2017 | Kashi et al. | |
| 9,700,595 B2 | 7/2017 | Lee et al. | |
| 9,763,976 B1 | 9/2017 | Obagi et al. | |
| 10,307,483 B2 | 6/2019 | Goss et al. | |
| 2001/0021380 A1 | 9/2001 | Phuenneke | |
| 2002/0151688 A1 | 10/2002 | Debart et al. | |
| 2003/0138417 A1 | 7/2003 | Kaisheva et al. | |
| 2003/0138421 A1 | 7/2003 | Van de Winkel et al. | |
| 2003/0143603 A1 | 7/2003 | Giles-Komar et al. | |
| 2003/0180253 A1 | 9/2003 | Chen et al. | |
| 2003/0180287 A1 | 9/2003 | Gombotz et al. | |
| 2003/0190316 A1 | 10/2003 | fiKakuta et al. | |
| 2003/0202975 A1 | 10/2003 | Tedder | |
| 2003/0206898 A1 | 11/2003 | Fischkoff et al. | |
| 2004/0023313 A1 | 2/2004 | Boyle et al. | |
| 2004/0033228 A1 | 2/2004 | Krause et al. | |
| 2004/0033535 A1 | 2/2004 | Boyle et al. | |
| 2004/0038878 A1 | 2/2004 | Tanikawa et al. | |
| 2004/0071702 A1 | 4/2004 | Van de Winkel et al. | |
| 2004/0126373 A1 | 7/2004 | Banerjee et al. | |
| 2004/0136990 A1 | 7/2004 | Banerjee et al. | |
| 2004/0181033 A1 | 9/2004 | Han et al. | |
| 2004/0197324 A1 | 10/2004 | Liu et al. | |
| 2004/0202655 A1 | 10/2004 | Morton et al. | |
| 2004/0228913 A1 | 11/2004 | Kumar et al. | |
| 2005/0175603 A1 | 8/2005 | Liu et al. | |
| 2005/0214278 A1 | 9/2005 | Kabuta et al. | |
| 2006/0127395 A1 | 7/2006 | Arvinte et al. | |
| 2006/0149042 A1 | 7/2006 | Konstantinov et al. | |
| 2006/0153846 A1 | 7/2006 | Krause et al. | |
| 2006/0182740 A1 * | 8/2006 | Yang et al. | 424/133.1 |
| 2007/0065567 A1 | 3/2007 | Segall et al. | |
| 2007/0071675 A1 | 3/2007 | Wu et al. | |
| 2007/0172475 A1 | 7/2007 | Matheus et al. | |
| 2007/0202051 A1 | 8/2007 | Schuschnig | |
| 2007/0243185 A1 | 10/2007 | Gombotz et al. | |
| 2007/0269463 A1 | 11/2007 | Donovan | |
| 2008/0003220 A1 | 1/2008 | Gokarn | |
| 2008/0071097 A1 | 3/2008 | Taugerbeck et al. | |
| 2008/0161242 A1 | 7/2008 | Randolph et al. | |
| 2008/0213282 A1 | 9/2008 | Jacob et al. | |
| 2008/0286280 A1 | 11/2008 | Kallmeyer et al. | |
| 2008/0311078 A1 | 12/2008 | Gokarn et al. | |
| 2009/0291062 A1 | 11/2009 | Fraunhofer et al. | |
| 2010/0137213 A1 | 6/2010 | Fernandez et al. | |
| 2011/0060290 A1 | 3/2011 | Bonk et al. | |
| 2011/0070227 A1 | 3/2011 | Novotney-Barry et al. | |
| 2011/0171217 A1 | 7/2011 | Badkar | |
| 2011/0224616 A1 | 9/2011 | Slate et al. | |
| 2012/0028877 A1 | 2/2012 | Gokarn et al. | |
| 2012/0089119 A1 | 4/2012 | Slate et al. | |
| 2012/0265142 A1 | 4/2012 | Slate et al. | |
| 2013/0023825 A1 | 1/2013 | Edwards et al. | |
| 2013/0273067 A1 | 10/2013 | Gokarn et al. | |
| 2014/0072560 A1 | 3/2014 | Arakawa et al. | |
| 2014/0186351 A1 | 7/2014 | Britta et al. | |
| 2014/0199303 A1 | 7/2014 | Choi et al. | |
| 2014/0255400 A1 | 9/2014 | Maloney et al. | |
| 2015/0045729 A1 | 2/2015 | Denzer et al. | |
| 2015/0118249 A1 | 4/2015 | Leach et al. | |
| 2015/0283241 A1 | 10/2015 | Deepak et al. | |
| 2015/0313996 A1 | 11/2015 | Park et al. | |
| 2016/0022914 A1 | 1/2016 | Mounce et al. | |
| 2016/0106844 A1 | 4/2016 | Bañado et al. | |
| 2016/0120751 A1 | 5/2016 | Mounce et al. | |
| 2016/0319011 A1 | 11/2016 | Gokarn et al. | |
| 2016/0339102 A1 | 11/2016 | Gokarn et al. | |
| 2016/0362484 A1 | 12/2016 | Gokarn et al. | |
| 2016/0362485 A1 | 12/2016 | Gokarn et al. | |
| 2016/0362486 A1 | 12/2016 | Gokarn et al. | |
| 2016/0367665 A1 | 12/2016 | Gokarn et al. | |
| 2016/0367666 A1 | 12/2016 | Gokarn et al. | |
| 2017/0051039 A1 | 2/2017 | Gombotz et al. | |
| 2017/0143828 A1 | 5/2017 | Fraunhofer et al. | |
| 2017/0348225 A1 | 12/2017 | Freitag et al. | |
| 2017/0368170 A1 | 12/2017 | Gokarn et al. | |
| 2018/0110856 A1 | 4/2018 | Goss et al. | |
| 2018/0256718 A1 | 9/2018 | Goss et al. | |
| 2019/0022217 A1 | 1/2019 | Goss et al. | |
| 2019/0144523 A1 | 5/2019 | Gombotz et al. | |
| 2019/0292237 A1 | 9/2019 | Gombotz et al. | |
| 2021/0007991 A1 | 1/2021 | Manning et al. | |

FOREIGN PATENT DOCUMENTS

| | | |
|---|---|---|
| EP | 0 025 321 | 3/1981 |
| EP | 0 025 719 | 3/1981 |
| EP | 0490 549 | 6/1992 |
| EP | 0614666 A1 | 9/1994 |
| EP | 0619324 | 10/1994 |
| EP | 0 665 019 | 8/1995 |

(56) References Cited

FOREIGN PATENT DOCUMENTS

| | | |
|---|---|---|
| EP | 0893450 A1 | 1/1999 |
| EP | 1 304 376 | 10/2000 |
| EP | 1 314 437 | 5/2003 |
| EP | 1475101 A1 | 11/2004 |
| EP | 0 909 564 | 6/2006 |
| EP | 2 926 834 A1 | 10/2015 |
| JP | S61-218528 | 9/1986 |
| JP | S63-145237 | 6/1988 |
| JP | S63-192724 | 8/1988 |
| JP | 2002-539770 | 11/2002 |
| JP | 6-256222 | 3/2004 |
| JP | 2004-532262 A | 10/2004 |
| JP | 2005-027671 | 2/2005 |
| JP | 2005-506963 | 3/2005 |
| WO | WO-92/02616 A1 | 2/1992 |
| WO | WO 97/029131 | 8/1997 |
| WO | WO 97/040850 | 11/1997 |
| WO | 98/03550 A1 | 1/1998 |
| WO | WO 98/01555 | 1/1998 |
| WO | WO 98/022136 | 5/1998 |
| WO | WO-00/29004 A1 | 5/2000 |
| WO | 00/46240 A2 | 8/2000 |
| WO | WO 00/46240 * | 8/2000 |
| WO | WO 00/061177 | 10/2000 |
| WO | WO 00/062790 | 10/2000 |
| WO | WO 01/24814 | 4/2001 |
| WO | WO 01/43773 | 6/2001 |
| WO | WO 01/44472 | 6/2001 |
| WO | WO 01/58473 | 8/2001 |
| WO | WO 01/60397 | 8/2001 |
| WO | WO 02/08417 | 1/2002 |
| WO | WO 02/13860 | 2/2002 |
| WO | WO 02/30463 | 4/2002 |
| WO | WO 02/47721 | 6/2002 |
| WO | WO-02/051979 A2 | 7/2002 |
| WO | WO 02/053596 | 7/2002 |
| WO | WO 02/053596 A2 * | 7/2002 |
| WO | 02/096457 A2 | 12/2002 |
| WO | WO 02/096457 A2 | 12/2002 |
| WO | WO 03/001563 | 1/2003 |
| WO | WO 03/002713 A1 | 1/2003 |
| WO | WO 03/017935 | 3/2003 |
| WO | WO 03/024388 | 3/2003 |
| WO | 03/068260 A1 | 8/2003 |
| WO | WO 03/093320 | 11/2003 |
| WO | WO 03/102132 | 12/2003 |
| WO | WO 04/001007 | 12/2003 |
| WO | WO 04/016286 | 2/2004 |
| WO | WO 2004/083248 | 9/2004 |
| WO | WO 04/110490 | 12/2004 |
| WO | WO 05/035572 | 4/2005 |
| WO | 2005/047331 A2 | 5/2005 |
| WO | WO 2005/047331 A2 | 5/2005 |
| WO | WO 05/049078 | 6/2005 |
| WO | WO 05/095454 | 10/2005 |
| WO | WO-2005/112893 | 12/2005 |
| WO | WO 2006/003999 | 1/2006 |
| WO | WO 06/031560 | 3/2006 |
| WO | WO-2006/024497 A1 | 3/2006 |
| WO | WO-2006/064373 A2 | 6/2006 |
| WO | WO 06/0182740 | 8/2006 |
| WO | WO 06/138181 | 12/2006 |
| WO | 2007/124082 A2 | 11/2007 |
| WO | 2008/079290 A2 | 7/2008 |
| WO | WO 2008/132616 | 11/2008 |
| WO | WO 09/073569 | 6/2009 |
| WO | 2010/102241 A1 | 9/2010 |
| WO | WO 2014/08393 | 1/2014 |
| WO | WO 2014/064637 | 5/2014 |
| WO | WO 2014/078627 | 5/2014 |
| WO | WO 2014/177548 | 11/2014 |
| WO | WO 2016/033496 | 3/2016 |
| WO | WO 2016/033507 | 8/2016 |
| WO | WO 2016/149139 | 9/2016 |
| WO | WO 2018/075818 | 4/2018 |

OTHER PUBLICATIONS

Cleland J L et al: A Specific Molar 1,27,28 Ratio of Stabilizer to Protein is Required for Storage Stability of a Lyophilized Monoclonal AntibodyII, Journal of Pharmaceutical Sciences, American Pharm Assoc,Washington, US, vol. 90, No. 3, (Mar. 1, 2001),pp. 310-321.

Chen Bei et al: "Influence of histidine on the stability and physical properties of a fully human antibody in aqueous and solid forms", Pharmaceutical Research, Kluwer Academic Publishers, New York, NY, US, vol. 20, No. 12, (Dec. 1, 2003), pp. 1952-1960.

Halvor N. Christensen: "Proteins as Buffers", Annals of the New York Academy of Sciences, vol. 133, No. 1 Current Conce, (Apr. 1, 1966), pp. 34-40.

Yati N R Gokarn et al: Self-buffering antibody formulations, Journal of Pharmaceutical Sciences, American Pharmaceutical Association, Washington, US, vol. 97, No. 8, (Aug. 1, 2008), pp. 3051-3066.

Kurnik et al, Buffer Exchange Using Size Exclusion Chromatography, Countercurrent Dialysis, and Tangential Flow Filtration: Models, Development, and Industrial Application, Biotechnology and Bioengineering, vol. 45, 149-157, 1995.

Barrera, P. et al., "Effects of treatment with a fully human antitumour necrosis factor α monoclonal antibody on the local and systemic homeostasis of interleukin 1 and TNFα in patients with rheumatoid arthritis", *Ann. Rheum. Dis.*, 60: 660-669 (2001).

Chang, B. S. and Hershenson, S., "Practical Approaches to Protein Formulation Development", in *Rationale Design of stable protein formulations-theory and practice*, (J. F. Carpenter and M. C. Manning, eds., Kluwer Academic/Plenum Publishers, New York, pp. 1-25 (2002).

Chang, B. S., "Ten Major Factors in Successful Protein Formulation Development", *Integrity Bio*, 3 pgs., (2012).

Cohen et al., "Preparation and properties of serum and plasma proteins. IV. A system for the separation into fractions of the protein and lipoprotein components of biological tissues and fluids", *Separation Into Fractions of Protein and Lipoprotein Components*, vol. 68, pp. 459-475, (Mar. 1946).

Spectrum Laboratories (http://www.spectrumlabs.com/lit/hfdial.pdf, Diafiltration (Buffer Exchange) Using Hollow Fiber Membranes instead of Dialysis Tubing—Automated Diafiltration, date unknown, pp. 1-6).

Millipore (Protein Concentration and Diafiltration by Tangential Flow Filtration, http://wolfson.huji.ac.il/purification/PDF/dialysis/MILLIPORE_TFF.pdf, 2003 pp. 1-24).

Ahrer et al., "Effects of ultra-/diafiltration conditions on present aggregates in human immunoglobulin G preparations", *Journal of Membrane Science*, 274: 108-115 (2006).

Lam et al., "Antioxidants for prevention of methionine oxidation in recombinant monoclonal antibody HER2", *J. Pharm. Sci.* 86(11):1250-1255 (1997).

Levine et al., "The use of surface tension measurements in the design of antibody-based product formulations", *J. Parenteral Science & Technology* 45(3):160-165 (1991).

Wang et al., "Antibody structure, instability, and formulation", *J. Pharm. Sci.* 96(1):1-26 (2007).

Wang, "Instability, stabilization, and formulation of liquid protein pharmaceuticals", *Int'l J. Pharmaceutics* 185:129-88 (1999).

Vollmers et al., A rapid method for purification of monoclonal human IgM from mass culture, *Hum. Antibod. Hybridomas*, 7(1):37-41 (1996).

Office Action dated Oct. 15, 2018 in Japanese Application No. 2017-218002 with English Translation.

Advisory Action dated Feb. 28, 2007 in U.S. Appl. No. 10/376,576.

Cleland, et al. The Development of Stable Protein Formulations: A Close Look at Protein Aggregation, Deamination and Oxidation, Clinical Reviews in Therapeutic Drug Carrier Systems, 10(4), pp. 307-377(1993).

Clinical Pharmacology and Therapeutics, vol. 66, No. 2, pp. 205-209, (1999).

Hora, et al. Lyophilized Formulations of Recombinant Tumor Necrosis Factor, Pharmaceutical Research, 9(1), pp. 33-36, (1992).

(56) References Cited

OTHER PUBLICATIONS

Kalden, J., Emerging Role of Anti-Tumor Necrosis Factor Therapy in Rheumatic Diseases, Arthritis Research, vol. 4, Sup. 2, pp. S34-S40, (2002).
Liu W, et al. Moisture-Induced Aggregation of Lyophilized Proteins in the Solid State, Biotechnology and Bioengineering, vol. 37, pp. 177-184, (1991).
Maksymowych, W., Novel Therapeutics in the Treatment of Spondyloarthritis, Investig Drugs, vol. 11, No. 7, pp. 478-486, (1999).
Manning, et al. Stability of Protein Pharmaceuticals Pharmaceutical Research, 6(11), pp. 903-918, (1989).
Moreland L et al. Etannercept Therapy in Rheumatoid Arthritis, A Randomized Controlled Trial, Amm Intern Med, vol. 130, pp. 478-486, (1999).
Moreland, L. et al,, Treatment of Rheumatoid Arthritis with a Recombinant Human Tumor Necrosis Factor Reactor, New England Journal of Medicine, vol. 337, pp. 141-147 (1997).
Notice of Abandonment dated Oct. 24, 2007 in U.S. Appl. No. 10/376,576.
Notice of Allowance dated Sep. 4, 2009 in U.S. Appl. No. 11/784,538.
Notice of Allowance dated Oct. 18, 2011 in U.S. Appl. No. 12/632,690.
Notice of Allowance dated May 2, 2014 in U.S. Appl. No. 13/401,496.
Notice of Allowance dated Aug. 4, 2016 in U.S. Appl. No. 14/478,926.
Office Action dated Nov. 17, 2005 in U.S. Appl. No. 10/376,576.
Office Action dated Aug. 9, 2006 in U.S. Appl. No. 10/376,576.
Office Action dated Apr. 29, 2009 in U.S. Appl. No. 11/784,538.
Office Action dated May 19, 2011 in U.S. Appl. No. 12/632,690.
Office Action dated Oct. 21, 2013 in U.S. Appl. No. 13/401,496.
Office Action dated Feb. 4, 2016 in U.S. Appl. No. 14/478,926.
Office Action dated Dec. 22, 2017 in U.S. Appl. No. 15/341,962.
Paborji, M. et al., Chemical and Physical Stability of Chimeric L6 a Mouse-Human Monoclonal Antibody, Pharmacuetial Research, Springer New York LLC, vol. 11, No. 5, pp. 764-771, (1994).
Quyyumi, A., Does Acute Improvement of Endothelial Dysfunction in Coronary Artery Disease Improve Myocardial Ischemia? A Double-Blind Comparison of Parenteral D- and L- Arginine, Journal of American College of Cardiology, 32(4), pp. 200-208, (1998).
Remmele, R., et al. Inyrtlrukin-1 Receptor (1L-1R) Liquid Formulation Development Using Differential Scanning Calorimetry, Pharmaceutical Research, vol. 2, No. 2, pp. 200-2008, (1998).
Response to Office Action dated May 17, 2006 in U.S. Appl. No. 10/376,576.
Response to Office Action dated Feb. 7, 2007 in U.S. Appl. No. 10/376,576.
Response to Office Action dated Jul. 24, 2009 in U.S. Appl. No. 11/784,538.
Response to Office Action dated Aug. 17, 2011 in U.S. Appl. No. 12/632,690.
Response to Office Action dated Apr. 21, 2014 in U.S. Appl. No. 13/401,496.
Response to Office Action dated Jun. 28, 2016 in U.S. Appl. No. 14/478,926.
Response to Restriction Requirement dated Sep. 27, 2005 in U.S. Appl. No. 10/376,576.
Response to Restriction Requirement dated Jul. 8, 2008 in U.S. Appl. No. 11/784,538.
Response to Restriction Requirement dated Feb. 2, 2009 in U.S. Appl. No. 11/784,538.
Response to Restriction Requirement dated Sep. 26, 2013 in U.S. Appl. No. 13/401,496.
Response to Restriction Requirement dated Nov. 7, 2017 in U.S. Appl. No. 15/341,962.
Restriction Requirement dated May 27, 2005 in U.S. Appl. No. 10/376,576.
Restriction Requirement dated Feb. 7, 2008 in U.S. Appl. No. 11/784,538.
Restriction Requirement dated Oct. 2, 2008 in U.S. Appl. No. 11/784,538.
Restriction Requirement dated Jun. 26, 2013 in U.S. Appl. No. 13/401,496.
Restriction Requirement dated Jun. 9, 2017 in U.S. Appl. No. 15/341,962.
Risihi V, et al. Role of Non-Compatible Osmolytes in the Stabilization of Proteins During Heat Stress, Biochemical Journal, vol. 329, pp. 137-143, (1998).
Robbins D, et al., Antibodies of Covalent Aggregates of Insulin in Blood of Insulin-Using Diabetic Patients, Diabetes, vol. 36, pp. 838-845, (1987).
Soejima, K, et al., An Efficient Refolding Method for the Preparation of Combinant Human Prethombin-2 and Characterization of the Recombinant Derived a-Thrombin, J. Biochem, vol. 130, pp. 269-277, (2001).
Supplementary European Search Report dated Jan. 23, 2006 in European Patent Application No. 03716244.
Wang, Y, et al. Parenteral Formations of Proteins and Peptides: Stability and Stabilizers, Journal of Parenteral Sciences & Technology, 42(2S), pp. S04-S26, (1988).
Yancey, P., et al. Living with Water Stress: Evolution of Osmolyte Systems, Science,, vol. 217, pp. 1214-1222, (1982).
Sandoz Inc.'s Answer, Affirmative Defenses and Demand for Jury Trial in *Immunex Corporation v. Sandoz Inc.*, filed Mar. 21, 2016 in United States District Court for The District of New Jersey, C.A. No. 2:16-cv-01118-CCC-MF, 54 Pages (Document 31).
EMBREL (etamercept) label, dated Dec. 2012.
EMBREL (etamercept) label, dated Nov. 2017.
Gallagher, E. et al., Reliability and Validity of a Visual Analog Scale for acute Abdominal Pain in the Ed,, American Journal of Emergency Medicine, pp. 287-290, (2002)/.
International Search Report dated Jan. 12, 2018 in International Application No. PCT/US2017/057472.
Physicians Desk Reference, for ENBREL Medical Economics, Inc., (2002).
Yu, A. et al. Pain Perception Following Subcutaneous Injections of Citrate-Buffered and Phosphate-Buffered Epoetin Alpha, The International Journal of Artifical Organs, vol. 21, No. 6, pp. 341-343, (1998).
Meeting Request dated Aug. 5, 2016 From Amgen to FDA.
Response to Meeting Request dated Aug. 5, 2016 From FDA to Amgen.
Amgen's Supplemental Biologies License Application.
Williams. J.M. et al. Benzyl alcohol attenuates the pain of lidocaine injections and prolongs anesthesia., J. Dermatol Surg Oncol., vol. 20, No. 11, pp. 730-733, (1994).
Preliminary Amendment dated Oct. 25, 2018 in U.S. Appl. No. 16/144,120.
Office Action dated Jul. 26, 2018 in U.S. Appl. No. 15/958,261.
U.S. Appl. No. 15/214,377, filed Jul. 19, 2016, Gokarn et al.
U.S. Appl. No. 15/227,880, filed Aug. 3, 2016, Gokarn et al.
U.S. Appl. No. 15/228,955, filed Aug. 4, 2016, Gokarn et al.
U.S. Appl. No. 15/230,039, filed Aug. 5, 2016, Gokarn et al.
U.S. Appl. No. 15/231,490, filed Aug. 8, 2016, Gokarn et al.
U.S. Appl. No. 15/232,733, filed Aug. 9, 2016, Gokarn et al.
U.S. Appl. No. 15/255,018, filed Sep. 1, 2016, Gokarn et al.
U.S. Appl. No. 15/698,408, filed Sep. 7, 2017, Gokarn et al.
U.S. Appl. No. 16/144,120, filed Sep. 27, 2018, Goss et al.
U.S. Appl. No. 60/700,265, filed Jul. 18, 2005, Siu et al.
AbbVie Biotechology Ltd., "Patent Owner's Preliminary Response," in *Coherus Biosciences Inc. v. AbbVie Biotechnology Ltd.*, IPR2016-01018, Paper No. 9 (PTAB Aug. 9, 2016).
Adalimumab Product Approval Information, http://www.fda.gov/Drugs/DevelopmentApprovalProcess/HowDrugsareDevelopedandApproved?ApprovalApplications/TherapeuticBiologicApplications/ucm080610.htm (accessed Jan. 23, 2017). It is noted that this item refers to a webpage, and may have been available in some form at an earlier point in time.
Adalimumab Drugs of the Future, 2001, 26: pp. 639-646.
Advisory Action dated Aug. 28, 2017 in U.S. Appl. No. 15/231,490.
Advisory Action dated Sep. 5, 2017 in U.S. Appl. No. 15/232,733.
Affidavit of Christopher Butler dated Feb. 21, 2017 in the Patent Trial and Appeal Board, United States Patent and Trademark Office, Petition Nos. PTAB-IPR2017-01008, PTAB-IPR2017-01009.

(56) References Cited

OTHER PUBLICATIONS

Affidavit of Marlene S. Bobka dated Feb. 21, 2017 in the Patent Trial and Appeal Board, United States Patent and Trademark Office, Petition Nos. PTAB-IPR2017-01008, PTAB-IPR2017-01009.
Affidavit of Michael Deas attaching English translation of OCTAGAM ® entry (75 008) in Rote Liste 2005 (Cantor Publishers 2005) as Exhibit A, and original German-language Rote Liste 2005 entry 75 008 as Exhibits B and C.
Akers et al., "Formulation Development of Protein Dosage Forms", Chapter 2, pp. 47-127, 2002.
Alberts, Molecular Biology of the Cell, Fourth Edition, New York, NY: Garland Publishing, Inc., pp. 1363-1384 (2002).
Amendment and Response to Non-Final Office Action dated Jun. 26, 2015 in U.S. Appl. No. 13/188,329.
Amendment and Response to Non-Final Office Action dated Mar. 10, 2015 in U.S. Appl. No. 13/188,329.
Amendment and Response to Final Office Action dated Nov. 17, 2017 in U.S. Appl. No. 15/231,490.
Amendment dated Aug. 24, 2015. U.S. Appl. No. 14/643,844.
Amersham Biosciences, "Ion exchange chromatography: Principles and methods" 1-157 (1999).
Andrew and Titus, "Fragmentation of Immunoglobulin G", Curr. Protoc. Cell Biol., Chapter 16;Unit 16.4, p. 16.4.1-16.4.10 (2000).
Antoni et al., "Side effects of anti-TNF therapy: Current knowledge." Clin Exp Rheumatol 2002; 20 (Suppl. 28). S152-S157.
Applicant Initiated Interview Summary dated Feb. 8, 2016 in U.S. Appl. No. 13/188,329.
Applicant-Initiated Interview Summary dated Nov. 26, 2012 in U.S. Appl. No. 12/325,049.
Application Data Sheet Dated Nov. 28, 2008 in U.S. Appl. No. 12/325,049.
Arakawa et al., "Elution of Antibodies from a Protein-A Column by Aqueous Arginine Solutions", Protein Expr. Purif. 36:244-248 (2004).
Aulton, Michael E. Pharmaceutics: The Science of Dosage Form Design pp. 359-380 (1988).
AVASTIN Label (Feb. 2004).
Avonex® (interferon beta-1a) Label, 1-23 (2001).
Avonex® (interferon beta-1a), Physicians' Desk Reference, PDR 57, Thomson PDR, Montvale, NJ, pp. 1006-1010 (2003).
AvvVie Biotechnology Ltd., "Annex A—The Humira Story," in Opposition Proceeding for EP1406656 (filed on Dec. 22, 2014).
Barnett, et al., "Reduction of Pain and Local Complications When Buffered Lidocaine Solution is Used as a Local Anesthetic in Conjunction with Hyperthermia Treatments: Results of a Randomized Trial," Int'l J. Radiation Oncology Biol. Phys. 23(3), pp. 585-591. 1992.
Bekker et al., "A Single-Dose Placebo-Controlled Study of AMG 162, a Fully Human Monoclonal Antibody to RANKL, in Postmenopausal Women", J. Bone Miner. Res. 19:1059-1066 (2004).
Berg et al., "Exploring Proteins" in Biochemistry, 5th edition, pp. 77-116, New York, W H Freeman (copyright date 2002).
Berne, Robert M et al. excerpt, Chapter 20 "Blood Components" in Physiology 3rd Edition pp. 327-338 (1993).
Bexxar® (tositumomab and iodine | 131 tositumomab) Label, 1-49 (2003).
Bexxar® (tositumomab and iodine | 131 tositumomab), Physicians' Desk Reference, PDR 60, pp. 1360-1366 (2006).
Binabaji et al., "Theoretical Analysis of the Ultrafiltration Behavior of Highly Concentrated Protein Solutions", Journal of Membrane Science 494:216-223 (2015).
Binabaji et al., "Ultrafiltration of Highly Concreated Antibody Solutions: Experiments and Modeling for the Effects of Module and Buffer Conditions", Biotech. Prog. 32:692-701 (2016).
Biologies License Application No. 125057/0, Submitted to the FDA on Mar. 28, 2002.
Bjorck et al., Purfication and Some Properties of Streptoccal Protein G, a Novel IgG-Biding Reagent J. Immunol. 133:969-74 (1984).
Boes, "Role of Natural and Immune IgM Antibodies in Immune Responses," Mol. Immunol., 37:1141-1149 (2000).

Brazeau, et al., "Current Perspectives on Pain upon Injection of Drugs," J. Pharm. Sci 87(6), pp. 667-677. Jun. 1998.
Brown, Theodore L. et al excerpt, Chapter 17 "Additional Aspects of Aqueous Equilibria" in Chemistry: The Central Science 8th Edition (2000).
Burton, D.R et al., Aspects of the Molecular Structure of IgG Subclasses, 19 Monogr. Allergy 7-35 (1986).
Butler & Hamilton, "Quantitation of Specific Antibodies: Methods of Express, Standards, Solid-Phase Considerations, and Specific Applications," Ch. 9 un Immunochemistry of Solid-Phase Immunoassay, CRC Press (John E. Butler ed., 1991).
Cada, ed., Adalimumab. Hospital Pharmacy 2003; 38: pp. 568-580.
Campath Label (Aug. 2006).
Campath® (alemtuzumab) Label, 1-14 (2004).
Campath® (alemtuzumab), Physicians' Desk Reference, PDR 57, Thomson PDR, Montvale, NJ, pp. 975-977 (2003).
Carnahan et al., "Epratuzumab, a Humanized Monoclonal Antibody Targeting CD22: Characterization of in Vitro Properties"; Clinical Cancer Research 9:3982s-3990s (2003).
Carpenter, et al., "Rational Design of Stable Lyophilized Protein Formulations: Some Practical Advice," Pharm. Res. 12(8), pp. 969-975.1997.
Carpenter, J. F. and Manning, M. C., eds., Pharmaceutical Biotechnology, "Rational Design of Stable Protein Formulations, Theory and Practice", vol. 13: Kluwer Academic/Plenum Publishers, New York, Boston, Dordrecht, London, Moscow (2002).
Carter, "Improving the Efficacy of Antibody-Based Cancer Therapy", Nat. Rev. Cancer 1:118-129 (2001).
Castellano et al., "The Role of RANK-Ligand Inhibition of Cancer: The Story of Denosumab", The Oncologist 16:136-145 (2011).
Chen, et al., "Aggregation Pathway of Recombinant Human Keratinocyte Growth Factor and Its Stabilization," Pharm. Res. 11(11), pp. 1581-1587. 1994.
Chi et al., "Physical Stability of Proteins in Aqueous Solution: Mechanism and Driving Forces in Nonnative Protein Aggregation", Pharm. Res. 20: 1325-1336 (2003).
Chong and Wong, "Immunobiologies in the Treatment of Psoriasis", Clin. Immunol. 123:129-138 (2007).
Christensen, "Protein as Buffers", Annals of the New York Academy of Sciences. 133(1) . Apr. 1, 1966, pp. 34-40.
Cleland & Langer, "Formulation and Delivery of Proteins and Peptides: Design and Development Strategies," Ch. 1 in Formulation and Delivery of Proteins and Peptides, ACS Symposium Series 567, 1-19 (1994).
Clinical Pharmacology and Biopharmaceutics Review(s), by Center for Drug Evaluation and Research and Center for Biologies Evaluation and Research, Application No. 125057/0, in Approval Package for Humira ® (Approved Dec. 31, 2002).
Clowse, et al., Efficacy and Safety of Epratuzumab in Moderately to Severely Active Systemic Lupus Erythematosus Arthritis & Rheumatology. 69:362-375 (2016).
CNJ-016 (Vaccinia Immune Globulin Intravenous) Label (Jan. 2010).
Corrected pp. 87-88 of declaration of Geoffrey Lee, Ph.D. dated Mar. 13, 2017 in Interference No. 106,057, involving U.S. Appl. No. 13/188,329 and U.S. Appl. No. 13/188,329 and U.S. Pat. No. 8,420,081.
Curtis et al., Injection-Site Burning and Stinging in Patients With Rheumatoid Arthritis UsingJnjectable Biologies. Curr Med Res Opin. Jan. 2011; 27: pp. 71-78.
Dantal, Intravenous Immunoglobulins: In-Depth Review of Excipients and Acute Kidney Injury Risk, Am. J. Nephrol. 2013; 38; 275-284.
Daugherty, et al., "Formulation and Delivery Issues for Monoclonal Antibody Therapeutics," Adv. Drug Deliv. Rev. 58, pp. 686-706. 2006.
Davies and Metzger, "Structural Basis of Antibody Function", Annu. Rev. Immunol. 1:87-117 (1983).
Dean, "Lange's Handbook of Chemistry," McGraw-Hill, p. 8.49-8.65 (9th ed. 1999).
Decision—Motions—Board Rule 121(a), dated Sep. 27, 2017 in Interference No. 106,057, involving U.S. Appl. No. 13/188,329 and U.S. Appl. No. 13/188,329 and U.S. Pat. No. 8,420,081.

(56) References Cited

OTHER PUBLICATIONS

Declaration of David D. Sherry, M.D dated Feb. 26, 2017. in the Patent Trial and Appeal Board, United States Patent and Trademark Office, Petition No. PTAB-IPR2017-01008.
Declaration of David D. Sherry, M.D dated Feb. 26, 2017. in the Patent Trial and Appeal Board, United States Patent and Trademark Office, Petition No. PTAB-IPR2017-01009.
Declaration of David D. Sherry, M.D. dated Jan. 31, 2017 in the Patent Trial and Appeal Board, United States Patent and Trademark Office, Petition No. PTAB-IPR2017-00827.
Declaration of David D. Sherry, M.D. dated Jan. 31, 2017 in the Patent Trial and Appeal Board, United States Patent and Trademark Office, Petition No. PTAB-IPR2017-00826.
Declaration of Geoffrey Lee, Ph.D. (supplemental), dated Feb. 16, 2017 in Interference No. 106,057, involving U.S. Appl. No. 13/188,329 and U.S. Appl. No. 13/188,329 and U.S. Pat. No. 8,420,081.
Declaration of Interference dated May 18, 2016, in Interference No. 106,057, involving U.S. Pat. No. 8,420,081 and U.S. Appl. No. 13/797,622.
Declaration of Klaus-Peter Radtke, Ph.D. dated Feb. 28, 2017, in the Patent Trial and Appeal Board, United States Patent and Trademark Office, Petition No. PTAB-IPR2017-01008.
Declaration of Klaus-Peter Radtke, Ph.D. dated Feb. 28, 2017, in the Patent Trial and Appeal Board, United States Patent and Trademark Office, Petition No. PTAB-IPR2017-01009.
Declaration of Klaus-Peter Radtke, Ph.D, dated Jan. 31, 2017, in the Patent Trial and Appeal Board, United States Patent and Trademark Office, Petition No. PTAB-IPR2017-00822.
Declaration of Klaus-Peter Radtke, Ph.D. dated Jan. 31, 2017, in the Patent Trial and Appeal Board, United States Patent and Trademark Office, Petition No. PTAB-IPR2017-00823.
Declaration of Klaus-Peter Radtke, Ph.D, dated Jan. 31, 2017, in the Patent Trial and Appeal Board, United States Patent and Trademark Office, Petition No. PTAB-IPR2017-00826.
Declaration of Klaus-Peter Radtke, Ph.D. dated Jan. 31, 2017, in the Patent Trial and Appeal Board, United States Patent and Trademark Office, Petition No. PTAB-IPR2017-00827.
Declaration of Mark C. Manning, Ph.D. dated May 6, 2016 from IPR2017-01008, Ex. 2004.
Declaration of Richard L. Remmele, Jr. dated Jul. 24, 2009 in U.S. Appl. No. 11/784,538, also Ex. 1044 in IPR2017-01823.
Petition for Inter Parties Review of U.S. Pat. No. 8,802,100 dated Jul. 20, 2017 by Sandoz, Inc., in the Patent Trial and Appeal Board, United States Patent and Trademark Office, No. IPR2017-01823.
Declaration of Richard L. Remmele, Jr, dated Jul. 5, 2016 from IPR2017-01823, Ex.1002.
Deposition Transcript of Geoffrey Lee, Ph.D., dated Mar. 13, 2017 in Interference No. 106,057, involving U.S. Appl. No. 13/188,329 and U.S. Appl. No. 13/188,329 and U.S. Pat. No. 8,420,081.
Development Pharmaceutics for Biotechnological and Biological Products (Annex to Note for Guidance on Development Pharmaceutics), by Committee for Proprietary Medicinal Products, The European Agency for the Evaluation of Medicinal Products (Oct. 21, 1999).
DiJoseph et al., "Antibody-Targeted Chemotherapy with CMC-544; a CD22-targeted Immuconjugate of Calichemicin for the Treatment of B-Lymphoid Malignancies", Blood 103:1807-1814 (2004).
Egan, "Biotechnology in Drug Research Experimental, Toxicological and Clinical Aspects", Arzneimittelforschung 49:779-790 (1999).
ENBREL ® Label (Nov. 1998).
ENBREL ® Label (Sep. 2002).
ENBREL ® Label (2004).
Endobulin S/D label, text revised Jul. 1999 (with machine translation).
European Medical Agency. Initial Scientific Discussion for the Approval of Trudexa. Copyright 2004, EMEA.
Executed Transcript of Deposition Transcript of Andrew Zydney dated Jan. 13, 2017 (with errata sheet) in Interference No. 106,057, involving U.S. Appl. No. 13/188,329 and U.S. Appl. No. 13/188,329 and U.S. Pat. No. 8,420,081.

Executed Transcript of Deposition Transcript of Peter Tessier dated Jan. 5, 2017 (with errata sheet) in Interference No. 106,057, involving U.S. Appl. No. 13/188,329 and U.S. Appl. No. 13/188,329 and U.S. Pat. No. 8,420,081.
Extended European Search Report dated Apr. 26, 2018 in European App No. 17205734.1-1118.
Fayos, et al., "On the Origin of the Thermostabilization of Proteins Induced by Sodium Phosphate," J. Am. Chem. Soc. 127(27), pp. 9690-9691. 2005.
Fesinmeyer, et al., Effect of Ions on Agitation- and Temperature-Induced Aggregation Reactions of antibodies. Pharmaceutical Research, Apr. 2009, vol. 26: pp. 903-913.
Fesinmeyer, RM, Presentation at AAPS National Biotechnology Conference, Jun. 24-27, 2007, San Diego Convention Center.
File History of Int'l Patent Application # PCT/US2006/022599, filed Jun. 8, 2006.
File History of U.S. Appl. No. 15/214,377, filed Jul. 19, 2016.
File History of U.S. Appl. No. 15/227,880, filed Aug. 3, 2016.
File History of U.S. Appl. No. 15/228,955, filed Aug. 4, 2016.
File History of U.S. Appl. No. 15/230,039, filed Aug. 5, 2016.
File History of U.S. Appl. No. 15/231,490, filed Aug. 8, 2016.
File History of U.S. Appl. No. 15/232,733, filed Aug. 9, 2016.
File History of U.S. Appl. No. 15/255,018, filed Sep. 1, 2016.
File History of U.S. Appl. No. 13/188,329, filed Jul. 21, 2011.
File History of U.S. Appl. No. 11/917,188, having a 371(c) date of Jun. 16, 2008.
File History of U.S. Appl. No. 12/325,049, filed Nov. 28, 2008.
File History of U.S. Appl. No. 13/797,690, filed Mar. 12, 2013.
Final Amendment date Jul. 26, 2016 in U.S. Appl. No. 13/188,329.
Final Office Action dated May 18, 2017 in U.S. Appl. No. 15/231,490.
First Declaration of Peter Tessier, Ph.D., dated Oct. 11, 2016.
Fisher Scientific Safety Data Sheet for Phosphate Buffered Saline Solution (creation date Sep. 22, 2009; Revision Date Apr. 10, 2014).
Flebogamma Label (Jan. 2004).
Fleischmann et al., "Does safety make a difference in selecting the right TNF antagonist?" Arthritis Research & Therapy 2004; vol. 6 Suppl 2 pp. S12-S28.
Fransson et al., Local Tolerance of Subcutaneous Injection. J. Pharm. Pharmacol. 1996: 48, pp. 1012-1015.
Fraunhofer Exhibit List 3 over Fraunhofer's U.S. Pat. No. 8,420,081 dated Oct. 31, 2016 in Interference No. 106,057, involving U.S. Appl. No. 13/188,329 and U.S. Appl. No. 13/188,329 and U.S. Pat. No. 8,420, 081.
Fraunhofer Motions List dated Jul. 27, 2016 in Interference No. 106,057, in 23 pages.
Fraunhofer Objections to Evidence 1, Served Feb. 7, 2017 n Interference No. 106,057, involving U.S. Appl. No. 13/188,329 and U.S. Appl. No. 13/188,329 and U.S. Pat. No. 8,420,081.
Fraunhofer Substantive Motion 1 (for judgment based on 35 U.S.C. § 135(b)(1) over Fraunhofer's U.S. Pat. No. 8,420,081) dated Oct. 12, 2016 in Interference No. 106,057, involving U.S. Appl. No. 13/188,329 and U.S. Appl. No. 13/188,329 and U.S. Pat. No. 8,420, 081.
Fraunhofer Substantive Motion 2 (for judgment based on 35 U.S.C. § 112 second paragraph) dated Oct. 12, 2016 in Interference No. 106,057, involving U.S. Appl. No. 13/188,329 and U.S. Appl. No. 13/188,329 and U.S. Pat. No. 8,420, 081.
Fraunhofer Substantive Motion 3 (to substitute proposed Count A for Count 1) dated Oct. 12, 2016 in Interference No. 106,057, involving U.S. Appl. No. 13/188,329 and U.S. Appl. No. 13/188,329 and U.S. Pat. No. 8,420, 081.
Fraunhofer Substantive Motion 4 (to vacate benefit of Gokarn U.S. Appl. No. 13/188,329) dated Oct. 12, 2016 in Interference No. 106,057, involving U.S. Appl. No. 13/188,329 and U.S. Appl. No. 13/188,329 and U.S. Pat. No. 8,420, 081.
Fraunhoffer Miscellaneous Motion 5 to Exclude Evidence dated Apr. 5, 2017 in Interference No. 106,057, involving U.S. Appl. No. 13/188,329 and U.S. Appl. No. 13/188,329 and U.S. Pat. No. 8,420,081.
Fraunhoffer Reply 1 dated Mar. 25, 2017 in Interference No. 106,057, involving U.S. Appl. No. 13/188,329 and U.S. Appl. No. 13/188,329 and U.S. Pat. No. 8,420,081.

(56) References Cited

OTHER PUBLICATIONS

Fraunhoffer Reply 2 dated Mar. 25, 2017 in Interference No. 106,057, involving U.S. Appl. No. 13/188,329 and U.S. Appl. No. 13/188,329 and U.S. Pat. No. 8,420,081.
Fraunhoffer Reply 3 dated Mar. 25, 2017 in Interference No. 106,057, involving U.S. Appl. No. 13/188,329 and U.S. Appl. No. 13/188,329 and U.S. Pat. No. 8,420,081.
Fraunhoffer Reply 4 dated Mar. 25, 2017 in Interference No. 106,057, involving U.S. Appl. No. 13/188,329 and U.S. Appl. No. 13/188,329 and U.S. Pat. No. 8,420,081.
Fraunhoffer Reply 5 dated Apr. 25, 2017 in Interference No. 106,057, involving U.S. Appl. No. 13/188,329 and U.S. Appl. No. 13/188,329 and U.S. Pat. No. 8,420,081.
Frenken et al., "Identification of the Component Part in an Epoetin Alfa Preparation that Causes Pain After Subcutaneous Injection." American J. Kidney Dis. 1992; 22: pp. 553-556.
GAMIMUNE Label (Oct. 2005).
Gammagard Liquid Label (Apr. 2005).
Gammagard S/D, Immune Globulin Intravenous (Human) label, initial US Approval 1994, revised 2014.
GAMUNEX Label (Nov. 2005).
Gatlin & Gatlin, "Formulation and Administration Techniques to Minimize Injection Pain and Tissue Damage Associated with Parenteral Products," Chapter 17 of Injectable Drug Development: Techniques to Reduce Pain and Irritation (Eds. Gupta & Brazeau) (1999).
Gebhart, "Biotech Company Preparing Several Drugs for Take-off," Drug Topics, vol. 145, No. 5, p. 50 (Mar. 5, 2001).
Gelfand, "Differences Between IGIV Products: Impact on Clinical Outcome," Int'l Immunopharmacology, 6:592-99 (2006).
Gokarn et al., "Excipients for Protein Drugs," Ch. 17 in Excipient Development for Pharmaceutical, Biotechnology, and Drug Delivery Systems (*Ashok Katdare & Mahesh* v. *Chaubal eds.*, 2006).
Gokarn Opposition 1 dated Jan. 31, 2017 in Interference No. 106,057, involving U.S. Appl. No. 13/188,329 and U.S. Appl. No. 13/188,329 and U.S. Pat. No. 8,420,081.
Gokarn Opposition 2 dated Jan. 31, 2017 In Interference No. 106,057, involving U.S. Appl. No. 13/188,329 and U.S. Appl. No. 13/188,329 and U.S. Pat. No. 8,420,081.
Gokarn Opposition 3 dated Jan. 31, 2017 in Interference No. 106,057, involving U.S. Appl. No. 13/188,329 and U.S. Appl. No. 13/188,329 and U.S. Pat. No. 8,420,081.
Gokarn Opposition 4 dated Jan. 31, 2017 in Interference No. 106,057, involving U.S. Appl. No. 13/188,329 and U.S. Appl. No. 13/188,329 and U.S. Pat. No. 8,420,081.
Gokarn Oppostion to Miscellaneous Motion 5 to Exclude Evidence dated Apr. 1, 2017 in Interference No. 106,057, involving U.S. Appl. No. 13/188,329 and U.S. Appl. No. 13/188,329 and U.S. Pat. No. 8,420,081.
Gottlieb, "Efficacy and Safety of Anti-TNF-a Agents in Psoriasis," in Anti-TNF-a Therapies in the Treatment of Dermatologic Diseases at 6 (2005) (Supplement to Skin & Allergy News; Produced In Affiliation with the Skin Disease Education Foundation's 29th Annual Hawaii Dermatology Seminar).
Granolleras et al., "Experience of Pain After Subcutaneous Administration of Different Preparations of Recombinant Human Erythropoietin: A Randomized, Double-Blind Crossover Study," Clinical Nephrology, 36:294-298 (1991).
Handbook of Pharmaceutical Excipients, Pharmaceutical Press (Raymond C. Rowe, Paul J, Sheskey, & Sian C. Owen eds., 5th ed. 2006).
Hanna, The IGIV-C Study Group, "Tolerability of a New Intravenous Immunogobulin Preparation (IGIV) in Pediatric and Adult Patients," presented at the 60th Anniversary Meeting of the American Academy of Allergy, Asthma & Immunology (Mar. 10, 2003), in J. Allergy Clinical Immunology, vol. 111, No. 2, part 2, a631.
Hardcastle, "Buffer Action of Proteins", J. Chem. Ed. 58: pp. 725-726 (1981).
Harinayaran et al., "Small Molecule Clearance in Ultrafiltration/ Diafiltration in Relation to Protein Interactions: Study of Citrate Binding to a Fab", Biotech. Bioeng. 102:1718-1722 (2009).

Harlow and Lane, Antibodies: A Laboratory Manual, Cold Spring Harbor, NY: Cold Spring Harbor Laboratory, pp. 1-22 (1988).
Helms, et al., "Destabilizing Loop Swaps in the CDRs of an Immunoglobin VL Domain," Protein Sci. 4, pp. 2073-2081. 1995.
HepaGam B Summary Basis for Approval (Jan. 2006).
Herceptin® (trastuzumab) Label, 1-28 (2002).
Herceptin® (trastuzumab), Physicians' Desk Reference, PDR 57, Thomson PDR, Montvale, NJ, pp. 1399-1402 (2003).
Humblet, Cetuximab: an IgG1 Monoclonal Antibody for the Treatment of Epidermal Growth Factor Receptorexpressing Tumours Expert Opin. Pharmacother., 5:1621-1633 (2004).
Humira ® Label (Feb. 2007).
Humira ® Label (Feb. 2008).
Humira ® Label (Nov. 2006).
Humira ® Label (Oct. 2005).
Humira Label (Jan. 2003).
Humira Label (Jan. 2008).
Humira Label (Nov. 2015).
Humira Label (Oct. 2016).
Humira Product label, dated Dec. 31, 2002.
Humira Product label, dated Jul. 30, 2004.
Humira® (adalimumab) Label, 1-16 (2002).
Humira® (adalimumab), Physicians' Desk Reference, PDR 58, Thomson PDR, Montvale, NJ, pp. 470-474 (2004).
Humphreys, "Top 200 Medicines—Special Report," Pharmalive, http://www.pharmalive.com/special-report-top-200-medicines/. Aug. 12, 2015.
Hypermol, "Dialysis: an introduction," Dialysis: Technical Datasheet, 1-2 (2008).
Injection Tips, Humira.com, http://www.humira.com/hu/hustore/cgi-bin/ProdSubEV_Cat_205043_SubCat_210170_NavRoot_205042_NavID_301.htm [http://web.archive.org/web/20050317083331/http://www.humira.com/hu/hustore/cgi-bin/ProdSubEV_Cat_205043_SubCat_210170_NavRoot_205042_NavID_301.htm (Archived Mar. 17, 2005). It is noted that this item refers to a webpage, and may have been available in some form at an earlier point in time,.
International Preliminary Report on Patentability dated Dec. 17, 2007 in PCT App. No. PCT/US2006/022599.
International Search Report and Written Opinion dated May 12, 2009 in PCT App. No. PCT/US2008/085066,.
International Search Report and Written Opinion dated Oct. 12, 2007 in PCT App. No. PCT/US2006/022599.
Ipp, et al., "Adverse Reactions to Diptheria, Tetanus, Pertussis-Polio Vaccination at 18 Months of Age: Effect of injection Site and Needle Length," Pediatrics 83(5): pp. 679-682. May 1989.
Jefferis et al., "Recognition Sites on Human IgG for Fcy Receptors: The Role of Glycosylation," Immunology Letters, 44:111-117 (1995).
Jorgensen, "Improvement of Patient Convenience in Treatment with Growth Hormone," J. Pediatric Endocrinology 7(2), pp. 175-180. 1994.
Jorgensen, et al., "Pain Assessment of Subcutaneous Injections," Ann. Pharmacotherapy 30, pp. 729-732. Jul./Aug. 1996.
Kamerzell, et al., "Increasing IgG Concentration Modulated the Conformational Heterogeneity and Bonding Network that Influence Solution Properties," J. Phys. Chem. B. 113(17), pp. 6109-6118. 2009.
Kaminiski, M.S., et al., Pivotal Study of Iodine I 131 Tositumomab for Chemotherapy-Refractory Low-Grade or Transformed Low-Grade B-Cell Non-Hodgkin's Lymphomas, Journal of Clinical Oncology, vol. 19, No. 19, pp. 3918-3928, 2001.
Kaminski, M.S., et al., Radioimmunotherapy of B-Cell Lymphoma with [131I] Anti-B1 (Anti-CD20) Antibody, The New England Journal of Medicine, vol. 329, No. 7, pp. 459-465, 1993.
Kappelgaard, et al., Liquid Growth Hormone: Preservatives and Buffers. Horm Res 2004;62(suppl 3): pp. 98-103.
Katdare et al., eds., Excipient Development for Pharmaceutical Biotechnology and Drug Delivery Systems, 1st Ed., Informa Healthcare USA, Inc., New York, 2006.
Kempeni, Preliminary results of early clinical trials with the fully human anti-TNF α monoclonal antibody D2E7. Ann. Rheum. Dis. 1999; 58(Suppl): 170-172.
Kim et al., Diffusivity of Protein in Aqueous Solution. Korean J. Chem. Eng., 1996; 13: pp. 288-297.

(56) References Cited

OTHER PUBLICATIONS

Koticha et al., "Rapid Antibody Purification Using Ultrafiltration and Centrifugal Affinity Columns," BioscienceTechnologies.com, accessible on the world wide web at www.biosciencetechnology.com/article/2006/07/rapid-antibody-purification-usingultrafiltration-and-centrifugal-affinity-cols. As this is a webpage, the earliest publication date is not apparent on the document itself. However, the document specifies a date of Jul. 17, 2006.
Kotz and Treichel, "Principles of Reactivity: Reactions Between Acids and Bases" Chem. & Chem. Reactivity, Chapter 18:Unit 18.3, pp. 851-858 (1999).
Kuzu, et al., "The Effect of Cold on the Occurrence of Bruising, Haematoma and Pain at the Injection Site in Subcutaneous Low Molecular Weight Heparin," Int't J. Nursing Studies 38, pp. 51-59. 2001.
Laursen et al., "Pain perception after subcutaneous injections of media containing different buffers,".
Lee, et al., "Toward Aggregation-resistant Antibodies by Design," Trends in Biotech. 31(11), pp. 612-620. 2013.
Li et al., Resurrecting Abandoned Proteins with Pure Water: CD and NMR Studies of Protein Fragments Solubilized in Salt-Free Water. Biophysical Journal Dec. 2006; 91: pp. 4201-4209.
Lide, CRC Handbook of Chemistry and Physics, 81st ed., Boca Raton, FL: CRC Press., pp. 7-1, 8-44 to 8-56 (2000).
Lista immunoglobuline in italia, Accessed from the world wide web at http://wp.aip-it.org/wp-content/uploads/2013/03/lista_Immunoglobuline_in_italia.pdf. This document is from the world wide web, and no date of publication is immediately apparent in the document. As this is a webpage, the earliest publication date is not apparent on the document itself. However, the document specifies that it was last updated Dec. 2007.
Liu et al. Reversible Self-Association Increases the Viscosity of a Concentrated Monoclonal Antibody in Aqueous Solution. J. Pharmacuetical. Sci. 2005; 94: pp. 1928-1940.
Lovrien et al. Selective Precipitation of Proteins, Current Protocols in Protein Science, 1997, at 4.5.1.
Manual of Patent Examining Procedure § 1101.02: "With a Patent" (2nd ed., Nov. 1953).
Manual of Patent Examining Procedure § 1101.02: "With a Patent" (3rd ed., Nov. 1961).
Manual of Patent Examining Procedure § 2173.03: "Correspondence Between Specification and Claims" (9th ed., Rev. 7, Nov. 2015).
Manual of Patent Examining Procedure § 2309.01: "Formulation of Counts [R-2]" (5th ed. rev. 7, Dec. 1987).
Manual of Patent Examining Procedure 2111.01.V: "How to Determine the Meaning of a Claim Term That Does Not Invoke 35 USC 112(f)".
McCue et al., "Three Generations of Immunoglobulin G Preparations for Clinical Use," Reviews of Infectious Diseases, 8:S374-81 (1986).
McDonnell. "Chapter 3: Production of Antibodies in Hybridoma and Non-hybridoma Cell Lines." In Animal Cell Culture, Cell Engineering 9, Springer International Publishing Switzerland 2015.
Meadows & Hollowell, "'Off-label' drug use: an FDA Regulatory Term, Not a Negative Implication of Its Medical Use," Int'l J. Impotence Research 20:135-144 (2008).
Mease, Adalimumab in the treatment of arthritis. Therapeutics and Clinical Risk Management 2007; 3: pp. 133-148.
Meyssami et al., "Prediction of PH Model Systems Pressurized with Carbon Dioxide", Biotechnol. Prog. 8:149-154 (1992).
Mezzasalma, et al., "Enhancing Recombinant Protein Quality and Yield by Protein Stability Profiling," J. Biomolecular Screening 12(3), pp. 418-428. 2007.
Miscellaneous Communication dated Aug. 3, 2016 in U.S. Appl. No. 13/188,329.
Mohan, "Buffers: A guide for the preparation and use of buffers in biological systems," Calbiochem, 1-32 (2003).

Nash et al. Randomized Crossover Comparison of Injection Site Pain with 40 mg/0.4 or 0.8mL Formulations of Adalimumab in Patients with Rheumatoid Arthritis. Rheumatol. Ther. Jun. 9, 2016.
NCI Dictionary of Cancer Terms, https://www.cancer.gov/publications/dictionaries/cancer-terms, downloaded Oct. 31, 2016; however, as this is a webpage, it may have been accessible in some form prior to Oct. 31, 2016.
Ng, Drugs: From Discovery to Approval, Wiley-Liss, Hoboken, N.J., pp. 159-280 (2004).
Niederkofler, et al., MSIA Workflow for Therapeutic Antibodies: Qualitative, Quantitative, and Functional Verification Data from HR/AM Detection of Intact, Reduced, and Peptide-level Forms of Adalimumab. Thermo Fisher Scientific Inc. Accessed on the world wide web at tools.thermofisher.com/content/sfs/brochures/MSIA-Workflow-for-Therapeutic-Antibodies.pdf. As this is a webpage, the earliest publication date is not apparent on the document itself. However, the document specifies a copyright date of 2014.
Non-Final Rejection dated Jan. 4, 2012 in U.S. Appl. No. 12/325,049.
Non-Final Rejection dated Mar. 2, 2011 in U.S. Appl. No. 12/325,049.
Note for Guidance on Development Pharmaceutics, by the Committee for Proprietary Medicinal Products (CPMP), The European Agency for the Evaluation of Medicinal Products (Jan. 28, 1998).
Notice of Abandonment dated Mar. 7, 2016 in U.S. Appl. No. 13/797,690.
Notice of Abandonment dated Nov. 1, 2011 in U.S. Appl. No. 11/917,188.
Notice of Allowance dated Apr. 25, 2016 in U.S. Appl. No. 13/797,622.
Notice of Allowance dated Nov. 26, 2012 in U.S. Appl. No. 12/325,049.
Nozaki et al., Examination of Titration Behavior, Methods Enzymol., 11: 715-734 (1967).
OCTAGAM Label (Mar. 2004).
Office Action dated May 18, 2017 in U.S. Appl. No. 15/230,039.
Office Action dated Jan. 20, 2017 in U.S. Appl. No. 15/228,955.
Office Action dated Apr. 2, 2015 in U.S. Appl. No. 13/188,329.
Office Action dated Apr. 27, 2016 in U.S. Appl. No. 13/188,329.
Office Action dated Apr. 28, 2016 in EP Patent App. No. 06772779.2.
Office Action dated Apr. 27, 2018 in U.S. Appl. No. 15/227,880.
Office Action dated Aug. 3, 2015 in U.S. Appl. No. 13/797,690.
Office Action dated Dec. 10, 2014 in U.S. Appl. No. 13/188,329.
Office Action dated Jan. 15, 2015 in U.S. Appl. No. 13/797,690.
Office Action dated Jul. 5, 2016 in CA Patent App. No 2,610,839.
Office Action dated Jul. 6, 2017 in U.S. Appl. No. 15/232,733.
Office Action dated Jun. 15, 2015 in EP Patent App. No. 08857510.5.
Office Action dated Jun. 18, 2014 in EP Patent App. No. 08857510.5.
Office Action dated Jun. 29, 2017 in U.S. Appl. No. 15/228,955.
Office Action dated Mar. 21, 2011 in U.S. Appl. No. 11/917,188.
Office Action dated May 24, 2017 in U.S. Appl. No. 15/227,880.
Office Action dated May 4, 2018 in U.S. Appl. No. 15/698,405.
Office Action dated Nov. 25, 2016 in U.S. Appl. No. 15/232,733.
Office Action dated Nov. 25, 2016 in U.S. Appl. No. 15/255,018.
Office Action dated Jul. 18, 2017 in Japanese Application No. JP 2015-216447 (with English translation).
Office Action dated Nov. 9, 2016 in U.S. Appl. No. 15/227,880.
Office Action dated Nov. 9, 2016 in U.S. Appl. No. 15/230,039.
Office Action dated Nov. 9, 2016 in U.S. Appl. No. 15/231,490.
Office Action dated Nov. 1, 2017 in U.S. Appl. No. 15/232,733.
Office Action dated Oct. 19, 2016 in JP Patent App. No 2015-216447.
Office Action dated Oct. 30, 2015 in EP Patent App. No. 08857510.5.
Office Action dated Oct. 8, 2015 in U.S. Appl. No. 13/797,622.
Office Action dated Oct. 6, 2017 in U.S. Appl. No. 15/698,405.
Office Action dated Sep. 17, 2015 in U.S. Appl. No. 13/188,329.
Office Communication dated Aug. 3, 2016 in U.S. Appl. No. 13/188,329.
Office Action dated Sep. 5, 2017 in U.S. Appl. No. 15/227,880.
Office Action dated Sep. 5, 2017 in U.S. Appl. No. 15/230,039.
Office Action dated Sep. 11, 2017 in U.S. Appl. No. 15/255,018.

(56) References Cited

OTHER PUBLICATIONS

Office Action dated Dec. 8, 2017 in U.S. Appl. No. 15/228,955.
Olthuis et al., "Characterization of Proteins by Means of the Buffer Capacity, Measured with an ISFET-based Coulometric Sensor-Actuator System," Biosensors & Bioelectronics, 9:743-751 (1994).
Order Conduct of the Proceeding dated Apr. 7, 2017 in the Patent Trial and Appeal Board, United States Patent and Trademark Office, Petition Nos. PTAB-IPR2017-00822, PTAB-IPR2017-00823, PTAB-IPR2017-00826, PTAB-IPR2017-00827, PTAB-IPR2017-01008, PTAB-IPR2017-01009.
Order Dismissing the Proceedings dated Apr. 11, 2017 in the Patent Trial and Appeal Board, United States Patent and Trademark Office, Petition Nos. PTAB-IPR2017-00826, PTAB-IPR2017-00827.
Order—Conference Call—Bd.R. 104(a), dated Oct. 17, 2017 Interference No. 106,057, involving U.S. Appl. No. 13/188,329 and U.S. Appl. No. 13/188,329 and U.S. Pat. No. 8,420,081.
Parham et al., "Monoclonal Antibodies: Purification, Fragmentation and Application to Structural and Functional Studies of Class I MHC Antigens" J. Immunol. Methods 53:133-173 (1982).
Parslow, "Immunoglobulins & Immunoglobulin Genes," Ch. 7 in Medical Immunology, Appleton & Lange (Daniel P. Stites, Abba I. Terr, & Tristram G. Parslow eds., 9th ed. 1997).
Patent Oppositions by Abbvie, Inc. dated May 3, 2017 in Australian App. No. 2015242973.
Patent Oppositions by Steven Borovec dated May 3, 2017 in Australian App. No. 2015242973.
Patent Owner's Preliminary Response dated Jun. 11, 2017 by Coherus BioSciences Inc, in the Patent Trial and Appeal Board, United States Patent and Trademark Office, Petition No. PTAB-IPR2017-00822.
Patent Owner's Preliminary Response dated Jun. 11, 2017 by Coherus BioSciences Inc, in the Patent Trial and Appeal Board, United States Patent and Trademark Office, Petition No. PTAB-IPR2017-00823.
Patent Owner's Preliminary Response dated Jun. 11, 2017 by Coherus BioSciences Inc, in the Patent Trial and Appeal Board, United States Patent and Trademark Office, Petition No. PTAB-IPR2017-01008.
Patent Owner's Preliminary Response dated Jun. 11, 2017 by Coherus BioSciences Inc, In the Patent Trial and Appeal Board, United States Patent and Trademark Office, Petition No. PTAB-IPR2017-01009.
Petition for Extension filed Jul. 21, 2011 in U.S. Appl. No. 11/917,188.
Petition for Inter Parties Review of U.S. Pat. No. 9,085,619 dated Jan. 31, 2017 42 by Coherus BioSciences Inc, in the Patent Trial and Appeal Board, United States Patent and Trademark Office, Petition No. PTAB-IPR2017-00827.
Petition for Inter Parties Review of U.S. Pat. No. 9,085,619 dated Jan. 31, 2017 by Coherus BioSciences Inc, in the Patent Trial and Appeal Board, United States Patent and Trademark Office, Petition No. PTAB-IPR2017-00822.
Petition for Inter Parties Review of U.S. Pat. No. 9,085,619 dated Jan. 31, 2017 by Coherus BioSciences Inc, in the Patent Trial and Appeal Board, United States Patent and Trademark Office, Petition No. PTAB-IPR2017-00823.
Petition for Inter Parties Review of U.S. Pat. No. 9,085,619 dated Jan. 31, 2017 by Coherus BioSciences Inc, In the Patent Trial and Appeal Board, United States Patent and Trademark Office, Petition No. PTAB-IPR2017-00826.
Petition for Inter Parties Review of U.S. Pat. No. 9,085,619 dated Mar. 2, 2017 by Coherus BioSciences Inc, in the Patent Trial and Appeal Board, United States Patent and Trademark Office, Petition No. PTAB-IPR2017-01008.
Petition for Inter Parties Review of U.S. Pat. No. 9,085,619 dated Mar. 2, 2017 by Coherus BioSciences Inc, in the Patent Trial and Appeal Board, United States Patent and Trademark Office, Petition No. PTAB-IPR2017-01009.

Petitioner's Unopposed Motion to Dismiss Petitions Without Prejudice dated Apr. 7, 2017 in the Patent Trial and Appeal Board, United States Patent and Trademark Office, Petition Nos. PTAB-IPR2017-00826, PTAB-IPR2017-00827.
Phillips and Signs, Curr. Protoc. Protein Sci., Unit 4.4, p. 4.4.1-4.4.15, John Wiley & Sons, Inc. (2004).
Physician's Desk Reference, pp. 470-474 (58th ed. 2004) ("2003 Humira Label").
Physicians' Desk Reference entry for GAMUNEX ®, p. 8720876 (59th ed. 2005).
Physicians' Desk Reference, PDR 59, Section 2 Thomson PDR, Montvale, NJ, pp. 101-127 (2005).
Physicians' Desk Reference, PDR 60, Section 2 Thomson PDR, Montvale, NJ, pp. 101-125 (2005).
Physicians' Desk Reference, pp. 558-559, 914-31,805-07, 2026-28,'2295-97, 2524-25 (56th ed. 2002).
Physicians' Desk Reference, pp. 925-928 (56th ed. 2002) ("Gamimune Label").
Pierce Biotechnology, Inc., "Dialysis; an overview," Technical Resource, 1-2 (2004).
Piper and Fenton, "PH Stability and Activity Curves of Pepsin with Special reference to Their Clinical Importance", Gut 6:506-508 (1965).
Pre-Appeal Brief Request for Review dated Jan. 17, 2017. U.S. Appl. No. 14/879,885.
Preliminary Amendment dated Aug. 5, 2009 in U.S, U.S. Appl. No. 12/325,049.
Preliminary Amendment dated Dec. 11, 2007 in U.S. Appl. No. 11/917,188.
Preliminary Amendment dated Mar. 12, 2013 in U.S. Appl. No. 13/797,622.
Preliminary Amendment dated Oct. 18, 2011 in U.S. Appl. No. 13/188,329.
Press Release, "Amgen and Immunomedics Announce Emphasis on Development if AMG 412 (Epratuzumab) as Combination Therapy While Closing Single Agent Trial," PRNewswire-FirstCall (Jan. 23, 2003).
Privigen Label (Oct. 2016).
Pulmozyne® (dronase alfa), Physicians' Desk Reference, PDR 60, Thomson PDR, Montvale, NJ, pp. 1245-1247 (2006).
Raibekas, et al., "Anion Binding and Controlled Aggregation of Human Interleukin-1 Receptor Antagonist," Biochemistry 4(29), pp. 9871-9879. 2005.
Raptiva® (efalizumab) Label, 1-34 (2003).
Raptiva® (efalizumab), Physicians' Desk Reference, PDR 59, Thomson PDR, Montvale, NJ, pp. 1350-1354 (2005).
Rau. Adalimumab (a fully human anti-tumour necrosis factor a monoclonal antibody) in the treatment of active rheumatoid arthritis: the initial results of five trials. Ann. Rehum. Dis. 2002; 61 (Suppl.): 1170-1173.
Redeclaration of Interference dated Aug. 4, 2016 in Interference No. 106,057, involving U.S. Appl. No. 13/188,329 and U.S. Appl. No. 13/188,329 and U.S. Pat. No. 8,420,081.
Remicade ® Label (Aug. 1998).
Remicade® (inflizimab) Label, 1-23 (2002).
Remicade® (inflizimab), Physicians' Desk Reference, PDR 57, Thomson PDR, Montvale, NJ, pp. 1178-1182 (2003).
Remmele et al., Active Dimer of Epratuzumab Provides Insight into the Complex Nature of a Antibody Aggregate, J Pharmaceutical Sciences, 95:126-145 (2006).
Replacement Declaration of Klaus-Peter Radtke, Ph.D. Dated Jan. 31, 2017, in the Patent Trial and Appeal Board, United States Patent and Trademark Office, Petition No. PTAB-IPR2017-00822.
Replacement Declaration of Klaus-Peter Radtke, Ph.D. Dated Jan. 31, 2017, in the Patent Trial and Appeal Board, United States Patent and Trademark Office, Petition No. PTAB-IPR2017-00823.
Replacement Petition for Inter Parties Review of U.S. Pat. No. 9,085,619 dated Jan. 31, 2017 by Coherus BioSciences Inc, in the Patent Trial and Appeal Board, United States Patent and Trademark Office, Petition No. PTAB-IPR2017-00822.
Replacement Petition for Inter Parties Review of U.S. Pat. No. 9,085,619 dated Jan. 31, 2017 by Coherus BioSciences Inc, in the

(56) References Cited

OTHER PUBLICATIONS

Patent Trial and Appeal Board, United States Patent and Trademark Office, Petition No. PTAB-IPR2017-00823.
Request for Rectification under Rule 91 dated Sep. 7, 2016 in International Application PCT/US2006/0022599.
Response to European Patent Office Action, filed Oct. 28, 2016 in European App. No. 06772779.2.
Response to Final Office Action dated Aug. 18, 2017 in U.S. Appl. No. 15/231,490.
Response to Final Office Action dated Aug. 18, 2017 in U.S. Appl. No. 15/232,733.
Response to Final Office Action dated Sep. 13, 2017 in U.S. Appl. No. 15/232,733.
Response to Final Office Action dated Sep. 6, 2017 in U.S. Appl. No. 15/227,880.
Response to Non-Final Office Action dated Oct. 20, 2017 in U.S. Appl. No. 15/227,880.
Response to Non-Final Office Action dated Apr. 21, 2017. U.S. Appl. No. 14/879,847.
Response to Non-Office Action dated Apr. 30, 2018 in U.S. Appl. No. 15/698,405.
Response to Non-Final Office Action dated May 8, 2017 in U.S. Appl. No. 15/227,880.
Response to Non-Final Office Action dated May 24, 2017 in U.S. Appl. No. 15/232,733.
Response to Non-Final Office Action dated May 24, 2017 in U.S. Appl. No. 15/255,018.
Response to Non-Final Office Action dated Jun. 14, 2017 in in U.S. Appl. No. 15/228,955.
Response to Non-Final Office Action dated May 8, 2017 in U.S. Appl. No. 15/230,039.
Response to Non-Final Office Action dated May 8, 2017 in U.S. Appl. No. 15/231,490.
Response to Non-Final Office Action dated Aug. 18, 2017 in U.S. Appl. No. 15/230,039.
Response to Non-Final Rejection dated Jun. 2, 2011 in U.S. Appl. No. 12/325,049.
Response to Non-Final Rejection dated May 21, 2012 in U.S. Appl. No. 12/325,049.
Response to Non-Final Office Action dated Nov. 13, 2017 in in U.S. Appl. No. 15/228,955.
Response to Restriction Requirement and Amendment dated Jan. 10, 2011 in U.S. Appl. No. 11/917,188.
Response to Restriction Requirement dated Dec. 16, 2010 in U.S. Appl. No. 12/325,049.
Response to Restriction Requirement dated Oct. 29, 2014 in U.S. Appl. No. 13/797,690.
Response to Restriction Requirement dated Sep. 29, 2014 in U.S. Appl. No. 13/188,329.
Restriction Requirement dated Dec. 9, 2010 in U.S. Appl. No. 11/917,188.
Restriction Requirement dated Oct. 18, 2010 in U.S. Appl. No. 12/325,049.
Re-Examination Report dated Mar. 2, 2018 in Australian App. No. 2015242973.
Rouet, et al., "Stability Engineering of the Human Antibody Repertoire," FEBS Letters 588, pp. 269-277. 2014.
Rousseaux et al., "Optimal Conditions for the Preparation of Fab and F(ab') Fragments of Monoclonal IgG of Different Rat IgG Subclasses", J. Immunol Methods 64:141-146 (1983).
Ruiz, et al., "Aggregation of Recombinant Human Interferon Alpha 2b in Solution: Technical Note," AAPS Pharm. Sci. Tech. 7(4), Article 99, pp. E1-E5. 2006.
Salinas, et al., "Understanding and Modulating Opalescence and Viscosity in a Monoclonal Antibody Formulation," J. Pharm. Sci. 99(1), pp. 82-93. 2010.
Saluja et al. Application of High-Frequency Rheology Measurements for Analyzing Protein-Protein Interactions in High Protein Concentration Solutions Using a Model Monoclonal Antibody (IgG2). J. Pharmaceutical Sci. Sep. 2006, Version of Record Online Jul. 17, 2006 95: pp. 1967-1983.
Saluja et al., "Ultrasonic Storage Modulus as a Novel Parameter for Analyzing Protein-Protein Interactions in High Protein Concentration Solutions: Correlation with Static and Dynamic Light Scattering Measurements," Biophysical Journal, Jan. 2007, 92: pp. 234-244.
Saluja et al., Ultrasonic Rheology of a Monoclonal Antibody (IgG2) Solution: Implications for Physical Stability of Proteins in High Concentration Formulations. J. Pharmaceutical Sci. 96: Dec. 2007. pp. 3181-3195.
Saluja, "Characterization of Protein-Protein Interactions for Optimizing Formulation and Physical Stability of High Protein Concentration Solutions" Dissertation, University of Connecticut, Jan. 2007.
Saluja, et al., Nature and consequences of protein-protein interactions in high protein concentration soultions. Intl. J. Pharmaceutics, 2008, 358: 1-15.
Scheffler et al., Improving Antibody Characterization by Orbitrap Mass Spectrometry. Thermo Scientific. CASSS Mass Spec 2012, Abstract p. 216 and poster. The CASSS Mass Spec conference took place Sep. 11-14, 2012.
Schwartz, Diafiltration for Desalting of Buffer Exchange, BioProcess Int'l, May 2003.
Schwartz, Diafiltration: A Fast, Efficient Method for Desalting or Buffer Exchange of Biological Samples. Pall Life Sciences Brochure, Copyright Date 2003.
Schwartzman & Morgan, "Does Route of Administration Affect the Outcome of TNF Antagonist Therapy?," Arthritis Research & Therapy, 6(Suppl. 2):S19-S23 (2004).
Segel, Biochemical calculations, 2nd ed., New York: John Wiley and Sons, Inc., pp. 1-93 (1976).
Sellers et al., "Dry Powders of Stable Protein Formulations from Aqueous Solutions Prepared Using Supercritical CO2-Assisted Aerosolization", J. Pharm. Sci. 90:785-797 (2001).
Senior Party Gokarn List of Proposed Motions dated Jul. 27, 2016 in Interference No. 106,057, in 76 pages.
Shao and Zydney, "Optimization of Ultrafiltration/Diafiltration Processes for Partially Bound Impurities," Biotech. Bioeng. 87:286-292 (2004).
Shire, "Formulation of Proteins and Monoclonal Antibodies (mAbs)," Monoclonal Antibodies, Meeting the Challenges In Manufacturing, Formulation, Delivery and Stability of Final Drug Product, Woodhead Publishing Series in Biomedicine 77, Chap, 4, pp. 93-120. Woodland Publishing, Cambridge, UK. 2015.
Shire, et al., "Challenges in the Development of High Protein Concentration Formulations" J. Pharmaceutical Sciences 2004, 93: pp. 1390-1402.
Statement of Grounds and Particulars by AbbVie, Inc. In Opposition to Australian App. No. 2015242973.
Stoner et al., "Protein-Solute Interactions Affect the Outcome of Ultrafiltration/Diafiltration Operations," J. Pharm. Sci., 93:2332-2342 (2004).
Substance Name: Epratuzumab [USAN:INN] ChemlDplus, A Toxnet Database, U.S. National Library of Mediciness., downloaded from the world wide web at https://chem.nlm.nih.gov/chemldplus/name/startswith/epratuzumab on Jan. 30, 2017. It is noted that this item refers to a webpage, and may have been available in some form at an earlier point in time.
Substitute First Declaration of Andrew Zydney, Ph.D., dated Oct. 28, 2016.
Substituted Clams dated Sep. 7, 2006 from File History of Application No. PCT/US2006/022599.
Summary Review for Regulatory Action, by Sarah Yim, Division of Pulmonary, Allergy, and Rheumatology Products (U.S. Food & Drug Administration), Humira ® (2015).
Summons to Attend Oral Proceedings Pursuant to Rule 115(1) EPC in European Application No. 06772779.2 dated Apr. 10, 2017.
Supplemental Response dated Aug. 9, 2011 in U.S. Appl. No. 12/325,049.
Synagis Label (Jul. 2004).

(56) References Cited

OTHER PUBLICATIONS

Tayyab et al., "Size Exclusion of Chromatography and Size Exclusion HPLC of Proteins", Biochemical Education, 19:149-152 (1991).
Thomson Reuters, "A Bioworld Special Report: Biosimilars: U.S. Market Opportunities and Critical Strategies 2016" (2016).
Thurlkill et al., "pK values of the ionizable groups of proteins" Protein Science 2006, 15: pp. 1214-1218.
Tsourounis, Biologic Therapies for the Treatment of Chronic Plaque Psoriasis, Formulary 40:184-199 (Jun. 2005).
TYSABRI Label (Nov. 2004).
U.S. Pharmacopeia, "Water for Pharmaceutical Purposes," USP 24, United Stated Pharmacopeial Convention, Inc., Rockville, MD, pp. 2154-2163 (2000).
U.S. Prosecution History of U.S. Appl. No. 13/774,735 (U.S. Pat. No. 8,883,146).
U.S. Prosecution History of U.S. Appl. No. 14/506,576 (U.S. Pat. No. 9,085,619).
U.S. Prosecution History of U.S. Appl. No. 61/004,992.
Van de Putte et al. "Efficacy and safety of the fully human anti-tumour necrosis factor alpha monoclonal antibody adalimumab (D2E7) in DMARD refractory patients with rheumatoid arthritis: a 12 week, phase II study," Ann Rheum Dis 2003;62:1168-1177, dated 2003.
Van de Putte, et al., A Single Dose Placebo Controlled Phase I Study of the Fully Human Anti-TNF Antibody D2E7 in Patients with Rheumatoid Arthritis, Arthritis Rheum., 41(9), S57 (Sep. 1998).
Van Reis and Zydney, "Protein Ultrafiltration," in Encyclopedia of Bioprocess Technology: Fermentation, Biocatalysis, and Bioseparation, ed. by M.C, Flickinger and S.W. Drew, pp. 2197-2214, John Wiley & Sons, Inc., New York (1999).
Van Reis and Zydney, "Protein Ultrafiltration," in Encyclopedia of Industrial Biotechnology: Bioprocess, Bioseparation, and Cell Technology, ed. by Flickinger and Drew, John Wiley & Sons, Inc. (2010).
Van Reis and Zydney, "Bioprocess Membrane Technology", J. Membrane Sci. 297:16-50 (2007).
Van Slyke, "On the Measurement of Buffer Values and on the Relationship of Buffer Value to the Dissociation Constant of the Buffer and the Concentration and Reaction of the Buffer Solution" Constant J. Biol. Chem. 52:525-570 (1922).
Vectibix Label (Sep. 2006).
Vermeer and Norde, "Ther Thermal Stability and Activity Curves of Pepsin with Special reference to Their Clinical Importance", Biophys. J. 78:394-404 (2000).
Veys et al., "Pain at the injection site of subcutaneously administered erythropoietin: phosphate-buffered epoetin alpha compared to citrate-buffered epoetin alpha and epoetin beta," Clinical Nephrology, 1998, 49:41-44.
Vidanovic et al., "Effects of nonionic surfactants on the physical stability of immunogluobulin G In aqueous solution during mechanical agitation", Pharmazie, vol. 58, pp. 399-404, 2003.
Vivaglobin Label (Jan. 2006).
Wang and Goodman, Basic & Clinical Immuniology, ed. Fudenberg, Stites, Caldwell and Wells, Los Altos, CA: Lange Medical Publication, pp. 15-40 (1976).
Wang et al., "Opalescence of an IgG1 Monoclonal Antibody Formulation is Mediated by Ionic Strength and Excipients", BioPharm International, pp. 36-47, Apr. 2009.
Weinblatt et al., Adalimumab, a Fully Human Anti-Tumor Necrosis Factor a Monoclonal Antibody for the Treatment of Rheumatoid Arthritis in Patients Taking Concomitant Methotrexate. Arthritis & Rheumatism, 49: 35-45, 2003.
Xolair ® (Omalizumab) Label, 1-17 (2003).
Xolair ® (Omalizumab), Physicians' Desk Reference, PDR 58, Thomson PDR, Montvale, NJ, pp. 1374-1376 (2004).
Yang, et al., "Development of ABX-EGF, a Fully Human Anti-EGF Receptor Monoclonal Antibody, for Cancer Therapy,", Grit. Rev. Oncol. Hematol. 38: 17-23 (2001).
Yu, et al., "Pain Perception Following Subcutaneous Injections of Citrate-Buffered and Phosphate-Buffered Epoetin Alpha," Int'l J. Artificial Organd 21(6), pp. 341-343. 1998.
Zeman and Zydney, "Microfiltration and Ultrafiltration: Principles and Applications", pp. 380-396; 544-564, Marcel Dekker, Inc., New York: (1996).
Zevalin ® Label, Physicians' Desk Reference. Thomas PDR, Montvale, N.J., 60th ed. 2006.
Zhao et al., "Recent U.S. Patents on Protein Drug Formulation: 2000-2007". Recent Patents on Drug Delivery & Formulation, vol. 2, pp. 200-208, 2008.
Zydney and Kuriyel, "Protein Concentration and Buffer Exchange," in Methods in Biotechnology, vol. 9, Downstream Protein Processing, ed. by M. Desai, pp. 23-34, Humana Press, Totowa, NJ (2000).
Zydney, "5.2 Ultrafiltration/Diafiltration", Slideshow Presentation at Novo Nordisk and Aventis Pasteur (2004).
Zydney, "Membrane Separations: Membrane Bioseparations," in Encyclopedia of Separation Science, pp. 1748-1755, Academic Press, Ltd., London (2000).
Decision Denying Institution of Inter Parties Review, dated Sep. 7, 2017 in the Patent Trial and Appeal Board, United States Patent and Trademark Office, Petition No. PTAB-IPR2017-00822.
Decision Denying Institution of Inter Parties Review, dated Sep. 7, 2017 in the Patent Trial and Appeal Board, United States Patent and Trademark Office, Petition No. PTAB-IPR2017-00823.
Decision Denying Institution of Inter Parties Review, dated Sep. 7, 2017 in the Patent Trial and Appeal Board, United States Patent and Trademark Office, Petition No. PTAB-IPR2017-01008.
Decision Denying Institution of Inter Parties Review, dated Sep. 7, 2017 in the Patent Trial and Appeal Board, United States Patent and Trademark Office, Petition No. PTAB-IPR2017-01009.
Claims filed Jul. 26, 2016 in U.S. Appl. No. 13/188,329.
Claims filed Sep. 7, 2017 in U.S. Appl. No. 15/214,377.
Claims filed Oct. 20, 2017 in U.S. Appl. No. 15/227,880.
Claims filed Jun. 14, 2017 in U.S. Appl. No. 15/228,955.
Claims filed Sep. 1, 2016 in U.S. Appl. No. 15/230,039.
Claims filed May 8, 2017 in U.S. Appl. No. 15/231,490.
Claims filed Sep. 13, 2017 in U.S. Appl. No. 15/232,733.
Claims filed May 24, 2017 in U.S. Appl. No. 15/255,018.
Claims filed Sep. 11, 2017 in U.S. Appl. No. 15/698,045.
Claims filed Feb. 2, 2017 in U.S. Appl. No. 15/423,503 (AbbVie).
Office Action dated Sep. 22, 2017 in U.S. Appl. No. 15/227,880.
Third Redeclaration dated Dec. 11, 2017 in Interference No. 106,057, involving U.S. Appl. No. 13/188,329 and U.S. Appl. No. 13/188,329 and U.S. Pat. No. 8,420,081.
Decision-125(b); Order-Miscellaneous dated Dec. 11, 2017 in Interference No. 106,057, involving U.S. Appl. No. 13/188,329 and U.S. Appl. No. 13/188,329 and U.S. Pat. No. 8,420,081.
Office Communication dated Dec. 1, 2017 in U.S. Appl. No. 15/231,490.
Response to Restriction Requirement dated Mar. 23, 2018 in U.S. Appl. No. 15/227,880.
Restriction Requirement dated Mar. 27, 2018 in U.S. Appl. No. 15/214,377.
Judgment dated Dec. 20, 2017 in Interference No. 106,057, involving U.S. Appl. No. 13/188,329 and U.S. Appl. No. 13/188,329 and U.S. Pat. No. 8,420,081.
Acknowledgment of Settlement Agreement dated Jan. 20, 2018 Interference No. 106,057, involving U.S. Appl. No. 13/188,329 and U.S. Appl. No. 13/188,329 and U.S. Pat. No. 8,420,081.
Response to Non-Final Office Action dated May 8, 2018 in in U.S. Appl. No. 15/228,955.
Final Office Action dated Jun. 11, 2018 in in U.S. Appl. No. 15/228,955.
Response to Office Action dated Mar. 30, 2018 in U.S. Appl. No. 15/698,405.
Claims filed Sep. 28, 2018 in U.S. Appl. No. 15/788,762.
Claims filed Oct. 25, 2018 in U.S. Appl. No. 16/144,120.
Claims filed Oct. 26, 2018 in U.S. Appl. No. 15/958,261.
Examination Report dated Jun. 19, 2018 in Australian Patent Application No. 2017202889.
International Preliminary Reporton Patentability dated Apr. 23, 2019 in International Application No. PCT/US2017/057472.

(56) References Cited

OTHER PUBLICATIONS

Notice of Allowance dated Nov. 29, 2018 in U.S. Appl. No. 15/958,261.
Notice of Allowance dated Jan. 25, 2019 U.S. Appl. No. 15/958,261.
Office Action dated Oct. 27, 2017 in European Patent Application No. 06772779.2.
Office Action dated Jul. 18, 2018 in U.S. Appl. No. 15/341,962.
Office Action dated Nov. 26, 2018 in U.S. Appl. No. 15/758,762.
Office Action t dated Mar. 5, 2019 in European Application No. EP 17205734.1.
Response to Office Action dated Oct. 26, 2018 in U.S. Appl. No. 15/958,261.
Restriction Requirement dated Nov. 27, 2017 in U.S. Appl. No. 15/227,880.
File History of U.S. Appl. No. 15/698,405.
File History of U.S. Appl. No. 16/144,120.
File History of U.S. Appl. No. 15/958,261.
File History of U.S. Appl. No. 15/788,762.
Office Action dated Aug. 6, 2019 in Japanese Application No. 2017-218002 with English Translation.
Response dated Jul. 12, 2019 to European Office Action of Mar. 5, 2019 for European Patent Application No. EP 17 205 734.1.
Intention to Grant dated Aug. 16, 2019 for European Patent Application No. EP 17 205 734.1.
Office Action dated Mar. 17, 2020 in Japanese Application No. 2017-218002 with English Translation.
Extended European Search Report dated Apr. 2, 2020 in Application No. 17862991.1.
Immunex Corporation, "Enbrel", dated Dec. 1, 2006, Retrieved from the Internet: URL:https://www.accessdata.fda.gov/drugsatfda_docs/label/2008/enbrel_pi.pdf, retrieved on Feb. 17, 2020.
Notice of Abandonment dated Jun. 11, 2019 in U.S. Appl. No. 15/788,762.
Notice of Acceptance dated Oct. 18, 2019 in South African Application No. 2019/02544.
Office Action dated Feb. 17, 2020 in Chilean Application No. 201901053 with English Translation.
Demand for Invalidation Trial against Japanese Patent No. 6293103, dated Jun. 30, 2020.
Description of Evidences in Demand for Invalidation Trial against Japanese Patent No. 6293103, dated Jun. 30, 2020.
K. Imabori, T. Yamakawa, K. Inoue (Eds.), Seikagaku Jiten [Dictionary of Biochemistry] (3rd edn.), Tokyo Kagaku Doujin, Tokyo (1998) 333-35, 986 (Exhibit A3).
I. Suzuki (Ed.), "Zoku, Iyakuhin-no-Kaihatsu,", Hirokawa Publishing Co., Tokyo, 1992. 19-68, 105-114, 134-135 (Exhibit A12) translation of p. 44 included.
Shinmura, I. (Ed.) Kojien, 5th edition. Nov. 11, 1998. 1126, 1192, 1339 (Exhibit A21).
Yoshimura et al. Diafiltration studies of protein solutions using IgG formulations: Test Report. Dated May 12, 2020. (Exhibit A24).
Office Action dated Aug. 20, 2020 in Eurasian Application No. 201990998 with English Translation.
Office Action dated Jun. 15, 2020 in Chilean Application No. 201901053 with English Translation.
Search Report dated May 11, 2020 in European Application No. 19217355.7.
Demand for Invalidation Trial against Japanese Patent No. 5856555, dated Mar. 31, 2020.
Description of Evidence in Demand for Invalidation Trial against Japanese Patent No. 5856555, dated Mar. 31, 2020.
K. Imabori, T. Yamakawa, K. Inoue (Eds.), Seikagaku Jiten [Dictionary of Biochemistry] (3rd edn.), Tokyo Kagaku Doujin, Tokyo (1998) 334-35 (Exhibit A3).
Isemura, "Tanpakushitsu Kagaku," vol. 2, Kyoritsu Shuppan Co., Ltd., (1st edn.) Tokyo, 1979, 40-47. (Exhibit A4).
Weltman et al., "Hydrogen Ion Titration of Rabbit Gamma-Globulin and Some of Its Subunits" Biochim Biophys Acta. Dec. 9, 1964;93:553-63 (Exhibit A5).
Gras et al., "Curvas de electrotitulacion de globulina gamma" R. esp. Fisiol. 1959. 15(4): 273-78. (Exhibit A6).
Gamimune® label (1986) (Exhibit A8).
Oncley et al., "The Separation of the Antibodies, Isoagglutinins, Prothrombin, Plasminogen and beta1-lipoprotein Into Subtractions of Human Plasma" 1949. J Am Chem Soc. Feb. 1949;71(2):541-50 (Exhibit A11).
I. Suzuki (Ed.), "Zoku, Iyakuhin-no-Kaihatsu,", Hirokawa Publishing Co., Tokyo, 1992. 19-68, 105-114, 134-135 (Exhibit A12).
Plummer, "Jikken de Manabu Seikagaku", 1981.45-51. [Japanese publication of Plummer "Introduction to Practical Biochemistry"] (Exhibit A18).
"Omalizumab" Biodrugs 2002. 15:380 (Exhibit A19).
Schwartz "Diafiltration : A Fast, Efficient Method for Desalting , or Buffer Exchange of Biological Samples" 2003 (Exhibit A20).
Shinmura, I. (Ed.), Kojien, 5th edition. Nov. 11. 1998. 1126, 1139 (Exhibit A21).
Expert Opinion of Prof. Fumio Arisaka, dated Mar. 30, 2020, in Demand for Invalidation Trial against Japanese Patent No. 5856555 (Exhibit A22).
Notice of Abandonment dated Aug. 10, 2018 in U.S. Appl. No. 13/188,329.
Notice of Abandonment dated Oct. 26, 2018 in U.S. Appl. No. 15/214,377.
Notice of Abandonment dated Nov. 30, 2018 in U.S. Appl. No. 15/227,880.
Notice of Abandonment dated Jan. 7, 2019 in U.S. Appl. No. 15/228,955.
Notice of Abandonment dated Apr. 2, 2018 in U.S. Appl. No. 15/230,039.
Notice of Abandonment dated Jul. 3, 2018 in U.S. Appl. No. 15/231,490.
Notice of Abandonment dated Jul. 5, 2018 in U.S. Appl. No. 15/232,733.
Notice of Abandonment dated May 23, 2018 in U.S. Appl. No. 15/255,018.
Notice of Abandonment dated Jun. 25, 2019 in U.S. Appl. No. 15/698,405.
Restriction Requirement dated Apr. 20, 2020 in U.S. Appl. No. 16/144,120.
File History of U.S. Appl. No. 15/341.962, filed Nov. 2, 2016.
File History of U.S. Appl. No. 16/246.202, filed Nov. 1, 2019.
File History of U.S. Appl. No. 16/396.352, filed Apr. 26, 2019.
Notice of Allowance dated Sep. 17, 2020 in U.S. Appl. No. 16/144,120.
Response to Demand for Invalidation Trial against Japanese Patent No. 5856555, filed Oct. 1, 2020 (with machine translation).
Lipman et al., Monoclonal Versus Polyclonal Antibodies: Distinguishing Characteristics, Applications, and Information Resources ILAR J.46(3):258-68. (2005).
Sek, D. Breaking old habits: Moving away from commonly used buffers in pharmaceuticals. Eur. Pharm. Rev. (accessed Oct. 5, 2020) dated Jul. 10, 2012.
Alves. Antibody conjugation and formulation. Antibody Therapeutics, vol. 2, No. 1, 33-39. (2019).
Bahrenburg et al. Buffer-free therapeutic antibody preparations provide a viable alternative to conventionally buffered solutions: From protein buffer capacity prediction to bioprocess applications Biotechnol. J. 10, 610-622 (2015).
Xolair label, revised 2018 (initial approval 2003) (available at https://www.accessdata.fda.gov/drugsatfda_docs/label/2018/103976s5231lbi.pdf).
Zevalin label, revised 2009 (initial approval 2002) (available at https://www.accessdata.fda.gov/drugsatfda_docs/label/2009/1250s1980156.pdf).
Humira Label (Japan), revised 2020 (initial approval 2018) (in Japanese) with machine translation.
Hooper, J. Intravenous immunoglobulins: evolution of commercial IVIG preparations. Immunol Allergy Clin North Am. Nov. 2008;28(4):765-78, viii.
Wolberg et al., Coagulation factor XI is a contaminant in intravenous immunoglobulin preparations. Am J Hematol. Sep. 2000;65(1):30-4.

(56) References Cited

OTHER PUBLICATIONS

Sharma et al., Hyperchloremic Acidosis. [Updated May 2, 20203]. In: StatPearls [Internet]. Treasure Island (FL): StatPearls Publishing; Jan. 2020-. Available from: https://www.ncbi.nlm.nih.gov/books/NBK482340/ (retrieved Oct. 5, 2020).
Centor RM. Serum Total Carbon Dioxide. In: Walker HK, Hall WD, Hurst JW, editors. Clinical Methods: The History, Physical, and Laboratory Examinations. 3rd edition. Boston: Butterworths; 1990. Chapter 196. Available from: https://www.ncbi.nlm.nih.gov/books/NBK308/ (retrieved Oct. 5, 2020).
Report of Re-Examination with English translation dated Nov. 26, 2020 in Japanese Patent Application No. 2017-218002 in 5 pages.
Notice of Allowance dated Nov. 5, 2020 in U.S. Appl. No. 16/144,120 in 10 pages.
Office Action with English Translation dated Dec. 1, 2020 In Korean Patent Application No. 10-2019-7014130.
Office Action with English Translation dated Dec. 17, 2020 In Indian Patent Application No. 201917015635.
Office Action with English Translation dated Nov. 30, 2020 In Chinese Patent Application No. 201780072322.9.
Written Answer To The Case with English Translation dated Dec. 10, 2020 filed in the response to the Demand for Invalidation Trial in Japanese Patent No. 6293103.
Request for Correction with English Translation dated Dec. 10, 2020 filed in the response to the Demand for Invalidation Trial in Japanese Patent No. 6293103.
Exhibit 19 Prescription drug injection for specified bio-derived products in 9 pages filed in the response to the Demand for Invalidation Trial in Japanese Patent No. 6293103.
Exhibit 21 Office Action Summary dated Sep. 15, 2008 in U.S. Appl. No. 11/338,138 in 14 pages filed in the response to the Demand for Invalidation Trial in Japanese Patent No. 6293103.
Exhibit 22 Amendment filed Jan. 24, 2006 in U.S. Appl. No. 11/338,138 in 9 pages filed in the response to the Demand for Invalidation Trial in Japanese Patent No. 6293103.
Exhibit 23 Written notice of reasons for refusal dated Nov. 28, 2020 in 8 pages filed in the response to the Demand for Invalidation Trial in Japanese Patent No. 6293103.
Exhibit 24 Amendment Submitted May 11, 2005 in Japanese Patent Application No. 2002-592966 in 18 pages filed in the response to the Demand for Invalidation Trial in Japanese Patent No. 6293103.
Exhibit 25 Opinion Form Submitted Jul. 3, 2009 in Japanese Patent Application No. 2002-592966 in 12 pages filed in the response to the Demand for Invalidation Trial in Japanese Patent No. 6293103.
Description of Evidence dated Dec. 10, 2020 in 14 pages filed in the response to the Demand for Invalidation Trial in Japanese Patent No. 6293103.
Demandant's Petition filed in Demand for Invalidation Trial in Japanese Patent No. 5856555, dated Dec. 28, 2020 (with English translation).
Biochemical Dictionary, 3rd ed., 1998, filed as Exhibit A28 in the Demand for Invalidation Trial against Japanese Patent No. 6293103, in 4 pages (with partial English translation).
Collins, K., "Charge Density-Dependent Strength of Hydration and Biological Structure", Biophysical Journal, vol. 72, Jan. 1997, pp. 65-76.
DiJoseph, J et al., "Antibody-targeted chemotherapy of B-cell lymphoma using calicheamicin conjugated to murine or humanized antibody against CD22", Cancer Immunology Immunotherapy, vol. 54, Jan. 2005, pp. 11-24.
Finlayson et al., "Reversibility of Human Immunoglobulin G Dimerization", In Lindgren et al., eds., Radiobiologic Investigations, Acta Radiologica, 1971, pp. 114-123.
"Gamimune® N, 5%,—Immune Globulin Intravenous (Human), 5% Solvent/Detergent Treated", Physcians' Desk Reference, 2002, Montvale, N.J., 56th ed., pp. 925-931.
Gottschalk, U., "Downstream Processing of Monoclonal Antibodies: from High Dilution to High Purity", BioPharm International, vol. 18, Issue 6, Jun. 2005, in 18 pages, (available at https://www.biopharminternational.com/view/downstream-processing-monoclonal-antibodies-high-dilution-high-purity).
Gronski et al., "On the Nature of IgG Dimers—I. Dimers in Human Polyclonal IgG Preparations: Kinetic Studies", Behring Inst. Mitt., 1988, No. 82, pp. 127-143.
Iwanami's Biology Dictionary, 4th ed., 1996, p. 1406, filed as Exhibit A37 in the Demand for Invalidation Trial against Japanese Patent No. 6293103, in 4 pages (with partial English translation).
Iwanami's Dictionary of Physics and Chemistry, 5th ed., 1998, p. 104, filed as Exhibit A27 in the Demand for Invalidation Trial against Japanese Patent No. 6293103, in 5 pages (with partial English translation).
Karas, M. et al., "Membrane-associated Insulin-like Growth Factor-binding Protein-3 Inhibits Insulinlike Growth Factor-I-induced Insulin-like Growth Factor-I Receptor Signaling in Ishikawa Endometrial Cancer Cells", The Journal of Biological Chemistry, vol. 272, No. 26, Jun. 1997, p. 16514-16520.
Kerry, P. J. et al., "Standardization of prekallikrein activator (PKA): the 1st International Standard for PKA", British Journal of Haematology, vol. 60, Jun. 1985, pp. 345-352.
Khayyamian, S. et al., "ICOS-ligand, expressed on human endothelial cells, costimulates Th1 and Th2 cytokine secretion by memory CD4+ T cells", PNAS, vol. 99, No. 9, Apr. 2002, pp. 6198-6203.
Nanzando's Medical Dictionary, 1998, p. 4 and p. 1326, filed as Exhibit A26 in the Demand for Invalidation Trial against Japanese Patent No. 6293103, in 4 pages (with partial English translation).
Naranda, T. et al., "A peptide derived from an extracellular domain selectively inhibits receptor internalization: Target sequences on insulin and insulin-like growth factor 1 receptors", PNAS, vol. 94, Oct. 1997, p. 11692-11697.
Penin et al., "Structural Biology of Hepatitis C Virus", Hepatology, Jan. 2004, vol. 39, Issue 1, pp. 5-19.
Reddy et al., "Computational Virology: From the inside out", Biochimica et Biophysica Acta, Jul. 2016, vol. 1858, Issue 7, Part B, pp. 1610-1618.
Ries-Kautt, M et al., "Relative Effectiveness of Various Ions on the Solubility and Crystal Growth of Lysozyme", The Journal of Biological Chemistry, vol. 264, No. 2, Jan. 1989, pp. 745-748.
Santa Cruz Biotechnology, Inc., Product Sheets for IGF-IRα (1H7): sc-461, IGF-IR (3B7): sc-462, and IGF-Irα (2C8): sc-463, in 3 pages (Available at https://www. scbt.com/p/igf-iralpha-antibody-1h7, https://www.scbt.eom/p/igf-ir-antibody-3b7, and https://www.scbt.com/p/igf-iralpha-antibody-2c8, respectively [retrieved on Mar. 12, 2021]). No publication date is apparent in these Product Sheets.
Sasaki et al., "ELISA Diagnosis for Mycoplasma pneumoniae Infection with Human Normal Immunoglobulin Products as Control Sera", The Journal of the Japanese Association for Infectious Diseases, Apr. 1990, vol. 64, No. 4, filed as Exhibit A29 in the Demand for Invalidation Trial against Japanese Patent No. 6293103, in 6 pages (with partial English translation).
Tsai et al., "Origin of the Isoelectric Heterogeneity of Monoclonal Immunoglobulin hi B4", Pharmaceutical Research, 1993, vol. 10, No. 11, pp. 1580-1586.
Vermeer et al., "The Thermal Stability of Immunoglobulin: Unfolding and Aggregation of a MultiDomain Protein", Biophys. J. 78:394-404 (2000).
Yoshimoto, H. et al., "Overexpression of Insulin-Like Growth Factor-1 (IGF-I) Receptor and the Invasiveness of Cultured Keloid Fibroblasts", American Journal of Pathology, vol. 154, No. 3, Mar. 1999, pp. 883-889.
Response to Final Office Action dated Aug. 24, 2017 in U.S. Appl. No. 15/227,880.
Office Action dated Nov. 24, 2020 in Japanese Application No. 2019-520794 with English Translation.
Notice of Allowance dated Feb. 25, 2021 in U.S. Appl. No. 16/144,120 in 10 pages.
Office Action dated Apr. 5, 2021 in Korean Patent Application No. 10-2019-7014130 with English Translation.
Office Action dated Apr. 16, 2021 in Eurasian Application No. 201990998 with English Translation.
Content of an Extended Registration of Japanese Patent No. 5840364, filed as Exhibit B47 in the Demand for Invalidation Trial against

(56) References Cited

OTHER PUBLICATIONS

Japanese Patent No. 5856555, in 2 pages (Available from the Internet Website of the Patent Information Platform retrieved Apr. 6, 2021), dated Oct. 23, 2019.
Statement Brief for the Oral Proceedings filed in the Demand for Invalidation Trial against Japanese Patent No. 5856555, dated Apr. 8, 2021, in 140 pages.
Description of Evidence filed in the Demand for Invalidation Trial against Japanese Patent No. 5856555, dated Apr. 8, 2021, in 13 pages.
Draft Notice of Issues to be Examined in the Demand for Invalidation Trial against Japanese Patent No. 5856555, dated Feb. 1, 2021.
Counterargument by the Demandant with English Translation dated Mar. 19, 2021, filed in the Demand for Invalidation Trial against Japanese Patent No. 6293103, in 392 pages.
Biochemical Dictionary, 3rd ed., 1998, p. 456, filed as Exhibit A41 in the Demand for Invalidation Trial against Japanese Patent No. 5856555, in 3 pages.
Kim, N. et al., "Effects of pH Buffer Concentration on the Thermal Stability of Etanercept Using DSC and DLS", Biol. Pharm. Bull., May 2014, vol. 37(5), pp. 808-816.
Lopez, E. et al., "Simultaneous Determination of the Major Organic Acids, Sugars, Glycerol, and Ethanol by HPLC in Grape Musts and White Wines", Journal of Chromatographic Science, May 1996, vol. 34(55), pp. 254-257.
Luo, M., Complete Collection of Pharmaceutical Excipients, Sichuan Science and Technology Publishing House, Dec. 2006, p. 1372.
Orlandi, R. et al., "Cloning immunoglobulin variable domains for expression by the polymerase chain reaction", Proc. Natl. Acad. Sci., May 1989, vol. 86, pp. 3833-3837.
Patel, K. et al., "Chemical pathways of peptide degradation. II. Kinetics of deamidation of an asparaginyl residue in a model hexapeptide", Pharm. Res., Jul. 1990, vol. 7(7), pp. 703-711.
Song, Y. et al., "Effect of 'pH' on the rate of asparagine deamidation in polymeric formulations: 'pH'-rate profile", J. Pharm Sci., Feb. 2001, vol. 90(2), pp. 141-156.
Exhibit 19 Prescription drug injection for specified bio-derived products in 9 pages, issued Aug. 2018, filed in the response to the Demand for Invalidation Trial in Japanese Patent No. 6293103.
Exhibit 23 Written notice of reasons for refusal dated Jan. 28, 2020 in 8 pages filed in the response to the Demand for Invalidation Trial in Japanese Patent No. 6293103.
Exhibit 24 Amendment Submitted Jul. 3, 2009 in Japanese Patent Application No. 2002-592966 in 18 pages filed in the response to the Demand for Invalidation Trial in Japanese Patent No. 6293103.
Office Action with English Translation dated Jun. 17, 2021 in Chinese Patent Application No. 201780072322.9.
Office Action dated May 25, 2021 in Korean Patent Application No. 10-2019-7014130 with English translation.
Statement Brief for the Oral Proceedings by Demandant filed in the Demand for Invalidation Trial against Japanese Patent No. 5856555, dated May 6, 2021, in 467 pages.
Description of Evidence by Demandant filed in the Demand for Invalidation Trial against Japanese Patent No. 5856555, dated May 6, 2021, in 15 pages.
Notice of Allowance dated Jun. 15, 2021 in U.S. Appl. No. 16/144,120 in 14 pages.
Petition by Demandant filed in the Demand for Invalidation Trial against Japanese Patent No. 5856555 in 40 pages, dated Jul. 9, 2021.
Demandee (Patentee) Explanatory Material Slides presented in the Demand for Invalidation Trial against Japanese Patent No. 5856555 in 177 pages, dated May 20, 2021.
Demandant Explanatory Material Slides presented in the Demand for Invalidation Trial against Japanese Patent No. 5856555 in 66 pages, dated May 20, 2021.
Declaration of Dr. R. Matthew Fesinmeyer in Support of Amgen Inc. filed in the Demand for Invalidation Trial against Japanese Patent No. 6293103 in 7 pages, dated Aug. 4, 2021.
Description of Evidences (2) filed in the Demand for Invalidation Trial against Japanese Patent No. 6293103 in 11 pages, dated Mar. 19, 2021.
Statement Brief by the Demandant filed in the Demand for Invalidation Trial against Japanese Patent No. 6293103 in 177 pages, dated Aug. 6, 2021.
Description of Evidences (3) filed in the Demand for Invalidation Trial against Japanese Patent No. 6293103 in 8 pages, dated Aug. 6, 2021.
Correction and Opinion for U.S. Appl. No. 11/338,138, filed as Exhibit A43 in the Demand for Invalidation Trial against Japanese Patent No. 6293103 in 18 pages, dated Jan. 7, 2009.
Gomez, G. et al., "Effect of Initial Buffer Composition on pH Changes During Far-From-Equilibrium Freezing of Sodium Phosphate Buffer Solutions", Pharmaceutical Research, vol. 18(1), Jan. 2001, pp. 90-97.
Pikal-Cleland, K. et al., "Lyophilization-induced protein denaturation in phosphate buffer systems: Monomeric and tetrameric 3-galactosidase", Journal of Pharmaceutical Sciences, vol. 90(9), Sep. 2001, pp. 1255-1268.
Petition by Demandee filed in the Demand for Invalidation Trial against Japanese Patent No. 5856555, dated Jun. 17, 2021, in 37 pages.
Description of Evidence by Demandee filed in the Demand for Invalidation Trial against Japanese Patent No. 5856555, dated Jun. 17, 2021, in 4 pages.
Description of Evidences by Demandee filed in the Demand for Invalidation Trial against Japanese Patent No. 6293103 in 9 pages, dated Aug. 6, 2021.
Statement Brief by Demandee filed in the Demand for Invalidation Trial against Japanese Patent No. 6293103 in 344 pages, dated Aug. 6, 2021.
Bellinghausen, I. et al., "Importance of the inducible costimulator molecule for the induction of allergic immune responses and its decreased expression on T helper cells after venom immunotherapy", Immunology, vol. 112(1), pp. 80-86, 2004.
Office Action for Australian Application No. AU 2017345490 in 2 pages, dated Jul. 30, 2021.
Office Action for Application No. JP 2020-122950 with English translation in 8 pages, dated Jul. 27, 2021.
Request for Correction filed in the Demand for Invalidation Trial against Japanese Patent No. 5856555 in 29 pages, dated Nov. 22, 2021.
Written Argument filed in the Demand for Invalidation Trial against Japanese Patent No. 5856555 in 73 pages, dated Nov. 22, 2021.
Notice of Reasons for Invalidation filed in the Demand for Invalidation Trial against Japanese Patent No. 5856555, dated Sep. 29, 2021, in 45 pages.
Office Action for Brazilian Application No. BR 1120190078584 with English translation in 6 pages, dated Sep. 15, 2021.
Office Action for Korean Application No. KR 10-2019-7014130 in 6 pages, dated Sep. 23, 2021.
Petition by Demandant filed in the Demand for Invalidation Trial against Japanese Patent No. 6293103 in 29 pages, dated Sep. 10, 2021.
Petition by Demandee filed in the Demand for Invalidation Trial against Japanese Patent No. 6293103 in 12 pages, dated Sep. 10, 2021.
Petition for Oral Proceedings by Demandant filed in the Demand for Invalidation Trial against Japanese Patent No. 6293103 in 107 pages, dated Aug. 20, 2021.
Slides for Oral Proceedings by Demandee filed in the Demand for Invalidation Trial against Japanese Patent No. 6293103 in 99 pages, dated Aug. 20, 2021.
Request for Correction and Corrected Claims filed in the Demand for Invalidation Trial against Japanese Patent No. 6293103 in 99 pages, dated Nov. 22, 2021.
Written Argument filed in the Demand for Invalidation Trial against Japanese Patent No. 6293103 in 99 pages, dated Nov. 22, 2021.
Notice of Allowance dated Nov. 1, 2021 in U.S. Appl. No. 16/144,120 in 10 pages.

(56) References Cited

OTHER PUBLICATIONS

Notice of Reasons for Invalidation filed in the Demand for Invalidation Trial against Japanese Patent No. 6293103 in 64 pages, dated Dec. 1, 2021.
Decision on whether or not to Approve Amendment filed in the Demand for Invalidation Trial against Japanese Patent No. 6293103 in 9 pages, dated Dec. 1, 2021.
Counterargument by Demandant with English translation filed in the Demand for Invalidation Trial against Japanese Patent No. 5856555 in 128 pages, dated Jan. 19, 2022.
Eurasian Office Action for EA Application No. 201990998 with English translation in 6 pages, dated Dec. 8, 2021.
Notice of Withdrawal with English translation filed in the Demand for Invalidation Trial against Japanese Patent No. 5856555 in 2 pages, dated Feb. 17, 2022.
Notice of Withdrawal with English translation filed in the Demand for Invalidation Trial against Japanese Patent No. 6293103 in 2 pages, dated Feb. 17, 2022.
Request for Correction with English translation filed in the Demand for Invalidation Trial against Japanese Patent No. 6293103 in 29 pages, dated Jan. 31, 2022.
Request for Withdrawal with English translation filed in the Demand for Invalidation Trial against Japanese Patent No. 5856555 in 5 pages, dated Feb. 10, 2022.
Request for Withdrawal with English translation filed in the Demand for Invalidation Trial against Japanese Patent No. 6293103 in 5 pages, dated Feb. 10, 2022.
Response to Notice of Reasons for Invalidation with English translation filed in the Demand for Invalidation Trial against Japanese Patent No. 6293103 in 29 pages, dated Jan. 31, 2022.
Notice of Allowance dated Mar. 4, 2022 in U.S. Appl. No. 16/144,120 in 11 pages.
Dani, B. et al., "Pharmaceutics, Preformulation, and Drug Delivery—High Concentration Formulation Feasibility of Human Immunoglobulin G for Subcutaneous Administration", Journal of Pharmaceutical Sciences, Jun. 2007, vol. 96, No. 6, pp. 1504-1517.
Office Action for Japanese Application No. 2017-218002 with English translation in 28 pages, dated Mar. 29, 2022.
Notice of Allowance dated Jun. 23, 2022, in U.S. Appl. No. 16/144,120 in 9 pages.
Office Action for Japanese Application No. 2020-122950 in 6 pages, dated May 31, 2022.
Acknowledgement Receipt Received in U.S. Appl. No. 17/810,225, dated Jun. 30, 2022.
Corrected Notice Of Allowability dated Jul. 27, 2022 in U.S. Appl. No. 16/144,120 in 3 pages.
Notice of Acceptance for Australian Application No. 2017345490 in 3 pages, dated Jun. 27, 2022.
Notice of Allowability for U.S. Appl. No. 16/144,120 in 3 pages, dated Jul. 20, 2022.
Notice of Patent Grant for Korean Application No. 10-2019-7014130 with English translation in 5 pages, dated Jun. 27, 2022.
Notice of Patent Grant for Korean Application No. 10-2021-7042112 with English translation in 6 pages, dated Apr. 6, 2022.
Notification of Readiness to Grant for Eurasian Application No. 201990998 with English translation in 2 pages, dated Jul. 20, 2022.
Office Action for Japanese Application No. 2021-080160 with English translation in 7 pages, dated Jun. 28, 2022.
Trial Decision received from the Intellectual Property Trial and Appeal Board (IPTAB) for Korean Application No. 10-2019-7014130 with English Translation in 41 pages, dated May 20, 2022.
Acknowledgement Receipt Received in U.S. Appl. No. 17/933,055 in 58 pages, dated Sep. 16, 2022.
Corrected Notice of Allowability for U.S. Appl. No. 16/144,120 in 3 pages, dated Sep. 14, 2022.
Corrected Notice of Allowability in U.S. Appl. No. 16/144,120, dated Oct. 12, 2022.
U.S. Appl. No. 17/810,225, Self-Buffering Antibody Formulations, filed Jun. 30, 2022.
U.S. Appl. No. 15/958,261, Pharmaceutical Formulations And Methods Of Making The Same, filed Apr. 20, 2018 (Issued).
U.S. Appl. No. 16/144,120, Pharmaceutical Formulations And Methods Of Making The Same, filed Sep. 27, 2018 (Issued).
U.S. Appl. No. 17/933,055, Pharmaceutical Formulations And Methods Of Making The Same, filed Sep. 16, 2022.
Office Action for Japanese Application No. 2021-080160 with English translation in 8 pages, dated Dec. 20, 2022.

\* cited by examiner

Figure 1. Buffer Capacity of Acetate in the pH 4.0 - 5.0 Range
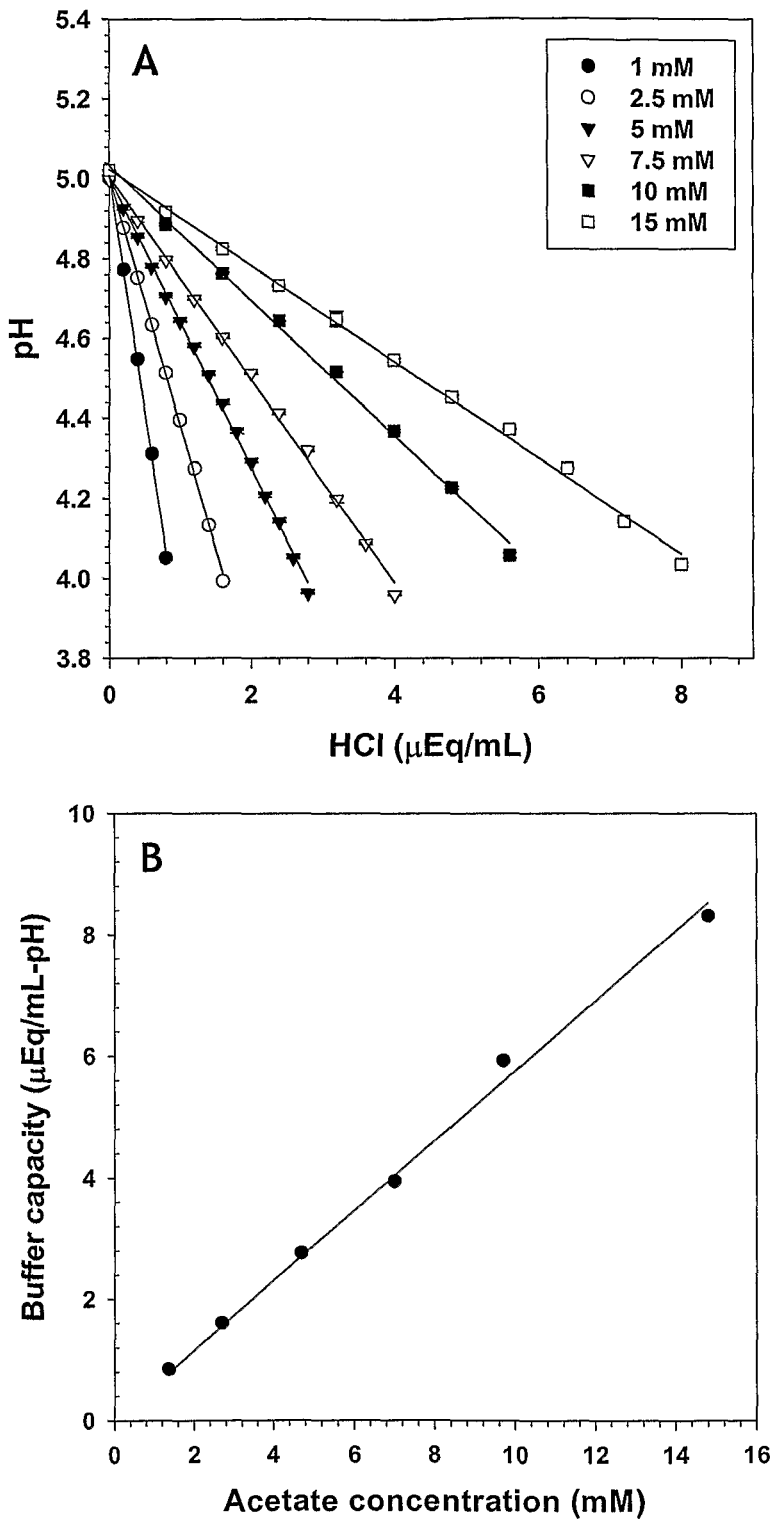

Figure 2. Buffer Capacity of Acetate in the pH 5.0 – 5.5 Range
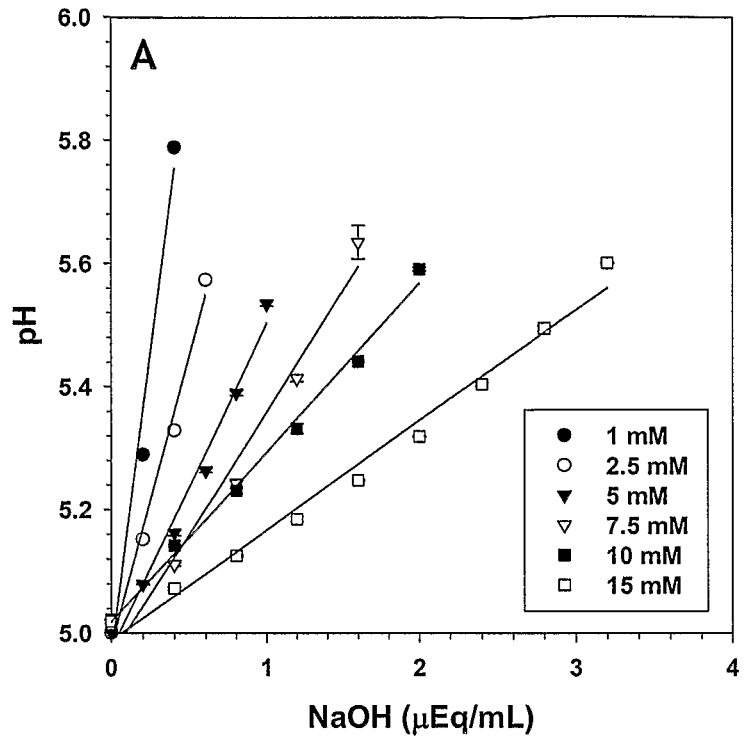
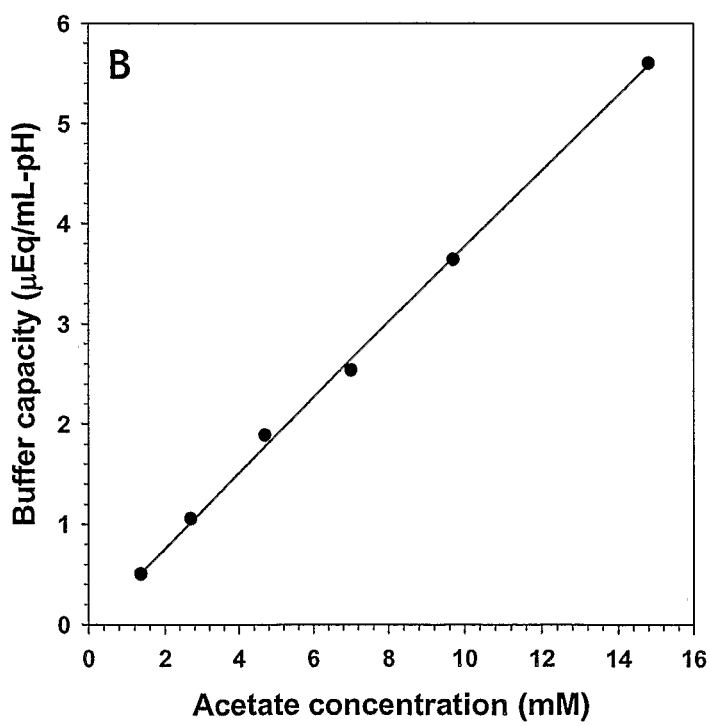

Figure 3. Determination of acetate concentration in acetate standards used for buffer capacity measurements
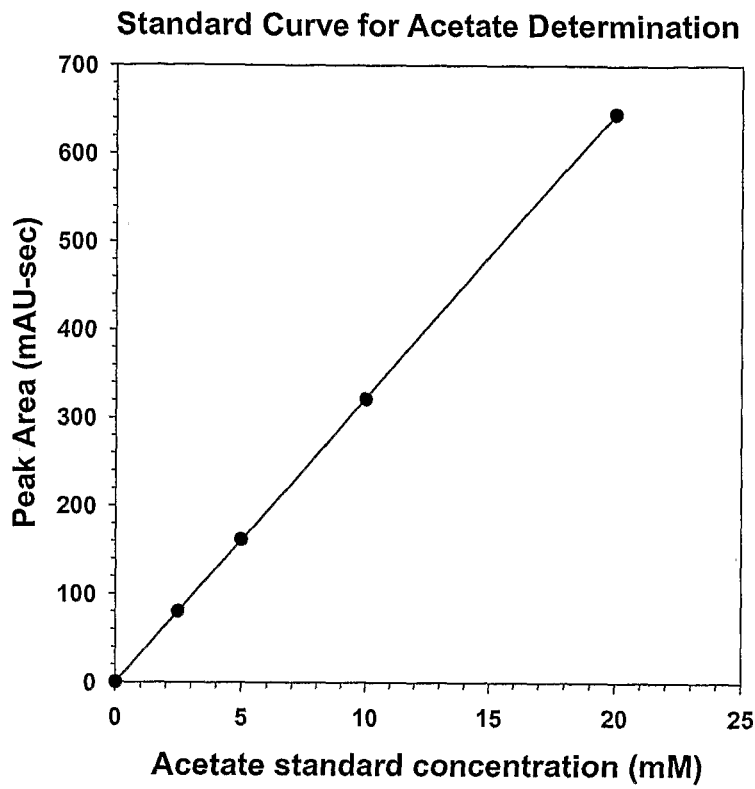
Experimentally determined acetate values for solutions used to determine acetate buffer capacity
| Acetate concentration (mM) | |
| --- | --- |
| Nominal | Experimental |
| 1 | 1.37 |
| 2.5 | 2.7 |
| 5 | 4.7 |
| 7.5 | 7.0 |
| 10 | 9.7 |
| 15 | 14.8 |

Figure 4. Acid titration of Ab-hOPGL Solutions
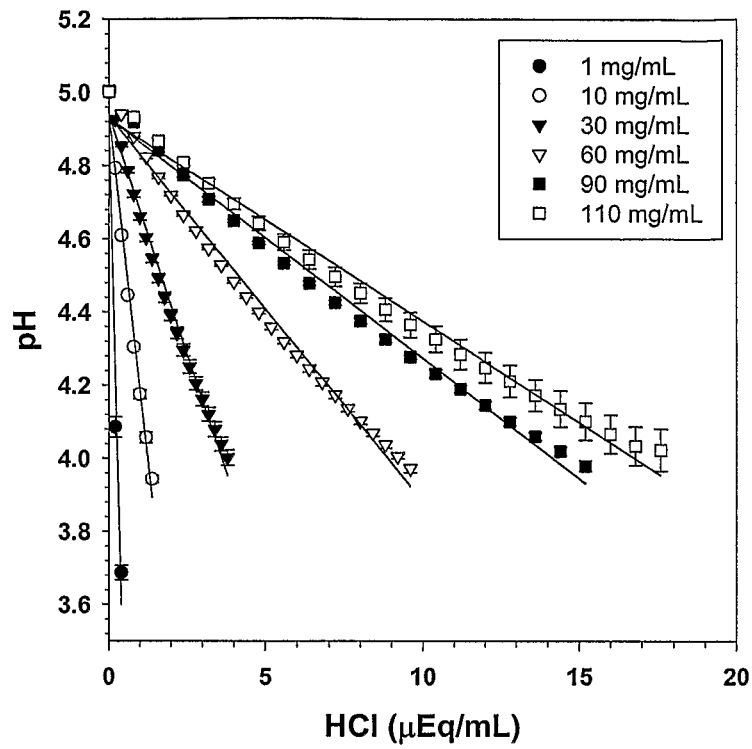
Figure 5. Base titration of Ab-hOPGL Solutions
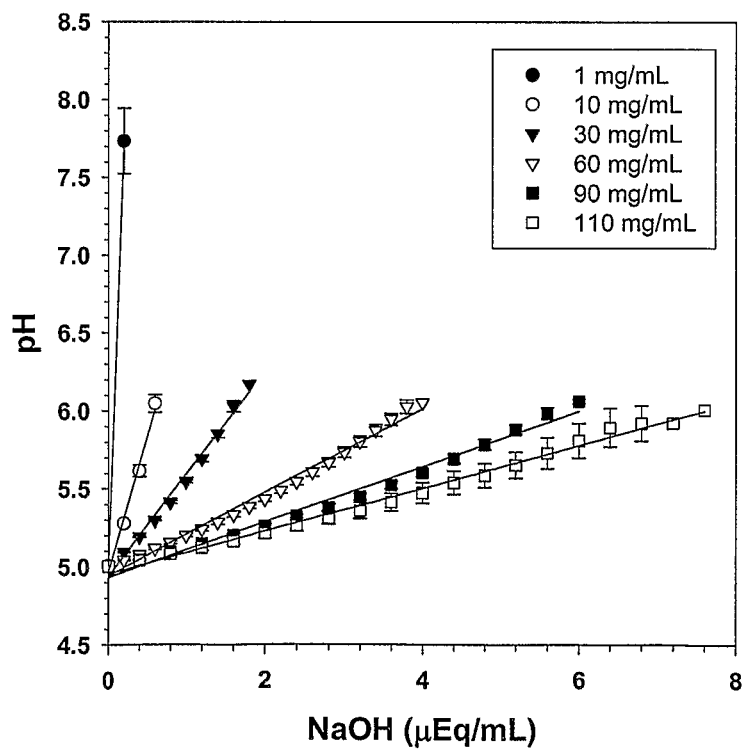

Figure 6. Determination of residual acetate levels in Ab-hOPGL Solutions for buffer capacity measurements
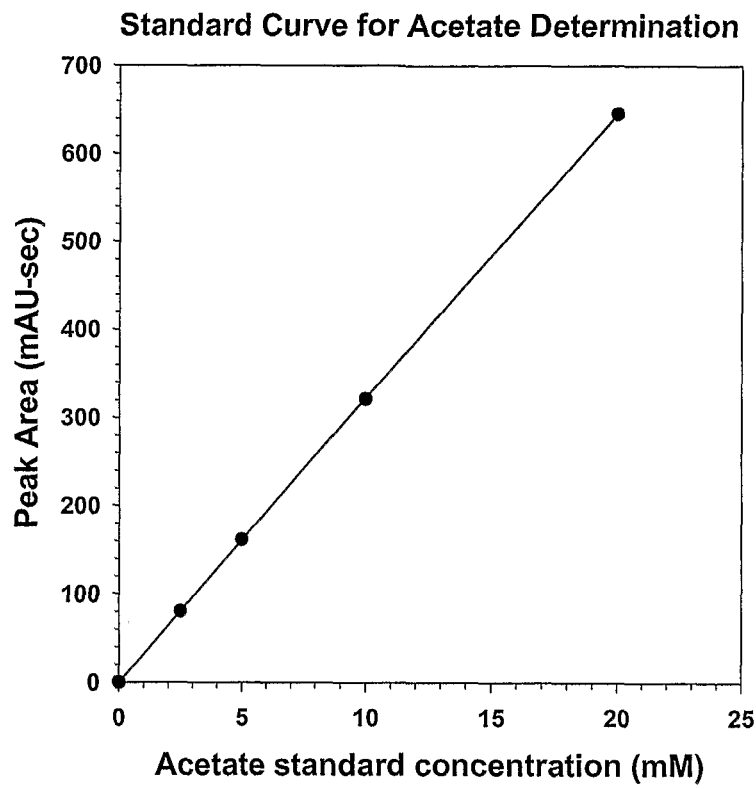
Residual acetate levels in Ab-hOPGL solutions used to determine buffer capacity
| Acetate concentration (mM) | |
| --- | --- |
| Nominal | Experimental |
| 1 | 0.05 |
| 10 | 0.20 |
| 30 | 0.51 |
| 60 | 1.16 |
| 90 | 1.71 |
| 110 | 1.82 |

Figure 7. Buffer capacity of Ab-hOPGL +/- residual acetate as a function of its concentration in the pH 4.0 – pH 5.0 range
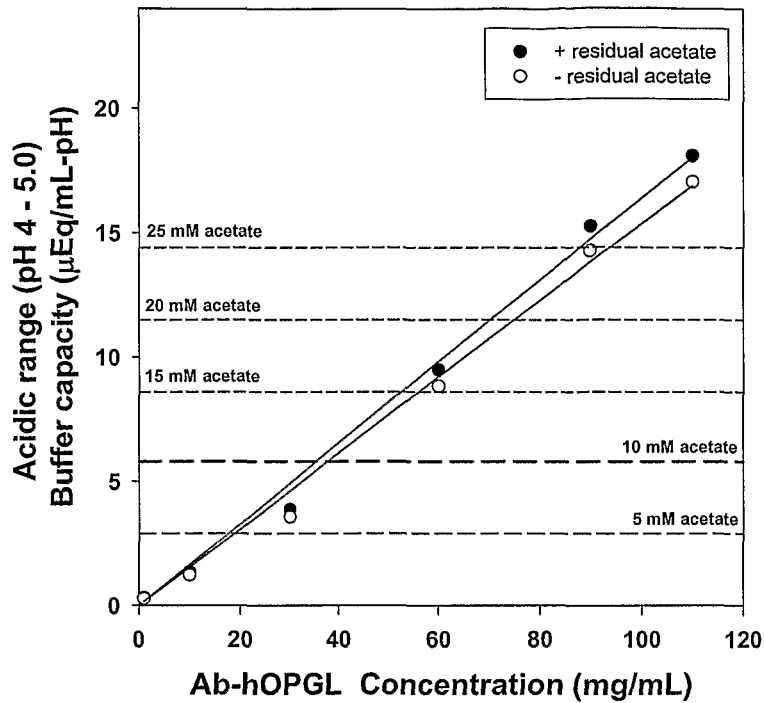
Figure 8. Buffer capacity of Ab-hOPGL +/- residual acetate as a function of its concentration in the pH 5.0 – pH 6.0 range
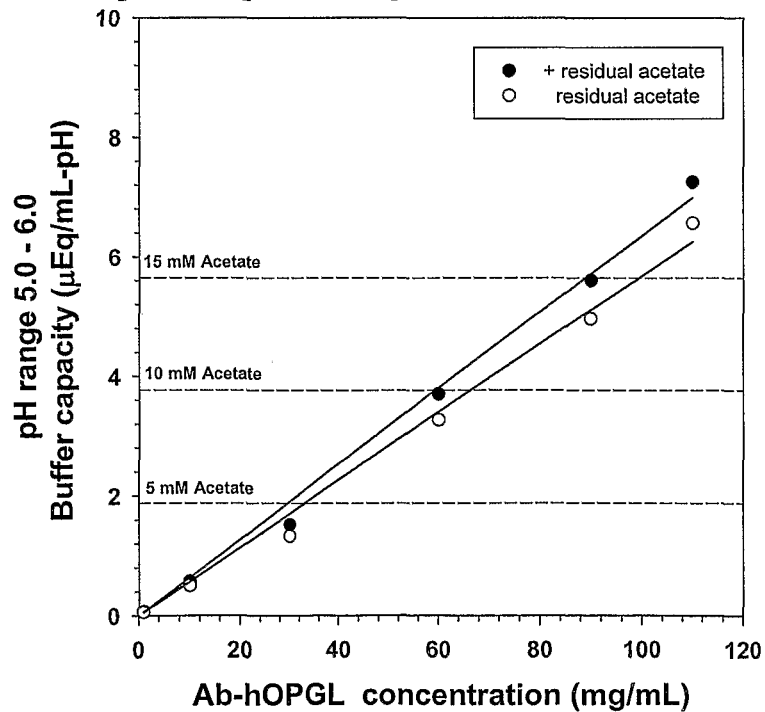

Figure 9. Stability of the Self-Buffered, 60 mg/mL, Ab-hOPGL Formulation Compared to Conventionally Buffered Formulations at 4 C
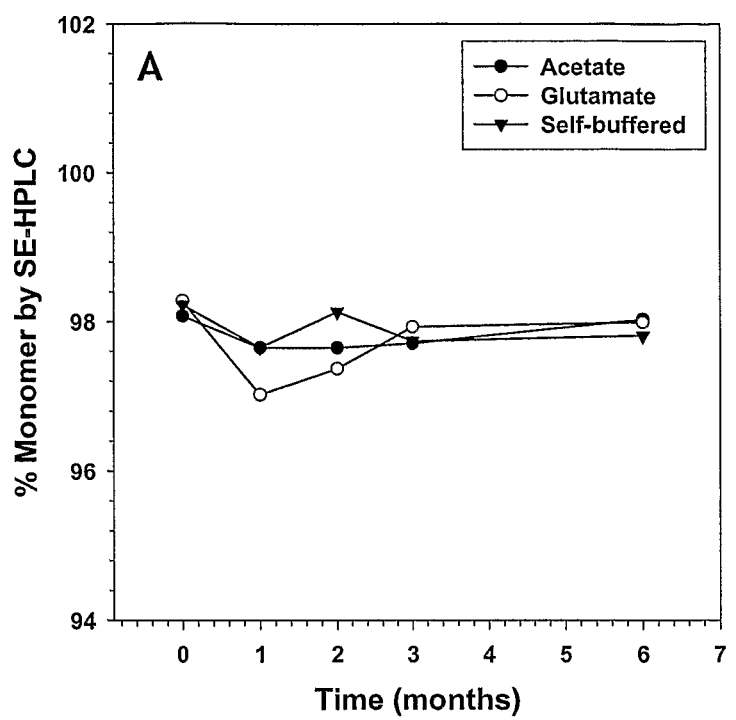
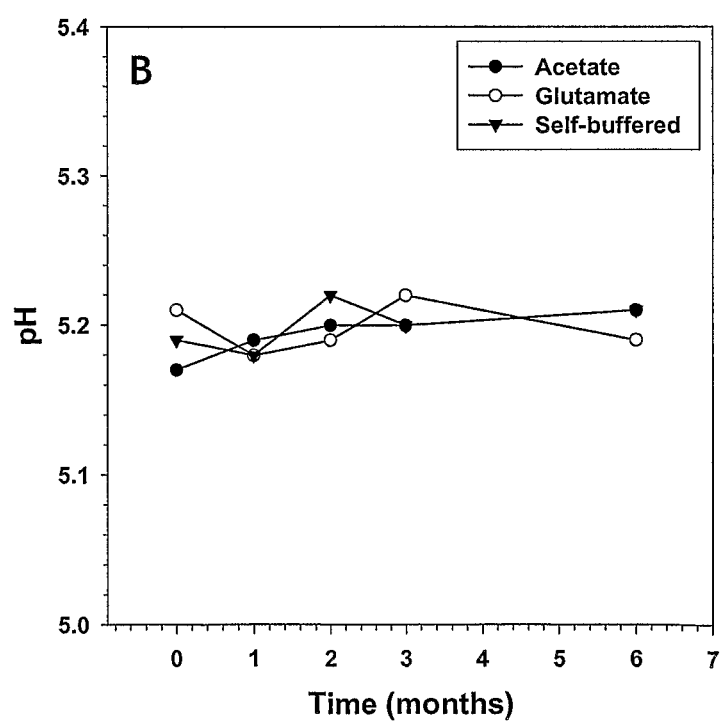

Figure 10. Buffer capacity of Ab-hB7RP1 Solutions in the pH 4.0 – 5.0 range
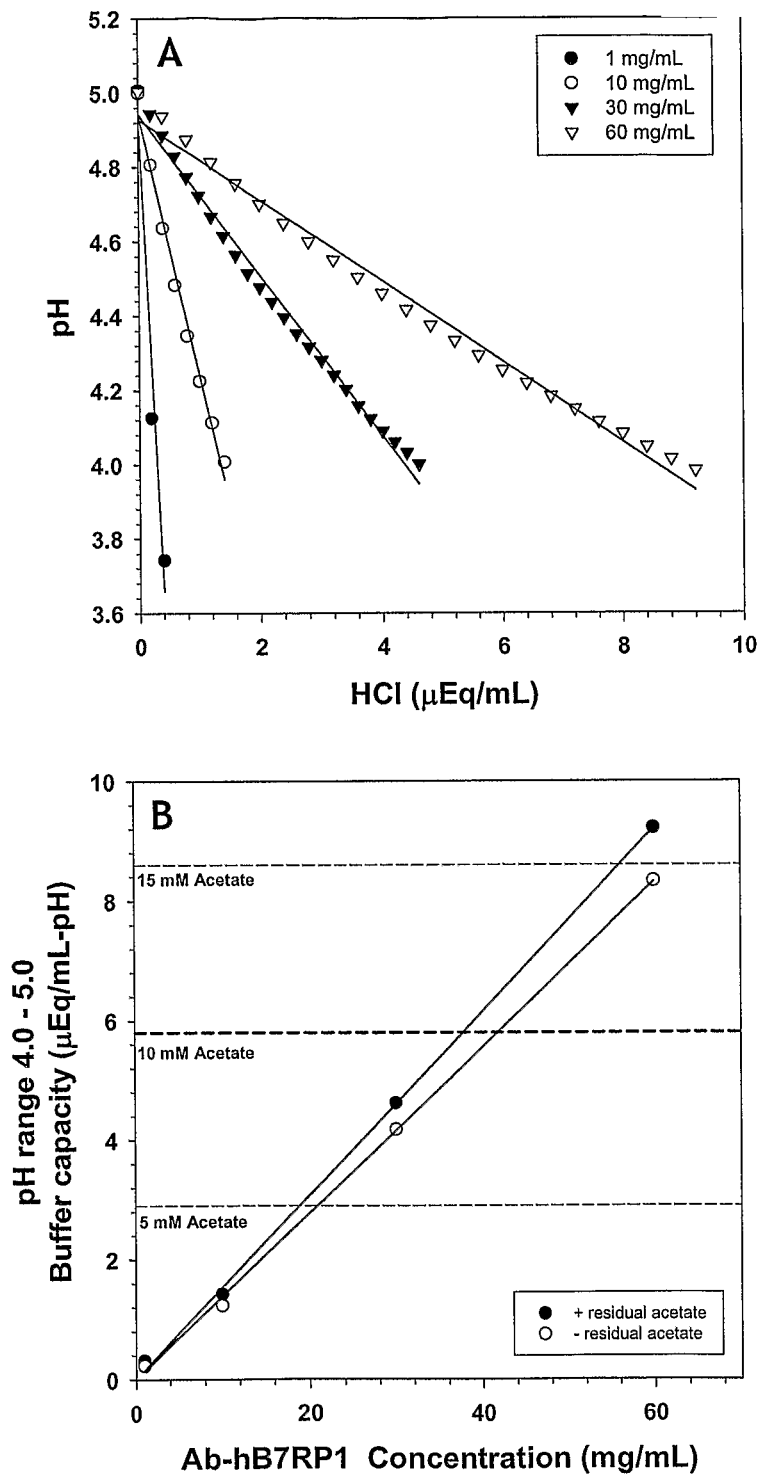

Figure 11. Buffer capacity of Ab-hB7RP1 Solutions in the pH 5.0-6.0 range
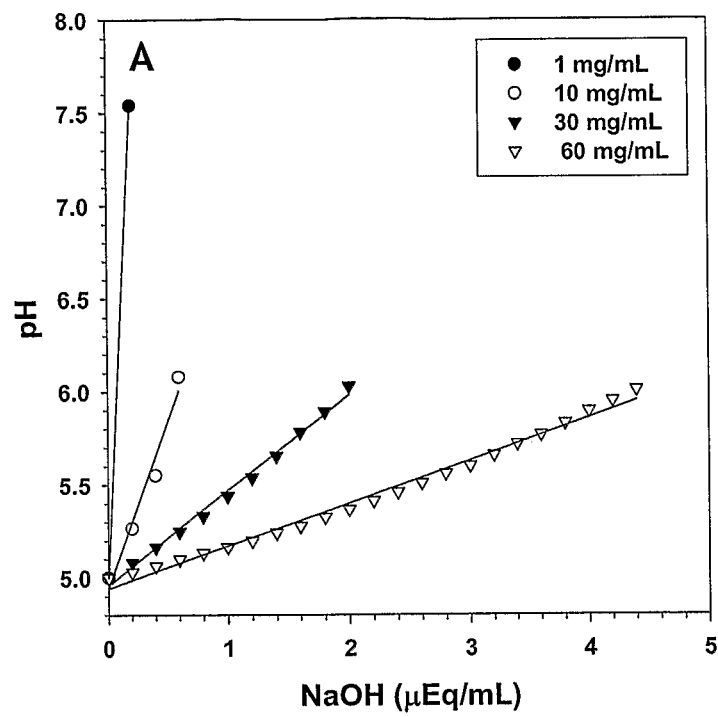
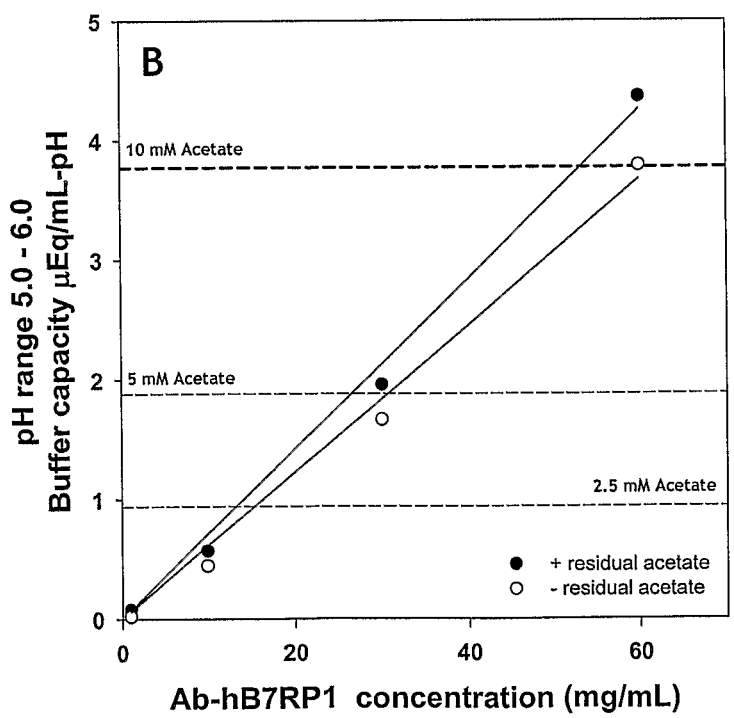

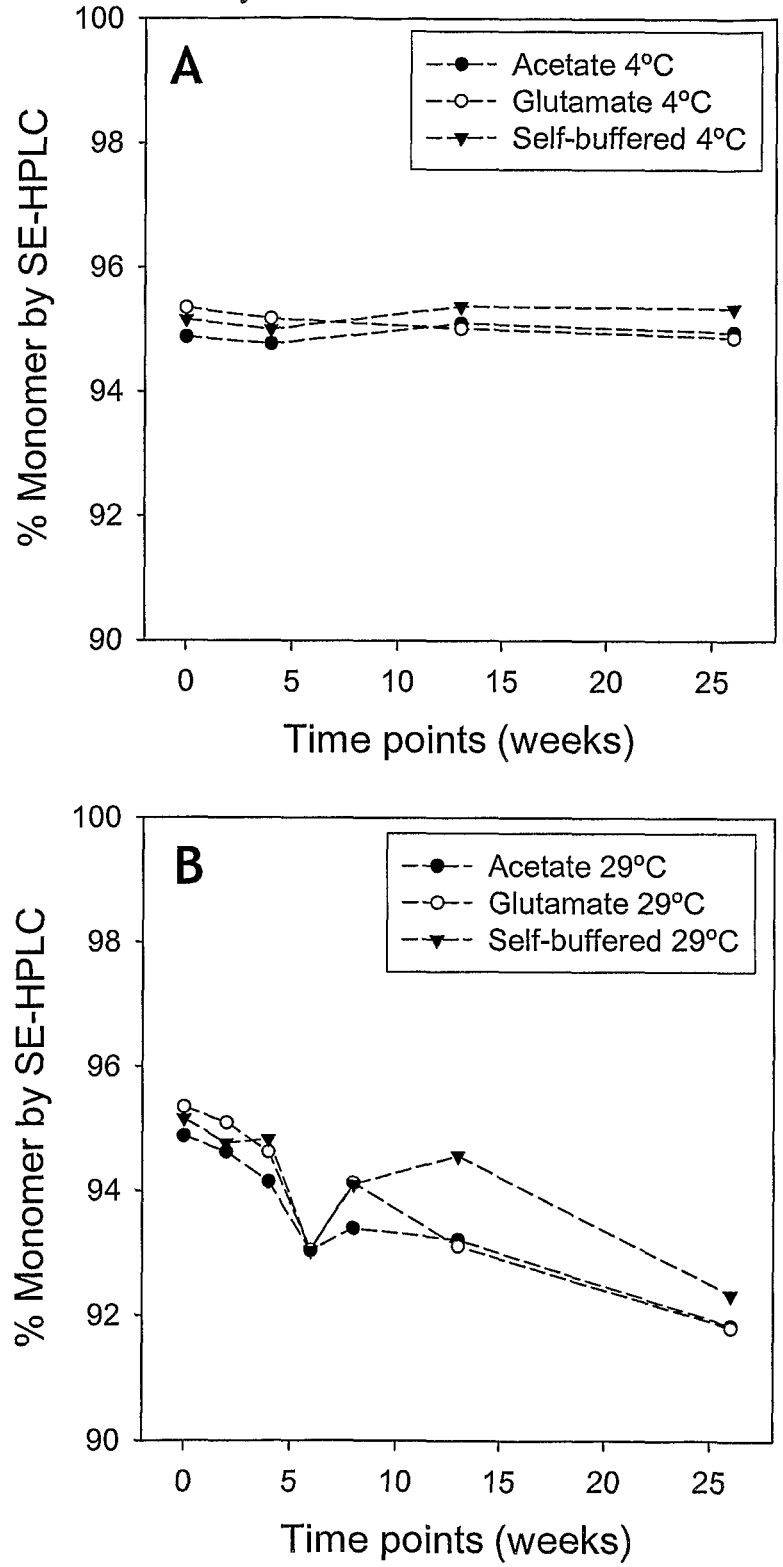
Figure 12. Stability of the Self-Buffered, 60 mg/mL, Ab-hB7RP1 Formulation Compared to Conventionally Buffered Formulations Figure 13. pH control of the Self-Buffered, 60 mg/mL, Ab-hB7RP1 Formulation
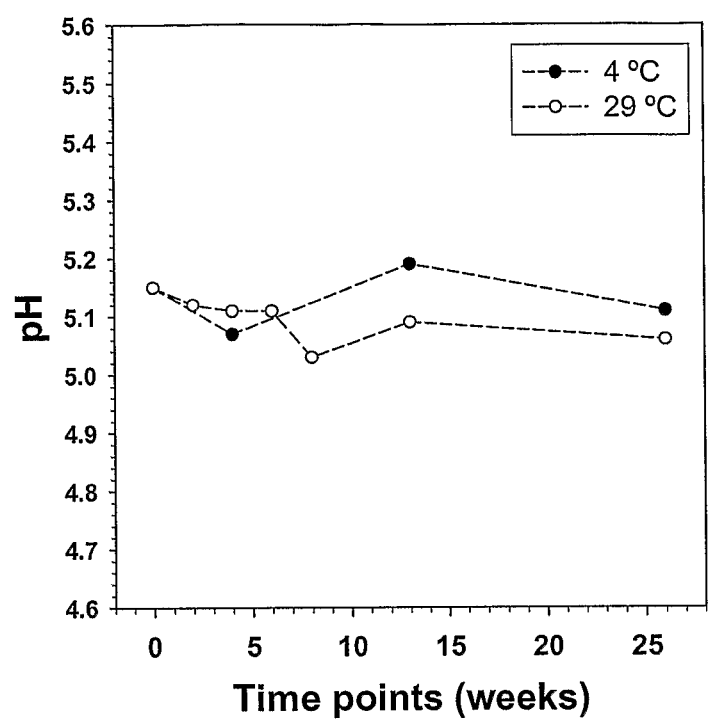

Figure 14. Buffer capacity of Ab-hCD22 solutions in the pH 4.0- 6.0 range
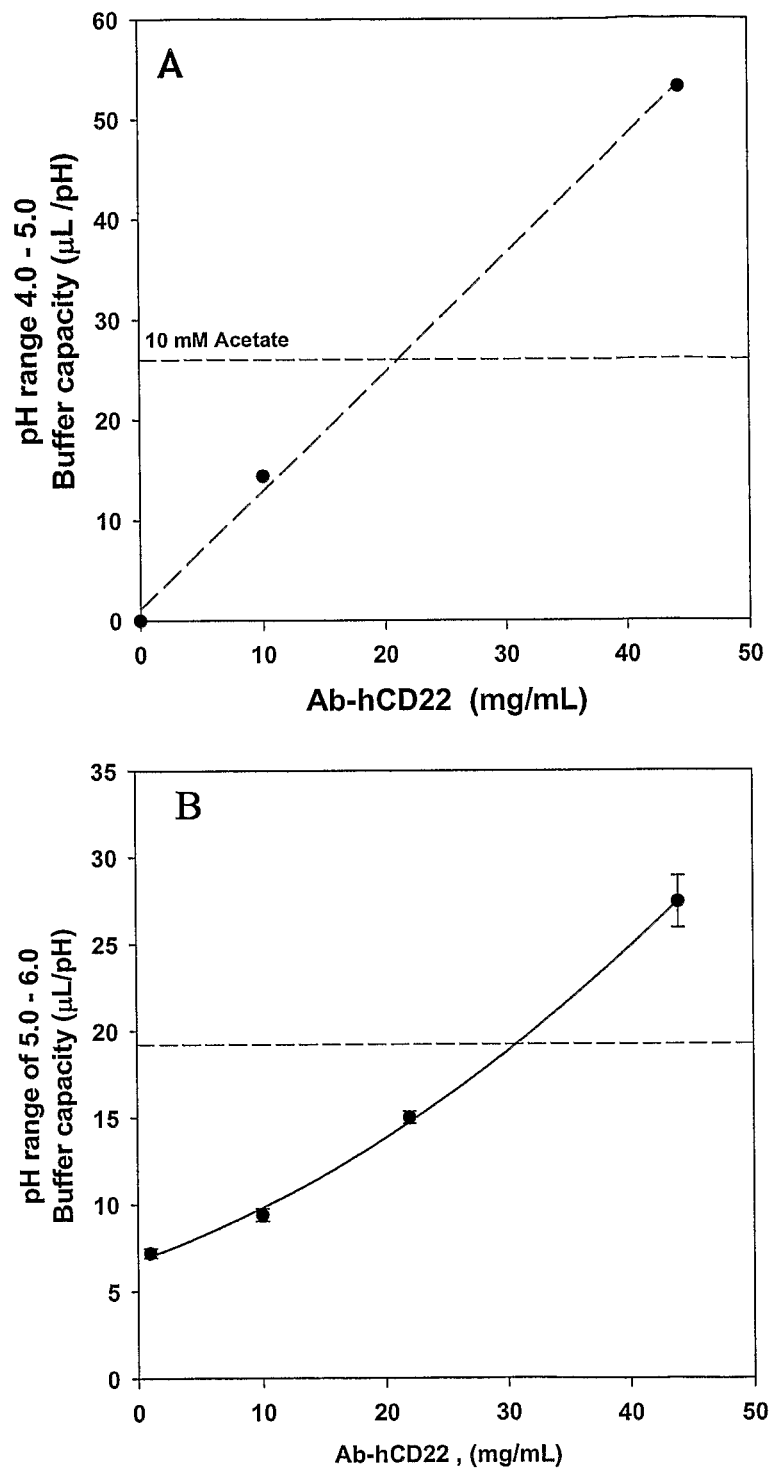

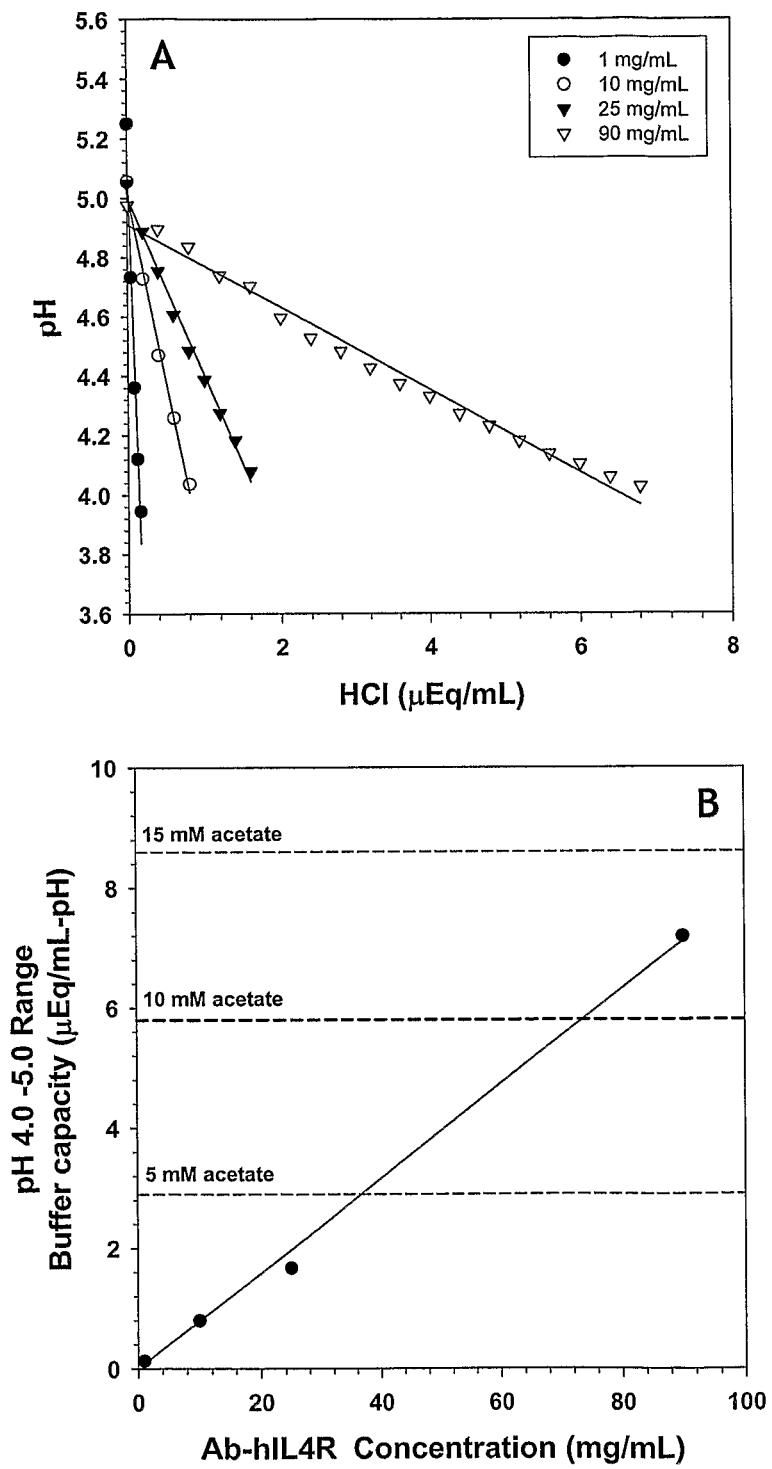
Figure 15. Buffer capacity of Ab-hIL4R Solutions in the pH 4.0 - 5.0 Range Figure 16. Buffer capacity of Ab-hIL4R Solutions in the pH 5.0 - 6.0 Range
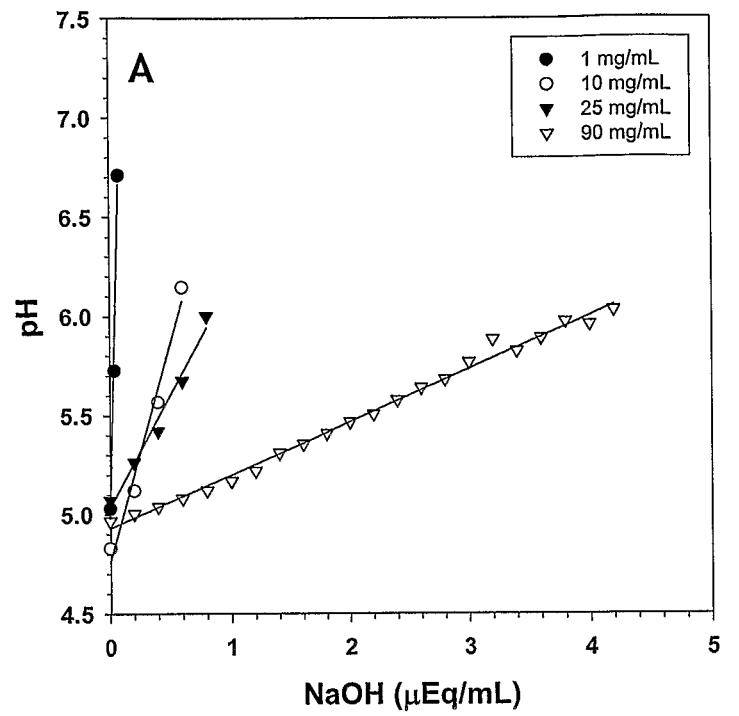
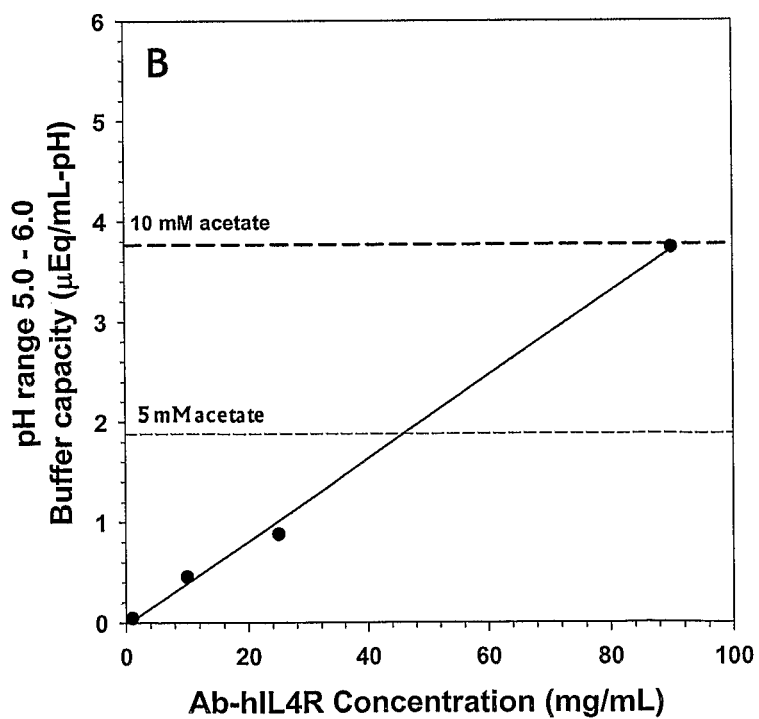

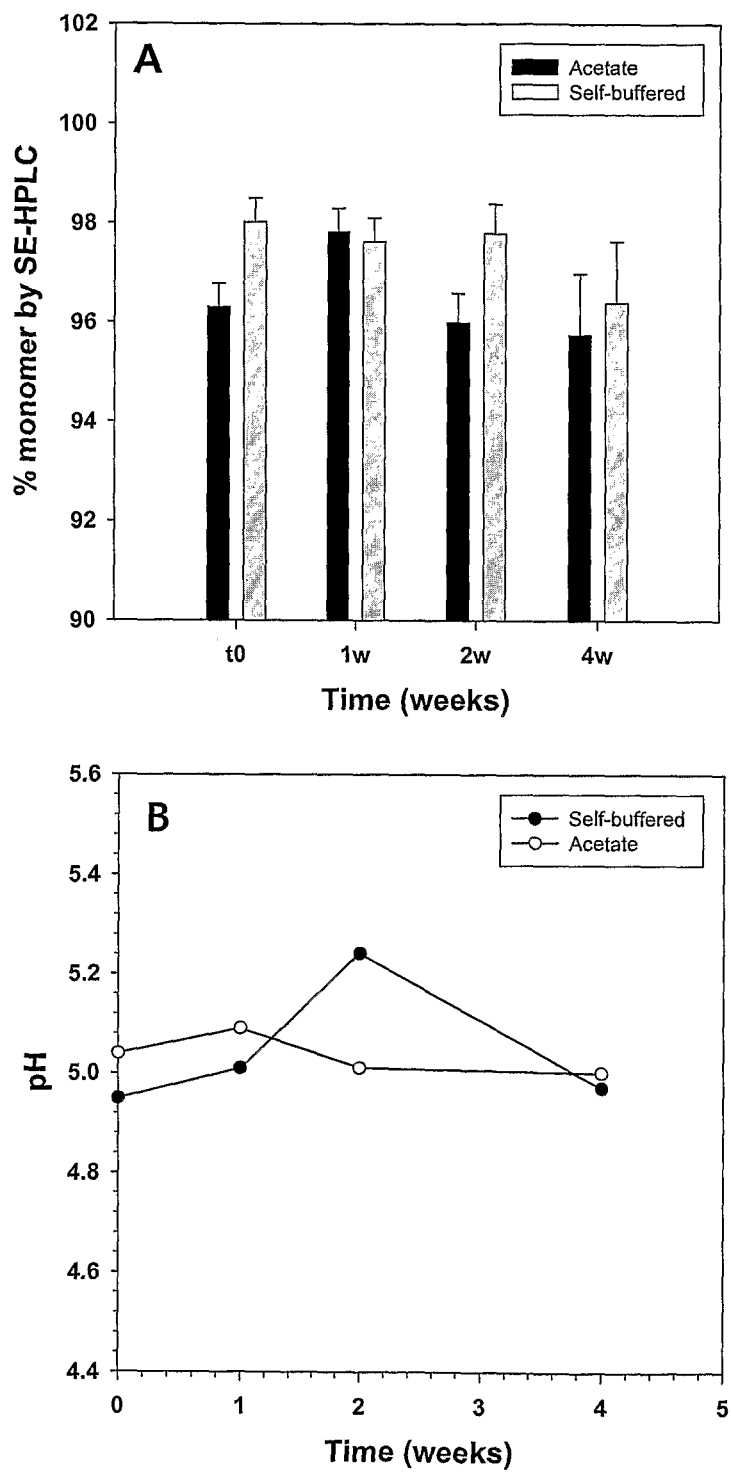
Figure 17. Accelerated Stability & pH control of the Self-Buffered, 70 mg/mL, Ab-hIL4R Formulation Compared to the Acetate Buffered Formulation at 37 C

Fig. 18A

Light Chain

METPAQLLFLLLLWLPDTTGEIVLTQSPGTLSLSPGERATLSCRASQSVRGRYLAWYQQKPGQA
PRLLIYGASSRATGIPDRFSGSGSGTDFTLTISRLEPEDFAVFYCQQYGSSPRTFGQGTKVEIK
RTVAAPSVFIFPPSDEQLKSGTASVVCLLNNFYPREAKVQWKVDNALQSGNSQESVTEQDSKDS
TYSLSSTLTLSKADYEKHKVYACEVTHQGLSSPVTKSFNRGEC (SEQ ID NO: 1)

Fig. 18B

Heavy Chain

MEFGLSWLFLVAILKGVQCEVQLLESGGGLVQPGGSLRLSCAASGFTFSSYAMSWVRQAPGKGL
EWVSGITGSGGSTYYADSVKGRFTISRDNSKNTLYLQMNSLRAEDTAVYYCAKDPGTTVIMSWF
DPWGQGTLVTVSSASTKGPSVFPLAPCSRSTSESTAALGCLVKDYFPEPVTVSWNSGALTSGVH
TFPAVLQSSGLYSLSSVVTVPSSNFGTQTYTCNVDHKPSNTKVDKTVERKCCVECPPCPAPPVA
GPSVFLFPPKPKDTLMISRTPEVTCVVVDVSHEDPEVQFNWYVDGVEVHNAKTKPREEQFNSTF
RVVSVLTVVHQDWLNGKEYKCKVSNKGLPAPIEKTISKTKGQPREPQVYTLPPSREEMTKNQVS
LTCLVKGFYPSDIAVEWESNGQPENNYKTTPPMLDSDGSFFLYSKLTVDKSRWQQGNVFSCSVM
HEALHNHYTQKSLSLSPGK (SEQ ID NO: 2)

Fig. 18C

Light Chain Variable Region

EIVLTQSPGTLSLSPGERATLSCRASQSVRGRYLAWYQQKPGQAPRLLIYGASSRATGIPDRFS
GSGSGTDFTLTISRLEPEDFAVFYCQQYGSSPRTFGQGTKVEIK (SEQ ID NO: 3)

Fig. 18D

Heavy Chain Variable Region

EVQLLESGGGLVQPGGSLRLSCAASGFTFSSYAMSWVRQAPGKGLEWVSGITGSGGSTYYADSV
KGRFTISRDNSKNTLYLQMNSLRAEDTAVYYCAKDPGTTVIMSWFDPWGQGTLVTVSS (SEQ
ID NO: 4)

SELF-BUFFERING ANTIBODY FORMULATIONS

REFERENCE TO RELATED APPLICATIONS

This application is a continuation of U.S. patent application Ser. No. 13/188,329 filed Jul. 21, 2011, which is a divisional of U.S. patent application Ser. No. 11/917,188 filed Jun. 16, 2008, which is a National Stage Entry of PCT/US2006/022599 filed Jun. 8, 2006, and claims full priority benefit of U.S. Provisional Application Ser. No. 60/690,582 filed 14 Jun. 2005, which is incorporated herein by reference in its entirety.

REFERENCE TO SEQUENCE LISTING

The present application includes a Sequence Listing in electronic format. The Sequence Listing is provided as file entitled AMGN001C1SEQLIST.txt created and last modified on Oct. 25, 2018, which is 8,613 bytes in size. The information in the electronic format of the Sequence Listing is incorporated herein by reference in its entirety.

FIELD OF THE INVENTION

The invention relates to the formulation of proteins, especially pharmaceutical proteins. In particular, it relates to self-buffering biopharmaceutical protein compositions, and to methods for designing, making, and using the compositions. It further relates to pharmaceutical protein compositions for veterinary and/or for human medical use, and to methods relating thereto.

BACKGROUND OF THE INVENTION

Many aspects of pharmaceutical production and formulation processes are pH sensitive. Maintaining the correct pH of a finished pharmaceutical product is critical to its stability, effectiveness, and shelf life, and pH is an important consideration in designing formulations for administration that will be acceptable, as well as safe and effective.

To maintain pH, pharmaceutical processes and formulations use one or more buffering agents. A variety of buffering agents are available for pharmaceutical use. The buffer or buffers for a given application must be effective at the desired pH. They must also provide sufficient buffer capacity to maintain the desired pH for as long as necessary. A good buffer for a pharmaceutical composition must satisfy numerous other requirements as well. It must be appropriately soluble. It must not form deleterious complexes with metal ions, be toxic, or unduly penetrate, solubilize, or absorb on membranes or other surfaces. It should not interact with other components of the composition in any manner which decreases their availability or effectiveness. It must be stable and effective at maintaining pH over the range of conditions to which it will be exposed during formulation and during storage of the product. It must not be deleteriously affected by oxidation or other reactions occurring in its environment, such as those that occur in the processing of the composition in which it is providing the buffering action, if carried over or incorporated into a final product, a buffering agent must be safe for administration, compatible with other components of the composition over the shelf-life of the product, and acceptable for administration to the end user.

Although there are many buffers in general use, only a limited number are suitable for biological applications and, of these, fewer still are acceptable for pharmaceutical processes and formulations. As a result, it often is challenging to find a buffer that not only will be effective at maintaining pH but also will meet all the other requirements for a given pharmaceutical process, formulation, or product.

The challenge of finding a suitable buffer for pharmaceutical use can be especially acute for pharmaceutical proteins. The conformation and activity of proteins are critically dependent upon pH. Proteins are susceptible to a variety of pH sensitive reactions that are deleterious to their efficacy, typically many more than affect small molecule drugs. For instance, to mention just a few salient examples, the side chain amides of asparagine and glutamine are deamidated at low pH (less than 4.0) and also at neutral or high pH (greater than 6.0). Aspartic acid residues promote the hydrolysis of adjacent peptide bonds at low pH. The stability and disposition of disulfide bonds is highly dependent on pH, particularly in the presence of thiols. Solubility, flocculation, aggregation, precipitation, and fibrillation of proteins are critically dependent on pH. The crystal habit important to some pharmaceutical formulations also is critically dependent on pH. And pH is also an important factor in surface adsorption of many pharmaceutical peptides and proteins.

Buffering agents that catalyze reactions that inactivate and/or degrade one or more other ingredients, moreover, cannot be used in pharmaceutical formulations. Buffers for pharmaceutical use must have not only the buffer capacity required to maintain correct pH, but also they must not buffer so strongly that their administration deleteriously perturbs a subject's physiological pH. Buffers for pharmaceutical formulations also must be compatible with typically complex formulation processes. For instance, buffers that sublime or evaporate, such as acetate and imidazole, generally cannot be relied upon to maintain pH during lyophilization and in the reconstituted lyophilization product. Other buffers that crystallize out of the protein amorphous phase, such as sodium phosphate, cannot be relied upon to maintain pH in processes that require freezing.

Buffers used to maintain pH in pharmaceutical end-products also must be not only effective at maintaining pH but also safe and acceptable for administration to the subject. For instance, several otherwise useful buffers, such as citrate at low or high concentration and acetate at high concentration, are undesirably painful when administered parenterally.

Some buffers have been found to be useful in the formulation of pharmaceutical proteins, such as acetate, succinate, citrate, histidine (imidazole), phosphate, and Tris. They all have undesirable limitations and disadvantages. And they all have the inherent disadvantage of being an additional ingredient in the formulation, which complicates the formulation process, poses a risk of deleteriously affecting other ingredients, stability, shelf-life, and acceptability to the end user.

There is a need, therefore, for additional and improved methods of maintaining pH in the production and formulation of pharmaceuticals and in pharmaceutical compositions, particularly in the production and formulation of biopharmaceutical proteins and in biopharmaceutical protein compositions.

SUMMARY

Therefore, it is among the various objects and aspects of the invention to provide, in certain of the preferred embodiments, protein formulations comprising a protein, particularly pharmaceutically acceptable formulations comprising a pharmaceutical protein, that are buffered by the protein itself, that do not require additional buffering agents to maintain a desired pH, and in which the protein is substantially the only buffering agent (i.e., other ingredients, if any, do not act substantially as buffering agents in the formulation).

In this regard and others, it is among the various objects and aspects of the invention to provide, in certain preferred embodiments, self-buffering formulations of a protein, particularly of a pharmaceutical protein, characterized in that the concentration of the formulated protein provides a desired buffer capacity.

It is further among the various objects and aspects of the invention to provide, in certain of the particularly preferred embodiments, self-buffering protein formulations, particularly pharmaceutical protein formulations, in which the total salt concentration is less than 150 mM.

It is further among the various objects and aspects of the invention to provide, in certain of the particularly preferred embodiments, self-buffering protein formulations, particularly pharmaceutical protein formulations, that further comprise one or more polyols and/or one or more surfactants.

It is also further among the various objects and aspects of the invention to provide, in certain of the particularly preferred embodiments, self-buffering formulations comprising a protein, particularly a pharmaceutical protein, in which the total salt concentration is less than 150 mM, that further comprise one or more excipients, including but not limited to, pharmaceutically acceptable salts; osmotic balancing agents (tonicity agents); surfactants, polyols, antioxidants; antibiotics; antimycotics; bulking agents; lyoprotectants; anti-foaming agents; chelating agents; preservatives; colorants; and analgesics.

It is additionally among the various objects and aspects of the invention to provide, in certain preferred embodiments, self-buffering protein formulations, particularly pharmaceutical protein formulations, that comprise, in addition to the protein, one or more other pharmaceutically active agents.

Various additional aspects and embodiments of the invention are illustratively described in the following numbered paragraphs. The invention is described by way of reference to each of the items set forth in the paragraphs, individually and/or taken together in any combination. Applicant specifically reserves the right to assert claims based on any such combination.

1. A composition according to any of the following, wherein the composition has been approved for pharmaceutical use by a national or international authority empowered by law to grant such approval preferably the European Agency for the Evaluation of Medical Products, Japan's Ministry of Health, Labor and Welfare, China's State Drag Administration, United States Food and Drug Administration, or their successor(s) in this authority, particularly preferably the United States Food and Drug Administration or its successor(s) in this authority.

2. A composition according to any of the foregoing or the following, wherein the composition is produced in accordance with good manufacturing practices applicable to the production of pharmaceuticals for use in humans.

3. A composition according to any of the foregoing or the following, comprising a protein, the protein having a buffer capacity per unit volume per pH unit of at least that of approximately: 2.0 or 3.0 or 4.0 or 5.0 or 6.50 or 8.00 or 10.0 or 15.0 or 20.0 or 30.0 or 40.0 or 50.0 or 75.0 or 100 or 125 or 150 or 200 or 250 or 300 or 350 or 400 or 500 mM sodium acetate buffer in pure water over the range of pH 5.0 to 4.0 or pH 5.0 to 5.5, preferably as determined in accordance with the methods described in Example 1 and 2, particularly preferably at least 2.0 mM, especially particularly preferably at least 3.0 mM, very especially particularly preferably at least 4.0 DIM or at least 5.0 mM, especially particularly preferably at least 7.5 mM, particularly preferably at least 10 mM, preferably at least 20 mM.

4. A composition according to any of the foregoing or the following wherein, exclusive of the buffer capacity of the protein, the buffer capacity per unit volume per pH unit of the composition is equal to or less than that of 1.0 or 1.5 or 2.0 or 3.0 or 4.0 or 5.0 mM sodium acetate buffer in pure water over the range of pH 4.0 to 5.0 or pH 5.0 to 5.5, preferably as determined in accordance with the methods described in Example 1 and 2, particularly preferably less than that of 1.0 very especially particularly preferably less than that of 2.0 mM, especially particularly preferably less than that of 2.5 mM, particularly preferably less than that of 3.0 mM, preferably less than that of 5.0 mM.

5. A composition according to any of the foregoing or the following comprising a protein wherein over the range of plus or minus 1 pH unit from the pH of the composition, the buffer capacity of the protein is at least approximately: 1.00 or 1.50 or 1.63 or 2.00 or 3.00 or 4.00 or 5.00 or 6.50 or 8.00 or 10.0 or 15.0 or 20.0 or 30.0 or 40.0 or 50.0 or 75.0 or 100 or 125 or 150 or 200 or 250 or 300 or 350 or 400 or 500 or 700 or 1,000 mEq per liter per pH unit, preferably at least approximately 1.00, particularly preferably 1.50, especially particularly preferably 1.63, very especially particularly preferably 2.00, very highly especially particularly preferably 3.00, very especially particularly preferably 5.0, especially particularly preferably 10.0, particularly preferably 20.0.

6, A composition according to any of the foregoing or the following comprising a protein wherein over the range of plus or minus 1 pH unit from the pH of the composition, exclusive of the protein, the buffer capacity per unit volume per pH unit of the composition is equal to or less than that of 0.50 or 1.00 or 1.50 or 2.00 or 3.00 or 4.00 or 5.00 or 6.50 or 8.00 or 10.0 or 20.0 or 25.0 mM sodium acetate buffer in pure water over the range pH 5.0 to 4.0 or pH 5.0 to 5.5, particularly preferably determined, in accordance with Example 1 and/or Example 2.

7. A composition according to any of the foregoing or the following, wherein over a range of plus or minus 1 pH unit from a desired pH, the protein provides at least approximately 55%, 60%, 65%, 70%, 75%, 80%, 85%, 90%, 95%, 97%, 98%, 99%, or 99.5% of the buffer capacity of the composition, preferably at least approximately 75%, particularly preferably at least approximately 85%, especially particularly preferably at least approximately 90%, very especially particularly preferably at least approximately 95%, very highly especially particularly preferably at least approximately 99% of the buffer capacity of the composition.

8. A composition according to any of the foregoing or the following, wherein the concentration of the protein is between approximately: 20 and 400, or 20 and 300, or 20 and 250, or 20 and 200, or 20 and 150 mg/ml, preferably between approximately 20 and 400 mg/ml, particularly preferably between approximately 20 and 250, especially particularly between approximately 20 and 150 mg/ml.

9. A composition according to any of the foregoing or the following, wherein the pH maintained by the buffering action of the protein is between approximately: 3.5 and 8.0, or 4.0 and 6.0, or 4.0 and 5.5, or 4.0 and 5.0, preferably between approximately 3.5 and 8.0, especially particularly preferably approximately 4.0 and 5.5.

10. A composition according to any of the foregoing or the following, wherein the salt concentration is less than: 150 mM or 125 mM or 100 mM or 75 mM or 50 mM or 25 mM, preferably 150 mM, particularly preferably 125 mM, especially preferably 100 mM, very particularly preferably 75 mM, particularly preferably 50 mM, preferably 25 mM.

11. A composition according to any of the foregoing or the following, further comprising one or more pharmaceutically acceptable salts; polyols; surfactants; osmotic balancing agents; tonicity agents; anti-oxidants; antibiotics; antimycotics; bulking agents; lyoprotectants; anti-foaming agents; chelating agents; preservatives; colorants; analgesics; or additional pharmaceutical agents.

12. A composition according to any of the foregoing or the following, comprising one or more pharmaceutically acceptable polyols in an amount that is hypotonic, isotonic, or hypertonic, preferably approximately isotonic, particularly preferably isotonic, especially preferably any one or more of sorbitol, mannitol, sucrose, trehalose, or glycerol, particularly especially preferably approximately 5% sorbitol, 5% mannitol, 9% sucrose, 9% trehalose, or 2.5% glycerol, very especially in this regard 596 sorbitol, 5% mannitol, 9% sucrose, 9% trehalose, or 2.5% glycerol.

13. A composition according to any of the foregoing or the following, further comprising a surfactant, preferably one or more fatty acid esters of sotbitan, polyethoxylates, and poloxamer 188, particularly preferably polysorbate 20 or polysorbate 80, preferably approximately 0.001 to 0.1% polysorbate 20 or polysorbate 80, very preferably approximately 0.002 to 0.02% polysorbate 20 or polysorbate 80, especially 0.002 to 0.02% polysorbate 20 or polysorbate 80.

14. A composition according to any of the foregoing or the following, wherein the protein is a pharmaceutical agent and the composition is a sterile formulation thereof suitable for treatment of a non-human or a human subject.

15. A composition according to any of the foregoing or the following, wherein the protein is a pharmaceutical agent effective to treat a disease and the composition is a sterile formulation thereof suitable for administration to a subject for treatment thereof.

16. A composition according to any of the foregoing or the following, wherein the protein does not induce a significantly deleterious antigenic response following administration to a subject.

17. A composition according to any of the foregoing or the following, wherein the protein does not induce a significantly deleterious immune response following administration to a subject.

18. A composition according to any of the foregoing or the owing, wherein the protein is a human protein.

19. A composition according to any of the foregoing or the following, wherein the protein is a humanized protein.

20. A method according to any of the foregoing or the following, wherein the protein is an antibody, preferably an IgA, IgD, IgE, IgG, or IgM antibody, particularly preferably an IgG antibody, very particularly preferably an IgG1, IgG2, IgG3, or IgG4 antibody, especially an IgG2 antibody.

21. A composition according to any of the foregoing or the following, wherein the protein comprises a: Fab fragment, $Fab_2$ fragment, $Fab_3$ fragment, Fe fragment, say fragment, bis-scFv(s) fragment, minibody, diabody, triabody, tetrabody, VhH domain, V-NAR domain, $V_H$ domain, $V_L$ domain, camel Ig, Ig NAR, or peptibody, or a variant, derivative, or modification of any of the foregoing.

22. A composition according to any of the foregoing or the following, wherein the protein comprises an Fe fragment or a part thereof or a derivative or variant of an Fe fragment or part thereof.

23. A composition according to any of the foregoing or the following, wherein the protein comprises a first binding moiety of a pair of cognate binding moieties, wherein the first moiety binds the second moiety specifically.

24. A composition according to any of the foregoing or the following, wherein the protein comprises (a) an Fc fragment or a part thereof or a derivative or variant of an Fc fragment or part thereof, and (b) a first binding moiety of a pair of cognate binding moieties.

25. A composition according to any of claim 1, 5, 7, 9, 11, 13, or 14, wherein the protein is selected from the group consisting of proteins that bind specifically to one or more CD proteins, HER receptor family proteins, cell adhesion molecules, growth factors, nerve growth factors, fibroblast growth factors, transforming growth factors (TGF), insulin-like growth factors, osteoinductive factors, insulins and insulin-related proteins, coagulation and coagulation-related proteins, colony stimulating factors (CSFs), other blood and serum proteins blood group antigens; receptors, receptor-associated proteins, growth hormone receptors, T-cell receptors; neurotrophic factors, neurotrophins, relaxins, interferons, interleukins, viral antigens, lipoproteins, integrins, rheumatoid factors, immunotoxins, surface membrane proteins, transport proteins, homing receptors, addressins, regulatory proteins, and immunoadhesins, 26. A composition according to any of the foregoing or the following, wherein the protein is selected from the group consisting of: OPGL specific binding proteins, myostatin specific binding proteins, IL-4 receptor specific binding proteins. IL1-R1 specific binding proteins, Ang2 specific binding proteins, NGF-specific binding proteins, CD22 specific binding proteins, IGF-1 receptor specific binding proteins, B7RP-1 specific binding proteins, IFN gamma specific binding proteins, TALL-1 specific binding proteins, stem cell factors, Flt-3 ligands, and IL-17 receptors.

27. A composition according to any of the foregoing or the following, wherein the protein is selected from the group consisting of proteins that bind specifically to one or more of: CD3, CD4, CD8, CD19, CD20, CD34; HER2, HER3, HER4, the EGF receptor; LEA-1, Mol, p150, 95, ICAM-1, VCAM, alpha v/beta 3 integrin; vascular endothelial growth factor ("VEGF"), growth hormone, thyroid stimulating hormone, follicle stimulating hormone, luteinizing hormone, growth hormone releasing factor, parathyroid hormone, mullerian-inhibiting substance, human macrophage inflammatory protein (MIP-1-alpha), erythropoietin (EPO), NGF-beta, platelet-derived growth factor (PDGF), aFGF, bFGF, epidermal growth factor (EGF), TGF-alpha, TGF-beta TGF-beta2, TGF-beta3, TGF-beta4, TGF-beta5, IGF-I, IGF-II, des(1-3)-IGF-I (brain IGF-I), insulin, insulin A-chain, insulin B-chain, proinsulin, insulin-like growth factor binding proteins: such as, among others, factor VIII, tissue factor, von Willebrands factor, protein C, alpha-L-antitrypsin, plasminogen activators, such urokinase and tissue plasminogen activator "t-PA"), bombazine, thrombin, and thrombopoietin; M-CSF, GM-CSF, G-CSF, albumin, IgE, flk2/flt3 receptor, obesity (OB) receptor, bone-derived neurotrophic factor (BDNF), NT-3, NT-4, NT-5, NT-6); relaxin A-chain, relaxin B-chain, prorelaxin; interferon-alpha, -beta, and -gamma; IL-1 to IL-10; AIDS envelope viral antigen; calcitonin, glucagon, atrial natriuretic factor, lung surfactant, tumor necrosis factor-alpha and -beta, enkephalinase, RANTES, mouse gonadotropin-associated peptide, Dnase, inhibin, and activin; protein A or D, bone morphogenetic protein (BMP), superoxide dismutase, decay accelerating factor (DAT).

28. A composition according to any of the foregoing or the following, wherein the protein is selected from the group consisting of: Actimmune (Interferon-gamma-1b), Activase (Alteplase), Aldurazme (Laronidase), Amevive (Alefacept), Avonex (Interferon beta-1a), BeneFIX (Nonacog alfa), Beromun (Tasonermin) Beatseron (Interferon-beta-1b), BEXXAR (Tositumomab), Tev-Tropin (Somatropin), Bioclate or RECOMBINATE (Recombinant), CEREZME (Imiglucerase), ENBREL (Etanercept), Eprex (epoetin alpha), EPOGEN/Procit (Epoetin alfa), FABRAZYME (Agalsidase beta), Fasturtec/Elitek ELITEK (Rasburicase), FORTEO (Teriparatide), GENOTROPIN (Somatropin), GlucaGen (Glucagon), Glucagon (Glucagon, rDNA origin), GONAL-F (follitropin alfa), KOGENATE FS (Octocog alfa), HERCEPTIN (Trastuzumab), HUMATROPE (SOMATROPIN), HUMIRA (Adalimumab), Insulin in Solution, INFERGEN® (Interferon alfacon-1), KINERET® (anakinra), Kogenate FS (Antihemophilic Factor), LEUKIN (SARGRAMOSTIM Recombinant human granulocyte-macrophage colony stimulating factor (rhuGM-CSF)), CAMPATH (Alemtuzumab), RITUXAN® (Rituximab), TNKase (Tenecteplase), MYLOTARG (gemtuzumab ozogamicin), NATRECOR (nesiritide), ARANESP (darbepoetin alfa), NEULASTA (pegfilgrastim), NEUMEGA (oprelvekin), NEUPOGEN (Filgrastim), NORDITROPIN CARTRIDGES (Somatropin), NOVOSEVEN (Eptacog alfa), NUTROPIIN AQ (somatropin), Oncaspar (pegaspargase), ONTAK (denileukin diftitox), ORTHOCLONE OKT (muromonab-CD3), OVIDREL (choriogonadotropin alfa), PEGASYS (peginterferon alfa-2a), PROLEUKIN (Aldesletikin), PULMOZYME (dornase alfa), Retavase (Reteplase), REBETRON Combination Therapy containing REBETOL® (Ribavirin) and INTRON® A (Interferon alfa-2b), REHIF (interferon beta-1a), REFACTO (Antihemophilic Factor), REFLUDAN (lepirudin), REMICADE (infliximab), REOPRO (abciximab) ROFERON®-A (Interferon alfa-2a), SINIULECT (baasiliximab), SOMAVERT (Pegivisomant), SYNAGIS® (palivizumab), Stemben (Ancestim, Stem cell factor), THYROGEN, INTRON® A (Interferon alfa-2b), PEG-INTRON® (Peginterferon alfa-2b), XIGRIS® (Drotrecogin alfa activated), XOLAIR® (Omalizumab), ZENAPAX® (daclizumab), and ZEVALIN® (Ibritumomab Thixetan).

29. A composition according to any of the foregoing or the following, wherein the protein is Ab-hCD22 or a fragment thereof, or a variant, derivative, or modification of Ab-hCD22 or of a fragment thereof; Ab-hIL4R or a fragment thereof, or a variant, derivative, or modification of Ab-hIL4R or of a fragment thereof; Ab-hOPGL or a fragment thereof, or a variant, derivative, or modification of Ab-hOPGL or of a fragment thereof, or Ab-hB7RP1 or a fragment thereof, or a variant, derivative, or modification of Ab-hB7RP1 or of a fragment thereof.

30. A composition according to any of the foregoing or the following, wherein the protein is: Ab-hCD22 or Ab-hIL4R or Ab-hOPGL or Ab-hB7RP1.

31. A composition according to any of the foregoing or the following comprising a protein and a solvent, the protein having a buffer capacity per unit volume per pH unit of at least that of 4.0 mM sodium acetate in water over the range of pH 4.0 to 5.0 or pH 5.0 to 5.5, particularly as determined by the methods described in Examples 1 and 2, wherein the buffer capacity per unit volume of the composition exclusive of the protein is equal to or less than that of 2.0 in M sodium acetate in water over the same ranges preferably determined in the same way.

32. A composition according to any of the foregoing or the following comprising a protein and a solvent, wherein at the pH of the composition the buffer capacity of the protein is at least 1.63 mEq per liter for a pH change of the composition of plus or minus 1 pH unit wherein the buffer capacity of the composition exclusive of the protein is equal to or less than 0.81 mEq per liter at the pH of the composition for a pH change of plus or minus 1 pH unit.

33. A lyophilate which upon reconstitution provides a composition in accordance with any of the foregoing or the following.

34. A kit comprising in one or more containers a composition or a lyophilate in accordance with any of the foregoing or the following, and instructions regarding use thereof.

35. A process for preparing a composition or a lyophilate according to any of the foregoing or the following, comprising removing residual buffer using a counter ion.

36. A process for preparing a composition or a lyophilate according to any of the foregoing or the following, comprising removing residual buffer using any one or more of the following in the presence of a counter ion: chromatography, dialysis, and/or tangential flow filtration.

37. A process for preparing a composition or a lyophilate according to any of the foregoing or the following, comprising removing residual buffer using tangential flow filtration.

38. A process for preparing a composition or a lyophilate according to any of the foregoing or the following comprising a step of dialysis against a solution at a pH below that of the preparation and, if necessary, adjusting the pH thereafter by addition of dilute acid or dilute base.

39. A method for treating a subject comprising administering to a subject in an amount and by a route effective for treatment a composition according to any of the foregoing or the following, including a reconstituted lyophilate.

BRIEF DESCRIPTION OF THE FIGURES

FIG. 1 depicts titration data and buffer capacity as a function of concentration for sodium acetate standard buffers over the range from pH 5.0 to 4.0. Panel A is a graph that depicts the pH change upon acid titration of several different concentrations of a standard sodium acetate buffer, as described in Example pH is indicated on the vertical axis. The amount of acid added to each solution is indicated on the horizontal axis in microequivalents of HCl added per ml of solution (µEq/ml). The linear least squares trend lines are depicted for each dataset. Acetate concentrations are indicated in the inset. Panel B is a graph that depicts the buffer capacity of the acetate buffers over the acidic pH range as determined from the titration data depicted in Panel A, as described in Example 1. Buffer capacity is indicated on the vertical axis as microequivlents of acid per ml of buffer solution per unit change in pH (µEq/ml-pH). Acetate concentration is indicated on the horizontal axis in mM.

FIG. 2 depicts titration data and buffer capacity as a function of concentrations for sodium acetate standard buffers over the range from pH 5.0 to 5.5. Panel A is a graph that depicts the pH change upon base titration of several different concentration of a standard sodium acetate buffer, as described in Example 2. pH is indicated on the vertical axis. The amount of base added to each solution is indicated on the horizontal axis in microequivalents of NaOH added per ml of solution (µEq/ml). The linear least squares trend lines are depicted for each dataset. Acetate concentrations are indicated in the inset. Panel B is a graph that depicts the buffer capacity of the acetate buffers over the basic pH range as determined from the titration data depicted in Panel A and described in Example 2. Buffer capacity is indicated on the vertical axis as microequivlents of base per ml of buffer solution per unit change in pH (µEq/ml-pH). Acetate concentration is indicated on the horizontal axis in mM.

FIG. 3 depicts the determination of acetate concentration in acetate buffer standards, as described in Example 3. The graph shows a standard curve for the determinations, with peak area indicated on the vertical axis and the acetate concentration indicated on the horizontal axis. The nominal and the measured amounts of acetate in the solutions used for the empirical determination of buffer capacity are tabulated below the graph.

FIG. 4 is a graph that depicts the pH change upon acid titration of several different concentrations of Ab-hOPGL over the range of pH 5.0 to 4.0, as described in Example 4. pH is indicated on the vertical axis. The amount of acid added to the solutions is indicated on the horizontal axis in microequivalents of HCl added per ml of buffer solution (µEq/ml). The linear least squares trend lines are depicted for each dataset. Ab-hOPGL concentrations are indicated in the inset.

FIG. 5 is a graph that depicts the pH change upon base titration of several different concentrations of Ab-hOPGL over the range 5.0 to 6.0, as described in Example 5. pH is indicated on the vertical axis. The amount of base added to the solutions is indicated on the horizontal axis in microequivalents of NaOH added per ml of buffer solution (µEq/ml). The linear least squares trend lines are depicted for each dataset. Ab-hOPGL concentrations are indicated in the inset.

FIG. 6 shows the residual acetate levels in Ab-hOPGL solutions used for determining buffer capacity. The graph shows the standard curve used for the acetate determinations as described in Example 6. The nominal and the experimentally measured acetate concentrations in the solutions are tabulated below the graph.

FIG. 7 is a graph depicting the buffer capacity of Ab-hOPGL plus or minus residual acetate in the pH range 5.0 to 4.0, The data were obtained as described in Example 7. The upper line shows Ab-hOPGL buffer capacity with residual acetate. The lower line shows Ab-hOPGL buffer capacity adjusted for residual acetate. The vertical axis indicates buffer capacity in microequivalents of acid per ml Ab-hOPGL solution per unit of pH (µEq/ml-pH). The horizontal axis indicates the concentration of Ab-hOPGL mg/ml. The buffer capacities of different concentrations of standard acetate buffers as described in Example are shown as horizontal lines. The concentrations of the buffers are indicated above the lines.

FIG. 8 is a graph depicting the buffer capacity of Ab-hOPGL plus or minus residual acetate in the basic pH range pH 5.0 to 6.0. The data were obtained as described in Example 8. The upper line depicts Ab-hOPGL buffer capacity with residual acetate. The lower line depicts Ab-hOPGL buffer capacity adjusted for residual acetate. The vertical axis indicates buffer capacity in microequivalents of base added per ml of buffer solution per unit of pH (µEq/ml-pH). The horizontal axis indicates the concentration of Ab-hOPGL in mg/ml. The buffer capacities of several concentrations of standard sodium acetate buffers as described in Example 2 are indicated by horizontal lines. The acetate concentrations are indicated above each line.

FIG. 9 depicts, in a pair of charts, pH and Ab-hOPGL stability in self-buffering and conventionally buffered formulations. Panel A depicts the stability of self-buffered Ab-hOPGL, Ab-hOPGL formulated in acetate buffer, and Ab-hOPGL formulated in glutamate as a function of storage time at 4° C. over a period of six months. The vertical axis indicates Ab-hOPGL stability in percent Ab-hOPGL monomer determined by SE-HPLC. Storage time is indicated on the horizontal axis. Panel B depicts the of the same three formulations measured over the same period of time. The determinations of protein stability and the measurements of pH are described in Example 9.

FIG. 10 depicts titration curves and buffer capacities for several concentrations of self-buffering Ab-hB7RP1 formulations over the range of 5.0 to 4.0. Panel A shows the titration data. pH is indicated on the vertical axis. The amount of acid added to the solutions is indicated on the horizontal axis in microequivalents of HCl added per nil of buffer solution (µEq/ml). The linear least squares trend lines are depicted for each dataset. The Ab-hB7RP1 concentrations are indicated in the inset. Panel B depicts the buffer capacities of Ab-hB7RP1 formulations. The upper line shows the buffer capacities for the formulations including the contribution of residual acetate. The lower line shows the buffer capacities for formulations after subtracting the contribution of residual acetate based on SE-HPLC determinations as described in Example 3. Linear least squares trend lines are shown for the two data sets. The vertical axis indicates buffer capacity in microequivalents of acid per ml of buffer solution per unit of pH (µEq/ml-pH). The concentration of Ab-hB7RP1 is indicated on the horizontal axis in ing/ml. The buffer capacities of several concentrations of standard sodium acetate buffers as described in Example 1 are shown by dashed horizontal lines. The acetate buffer concentration are shown below each line. The results were obtained as described in Example 10.

FIG. 11 depicts titration curves and buffer capacities for several concentrations of self-buffering Ab-hB7RP1 formulations over the range of pH 5.0 to 6.0. Panel A shows the titration data. pH is indicated on the vertical axis. The amount of base added to the solutions is indicated on the horizontal axis in microequivalents of NaOH added per ml of buffer solution (µEq/ml). The linear least squares trend lines are depicted for each dataset. The Ab-hB7RP1 concentrations are indicated in the inset. Panel B depicts the buffer capacities of Ab-hB7RP1 formulations. The upper line shows the buffer capacities for the formulations containing residual acetate. The lower line shows the buffer capacities for formulations adjusted to remove the contribution of residual acetate. Linear least squares trend lines are Shown for the two data sets. The vertical axis indicates buffer capacity in microequivalents of base per ml of buffer solution per unit of pH (µEq/ml-pH). The concentration of Ab-hB7RP1 is indicated on the horizontal axis in mg/ml. The buffer capacities of several concentrations of standard sodium acetate buffers as described in Example 2 are shown by dashed horizontal lines. The acetate buffer concentrations are shown above each line. The results were obtained as described in Example 11.

FIG. 12 depicts Ab-hB7RP1 stability in self-buffering and conventionally buffered formulations at 4° C. and 29° C. Panel A depicts the stability of self-buffered Ab-hB7RP Ab-hB7RP1 formulated in acetate buffer, and Ab-hB7RP formulated in glutamate as a function of storage, at 4° C. over a period of six months. The vertical axis depicts Ab-hB7RP1 monomer in the samples determined by SE-HPLC. Time is indicated on the horizontal axis, Panel B depicts the stability of the same three formulations as a function of storage at 29° C. over the same period of time.

Axes in Panel B are the same as in Panel A. The determinations of protein stability by HPLC-SE are described in Example 12.

FIG. 13 depicts pH stability in self buffer formulations of Ab-hB7RP1 at 4° C. and 29° C. The vertical axis indicates pH. Time, in weeks, is indicated on the horizontal axis. Temperatures of the datasets are indicated in the inset. The data were obtained as described in Example 13.

FIG. 11 depicts the buffer capacity of self-buffering formulations of Ab-hCD22 as a function of Ab-hCD22 concentration over the range of pH 4.0 to 6.0. Panel A depicts the buffer capacities of self-buffering Ab-hCD22 formulations as a function of Ab-hCD22 concentration over the range of pH 4.0 to 5.0. Panel B depicts the buffer capacities of self-buffering Ab-hCD22 formulations as a function of concentration over the range of pH 5.0 to 6.0. In both panels the vertical axis indicates buffer capacity in microequivalents of base per nil of buffer solution per unit of pH (µEq/ml-pH), and the horizontal axis indicates Ab-hCD22 concentrations in signal. For reference, the buffer capacity of 10 mM sodium acetate as described in Example 1 is shown in both panels by a dashed horizontal line. The results shown in the Figure were obtained as described in Example 14.

FIG. 15 depicts titration curves and buffer capacities for several concentrations of self-buffering Ab-hIL4R formulations over the range of pH 5.0 to 4.0. Panel A shows the titration data. pH is indicated on the vertical axis. The amount of acid added to the solutions is indicated on the horizontal axis in microequivalents of HCl added per ml of buffer solution (µEq/ml). The linear least squares trend lines are depicted for each dataset. The Ab-hIL4R concentrations are indicated in the inset. Panel B depicts the buffer capacities of Ab-hIL4R as a function of concentration. The linear least squares trend line is shown for the dataset. The vertical axis indicates buffer capacity in microequivalents of base per ml of buffer solution per unit of pH (µEq/ml-pH). The concentration of Ab-hIL4R is indicated on the horizontal axis in mg/ml. The buffer capacities of several concentrations of standard sodium acetate buffers as described in Example 1 are shown by dashed horizontal lines. The acetate buffer concentrations are shown above each line. The results were obtained as described in Example 15.

FIG. 16 depicts titration curves and buffer capacities for several concentrations of self-buffering Ab-hIL4R formulations over the range of pH 5.0 to 6.0. Panel A shows the titration data, pH is indicated on the vertical axis. The amount of base added to the solutions is indicated on the horizontal axis in microequivalents of NaOH added per ml of buffer solution (µEq/ml). The linear least squares trend lines are depicted for each dataset. The Ab-hIL4R concentrations are indicated in the inset. Panel B depicts the buffer capacities of Ab-hIL4R as a function of concentration. The linear least squares trend line is shown for the dataset. The vertical axis indicates buffer capacity in microequivalents of base per ml of buffer solution per unit of pH (µEq/ml-pH). The concentration of Ab-hIL4R is indicated on the horizontal axis in mg/ml. The buffer capacities of several concentrations of standard sodium acetate buffers as described in Example 2 are shown by dashed horizontal lines. The acetate buffer concentrations are shown above each line. The results were obtained as described in Example 16.

FIG. 17 depicts Ab-hIL4R and pH stability in acetate buffered and self-buffered formulations of Ab-hIL4R at 37° C. as a function of time. Panel A is a bar graph showing Ab-hIL4R stability over four weeks at 37° C. The vertical axis indicates stability in percent monomeric Ab-hIL4R as determined by SE-HPLC. The horizontal axis indicates storage time in weeks. The insert identifies the data for the acetate and for the self-buffered formulations. Panel B shows the pH stability of the same formulations for the same conditions and time periods. The pH is indicated on the vertical axis. Storage time in weeks is indicated on the horizontal axis. Data for the acetate and self-buffered formulations are indicated in the inset. The data were obtained as described in Example 17.

FIGS. 18A-D are schematic diagrams depicting a sequences of an antibody to OPGL.

GLOSSARY

The meanings ascribed to various terms and phrases as used herein are illustratively explained below.

"A" or "an" herein means "at least one;" "one or more than one."

"About," unless otherwise stated explicitly wherein, means ∀ 20%. For instance about 100 herein means 80 to 120, about 5 means 4 to 6, about 0.3 means 0.24 to 0.36, and about 60% means 48% to 72% (not 40% to 80%).

"Agonist(s)" means herein a molecular entity that is different from a corresponding stimulatory ligand but has the same stimulatory effect. For instance (although agonists work through other mechanisms), for a hormone that stimulates an activity by binding to a corresponding hormone receptor, an agonist is a chemically different entity that binds the hormone receptor and stimulates its activity.

"Antagonist(s)" means herein a molecular entity that is different from a corresponding ligand and has an opposite effect. For instance (although antagonists work through other mechanisms), one type of antagonist of a hormone that stimulates an activity by binding to a corresponding hormone receptor is a chemical entity that is different from the hormone and binds the hormone receptor but does not stimulate the activity engendered by hormone binding, and by this action inhibits the effector activity of the hormone.

"Antibody(s)" is used herein in accordance with its ordinary meaning in the biochemical and biotechnological arts.

Among antibodies within the meaning of the term as it is used herein, are those isolated from biological sources, including monoclonal and polyclonal antibodies, antibodies made by recombinant DNA techniques (also referred to at times herein as recombinant antibodies), including those made by processes that involve activating an endogenous gene and those that involve expression of an exogenous expression construct, including antibodies made in cell culture and those made in transgenic plants and animals, and antibodies made by methods involving chemical synthesis, including peptide synthesis and semi-synthesis. Also within the scope of the term as it is used herein, except as otherwise explicitly set forth, are chimeric antibodies and hybrid antibodies, among others.

The prototypical antibody is a tetrameric glycoprotein comprised of two identical light chain-heavy chain dimers joined together by disulfide bonds. There are two types of vertebrate light chains, kappa and lambda. Each light chain is comprised of a constant region and a variable region. The two light chains are distinguished by constant region sequences. There are five types of vertebrate heavy chains: alpha, delta, epsilon, gamma, and mu. Each heavy chain is comprised of a variable region and three constant regions. The five heavy chain types define five classes of vertebrate antibodies (isotypes): IgA, IgD, IgE, IgG, and IgM. Each isotype is made up of, respectively, (a) two alpha, delta, epsilon, gamma, or mu heavy chains, and (b) two kappa or two lambda light chains. The heavy chains in each class associate with both types of light chains; but, the two light chains in a given molecule are both kappa or both lambda. IgD, IgE, and IgG generally occur as "free" heterotetrameric glycoproteins. IgA and IgM generally occur in complexes comprising several IgA or several IgM heterotetramers associated with a "J" chain polypeptide. Some vertebrate isotypes are classified into subclasses, distinguished from one another by differences in constant region sequences. There are four human IgG subclasses, IgG1, IgG2, IgG3, and IgG4, and two IgA subclasses, IgA1 and IgA2, for example. All of these and others not specifically described above are included in the meaning of the term "antibody(s)" as used herein.

The term "antibody(s)" further includes amino acid sequence variants of any of the foregoing as described further elsewhere herein.

"Antibody-derived" as used herein means any protein produced from an antibody, and any protein of a design based on an antibody. The term includes in its meaning proteins produced using all or part of an antibody, those comprising all or part of an antibody, and those designed in whole or in part on the basis of all or part of an antibody. "Antibody-derived" proteins include, but are not limited to, Fc, Fab, and Fab$_2$ fragments and proteins comprising the same, $V_H$ domain and $V_L$ domain fragments and proteins comprising the same, other proteins that comprise a variable and/or a constant region of an antibody, in whole or in part, scFv(s) intrabodies, maxibodies, minibodies, diabodies, amino acid sequence variants of the foregoing, and a variety of other such molecules, including but not limited to others described elsewhere herein.

"Antibody-related" as used herein means any protein or mimetic resembling in its structure, function, or design an antibody or any part of an antibody. Among "antibody-related" proteins as the term is used herein are "antibody-derived" proteins as described above. It is to be noted that the terms "antibody-derived" and "antibody-related" substantially overlap; both terms apply to many such proteins, Examples of "antibody-related" proteins, without implying limitation in this respect, are peptibodies and receptibodies. Other examples of "antibody-related" proteins are described elsewhere herein.

"Antibody polypeptide(s)" as used herein, except as otherwise noted, means a polypeptide that is part of an antibody, such as a light chain polypeptide, a heavy chain polypeptide and a 0.1 chain polypeptide, to mention a few examples, including among others fragments, derivatives, and variants thereof, and related polypeptides.

"Approximately" unless otherwise noted means the same as about.

"Binding moiety(s)" means a part of a molecule or a complex of molecules that binds specifically to part of another molecule or complex of molecules. The binding moiety may be the same or different from the part of the molecule or complex of molecules to which it binds. The binding moiety may be all of a molecule or complex of molecules as well.

"Binds specifically" is used herein in accordance with its ordinary meaning in the art and means, except as otherwise noted, that binding is stronger with certain specific moieties than it is to other moieties in general, that it is stronger than non-specific binding that may occur with a wide variety of moieties, and that binding is selective for certain moieties and does not occur to as strong an extent with others. In the extreme case of specific binding, very strong binding occurs with a single type of moiety, and there is no non-specific binding with any other moiety.

"Co-administer" means an administration of two or more agents in conjunction with one another, including simultaneous and/or sequential administration.

"Cognate(s)" herein means complementary, fitting together, matching, such as, for instance, two jigsaw puzzles that fit one another, the cylinder mechanism of a lock and the key that opens it, the substrate binding site of an enzyme and the substrate of the enzyme, and a target and target binding protein that binds specifically thereto.

"Cognate binding moieties" herein means binding moieties that bind specifically to one another. Typically, but not always, it means a pair of binding moieties that bind specifically to one another. The moieties responsible for highly selective binding of a specific ligand and ligand receptor provide an illustrative example of cognate binding moieties. Another example is provided by the moieties that binds an antigen and an antibody.

"Composition" means any composition of matter comprising one or more constituents, such as a formulation.

"Comprised of" is a synonym of "comprising" (see below).

"Comprising" means including, without further qualification, limitation, or exclusion as to what else may or may not be included. For example, "a composition comprising x and y" means any composition that contains x and y, no matter what else it may contain. Likewise, "a method comprising x" is any method in which x is carried out, no matter what else may occur.

"Concentration" is used herein in accordance with its well-known meaning in the art to mean the amount of an item in a given amount of a mixture containing the item, typically expressed as a ratio. For example, concentration of a solute, such as a protein in a solution, can be expressed in many ways, such as (but not limited to): (A) Weight Percent (i)=weight of solute per 100 units of solvent volume; (B) Weight Percent (ii)=weight of solute per 100 units of total weight; (C) Weight Percent (iii)=weight of solute per 100 units of solvent by weight; (D) Mass Percent=mass of solute per 100 mass units of solution; (E) Mole Fraction=moles of solute per total moles of all components; (F) Molarity moles of solute per liter of solution (i.e., solute plus solvent); (G) Molality=moles of solute per Kg of solvent; and (H) Volume Molality=moles of solute per liter of solvent.

"Control region(s)" is used herein in accordance with its well-known meaning in the art, and except as noted otherwise, refers to regions in DNA or proteins that are responsible for controlling one or more functions or activities thereof. For instance, "expression control region" with reference to the control of gene expression, means the regions in DNA that are required for transcription to occur properly and that are involved in regulating when transcription occurs, how efficiently it occurs, when it is stopped, and the like.

"De novo" is used herein in accordance with its well-known meaning in the art, to denote something made from new. For instance, a de novo amino acid sequence is one not derived from a naturally occurring amino acid sequence, although, such a de nova sequence may have similarities with a naturally occurring sequence. De novo amino acid sequences can be generated, for instance, by a priori design, by combinatorial methods, by selection methods. They can be made, for example, by chemical synthesis, by semi-synthesis, and by a variety of recombinant DNA techniques, all of which are well know to those skilled in the art.

"Deleterious" means, as used herein, harmful. By way of illustration, "deleterious" processes include, for example, harmful effects of disease processes and harmful side effects of treatments.

"Derivative(s)" is used herein to mean derived from, in substance, form, or design, such as, for instance, a polypeptide that is based on but differs from a reference polypeptide, for instance, by alterations to its amino acid sequence, by fusion to another polypeptide, or by covalent modification.

"Disease(s)" a pathology, a condition that deleteriously affects health of a subject.

"Disorder(s)" a malediction, a condition that deleteriously alters health.

"Dysfunction" means, as used herein, a disorder, disease, or deleterious effect of an otherwise normal process.

"Effective amount" generally means an amount which provides the desired local or systemic effect. For example, an effective amount is an amount sufficient to effectuate a beneficial or desired clinical result. The effective amount can be provided all at once in a single administration or in fractional amounts that provide the effective amount in several administrations. The precise determination of what would be considered an effective amount may be based on factors individual to each subject, including their size, age, injury, and/or disease or injury being treated, and amount of time since the injury occurred or the disease began. One skilled in the art will be able to determine the effective amount for a given subject based on these considerations which are routine in the art. As used herein, "effective dose" means the same as "effective amount."

"Effective route" generally means a route which provides for delivery of an agent to a desired compartment, system, or location. For example, an effective mute is one through which an agent can be administered to provide at the desired site of action an amount of the agent sufficient to effectuate a beneficial or desired clinical result.

"Endogenous" (such as endogenous gene) is used herein to refer to, for instance, genes and other aspects of DNA, such as control regions, that naturally occur in a genome and organism, unless otherwise indicated.

"Exogenous" (such as exogenous gene), unless otherwise indicated, is used herein generally to mean, for instance, DNA from an outside source, such as DNA introduced to a cell and incorporated into its genome.

"FBS" means fetal bovine serum.

"Formulation(s)" means a combination of at least one active ingredient with one or more other ingredients for one or more particular uses, such as storage, further processing, sale, and/or administration to a subject, such as, for example, administration to a subject of a specific agent in a specific amount, by a specific route, to treat a specific disease.

"Fragment(s)" herein means part of a larger entity, such as a part of a protein; for instance, a polypeptide consisting of less than the entire amino acid sequence of a larger polypeptide. As used herein, the term includes fragments formed by terminal deletion and fragments formed by internal deletion, including those in which two or more non-contiguous portions of a polypeptide are joined together to form a smaller polypeptide, which is a fragment of the original.

"Fusion protein(s)" herein means a protein formed by fusing all or part of two polypeptides, which may be either the same or different. Typical fusion proteins are made by recombinant DNA techniques, by end to end joining of nucleotides encoding the two (or more) polypeptides.

"Genetically engineered" herein means produced using a deliberate process of genetic alteration, such as by recombinant DNA technology, classical methods of genetic manipulation, chemical methods, a combination of all three, or other methods.

"Homolog(s)" herein means having homology to another entity, such as a protein that is homologous to another protein. Homologous means resembling in structure or in function.

"Ionization" herein means the change of net charge on a substance by at least one, including loss or gain of charge, such as the ionization of acetic acid in low pH solution, from HOAc to OAc$^-$ and H$^+$.

"k" herein denotes an equilibrium co-efficient, in accordance with its standard meaning in chemistry.

"$k_a$" herein denotes the dissociation constant of a particular hydrogen of a molecule, in accordance with its standard meaning in chemistry, such as, for example, the dissociation constant of the acidic hydrogen of acetic acid.

"$k_d$" herein denotes a dissociation constant of a pair of chemical entities (or moieties), in accordance with its standard meaning in chemistry.

"Kit" means a collection of items used together for a given purpose or purposes.

"Ligand(s)" herein means a molecular entity that binds selectively and stoichiometrically to one or more specific sites on one more other molecular entities. Binding typically is non-covalent, but can be covalent as well. A very few examples, among many others, are (a) antigens, which typically bind non-covalently to the binding sites on cognate antibodies; (h) hormones, which typically bind hormone receptors, non-covalently; (c) lectins, which bind specific sugars, non-covalently; (d) biotins, which bind multiple sites on avidin and other avidin-like proteins, non-covalently; (e) hormone antagonists, which bind hormone receptors and inhibit their activity and/or that of the corresponding hormone; and (f) hormone agonists, which similarly bind hormone receptors but stimulate their activity.

"Ligand-binding moiety(s)" herein means a molecular entity that binds a ligand, typically, a part of a larger molecular entity that binds the ligand, or a molecular entity derived therefrom.

"Ligand-binding protein(s)" herein means a protein that binds a ligand.

"Ligand moiety(s)" herein means a molecular entity that binds to a ligand-binding molecular entity in much the same way as does the corresponding ligand. A ligand moiety can be all of a ligand, or part of it, derived from a ligand, or generated de novo. Typically, however, the ligand moiety is more or less exclusively the aspect thereof that binds corresponding ligand-binding entities. The ligand moiety need not comprise, and the term generally does not denote, structural features other than those required for ligand binding.

"mEq" herein means milliequivalent(s).

"μEq" herein means microequivalent(s).

"Mimetic(s)" herein means a chemical entity with structural or functional characteristics of another, generally unrelated chemical entity. For instance, one kind of hormone mimetic is a non-peptide organic molecule that binds to the corresponding receptor in the same way as the corresponding hormone.

"mM" means millimolar; $10^{-3}$ moles per liter.

"Modified protein(s)," "modified polypeptide(s)," or "modified fragment(s)" herein means a protein or a polypeptide or a fragment of a protein or polypeptide comprising a chemical moiety (structure) other than those of the twenty naturally occurring amino acids that form naturally occurring proteins. Modifications most often are covalently attached, hut can also be attached non-covalently to a protein or other polypeptide, such as a fragment of a protein.

"Moiety(s)" herein means a molecular entity that embodies a specific structure and/or function, without extraneous components. For instance, in most cases, only a small part of a ligand-binding protein is responsible for ligand binding. This part of the protein, whether continuously encoded or discontinuously, is an example of a ligand-binding moiety.

"Naturally occurring" means occurs in nature, without human intervention.

"Non-naturally occurring" means does not occur in nature or, if it occurs in nature, is not in its naturally occurring state, environment, circumstances, or the like.

"PBS" means phosphate buffered saline.

"Peptibody" refers to a molecule comprising an antibody Fc domain (i.e., $C_H2$ and $C_H3$ antibody domains) that excludes antibody $C_H1$, $C_L$, $V_H$, and $V_L$ domains as well as Fab and F(ab)2, wherein the Fc domain is attached to one or more peptides, preferably a pharmacologically active peptide, particularly preferably a randomly generated pharmacologically active peptide. The production of peptibodies is generally described in PCT publication WO00/24782, published May 4, 2000, which is herein incorporated by reference in its entirety, particularly as to the structure, synthesis, properties, and uses of peptibodies.

"Peptide(s)" herein means the same as polypeptide; often, but not necessarily, it is used in reference to a relatively short polypeptide, "pH" is used in accordance with its well-known and universal definition as follows:

$$pH = -\log [H_3O^+].$$

"Pharmaceutical" as used herein means is acceptable for use in a human or non-human subject for the treatment thereof, particularly for use in humans, and approved therefor by a regulatory authority empowered to regulate the use thereof such as for example, the Food and Drug Administration in the United States, European Agency for the Evaluation of Medicinal Products, Japan's Ministry of Health, Labor and Welfare, or other regulatory agency such as those listed in R, Ng, DRUGS: FROM DISCOVERY TO APPROVAL, Wiley-Liss (Hoboken, N.J.) (2004), which is herein incorporated by reference in its entirety, particularly as to regulatory authorities concerned with drug approval, especially as listed in Chapter 7. As used herein the phrase "wherein the composition has been approved for pharmaceutical use by an authority legally empowered to grant such approval" means an entity or institution or the like, established by law and by law charged with the responsibility and power to regulate and approve the use of drugs for use in humans, and in some cases, in non-humans. Approval by any one such agency anywhere meets this qualification. It is not necessary for the approving agency to be that of the state in which, for instance, infringement is occurring. Example of such entities include the U.S. Food and Drug Administration and the other agencies listed herein above.

As used herein, "pharmaceutical" also may refer to a product produced in accordance with good manufacturing practices, such as those described in, among others, Chapter 9 and Chapter 10, of R. Ng, DRUGS: FROM DISCOVERY TO APPROVAL, Wiley-Liss (Hoboken, N.J.) (2004), which is herein incorporated by reference in its entirety, particularly in parts pertinent to good manufacturing practices for pharmaceutical protein formulations, in particular, as set forth in Chapters 9 and 10.

"Pharmaceutically acceptable" is used herein in accordance with its well-known meaning in the art to denote that which is acceptable for medical or veterinary use, preferably for medical use in humans, particularly approved for such use by the US Food and Drug Administration or other authority as described above regarding the meaning of "pharmaceutical,"

"Polypeptide(s)" see "Protein(s)."

"Precursor(s)" is used herein in accordance with its well-known meaning in the art to denote an entity from which another entity is derived. For instance, a precursor protein is a protein that undergoes processing, such as proteolytic cleavage or modification, thereby giving rise to another precursor protein (which will undergo further processing) or a mature protein.

"Protein(s)" herein means a polypeptide or a complex of polypeptides, in accordance with its well-known meaning in the art. As used herein, "protein(s)" includes both straight chain and branched polypeptides. It includes unmodified and modified polypeptides, including naturally occurring modifications and those that do not occur naturally. Such modifications include chemical modifications of the termini, the peptide backbone, and the amino acid side chains; amino acid substitutions, deletions and additions; and incorporation of unusual amino acids and other moieties, to name just a few such modifications. It also includes "engineered" polypeptides and complexes thereof, such as, but not limited to, any polypeptide or complex of polypeptides that has been deliberatively altered in its structure by, for instance, recombinant DNA techniques, chemical synthesis, and/or covalent modification, including deliberate alteration of amino acid sequence and/or posttranslational modifications.

"Protonation" means the addition of at least one hydrogen.

"Self-buffering" means the capacity of a substance, such as a pharmaceutical protein, to resist change in pH sufficient for a given application, in the absence of other buffers.

"Semi-de novo" herein means (a) partly designed in accordance with a particular reference and or produced from a precursor, and (b) partly designed without reference to a particular reference (such as designed solely by general principles and not based on any particular reference). For example, a polypeptide made by producing a first peptide in a bacterial expression system, producing a second peptide by chemical synthesis, and then joining the two peptides together to form the polypeptide.

"Semi-synthesis" means as used herein a combination of chemical and non-chemical methods of synthesis.

"Subject" means a vertebrate, such as a mammal, such as a human. Mammals include, but are not limited to, humans, farm animals, sport animals, and pets. Subjects in need of treatment by methods and/or compositions of the present invention include those suffering from a disorder, dysfunction, or disease, or a side effect thereof or from a side effect of a treatment thereof.

"Substantially" is used herein in accordance with its plain and ordinary definition to mean to a great extent or degree. For example, substantially complete means complete to a great extent, complete to a great degree. By way of further illustration, substantially free of residue means to a great extent free of residue, free of residue to a great degree. Should numerical accuracy be required, depending on context, "substantially," as used herein means, at least, 80% or more, particularly 90% or more, very particularly 95% or more.

"Therapeutically effective" is used herein in accordance with its well-known meaning in the art to denote that which achieves an improvement in the prognosis or condition of a subject or that otherwise achieves a therapeutic objective, including, for instance, a reduction in the rate of progress of a disease even if a subject's condition, nonetheless, continues to deteriorate.

"Therapeutically effective amount" generally is used to qualify the amount of an agent to encompass those amounts that achieve an improvement in disorder severity. For example, effective neoplastic therapeutic agents prolong the survivability of the subject, inhibit the rapidly-proliferating cell growth associated with the neoplasm, or effect a regression of the neoplasm, Treatments that are therapeutically effective within the meaning of the term as used herein, include treatments that improve a subject's quality of life even if they do not improve the disease outcome per se.

"Treat," "treating," or "treatment" are used broadly in relation to the invention and each such term encompasses, among others, preventing, ameliorating, inhibiting, or curing a deficiency, dysfunction, disease, or other deleterious process, including those that interfere with and/or result from a therapy.

"Variant(s)" herein means a naturally occurring or synthetic version of, for instance, a protein that is structurally different from the original but related, in structure and/or function, such as an allelic variant, a paralog, or a homolog of a protein.

DESCRIPTION OF THE INVENTION

The invention provides for the first time self-buffering protein formulations, particularly biopharmaceutical protein formulations, methods for making the formulations, and methods for using the formulations, among other things. Any protein that provides sufficient buffer capacity within the required pH range at a concentration suitable for its intended use can be prepared as a self-buffering protein formulation in accordance with the invention. The invention can be practiced with a variety of proteins, including both naturally-occurring proteins and "engineered" proteins, particularly biopharmaceutical proteins, as discussed further below.

The utility of proteins, particularly biopharmaceutical proteins, to be formulated in self-buffering compositions, particularly pharmaceutically acceptable compositions, has not been recognized prior to the invention herein disclosed. The influence of proteins in the regulation of physiological pH has been recognized and studied for some time. However, it has not heretofore been recognized that proteins, particularly biopharmaceutical proteins, can have enough buffer capacity to maintain a formulation within a desired pH range, without additional buffering agents.

Biopharmaceutical proteins for use in the United States are formulated as buffered solutions, unbuffered solutions, amorphous or crystalline suspensions, and lyophilates.

Most of the buffered solution formulations use a conventional buffering agent. Two proteins, Pulmozyme® and Humulin®, are formulated as solutions without conventional buffering agents, Neither of these proteins provides substantial self-buffering capacity in the formulations.

Pulmozyme® has a molecular weight of about 37,000 Daltons and contains 5 histidines, 22 aspartic acids, and 12 glutamic acids, among its 260 amino acids. The buffering capacity of the protein within 0.5 pH units of pH 6.3 is determined substantially by its histidine content. On this basis, the upper limit of the self-buffering capacity of the formulation is determined by the effective concentration of the histidine residues, 0.15 in M. The molar concentration of aspartic acid and glutamic acid in the formation is 0.9 mM. The total molar concentration of all three amino acids together, thus, is just a little over 1 mM, at the concentration of the formulation.

Humulin® is formulated at 3.5 g/ml. It has a molecular weight of about 6,000 Daltons and contains 2 aspartic acids, 8 glutamic acids, and 2 histidines. None of these amino acids is a particularly effective buffer at the pH of the formulation: 7.0 to 7.8. At this concentration the molar concentration of histidines, ich are closest in $pK_a$ to the pH of the formulation, is 1.16 mM.

The biopharmaceutical lyophilates are reconstituted prior to use forming solutions or suspensions. Most of the lyophilates contain conventional buffers that maintain the proper pH of the reconstituted formulations. A few others, in which the protein concentration is low or the pH must be low (less than 3) or high (greater than 9.5), are, effectively unbuffered.

Thus, buffering is achieved in current biopharmaceutical protein formulations using conventional buffering agents. The ability of proteins by themselves to buffer pharmaceutical protein formulations has not been fully appreciated and has not been used for the manufacture of protein pharmaceuticals.

The determination of protein buffer capacity, typically, is important to developing self-buffering protein formulations in accordance with the invention. Pertinent thereto, methods for measuring buffer capacity and thr determining the buffer capacity of proteins are described below. To allow ready comparability of data, protein buffer capacity must be expressed in comparable units and/or related to a buffer standard. Accordingly, the following section describes pH metrics and standards that meet these requirements, in accordance with the invention.

1. Buffering

A widely accepted definition of buffering is the resistance to change in pH of a composition upon addition of acid or base, Buffer capacity thus often is defined as the ability of a composition to resist pH change.

Typically buffer capacity is expressed in terms of the amount of strong acid or base required to change the pH of a composition a given amount, Van Slyke provided the most widely used quantitative measure of buffer capacity, according to which, for a solution, buffer capacity is expressed as the amount of strong acid or base required to change the pH of one liter of the solution by one pH unit under standard conditions of temperature and pressure.

According to this measure, for instance, the buffer capacity of 1 liter of 5 mM HOAc, 5 mM NaOAc, pH 4.76 in pure water is $4.09 \times 10^{-3}$ moles of a univalent strong base (i.e., $4.09 \times 10^{-3}$ equivalents of base), which can be calculated as follows.

The Henderson-Hasselbaleh equation for the solution is:

$$pH = \log\{[5\text{ mM}]NaOAc/[5\text{ mM}]HOAc\} + 4.76$$

Accordingly, the concentration, X, of a univalent strong base required to increase the pH of this buffer is:

$$4.76 \text{ to } 5.76 \text{ is } 5.76 = \log\{[5\text{ mM}+X\text{ mM}]NaOAc/[5\text{ mM}-X\text{ mM}]HOAc\} + 4.76$$

Thus:

$$1.00 = \log\{[5\text{ mM}+X\text{ mM}]NaOAc/[5\text{ mM}-X\text{ mM}]HOAc\}$$

$$10.0 = [5\text{ mM}+X\text{ mM}]NaOAc/[5\text{ mM}-X\text{ mM}]HOAc$$

$$10.0 = (5\text{ mM}+X\text{ mM})/(5\text{ mM}-X\text{ mM})$$

50 mM−10X mM=5 mM+X mM 11X mM=45 mM

X=4.09 in M, which, for one liter yields:

(4.09×10⁻³ moles/liter)(1 liter)(1 equivalent/mole)=
4.09×10⁻³ equivalents

Thus, according to this measure, the buffer capacity of 1 liter of a 10 mM acetate buffer containing 5 mM NaOAc and 5 mM HOAC at a pH of 4.76 in pure water is $4.09 \times 10^{-3}$ equivalents of base per liter per pH unit. Put other ways, the buffer capacity of the solution is 4.09 milliequivalents of base per liter per pH unit, 4.09 microequivalents of base per milliliter per pH unit, 0.409 microequivalents of base per 100 microliters per pH unit, 40.9 nanomoles of base per 10 microliters per pH unit, and 4.09 nanmoles of base per microliter per pH unit.

The same calculation yields the following buffer capacity thr other concentrations of this acetate buffer at pH 4.76, A 2 mM acetate buffer as above has a buffer capacity of 0.818 mEq per liter per pH unit. At 4 mM the buffer capacity is 1.636 mEq per liter per pH unit. The capacity at 5 mM is 2.045 mEq per liter per pH unit. At 7.5 mM the capacity is 3.068 mEq per liter per pH unit. At 10 mM the acetate buffer has a buffer capacity of 4.091 mEq per liter per pH unit. At 15 mM its capacity is 6.136 mEq per liter per pH unit.

It is worth noting that an acetate buffer solution at the $pK_a$ of acetic acid (pH 4.76) is equimolar in acetic acid and acetate base. (i.e., at the $pK_a$ the acid and base are present in equal amounts). As a result, the resistance to change in pH (buffer capacity) of an acetate buffer at the $pK_a$ of acetic acid is the same for addition of acid and base. The equipoise to acid and base is a general characteristic of buffering agents in buffers at a pH equal to their $pK_a$.

At any other pH a buffer will contain different amounts of acid and base forms and, therefore, its resistance to change (i.e., its buffer capacity) upon addition of acid will not be the same as its resistance to change upon addition of base. As a result, it is preferable to define the capacity of such buffers in terms of (i) the amount of acid required to lower the pH by one unit, and (ii) the amount of base required to raise the pH by one unit.

The partitioning in a buffer between acid and base forms in a given composition, such as a pH standard, can be calculated at any pH and buffer concentration using the procedures set forth above in describing the buffer capacity of 10 mM NaOAc at pH 4.76 plus or minus (containing equimolar amounts of acetic acid and sodium acetate). And the results can be used to define the buffer capacity of a standard for reference use.

Thus, for instance, the partitioning of acetic acid into acetic acid and acetate base in a solution at pH 5.0 can be calculated readily using the foregoing procedures, and from this the buffer capacity can be calculated for both base and for acid addition. Calculated this way, the theoretical buffer capacity of 10 mM sodium acetate buffer over the range from pH 5.0 to 5.5 is approximately 2.1 mM per 0.5 pH unit and 4.2 mM per pH unit. Put another way, the buffer capacity of the buffer, theoretically, is approximately 4.2 µEq per ml of buffer solution per unit of pH change. Similarly, the theoretical buffer capacity of 10 mM sodium acetate buffer over the range from pH 5.0 to 4.0 is 4.9 mM, and, put another way, 4.9 µEq per ml of buffer per unit of pH change over a given range of pH.

While such calculations often are quite useful in many cases, empirical standards and empirical determinations are preferred. Among particularly preferred empirical standards are sodium acetate buffers over the range of pH 5.0 to 4.0 and pH 5.0 to 5.5 as exemplified in Examples 1 and 2. Especially preferred are sodium acetate buffers in accordance therewith in which the total acetate concentration is, in particular, 10 mM, preferably 5 mM, especially 4 mM, among others as set forth elsewhere herein.

Acetate buffers at pH 5.0 are more resistant to change in pH upon addition of acid than upon addition of base, as discussed above. In a preferred empirical standard of buffer capacity, the buffer capacity of a standard acetate buffer such as these is defined as: (i) the slope of the least squares regression line calculated for base titration data for the buffer from pH 5.0 to pH 5.5, and (ii) the slope of the least squares regression line calculated for acid titration data for the buffer from pH 5.0 to pH 4.0. The preparation of standard acetate buffers and t determination of their buffer capacities are described in Examples 1, 2, and 3. It is to be appreciated that much the same methods can be used to establish and use buffer capacity standards using other suitable buffering agents.

In measuring the buffer capacity of a self-buffering protein composition in accordance with the invention, it often is convenient to express the buffer capacity in terms of the concentration of a standard buffer at the same pH having the same buffer capacity. When a standard is used that is not at the $pK_a$ of the buffering agent, such as a sodium acetate buffer initially at pH 5.0, in accordance with the invention the self-buffering composition is defined as having a buffer capacity equal to or greater than that of the standard, if either its buffer capacity upon base titration or its buffer capacity upon acid titration (or both) is equal to or exceeds the corresponding buffer capacity of the standard.

It is to be further appreciated that the pH of self-buffering protein compositions in accordance with the invention generally will not be at the $pK_a$ of the self-buffering protein, or any acid-base substituent therein. Indeed proteins are polyprotic and, as discussed herein, often will have several substituents, each with a somewhat different $pK_a$ that contribute to its buffer capacity in a given pH range. Accordingly, the buffer capacity of self-buffering protein formulations in accordance with the invention preferably is determined empirically by both acid titration and base titration over a given range of pH change from the desired pH of the composition. In preferred embodiments in this regard, the buffer capacity is determined by titrating with acid and separately with base over a change of respectively + and −1 pH unit from the starting of the formulation. In particularly preferred embodiments, the titration data is collected for a change in pH of plus or minus 0.5 pH units. As described in the Examples, the buffer capacity is the slope of the least squares regression line for the data for pH as a function of equivalents of acid or base added to the composition over the range of titration.

a. Empirical Measures and Standards of Buffer Capacity

In certain preferred embodiments of the invention, the measure of buffer capacity is an empirical standard. Among preferred empirical standards in this regard are a particular volume of an aqueous solution at a particular temperature and a particular pH, containing a particular buffering agent at a particular concentration and either no other components than water, or one or more other particular components, each at a particular concentration.

A particularly preferred specific standard for determining buffer capacity in accordance with various aspects and preferred embodiments of the invention is 10 mM sodium acetate pH 5.00 in pure water free of other constituents at 21° C. in equilibrium with ambient air at 1 atmosphere, as described in Examples 1 and 2, preferably expressed in equivalents per unit volume per pH unit, such as µEq/ml-pH. Buffer capacity of the standard should be measured empirically as described in Examples 1, 2, and 3, and as further discussed elsewhere herein.

A particularly preferred specific standard thr determining buffer capacity in accordance with various aspects and preferred embodiments of the invention is 10 mM sodium acetate pH 4.76 in pure water free of other constituents at 21° C. in equilibrium with ambient air at 1 atmosphere, as described in Examples 1 and 2, preferably expressed in equivalents per unit volume per pH unit, such as µEq/ml-pH. Buffer capacity of the standard should be measured empirically as described in Examples 1, 2, and 3, and as further discussed elsewhere herein. According to the Henderson-Hasselbalch equation, as noted above, the calculated buffer capacity of this standard over the range of pH 4.76 plus or minus 1 pH unit is 4.09 microequivalents per milliliter per pH unit (4.09 µEq/ml-pH).

A variety of other buffers are available for use as standards in other ranges of pH in accordance with various aspects and preferred embodiments of the invention in this regard. Reference buffers are particularly preferred in this regard, such as those well-known and routinely employed for analytical chemistry determinations. A variety of such buffering agents are set forth in textbooks on analytical chemistry and in monographs on the accurate determination of pH and buffer capacity.

Also useful in the invention in this regard are biological buffers, such as those described in, among other texts: TEITZ TEXTBOOK OF CLINICAL CHEMISTRY, $3^{rd}$ Ed., Burtis and Ashwood, eds., W.B. Saunders Company, Philadelphia, Pa. (1999), in particular in Tables 50-13 to 50-16, which are herein incorporated by reference in their entireties as to buffering agents and buffers and their use as pH and/or buffer capacity standards in accordance with the invention in this respect; THE TOOLS OF BIOCHEMISTRY, Terrance G. Cooper, John Wiley & Sons, New York, N.Y. (1977), in particular Chapter 1, pages 1-35, which is herein incorporated by reference in its entirety as to buffering agents and buffers and their use as pH and buffer capacity standards in accordance with the invention in this respect, most particularly as to Tables 1-3, 1-4, and 1-5 and text relating thereto, and PROTEIN PURIFICATION PRINCIPLES AND PRACTICE, $3^{rd}$ Ed., Robert K. Scopes, Springer-Verlag, New York, N.Y. (1994), in particular pages 160-164, especially therein Tables 6.4 and 6.5 and text relating thereto, Chapter 12, section 3, pages 324-333, especially therein Tables 12-4 and 12-5 and text relating thereto, and all of Appendix C: Buffers for Use in Protein Chemistry, which are herein incorporated by reference in their entirety as to buffering agents and buffers and their use in accordance with the invention in this respect.

Since some dissolved gases in water react with $OH^-$ and/or $H_3O^+$, however, the empirically determined buffer capacity of the standard solution may vary somewhat from the theoretical value. Hence, the definition of the standard requires that the solution be in equilibrium with the atmosphere at a pressure of 1 atmosphere. In addition, the buffer standard must be held in and contacted only with materials that do not alter its components or its buffer capacity, such as those that leach acids, bases, or other reactants that may alter the effective concentration or activity of the acetate buffer in any way that would alter its buffer capacity. Given both of the foregoing, atmospheric equilibration and inertness of the container, buffer capacity of the standard will scale directly and linearly with its volume. Accordingly, the buffer capacity of 100 ml will be 1/10 that of 1.00 liter, and the buffer capacity of 10 ml will be 1/100 that of 1.00 liter. Accordingly, the volume of the standard can be adjusted for convenience and then normalized back to 1 liter as desired.

It may not always be convenient to make the foregoing 10 mM acetate buffer capacity standard for field use. However, a variety of other buffer capacity standards can be made and used in the same way as the acetate buffer, using a variety of other buffering agents. Provided only that the buffering standards are prepared properly, they can be calibrated against the acetate buffering standard described above and then used in the field. The results obtained with such alternative standards may then be expressed in terms of the foregoing acetate standard without substantial distortion or error.

The buffer capacity of such alternative standards also can be calibrated by calculation. To do so, the buffer capacity of the alternative standard is determined directly and expressed in mEq per unit volume per unit of pH. Determinations based on the alternative standard then can be normalized to the acetate standard using the ratio between the buffering capacities expressed in mEq per unit volume per unit of pH of the alternative and the acetate standards.

Using such methods, which are commonly employed in metrology to relate field standards back to a reference standard, the acetate buffer standard described above provides a portable, scalable, reliable, and accurate reference for determining the buffer capacity of any composition that readily can be compared with disparate measures made on other compositions using similar methods.

b. Preparation of Buffer Capacity Standards

Buffer capacity standards can be prepared using well-established methods of analytical chemistry. See for instance, ANALYTICAL CHEMISTRY, $3^{rd}$ Ed., Douglas A. Skoog and Donald M. West, Holt, Rinehart and Winston, New York (1979), particularly chapter 9 (pages 186-226), chapter 10 (pages 227-233), and methods described on pages 583-588; TEITZ TEXTBOOK OF CLINICAL CHEMISTRY, $3^{rd}$ Ed., Burtis and Ashwood, eds., W.B. Saunders Company, Philadelphia, Pa. (1999), in particular Chapter 1 regarding general laboratory techniques for preparing and calibrating buffers and Tables 50-13 to 50-16; THE TOOLS OF BIOCHEMISTRY, Terrance G. Cooper, John Wiley & Sons, New York, N.Y. (1977), in particular Chapter 1, pages 1-35, and Tables 1-3, 1-4, and 1-5 and text relating thereto; PROTEIN PURIFICATION PRINCIPLES AND PRACTICE, $3^{rd}$ Ed., Robert K. Scopes, Springer-Verlag, New York, N.Y. (1994), in particular pages 160-164, especially therein Tables 6.4 and 6.5 and text relating thereto, Chapter 12, section 3, pages 324-333, especially therein Tables 12-4 and 12-5 and text relating thereto, and all of Appendix C: Buffers for Use in Protein Chemistry; and REMINGTON; THE SCIENCE AND PRACTICE OF PHARMACY, $21^{st}$ Ed., Beringer et al. Editors, Lippincott, Williams & Wilkins, Philadelphia, Pa. (2005), particularly in parts relating to buffering agents, buffers, buffer capacity and the like; each of which is herein incorporated by reference in its entirety particularly as to the preparation and use of buffers and buffer capacity standards in accordance with the invention in this respect.

The water used for preparing buffer capacity standards should be highly purified, preferably Type I water, such as milliQ water, or triple distilled water. The buffer reagents should be pure and, in particular, free of any substance that can alter the pH or buffer capacity of the standard solution, such as Reference Grade or ACS Reagent Grade reagents suitable for use in demanding analytic chemical analyses, as described in the foregoing references, TEITZ and REMINGTON cited above in particular, which are hereby incorporated by reference in their entireties particularly in parts pertinent to analytical grade water and reagents.

The exact compositions of the buffer reagents must be well established. The molecular weight of the buffer reagents must be known accurately for each buffer reagent. The molecular weights must be for the exact reagent that will be used and must include the weight of adducts such as hydrates that are present in the reagent. The effective number of hydrogen donors or hydrogen acceptors per molecule must be known accurately for each buffer reagent. The proportional distribution of different forms, such as hydrates, must be known for each reagent that contains a mixture of such forms, Concentrations of liquid buffer reagents much be known exactly, preferably in moles/volume and in molts/mass (e.g., moles/liter and moles/gm or kg. Hygroscopic agents must be dried to remove moisture so that reagent can be accurately weighed.

Generally speaking, the information provided by well-established vendors of reagents and reference grade chemicals is sufficiently accurate for the preparation of buffer capacity standards as described, above. And, well-known standard, techniques routinely employed in analytical chemistry can be used to dry "hygroscopic reagents" so that they can be weighed accurately.

As described therein, well established and routinely employed, analytical chemistry methods can be employed to prepare and calibrate acid and base solutions, such as 1 N HCl and 1 N NaOH (to name just two) for titrating buffer capacity standard solutions, as well as sample protein solutions, to determine buffer capacity. It should be noted that the preparation of NaOH solutions for titration should be done so as to eliminate inaccuracies that arise from the interaction of certain dissolved gases with basic solutions, and the pH altering effects of their solvation. See for instance Skoog and West (1979) and other references cited above regarding the preparation and calibration of buffers and buffer standards, which are herein incorporated by reference in their entireties particularly in parts pertinent to the preparation of standard solutions for titration, as discussed above.

c. Empirical Measurement of Buffer Capacity

Titration of standards and samples to determine buffer capacity can be done using well-known, routine methods. Titrations can be carried out manually. They also can be carried, out using: an autotitrator. A wide variety of autotitrators that are suitable for use in the invention in this regard are commercially available from numerous vendors. Methods suitable for use in the invention in this regard are the same as those described in the references cited above regarding preparation and calibration of buffer standards, each of which is incorporated herein by reference in its entirety particularly in parts pertinent to the titration of known and unknown solutions to determine their buffer capacity.

2. Buffering by Proteins and Protein Buffer Capacity a. Determination of Protein Hydrogen Equilibria and Buffer Capacity Proteins invariably contain many acidic and basic constituents. As a result hydrogen ion equilibrium of proteins is highly complex. In fact, a complete description of the hydrogen ion equilibria of a protein in a given environment is beyond the reach of current theoretical and computational methods. Empirical measurements of protein buffer capacities, thus are preferred. Methods developed thr precise empirical measurement of protein hydrogen equilibria, which can be and are routinely employed by those skilled in the art, are well-suited to measuring the buffering properties of proteins pertinent to the development of self-buffering protein formulations in accordance with the invention. Thus, the pH titration curves of proteins can be determined in accordance with the invention by well-known methods such as those described in and exemplified by pH titration studies of Tanford and co-workers on ribonuclease. See C. Tanford, "Hydrogen Ion Titration Curves of Proteins," in T. Shedlovsky (ed.), ELECTROCHEMISTRY IN BIOLOGY AND MEDICINE, John Wiley and Sons, New York, 1955, Ch. 13; C. Tanford and J. D. Hauenstein, *J. Am. Chem. Soc.* 78, 5287 (1956), C. Tanford, PHYSICAL CHEMISTRY OF MACROMOLECULES, John Wiley and Sons, New York, 1961, particularly pages 554-567, all of which are herein incorporated by reference particularly in parts pertinent to hydrogen ion titration of proteins and to the determination of buffering action and buffer capacity of proteins.

However, the present invention does not require such precise determinations as those described in the foregoing references. Rather, the buffering properties and buffer capacity of proteins in accordance with the invention can be determined using the methods described in standard references on analytical chemistry and biochemistry, such as, for instance, Skoog (1979), Cooper (1977), and Scopes (1994), cited above, each of which is herein incorporated by reference in its entirety particularly as to the empirical determination of titration curves, particularly of proteins within a given range of pH in accordance with the invention.

The determination of titration curves and buffer capacity in accordance with the invention is described in detail for numerous acetate buffers and a variety of pharmaceutical proteins in the Examples below. Thus, the pH titration curves of proteins can be determined empirically in accordance with such methods as described in the foregoing references over particular limited ranges of pH that are of interest to a given formulation. In many respects these methods are the same as those used in analytical chemistry for the titration of small molecules such as acetate buffers (as illustrated in the Examples). Somewhat greater care must be taken, however, in handling proteins to maintain the conformation and function required for effective formulation.

Protein titrations may be carried out manually or using automated titrators. Equipment for manual titration and automated titrators are readily available from a large number of suppliers and vendors. Methods suitable for determining pH titration curves and buffer capacity of proteins are exemplified in the Examples by reference to titration of acetate buffer standards and to titration of several different therapeutic proteins over defined ranges of pH. These methods can be employed to determine the hydrogen ionization behavior and buffer capacity of any other protein in accordance with the invention.

It is a particular aspect of the invention to determine the buffer capacity of proteins as a function of concentration in solution. In a preferred method in this regard, solutions of a given protein are prepared in a graded series of concentrations. A pH titration curve is determined for the protein at each concentration over the pH range of interest. Preferably titration curves are determined for the range of interest using both base titration and acid titration. The data are, in certain preferred embodiments, plotted on a graph of equivalents of acid or base added versus the measured pH of each solution. Typically, for ranges of about 0.5 to 1.0 pH unit, the titration data for each concentration closely fit a straight line, preferably determined by a least squares regression analysis. In preferred embodiments in this regard, buffer capacity for the protein at each concentration is equated to the slope of the regression line, expressed in units of equivalents per ml per pH unit (or fractions thereof). Also useful in the invention in this regard is the relationship between the buffer capacity of the protein and its concentration. In certain preferred embodiments, this relationship is determined by a least squares regression analysis of the best straight line fit of the buffer capacity data determined in accordance with the foregoing plotted on a graph of buffer capacity versus protein concentration.

Empirical data on the buffer capacity of proteins in accordance with the invention preferably is related to the buffer capacity of a standard acetate buffer. That is, in particularly preferred embodiments of the invention in this regard, the buffer capacity of a given protein at a given concentration in a given formulation, determined as above, is equated to the concentration of a standard acetate buffer having the same buffer capacity.

While empirical determinations as described herein are generally crucial aspect of formulating self-buffering compositions in accordance with various aspects and preferred embodiments of the invention, theoretical and computational methods also can be productively employed to guide the design, manufacture, and use of such compositions in conjunction with empirical determinations), as described below.

b. Prediction of Protein Hydrogen Ion Equilibria and Buffer Capacity

The ionization of hydrogen in proteins is complex but can be broken down in general terms into pH ranges defined by the ionizable hydrogens of amino acid side chains, and the terminal amino and carboxyl groups. The $pK_a$ of terminal carboxyls in polypeptides typically ranges around 3.1. The $pK_a$ of the acidic hydrogens in the side chains of aspartic acid and glutamic acid range around 4.4. The $pK_a$ of histidine in polypeptides ranges around 6.0. The terminal amino group hydrogen ionization $pK_a$ typically ranges around 7.5. The sulfhydryl in cysteine has a $pK_a$ range around 8.5. The tyrosine hydroxyl and the lysine amine both have $pK_a$s ranging around 10. The $pK_a$ of arginine ranges around 12.

Conformational folding typically partitions large polypeptides and proteins in polar solvents into exposed solvent-accessible regions and more or less non-polar core regions that have little or no contact with the ambient environment. Folding produces many environments between these two extremes. Furthermore, the micro environment around a given amino acid side chain in a protein typically is affected by one or more of: solvent effects; binding of ions; chelation; complexation; association with co-factors; and post-translational modifications; to name just a few possibilities. Each of these can influence the $pK_a$ of a given amino acid ionization in a protein. The $pK_a$s for specific residues in a given protein, thus, can vary dramatically from that of a free amino acid.

Indeed, the perturbation of $pK_a$s by microenvironments of amino acids in proteins has been used to study the folding of proteins and the disposition and charge state of specific amino acids in folded proteins. The protein titration curves reported by Tanford and others are complex with a few broad features in common. Typically only some of the ionizable protons are accounted for in the titration curves. Others apparently are located in the core and are inaccessible to solvent. The $pK_a$s of individual side chains of the same type that can be detected in some cases can be distinguished from one another. Nonetheless, while detectably different, their $pK_a$s generally are close to that of the free amino acid.

The strongest buffering action of proteins does not generally occur at the isoelectric point, as may be mistakenly supposed. In fact, buffering depends on the amino acid side chain hydrogens and the terminal hydrogens, and therefore occurs in ranges spanning the $pK_a$s of the ionizable hydrogens in the free amino acids, as discussed above. The most important of these, for formulating compositions of proteins, especially certain pharmaceutical proteins that are more soluble and/or more stable, among other things, at weakly acidic pH (pH 4 to 6), is buffering action that occurs in the range of the $pK_a$s of the carboxyl hydrogen of the amino acids aspartic acid and glutamic acid; that is, pH 4.0 to 5.5, particularly around 4.5.

There are a variety of ways available for estimating the buffer capacity of a given protein in a given solution at a given pH. Methods range from highly technical and complex computer models to those that can be carried out on a hand calculator. None of the methods is complete or entirely accurate; but, they can in some instances provide useful estimates.

For instance, a potentially useful idea of buffer capacity in some instances may be calculated for a protein in a solution based on its amino acid composition, the $pK_a$s (in the solvent in question) of the terminal amine and carboxy groups and the amino acid side hydrogen donors and acceptors, the concentration of the protein, and the pH of the solution.

For example, a potentially useful estimate of the buffer capacity of a protein at pH in the range of the $pK_a$ of the side chain carboxyl hydrogen of glutamic acid (as a free amino acid), can be gained from the molecular weight of the protein and the number of glutamic acid residues it contains. Dividing the former by the latter provides the weight per equivalent of glutamic acid and, therefore, the weight per equivalent of ionizable hydrogen at the $pK_a$ of glutamic acid. Since glutamic acid and aspartic acid side chain carboxyl groups have nearly the same $pK_a$s, results of such calculations for the two should be added together to yield an estimate of buffer capacity in a range around both their $pK_a$s. The estimated buffer capacity of a solution of the protein at the $pK_a$ can be calculated from the protein's concentration in the solution and the intrinsic factor just provided, namely weight per equivalent of ionizable hydrogen. Dividing the concentration by the weight per equivalent yields an estimate for the buffer capacity in units of Eq/volume. Such estimates often will be too high, since some residues usually are sequestered in regions of the protein not accessible to the solvent, and, therefore, do not contribute to its actual buffer capacity. It may be possible in certain instances to account for the effect of sequestering on buffer capacity. For instance, a fractional co-efficient that reflects theoretical or empirical estimates of sequestering can be applied to adjust the original calculation.

Such calculations generally will be of less utility and less accurate than empirical determinations of protein buffer capacity, in accordance with the methods described elsewhere herein, But they can be useful to provide rough maximum estimates of the buffer capacity of proteins in solution.

3. Proteins

The invention herein disclosed may be practiced with any protein that provides sufficient buffer capacity in a desired pH range within the parameters of protein concentration and the like required for a desired formulation. Among preferred proteins in this regard are pharmaceutical proteins for veterinary and/or human therapeutic use, particularly proteins for human therapeutic use. Also among preferred proteins are proteins that are soluble in aqueous solutions, particularly those that are soluble at relatively high concentrations and those that are stable for long periods of time. Additionally, among preferred proteins are those that have a relatively high number of solvent accessible amino acids with side chain hydrogen ionization constants near the pH of the desired buffering action.

Further among preferred proteins of the invention are proteins for pharmaceutical formulations that do not induce a highly deleterious antigenic response following administration to a subject. Preferred in this regard are proteins for veterinary and/or human medical use, particularly, regarding the latter, humanized and human proteins.

Further among preferred proteins of the invention are proteins that bind selectively to specific targets, including ligand-binding proteins and protein ligands. Antigen-binding proteins, proteins derived therefrom, and proteins related thereto are among the particularly preferred embodiments of the invention in this regard. Highly preferred proteins of the invention in this regard are antibodies and proteins derived from antibodies or incorporating antibodies, in whole or part, including, to name just a few such entities: monoclonal antibodies, polyclonal antibodies, genetically engineered antibodies, hybrid antibodies, hi-specific antibodies, single chain antibodies, genetically altered antibodies, including antibodies with one or more amino acid substitutions, additions, and/or deletions (antibody muteins), chimeric antibodies, antibody derivatives, antibody fragments, which may be from any of the foregoing and also may be similarly engineered or modified derivatives thereof, fusion proteins comprising an antibody or a moiety derived from an antibody or from an antibody fragment, which may be any of the foregoing or a modification or derivative thereof, conjugates comprising an antibody or a moiety derived from an antibody, including any of the foregoing, or modifications or derivatives thereof, and chemically modified antibodies, antibody fragments, antibody fusion proteins, and the like, including all of the foregoing.

a. Antibodies, Antibody-Derived, and Antibody-Related Proteins and the Like

Among particularly preferred proteins in accordance with the invention are antibody polypeptides, such as heavy and light chain polypeptides that have the same amino acid sequence as those that occur in and make up naturally-occurring antibodies, such as those that occur in sera and antisera, including such polypeptides and proteins isolated from natural sources, as well as those that are made by hybridoma technologies, by activation of an endogenous gene by homologous or non-homologous recombination, for instance), by expression of an exogenous gene under the control of an endogenous transcription control region, by expression of an exogenous expression construct, by semi-synthesis and by de novo synthesis, to name some techniques commonly employed for making antibodies and antibody-related polypeptides and proteins that can be used to produce antibody polypeptides and proteins in accordance with the invention.

Included among these antibody-related polypeptides and proteins are those in whole or part having a de novo amino acid sequence, those that comprise all or one or more parts of an antibody (that is: a continuous chain of amino acids having the same sequence as any four or more residues in the amino acid sequence of a naturally occurring antibody polypeptide), those having an amino acid sequence that matches in some way that of a naturally occurring antibody, but differs from it in other ways, those that have the same but different amino acid sequences as a naturally occurring counterpart or sequence relating thereto, but differ from the counterpart in one or more post-translational modifications, and those comprised in part of any of the foregoing (in part or in whole) fused to one or more polypeptide regions that can be of or derived from or related to a second, different antibody polypeptide, and can be of or derived from any other polypeptide or protein, whether naturally occurring, resembling but differing therefrom, having a semi-de novo amino acid sequence and/or a de novo sequence, among others. Such hybrids are generally referred to herein as fusion polypeptides and/or fusion proteins.

Further among preferred proteins in accordance with the invention herein described are modified proteins in accordance with all of the foregoing. Included among such modified proteins are proteins modified chemically by a non-covalent bond, covalent bond, or both a covalent and non-covalent bond. Also included are all of the foregoing further comprising one or more post-translational modifications which may be made by cellular modification systems or modifications introduced ex vivo by enzymatic and/or chemical methods, or introduced in other ways.

Among preferred proteins of the invention in this regard are Fab fragment(s), such as those produced by cleaving a typical dimeric $(LH)_7$ antibody with certain protease that leave the light chain intact while cleaving the heavy chains between the variable region and the adjacent constant region, "above" the disulfide bonds that hold the heavy chains together. Such cleavage releases one Fc fragment comprising the remaining portions of the heavy chains linked together, and two dimeric Fab fragments each comprising an intact light chain and the variable region of the heavy chain. Fab fragments also can be produced by other techniques that do not require isolation of a naturally occurring antibody and/or cleavage with a protease.

Also preferred are $Fab_2$ fragment(s) such as those produced in much the same manner as Fab fragments using a protease that cleaves "between or below" the disulfide bonds. As a result, the two Fab fragments are held together by disulfide bonds and released as a single $Fab_2$ fragment. $Fab_2$ fragments can be produced by many other techniques including those that do not require isolation of an intact antibody or cleavage with a protease having the required specificity. Furthermore, both mono- and bi-specific $Fab_2$ fragments can now be made by a variety of routine techniques.

Also among preferred proteins in this regard are $Fab_3$ fragments, which are engineered antibody fragments in which three Fab fragments are linked together. $Fab_3$ fragments can be mono-, bi-, or tri-specific. They can be made in a variety of ways well-known to those of skill in the pertinent arts.

Among other preferred proteins in this regard are Fc fragments(s), such as those produced by cleavage with a protease in the same manner used for the production of either Fab fragments or $Fab_2$ fragments. However, for the production of Fc fragments, the dimeric heavy chain containing fragments are isolated rather than the light chain containing fragments. Fc fragments lack antigen combining sites, but comprise effector regions that play a role in physiological processes involving antibodies, Fc fragments can be made by a variety of techniques that are well-known and routinely employed by those of skill in the art for this purpose.

Among other preferred proteins in this regard are single-chain variable fragments ("scFv(s)"), scFv(s) are fusion proteins made by joining the variable regions of the heavy and light chains of an immunoglobulin. The heavy and light chains in an scFv typically are joined by a short serine, glycine linker. scFv(s) have the same specificity as the antibodies from which they were derived. Originally produced through phage display, scFv(s) now can be made by a variety of well-known methods.

Also preferred are Bis-scFv(s) which are fusions of two scFv(s). Bis-scFv(s) can be mono- or bi-specific. A variety of methods are well-known and can be applied in making Bis-say(s) in accordance with the invention.

Also preferred in accordance with the invention in this regard are minibodies; mono- and bi-specific diabodies; mono-, hi-, and tri-specific triabodies; mono-, bi-, tri-, and tetra-specific tetrabodies; VhH domains; V-NAR domains; $V_H$ domains; $V_L$ domains; camel Igs; Ig NARs; and others.

Also among preferred embodiments in accordance with various aspects and preferred embodiments of the invention in these and other regards are proteins comprising one or more CDR and/or CDR-derived and/or CDR-related regions of an antibody or one or more FR and/or FR-derived and/or FR-related regions of an antibody. In this regard CDR means complementary determining region; that is, a hypervariable region of a light or heavy chain of an antibody, typically about 9 to 12 amino acids in length that usually is an important part of an antigen specific binding moiety of an antibody. FR in this regard means a framework region of an antibody; that is, a region of about 15 to 20 amino acids that separates CDRs in the antigen specific binding moiety of an antibody. The terms CDR-derived and CDR-related, and the terms FR-derived and FR-related have the same meanings as to CDR and FR, respectively, as set forth in the above Glossary for the terms antibody-derived and antibody-related as to the term antibody.

Regarding antibodies, antibody-derived, and antibody-related proteins in accordance with the foregoing and with other aspects of the invention herein disclosed, see, for instance, *Protein Engineering: Principles and Practice*, Jeffrey L, Cleland and Chares S. Craik, eds. Wiley-Liss, Inc., New York (1996), particularly therein Kelley, Robert F., "Engineering Therapeutic Antibodies." Chapter 15, pp. 399-434 and Hollinger, P. & Hudson, P., "Engineered antibody fragments and the rise of single domains," *Nature Biotechnology*, September 2005, 1126-1136, each of which is herein incorporated by reference in its entirety particularly in parts pertinent to the structure and engineering of antibodies, particularly biopharmaceutical antibodies, and antibody-derived and antibody-related proteins, particularly antibody-derived and antibody-related pharmaceutical proteins in accordance with the invention herein described.

As to all of the foregoing, particularly preferred in the invention are human, humanized, and other proteins that do not engender a significantly deleterious immune responses when administered to a human. Also preferred in the invention are proteins in accordance with all the foregoing that similarly do not cause a significantly deleterious immune responses on administration to non-humans.

Among very particularly preferred proteins in accordance with the invention in these regards are fusion proteins comprising antibodies and/or antibody-derived proteins, polypeptides, or fragments or the like, including all of those described above. Among very particularly preferred fusion proteins of the invention in this regard are fusion proteins comprising an antibody or antibody-derived protein or fragment such as those described above and a ligand-binding moiety, such as those illustratively described herein.

b. Target Binding Proteins

Also among preferred proteins of the invention in this regard are antibodies and other types of target binding proteins, and proteins relating thereto or derived therefrom, and protein ligands, and proteins derived therefrom or relating thereto. Among especially preferred ligand-binding proteins in this regard are proteins that bind signal and effector proteins, and proteins relating thereto or derived therefrom.

Among such binding proteins, including antibodies, including proteins derived therefrom and proteins related thereto, are those that bind to one or more of the following, alone or in any combination:

(i) CD proteins including but not limited to CD3, CD4, CD8, CD19, CD20, and CD34;
(ii) HER receptor family proteins, including, for instance, HER2, HER3, HER4, and the EGF receptor;
(iii) cell adhesion molecules, for example, LEA-1, Mol, p150,95, VLA-4, ICAM-1, VCAM, and alpha v/beta 3 integrin;
(iv) growth factors, including but not limited to, for example, vascular endothelial growth factor ("VEGF"); growth hormone, thyroid stimulating hormone, follicle stimulating hormone, luteinizing hormone, growth hormone releasing factor, parathyroid hormone, mullerian-inhibiting substance, human macrophage inflammatory protein (MIP-1-alpha), erythropoietin (EPO), nerve growth factor, such as NGF-beta, platelet-derived growth factor (PDGF), fibroblast growth factors, including, for instance, aFGF and bFGF, epidermal growth factor (EGF), transforming growth factors (TGF), including, among others, TGF-alpha and TGF-beta, including TGF-beta1, TGF-beta2, TGF-beta3, TGF-beta4, or TGF-beta5, insulin-like growth factors-I and -II (IGF-I and IGF-II), des(1-3)-IGF-I (brain IGF-I), and osteoinductive factors;
(v) insulins and insulin-related proteins, including but not limited to insulin, insulin A-chain, insulin B-chain, proinsulin, and insulin-like growth factor binding proteins;
(vi) coagulation and coagulation-related proteins, such as, among others, factor VIII, tissue factor, von Willebrands factor, protein C, alpha-1-antitrypsin, plasminogen activators, such as urokinase and tissue plasminogen activator ("t-PA"), bombazine, thrombin, and thrombopoietin;
(vii) colony stimulating factors (CSFs), including the following, among others, M-CSF, GM-CSF, and G-CSF;
(viii) other blood and serum proteins, including but not limited to albumin, IgE, and blood group antigens;
(ix) receptors and receptor-associated proteins, including, for example, flk2/flt3 receptor, obesity (OB) receptor, growth hormone receptors, and T-cell receptors;
(x) neurotrophic factors, including but not limited to, bone-derived neurotrophic factor (BDNF) and neurotrophin-3, -4, -5, or -6 (NT-3, NT-4, NT-5, or NT-6);
(xi) relaxin A-chain, relaxin B-chain, and prorelaxin;
(xii) interferons, including for example, interferon-alpha, -beta, and -gamma;
(xiii) interleukins (Ws), e.g., IL-1 to IL-10;
(xiiv) viral antigens, including but not limited to, an AIDS envelope viral antigen;
(xv) lipoproteins, calcitonin, glucagon, atrial natriuretic factor, lung surfactant, tumor necrosis factor-alpha and -beta, enkephalinase, RANTES (regulated on activation normally T-cell expressed and secreted), mouse gonadotropin-associated peptide, Dnase, inhibin, and activin;

(xvi) integin, protein A or D, rheumatoid factors, immunotoxins, bone morphogenetic protein (BMP), superoxide dismutase, surface membrane proteins, decay accelerating factor (DAF), AIDS envelope, transport proteins, homing receptors, addressins, regulatory proteins, immunoadhesins, antibodies; and (xvii) biologically active fragments or variants of any of the foregoing.

As to all of the foregoing, particularly preferred are those that are effective therapeutic agents, particularly those that exert a therapeutic effect by binding a target, particularly a target among those listed above, including targets derived therefrom, targets related thereto, and modifications thereof.

c. Particular Illustrative Proteins

Among particular illustrative proteins are certain antibody and antibody-related proteins, including peptibodies, such as, for instance, those listed immediately below and elsewhere herein:

OPGL specific antibodies and peptibodies and the like (also referred to as RANKL specific antibodies, peptibodies and the like), including fully humanized and human OPGL specific antibodies, particularly fully humanized monoclonal antibodies, including but not limited to the antibodies described in International Publication Number WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain as set forth therein in FIG. 2 and/or the heavy chain, as set forth therein in FIG. 4, each of which is individually and specifically incorporated by reference herein in its entirety fully as disclosed in the foregoing publication. Acid and base titrations of an OPGL specific antibody ("Ab-hOPGL") over the pH ranges of 4.5 to 5.0 and 5.0 to 5.5 are described in the Examples below. The calculation of buffer capacity of Ab-hOPGL in these pH ranges also is described in the Examples below.

Myostatin binding agents or peptibodies, including myostatin specific peptibodies, particularly those described in US Application Publication Number 2004/0181033, which is incorporated by reference herein in its entirely particularly in parts pertinent to myostatin specific peptibodies, including but not limited to peptibodies of the mTN8-19 family, including TN8-19-1 through TN8-19-40, TN8-19 cool and TN8-19 peptibodies of the mL2 family; the mL15 family; the mL17 family; the mL20 family; the mL21 family; the mL24 family, each of which is individually and specifically incorporated by reference herein in its entirety fully as disclosed in the foregoing publication.

IL-4 receptor specific antibodies, particularly those that inhibit activities mediated by binding of IL-4 and/or IL-13 to the receptor, including those described in International Publication No. WO 2005/047331 of International Application Number PCT/US2004/03742; which is incorporated herein by reference in its entirety particularly in parts pertinent to receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1M 1; L2H1; L2H2; L2H3; L2H4; L2H5; L2H6; L2H7; L2H8; L2H9; L2H10; L2H11; L2H12; L213; L2H14; L3H1; L4H1; L5H1; L6H1, each of which is individually and specifically incorporated by reference herein in its entirety fully as disclosed in the foregoing publication. Acid and base titrations over the pH ranges of 4.5 to 5.0 and 5.0 to 5.5, and the calculation of buffer capacity in this range of an IL-4 receptor specific antibody ("Ab-hIL4R") are described in the Examples below.

Interleukin 1-receptor ("IL1-R1") specific antibodies, peptibodies and related proteins and the like, including but not limited to those described in U.S. Application Publication Number US2004/097712A1 which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned U.S. application publication.

Ang2 specific antibodies and peptibodies and related proteins and the like, including but not limited to those described in International Publication Number WO 03/057134 and U.S. Application Publication Number US2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2×L1(N); 2×L1(N) WT; Con4 (N), Con4 (N) 1K WT, 2×Con4 (N) 1K; L1(C); L1(C) 1K; 2×L1 (C); Con4 (C); Con4 (C) 1K; 2×Con4 (C) 1K; Con4-L1 (N); Con4-L1 (C); TN-12-9 (N); C17 (N); TN8-8(N); TN8-14 (N); Con 1 (N), also including anti-Ang 2 antibodies and formulations such as those described in International Publication Number WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AblA1; AblF; AblKAblP; and AblP, in their various permutations as described therein, each of which is individually and specifically incorporated by reference herein in its entirety fully as disclosed in the foregoing publication.

NOF specific antibodies, including, in particular, but not limited to those described in US Application Publication Number US2005/0074821, which is incorporated herein by reference in its entirety particularly as to NGF-specific antibodies and related proteins in this regard, including in particular, but not limited to, the NGF-specific antibodies therein designated 4D4, 4G6, 6H9, 7H2, 4D10 and 14D11, each of which is individually and specifically incorporated by reference herein in its entirety fully as disclosed in the foregoing publication.

CD specific antibodies and related, proteins, such as those described in U.S. Pat. No. 5,789,554 which is incorporated herein by reference in its entirety as to CD22 specific antibodies and related proteins, particularly human CD22 specific antibodies, such as but not limited to humanized, and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0. Illustrative of the invention, acid and base titrations of a CD22-specific antibody ("Ab-hCD22") over the pH ranges of 4.5 to 5.0 and 5.0 to 5.5 are described, in the Examples below. The calculation of buffer capacity of Ab-hCD22 in these pH ranges also is described in the Examples below.

IGF-1 receptor specific antibodies and related proteins such as those described in International Patent Application Number PCT/US2005/046493, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18F18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, and L52H52, each of which is individually and specifically incorporated by reference herein in its entirety fully as disclosed in the foregoing International Application.

B-7 related protein 1("B7RP-1") specific antibodies, (B7RP-1 also is referred to in the literature as B7H2, ICOSL, B7h, and CD275) particularly B7RP-specific fully human monoclonal IgG2 antibodies, particularly fully human IgG2 monoclonal antibody that binds an epitope in the first immunoglobulin-like domain of B7RP-1, especially those that Inhibit the interaction of B7RP-1 with its natural receptor, ICOS, on activated T cells in particular, especially, in all of the foregoing regards, those disclosed in U.S. Provisional Application No. 60/700,265, filed 18 Jul. 2005, which is incorporated herein by reference in its entirety as to such antibodies and related proteins, including but not limited to antibodies designated therein as follow: 16H; 5D; 2H; 43H; 41H; and 15H, each of which is individually and specifically incorporated by reference herein in its entirety fully as disclosed in the foregoing U.S. Provisional Application. Acid and base titrations and determination of buffer capacity of a B7RP-1 specific antibody ("Ab-hB7RP1") are illustrated in the Examples below.

IL-15 specific antibodies, peptibodies and related proteins, such as, in particular, humanized monoclonal antibodies, particularly antibodies such as those disclosed in U.S. Application Publication Numbers: US2003/0138421; US2003/023586; US2004/0071702, each of which is incorporated herein by reference in its entirety as to IL-15 specific antibodies and related proteins, including peptibodies, including particularly, for instance, but not limited to, HuMax IL-15 antibodies and related, proteins, such as, for instance, 146B7.

IFN gamma specific antibodies, especially human IFN gamma specific antibodies, particularly fully human anti-IFN gamma antibodies, such as, for instance, those described in US Application Publication Number US2005/0004353, which is incorporated herein by reference in its entirety as to IFN gamma specific antibodies, particularly, for example, the antibodies therein designated 1118; 1118*; 1119; 1121; and 1121* each of which is individually and specifically incorporated by reference herein in its entirety fully as disclosed in the foregoing US Application Publication.

TALL-1 specific antibodies and other TALL specific binding proteins such as those described in U.S. Application Publication Number 2003/0195156 which is incorporated herein by reference in its entirety as to TALL-1 binding proteins, particularly the molecules of Tables 4 and 5B, each of which is individually and, specifically incorporated by reference herein in its entirety fully as disclosed in the foregoing US Application Publication.

Stem Cell Factor (s) ("SCF") and related proteins such as those described in U.S. Pat. Nos. 6,204,363 and 6,207,802, each of which is incorporated herein by reference in its entirety as to stem cell factors and related proteins, particularly, for example, the stem cells factor "STEMGEN™."

Flt3-Ligands, ("Flt3L") and related proteins such as those described, in U.S. Pat. No. 6,632,424 which is incorporated herein by reference as to Flt3-ligands and related proteins in this regard.

IL-17 receptors and related proteins ("IL-17R"), such as those described in U.S. Pat. No. 6,072,033 which is incorporated herein by reference as to Flt3-ligands and related proteins in this regard.

Etanercept, also referred to as Embrel, and related proteins.

Actimmune (Interferon-gamma-1b), Activase (Alteplase), Aldurazme (Laronidase), Amevive (Alefacept), Avonex (Interferon beta-1a), BeneFIX (Nonacog alfa), Beromun (Tasonermin), Beatseron (Interferon-beta-1b), BEXXAR (Tositumomab), Tev-Tropin (Somatropin), Bioclate or RECOMBINATE (Recombinant), CEREZME (Imiglucerase), ENBREL (Etanercept), Eprex (epoetin alpha), EPOGEN/Procit (Epoetin alfa), FABRAZYME (Agalsidase beta), Fasturtec/Elitek ELITEK (Rasburicase), FORTEO (Teriparatide), GENOTROPIN (Somatropin), GlucaGen (Glucagon), Glucagon (Glucagon, rDNA origin), GONAL-F (follitropin alfa), KOGENATE FS (Octocog alfa), HERCEPTIN (Trastuzumab), HUMATROPE (SOMATROPIN), HUMIRA (Adalimumab), Insulin in Solution, INFERGEN® (Interferon alfacon-1), KINERET® (anakinra), Kogenate FS (Antihemophilic Factor), LEUKIN (SARGRAMOSTIM Recombinant human granulocyte-macrophage colony stimulating factor (rhuGM-CSF)), CAMPATH (Alemtuzumab), RITUXAN® (Rituximab), TNKase (Tenecteplase), MYLOTARG (gemtuzumab ozogamicin), NATRECOR (nesiritide), ARANESP (darbepoetin alfa), NEULASTA (pegfilgrastim), NEUMEGA (oprelvekin), NEUPOGEN (Filgrastim), NORDITROPIN CARTRIDGES (Somatropin), NOVOSEVEN (Eptacog alfa), NUTROPIIN AQ (somatropin), Oncaspar (pegaspargase), ONTAK (denileukin diftitox), ORTHOCLONE OKT (muromonab-CD3), OVIDREL, (choriogonadotropin alfa), PEGASYS (peginterferon alfa-2a), PROLEUKIN (Aldesleukin), PULMOZYME (dornase alfa). Retavase (Reteplase), REBETRON Combination Therapy containing REBETOL® (Ribavirin) and INTRON® A (Interferon alfa-2b), REBIF (interferon beta-1a), REFACTO (Antihemophilic Factor), REFUTDAN (lepirudin), REMICADE (infliximab), REOPRO (abciximab) ROFERON®-A (Interferon alfa-2a), SIMULECT (baasiliximab), SOMAVERT (Pegivisomant), SYNAGIS® (palivizumab), Stemben (Ancestim, Stem cell factor), THYROGEN, INTRON® A (Interferon alfa-2b), PEG-INTRON® (Peginterferon alfa-2b), XIGRIS® (Drotrecogin alfa activated), XOLAIR® (Omalizumab), ZENAPAX® (daclizumab), ZEVALIN® (Ibritumomab Tiuxetan).

d. Sequence Variation

Particularly preferred proteins in regard to all of the foregoing and the following, include those that comprise a region that is 70% or more, especially 80% or more, more especially 90% or more, yet more especially 95% or more, particularly 97% or more, more particularly 98% or more, yet more particularly 99% or more identical in amino acid sequence to a reference amino acid sequence of a binding protein, as illustrated above, particularly a pharmaceutical binding protein, such as a GenBank or other reference sequence of a reference protein.

Identity in this regard can be determined using a variety of well-known and readily available amino acid sequence analysis software. Preferred software includes those that implement the Smith-Waterman algorithms, considered a satisfactory solution to the problem of searching and aligning sequences. Other algorithms also may be employed, particularly where speed is an important consideration. Commonly employed programs for alignment and homology matching of DNAs, RNAs, and polypeptides that can be used in this regard include PASTA, TFASTA, BLASTN, BLASTP, BLASTX, TBLASTN, PROSRCH, BLAZE, and MPSRCH, the latter being an implementation of the Smith-Waterman algorithm for execution on massively parallel processors made by MasPar.

The BLASTN, BLASTX, and BLASTP programs are among preferred programs for such determinations, the former for polynucleotide sequence comparisons and the latter two for polypeptide sequence comparisons; BLASTX for comparison of the polypeptide sequences from all three reading frames of polynucleotide sequence and BLASTP for a single polypeptide sequence.

BLAST provides a variety of user definable parameters that are set before implementing a comparison. Some of them are more readily apparent than others on graphical user interfaces, such as those provided by NCBI BLAST and other sequence alignment programs that can be accessed on the internet. The settings and their values are set out and explained on the service web sites and are explained and set out in particular detail in a variety of readily available texts, including but not limited to BIOINFORMATICS: SEQUENCE AND GENOME ANALYSIS, 2$^{nd}$ Ed., David W. Mount, Cold Spring Harbor Laboratory Press, Cold Spring Harbor, N.Y. (2004), especially Chapters 3, 4, 5, and 6 as to comparison of protein and nucleic acid sequences in general and as to BLAST comparisons and searches in particular; SEQUENCE ANALYSIS IN A NUTSHELL: A GUIDE TO COMMON TOOLS AND DATABASES, Scott Markel and Darryl León, O'Reilly & Associates, Sebastopol, Calif. (2003), especially Chapter 7 as to BLAST in particular, each of which is herein incorporated by reference in its entirety particularly in parts pertinent to comparison of nucleotide and polypeptide sequences and to determining their degree of identity, similarity, homology and/or the like, especially as to comparison of a test sequence and a reference sequence to calculate a degree (percent) of identity between them.

In preferred embodiments of the invention in this regard, relatedness of sequences is defined as the identity score in percent returned by any one or another of the aforementioned BLAST comparison searches with e=10 and all other parameters set to their default values on the NCBI web server as set forth in SEQUENCE ANALYSIS IN A NUTSHELL: A GUIDE TO COMMON TOOLS AND DATABASES, Scott Markel and Darryl León, O'Reilly & Associates, Sebastopol, Calif. (2003), pages 47-51 which are incorporated herein by reference in their entireties and in all particulars of the preferred settings for parameters of the present invention for comparing sequences using BLAST, such as those on NCBI BLAST.

The following references provide additional information on sequence comparisons in this regard, and in others, GUIDE TO HUMAN GENOME COMPUTING, Ed. Martin J. Bishop, Academic Press, Harcourt Brace & Company Publishers, New York (1994), which is incorporated herein by reference in its entirety with regard to the foregoing, particularly in parts pertinent to determining identity and or homology of amino acid or polynucleotide sequences, especially Chapter 7. The BLAST programs are described in Altschul et al., "Basic Local Alignment Research Tool," or *J Mol Biol* 215: 403-410 (1990), which is incorporated by reference herein in its entirety. Additional information concerning sequence analysis and homology and identity determinations are provided in, among many other references well-known and readily available to those skilled in the art: NUCLEIC ACID AND PROTEIN SEQUENCE ANALYSIS: A PRACTICAL APPROACH, Eds. M. J. Bishop and C. J. Rawings, IRL Press, Oxford, UK (1987); PROTEIN STRUCTURE: A PRACTICAL APPROACH, Ed, T. E, Creighton, IRL, Press, Oxford, UK (1989); Doolittle, R. F.: "Searching through sequence databases." *Met Enz.* 183: 99-110 (1990); Meyers and Miller: "Optimal alignments in linear space" *Comput. Applica. in Blosci* 4: 11-17 (1988); Needleman and Wunsch: "A general method applicable to the search for similarities in amino acid sequence of two proteins," *J Mol Biol* 48: 443-453 (1970) and Smith and Waterman "Identification of common molecular subsequences," *J Mol Biol* 147: 1950 et seq. (1981), each of which is incorporated herein by reference in its entirety with reference to the foregoing, particularly in parts pertinent to sequence comparison and identity and homology determinations.

Particularly preferred embodiments in this regard have 50% to 150% of the activity of the aforementioned reference protein, particularly highly preferred embodiments in this regard have 60% to 125% of the activity of the reference protein, yet more highly preferred embodiments have 75% to 110% of the activity of the reference protein, still more highly preferred embodiments have 85% to 125% the activity of the reference, still more highly preferred embodiments have 90% to 110% of the activity of the reference.

4. Formulations

Many reagents and methods conventionally employed for the formulation of protein pharmaceuticals can be used for the formulation of self-buffering protein compositions in accordance with various aspects and preferred embodiments of the invention. However, in self-buffering protein formulations in accordance with the invention, buffering is provided substantially entirely by the protein itself, not by a buffering agent, as is the case with conventional formulations. Moreover, self-buffering protein formulations in accordance with various aspects and preferred embodiments of the invention are substantially free of such buffering agents.

In many other respects, however, self-buffering protein compositions in accordance with various aspects and embodiments of the invention can be formulated using reagents and methods conventionally employed for the formulation of proteins, in particular, reagents and methods employed for the formulation of pharmaceuticals, including pharmaceuticals for veterinary and human use, especially those reagents and methods suitable for formulating protein pharmaceuticals for veterinary and especially for human use.

In accordance therewith, many methods and ingredients for formulating and using pharmaceuticals that are well-known and routine in the pertinent arts can be used in designing, making, and using self-buffering protein formulations in accordance with various aspects and preferred embodiments of the invention relating thereto. Such methods and ingredients are described in, to name just a few readily available references in this regard, REMINGTON:

THE SCIENCE AND PRACTICE OF PHARMACY, 21$^{st}$ Ed.; Beringer et al. Editors, Lippincott, Williams & Wilkins, Philadelphia, Pa. (2005); ANSEL'S PHARMACEUTICAL DOSAGE FORMS AND DRUG DELIVERY SYSTEMS, 8$^{th}$ Ed., Allen et al., Editors, Lippincott, Williams & Wilkins, Philadelphia, Pa. (2005); and PHARMACEUTICAL FORMULATION OF PEPTIDES AND PROTEINS, Sven Frokjaer and Lars Hovgaard, Editors, CRC Press, Boca Raton, Fla. (2000), each of which is herein incorporated in its entirety particularly in parts pertinent to conventional ingredients and methods that may be used in self-buffering formulations of proteins in accordance with various aspects and preferred embodiments of the invention relating thereto.

Additional methods and ingredients that can be useful in this regard are disclosed in, among others, U.S. Pat. No. 6,171,586; WO 2005/044854; U.S. Pat. No. 6,288,030; U.S. Pat. No. 6,267,958; WO 2004/055164; U.S. Pat. No. 4,597,966; US 2003/0138417; U.S. Pat. No. 6,252,055; U.S. Pat. No. 5,608,038; U.S. Pat. No. 6,875,432; US 2004/0197324; WO 02/096457; U.S. Pat. No. 5,945,098; U.S. Pat. No. 5,237,054; U.S. Pat. No. 6,485,932; U.S. Pat. No. 6,821,515; U.S. Pat. No. 5,792,838; U.S. Pat. No. 5,654,403; U.S. Pat. No. 5,908,826; EP 0 804 163; and WO 2005/063291, each of which is incorporated herein by reference in its entirety particularly in parts pertinent to pharmaceutically acceptable self-buffering protein formulations in accordance with the invention.

Various specific aspects of the ingredients and specific types of formulations are further described below, by way of illustration. The description thus provided is not exhaustive of the methods and compositions possible for self-buffering protein formulations in accordance with the various aspects and embodiments of the invention, nor is it in any way exclusive.

In preferred embodiments of a vane of aspects of the invention, formulations of self-buffering proteins comprise a protein and a carrier, which also may be referred to herein variously, as the case may be, as one or more of: a vehicle, a primary vehicle, a diluent, a primary diluent, a primary carrier, a solvent and/or a primary solvent. In the broadest sense the carrier may be a gas, a liquid, or a solid, as suits the phase of the composition and/or its use(s). In some embodiments of the invention in this regard, the carrier is a solid, such as a powder in which a protein may be dispersed. In preferred embodiments in this regard, the carrier is a liquid, particularly a liquid in which the self-buffering protein is highly soluble, particularly at concentrations that provide the desired buffer capacity. Liquid carriers may be organic or non-organic. Preferably they are aqueous, most preferably they are largely or entirely comprised of pure water.

It will be appreciated that formulations for pharmaceutical use in accordance with various aspects and embodiments of the invention must be compatible with the processes and conditions to which they will be subjected, such as, for instance, sterilization procedures (generally applied before mixing with an active agent), and conditions during storage.

Almost invariably, formulations in accordance with numerous aspects and embodiments of the invention will contain additional ingredients including but not limited in any way to excipients and other pharmaceutical agents, Nevertheless, it is to be understood that formulations in accordance with the invention are self-buffering formulations in which the buffer capacity is provided substantially or entirely by the primary protein itself, as described elsewhere herein.

Formulations in accordance with various aspects and embodiments of the invention may contain, among others, excipients, as described below, including but not limited to ingredients for modifying, maintaining, or preserving, for example, osmolality, osmolarity, viscosity, clarity, color, tonicity, odor, sterility, stability, rate of dissolution or release, adsorption or penetration of the formulations and/or primary polypeptide and/or protein.

Formulations will, of course, depend upon, for example, the particular protein being formulated, the other active agents, such as other pharmaceuticals, that will be comprised in the formulation, the intended route of administration, the method of administration to be employed, the dosage, the dosing frequency, and the delivery format, among others.

Formulations in accordance with certain of the preferred embodiments in various aspects of the invention provide compositions comprising a protein preferably a pharmaceutical protein and a solvent, the protein having a buffer capacity per unit volume of at least that of approximately: 2.0 or 3.0 or 4.0 or 5.0 or 6.50 or 8.00 or 10.0 or 15.0 or 20.0 or 30.0 or 40.0 or 50.0 or 75.0 or 1.00 or 125 or 150 or 00 or 250 or 300 or 350 or 400 or 500 or 700 or 1,000 or 1,500 or 2,000 or 2,500 or 3,000 or 4,000 or 5,000 mM sodium acetate buffer as determined over the range of pH 5.0 to 4.0 pH or 5.0 to 5.5 as described in Example 1 or 2 and elsewhere herein.

Formulations in accordance with certain of the preferred embodiments in various aspects of the invention provide self-buffering protein compositions, particularly pharmaceutical protein compositions, wherein, exclusive of the buffer capacity of the protein, the buffer capacity per unit volume of the composition is equal to or less than that of 1.0 or L5 or 2.0 or 3.0 or 4.0 or 5.0 mM sodium acetate buffer as determined, over the range of pH 5.0 to 4.0 or pH 5.0 to 5.5 as described in Example 1 or 2 and elsewhere herein.

Formulations in accordance with certain of the preferred embodiments in various aspects of the invention provide self-buffering protein compositions, particularly pharmaceutical protein compositions, comprising a protein and a solvent, wherein at the pH of the composition the buffer capacity of the protein is at least approximately: 1.00 or 1.50 or 1.63 or 2.00 or 3.00 or 4.00 or 5.00 or 6.50 or 8.00 or 10.0 or 15.0 or 20.0 or 30.0 or 40.0 or 50.0 or 75.0 or 100 or 125 or 150 or 200 or 250 or 300 or 350 or 400 or 500 or 700 or 1,000 or 1,500 or 2,000 or 2,500 or 3,000 or 4,000 or 5,000 mEq per liter and per change in pH of one pH unit.

Formulations in accordance with certain of the preferred embodiments in various aspects of the invention provide self-buffering protein compositions, particularly pharmaceutical protein compositions, comprising a protein and a solvent, wherein at the pH of the composition, exclusive of the protein, the buffer capacity per unit volume of the composition is equal to or less than that of a 0.50 or 1.00 or 1.50 or 2.00 or 3.00 or 4.00 or 5.00 or 6.50 or 8.00 or 10.0 or 20.0 or 25.0 mM acetate buffer as determined over the range of pH 5.0 to 4.0 or pH 5.0 to 5.5 as described in Example 1 or 2 and elsewhere herein.

Formulations in accordance with certain of the preferred embodiments in various aspects of the invention provide self-buffering protein compositions, particularly pharmaceutical protein compositions, comprising a protein and a solvent, wherein at a desired pH, the protein provides at least approximately 55%, 60%, 65%, 70%, 75%, 80%, 85%, 90%, 95%, 97%, 98%, 99%, or 99.5% of the buffer capacity of the composition.

Formulations in accordance with certain of the preferred embodiments in various aspects of the invention provide self-buffering protein compositions, particularly pharmaceutical protein compositions, comprising a protein and a solvent, wherein the concentration of the protein is between approximately: 20 and 400, or and 300, or 20 and 250, or 20 and 200, or 20 and 150 mg/ml.

Formulations in accordance with certain of the preferred embodiments in various aspects of the invention provide self-buffering protein compositions, particularly pharmaceutical protein compositions, comprising a protein and a solvent, wherein the pH maintained by the buffering action of the protein is a pH between approximately: 3.5 and 8.0, or 4.0 and 6.0, or 4.0 and 5.5, or 4.5 and 5.5.

Formulations in accordance with certain of the preferred embodiments in various aspects of the invention provide self-buffering protein compositions, particularly pharmaceutical protein compositions, comprising a protein and a solvent, wherein the salt concentration is less than: 150 mM or 125 mM or 100 mM or 75 mM or 50 mM or 25 mM.

Formulations in accordance with certain of the preferred embodiments in various aspects of the invention provide self-buffering protein compositions, particularly pharmaceutical protein compositions, comprising a protein and a solvent, and further comprising one or more pharmaceutically acceptable salts; osmotic balancing agents (tonicity agents); anti-oxidants; antibiotics; antimycotics; bulking agents; lyoprotectants; anti-foaming agents; chelating agents; preservatives; colorants; analgesics; or additional pharmaceutical agents.

Formulations in accordance with certain of the preferred embodiments in various aspects of the invention provide self-buffering protein compositions, particularly pharmaceutical protein compositions, comprising a protein and a solvent, and further comprising one or more pharmaceutically acceptable polyols in an amount that is hypotonic, isotonic, or hypertonic, preferably approximately isotonic, particularly preferably isotonic, especially preferably any one or more of sorbitol, mannitol, sucrose, trehalose, or glycerol, particularly especially preferably approximately 5% sorbitol, 5% mannitol, 9% sucrose, 9% trehalose, or 2.5% glycerol, very especially in this regard 5% sorbitol, 5% mannitol, 9% sucrose, 9% trehalose, or 2.5% glycerol.

Formulations in accordance with certain of the preferred embodiments in various aspects of the invention provide self-buffering protein compositions, particularly pharmaceutical protein compositions, comprising a protein and a solvent, and further comprising one or more pharmaceutically acceptable surfactants, preferably one or more of polysorbate 20, polysorbate 80, other fatty acid esters of sorbitan, polyethoxylates, and poloxamer 1.88, particularly preferably polysorbate 20 or polysorbate 80, preferably approximately 0.001 to 0.1% polysorbate 20 or polysorbate 80, very preferably approximately 0.002 to 0.0296 polysorbate 20 or polysorbate 80, especially 0.002 to 0.02% polysorbate 20 or polysorbate 80.

Formulations in accordance with certain of the preferred embodiments in various aspects of the invention provide self-buffering protein compositions, particularly pharmaceutical protein compositions, comprising a protein and a solvent, wherein the protein is a pharmaceutical agent and the composition is a sterile formulation thereof suitable for treatment of a veterinary or a human medical subject.

Also among formulations in accordance with various aspects and embodiments of the invention herein described are lyophilized compositions in accordance with the foregoing, particularly lyophilized compositions that when reconstituted provide a formulation as described above and elsewhere herein.

a. Excipients and Other Additional Ingredients

As discussed above, certain embodiments in accordance with aspects of the invention provide self-buffering protein compositions, particularly pharmaceutical protein compositions, that comprise, in addition to the protein, particularly a pharmaceutical protein, one or more excipients such as those illustratively described in this section and elsewhere herein. Excipients can be used in the invention in this regard for a wide variety of purposes, such as adjusting physical, chemical, or biological properties of formulations, such as adjustment of viscosity, and or processes of the invention to improve effectiveness and or to stabilize such formulations and processes against degradation and spoilage due to, for instance, stresses that occur during manufacturing, shipping, storage, pre-use preparation, administration, and thereafter.

A variety of expositions are available on protein stabilization and formulation materials and methods useful in this regard, such as Arakawa et al., "Solvent interactions in pharmaceutical formulations," *Pharm Res.* 8(3):285'91 (1991); Kendrick et al., "Physical stabilization of proteins in aqueous solution," in: RATIONAL DESIGN OF STABLE PROTEIN FORMULATIONS: THEORY AND PRACTICE, Carpenter and Manning, eds. *Pharmaceutical Biotechnology.* 13: 61-84 (2002), and Randolph et "Surfactant-protein interactions,"*Pharm Biotechnol.* 13: 159-75 (2002), each of which is herein incorporated by reference in its entirety, particularly in parts pertinent to excipients and processes of the same for self-buffering protein formulations in accordance with the current invention, especially as to protein pharmaceutical products and processes for veterinary and/or human medical uses.

Various excipients useful in the invention are listed in Table 1 and further described below.

TABLE 1

Types of Excipients and Their Functions

| Type | Function | |
|---|---|---|
| | Liquids | Lyophilates |
| Tonicity Agents/ Stabilizers | Provides isotonicity to the formulation such that it is suitable for injection | Stabilizers include cryo and lyoprotectants |
| | Examples include polyols, salts, and amino acids | Examples include polyols, sugars and polymers |
| | Help maintain the protein in a more compact state (polyols) | Cryoprotectants protect proteins from freezing stresses |
| | Minimize electrostatic, solution protein-protein interactions (salts) | Lyoprotectants stabilize proteins in the freeze-dried state |

TABLE 1-continued

Types of Excipients and Their Functions

| Type | Function | |
|---|---|---|
| | Liquids | Lyophilates |
| Bulking Agents | Not applicable | Used to enhance product elegance and to prevent blowout<br>Provides structural strength to the lyo cake<br>Examples include mannitol and glycine |
| Surfactants | Prevent/control aggregation, particle formation and surface adsorption of drug<br>Examples include polysorbate 20 and 80 | Employed if aggregation during the lyophilization process is an issue<br>May serve to reduce reconstitution times<br>Examples include polysorbate 20 and 80 |
| Anti-oxidants | Control protein oxidation | Usually not employed, molecular reactions in the lyophilized cake are greatly retarded |
| Metal Ions/ Chelating Agents | A specific metal ion is included in a liquid formulation only as a co-factor<br>Divalent cations such as zinc and magnesium are utilized in suspension formulations<br>Chelating agents are used to inhibit heavy metal ion catalyzed reactions | May be included if a specific metal ion is included only as a co-factor<br>Chelating agents are, generally not needed in lyophilized formulations |
| Preservatives | Important particularly for multi-dose formulations<br>Protects against microbial growth,<br>Example: benzyl alcohol | For multi-dose formulations only<br>Provides protection against microbial growth in formulation<br>Is usually included in the reconstitution diluent (e.g. bWFI) | i. Salts

Salts may be used in accordance with certain of the preferred embodiments of the invention to, for example, adjust the ionic strength and/or the isotonicity of a self-buffering formulation and/or to improve the solubility and/or physical stability of a self-buffering protein or other ingredient of a self-buffering protein composition in accordance with the invention.

As is well known, ions can stabilize the native state of proteins by binding to charged residues on the protein's surface and by shielding charged and polar groups in the protein and reducing the strength of their electrostatic interactions, attractive, and repulsive interactions. Ions also can stabilize the denatured state of a protein by binding to, in particular, the denatured peptide linkages (—CONH) of the protein. Furthermore, ionic interaction with charged and polar groups in a protein also can reduce intermolecular electrostatic interactions and, thereby, prevent or reduce protein aggregation and insolubility.

Ionic species differ significantly in their effects on proteins. A number of categorical rankings of ions and their effects on proteins have been developed that can be used in formulating self-buffering protein compositions in accordance with the invention. One example is the Hofmeister series, which ranks ionic and polar non-ionic solutes by their effect on the conformational stability of proteins in solution. Stabilizing solutes are referred to as "kosmotropic." Destabilizing solutes are referred to as chaotropic, Kosmotropes commonly are used at high concentrations e.g., >1 molar ammonium sulfate) to precipitate proteins from solution ("salting-out"). Chaotropes commonly are used to denture and/or to solubilize proteins ("salting-in"). The relative effectiveness of ions to "salt-in" and "salt-out" defines their position in the Hofmeister series.

In addition to their utilities and their drawbacks (as discussed above) salts also are effective for reducing the viscosity of protein formulations and can be used in the invention for that purpose.

In order to maintain isotonicity in a parenteral formulation in accordance with preferred embodiments of the invention, improve protein solubility and/or stability, improve viscosity characteristics, avoid deleterious salt effects on protein stability and aggregation, and prevent salt-mediated protein degradation, the salt concentration in self-buffering formulations in accordance with various preferred embodiments of the invention are less than 150 mM (as to monovalent ions) and 150 mEq/liter for multivalent ions. In this regard, in certain particularly preferred embodiments of the invention, the total salt concentration is from about 75 mEq/L: to about 140 mEq/L.

ii. Amino Acids

Free amino acids can be used in protein formulations in accordance with various preferred embodiments of the invention as, to name a few, bulking agents, stabilizers and antioxidants. However, amino acids comprised in self-buffering protein formulations in accordance with the invention do not provide buffering action. For this reason, those with significant buffer capacity either are not employed, are not employed at any pH around which they have significant buffering activity, or are used at low concentration so that, as a result, their buffer capacity in the formulation is not significant. This is particularly the case for histidine and other amino acids that commonly are used as buffers in pharmaceutical formulations.

Subject to the foregoing consideration, lysine, proline, serine, and alanine can be used for stabilizing proteins in a formulation. Glycine is useful in lyophilization to ensure correct cake structure and properties. As a result it is a common ingredient in lyophilized formulations and reconstituted lyophilates, such as Neumega®, Genotropin®, and Humatrope®. Arginine may be useful to inhibit protein aggregation, in both liquid and lyophilized formulations, such as Activase®, Avonex®, and Enbreil® liquid. Methionine is useful as an antioxidant.

iii Polyols

Polyols include sugars, e.g., mannitol, sucrose, and sorbitol and polyhydric alcohols such as, for instance, glycerol and propylene glycol, and, for purposes of discussion herein, polyethylene glycol (PEG) and related substances. Polyols are kosmotropic. They are useful stabilizing agents in both liquid and lyophilized formulations to protect proteins from physical and chemical degradation processes. Polyols also are useful for adjusting the tonicity of formulations.

Among polyols useful in the invention in this regard, is mannitol, commonly used to ensure structural stability of the cake in lyophilized formulations, such as, for example Leukine®, Enbreil®-Lyo, and Betaseron®. It ensures structural stability to the cake. It is generally used with a lyoprotectant, e.g., sucrose. Sorbitol and sucrose are among preferred agents for adjusting tonicity and as stabilizers to protect against freeze-thaw stresses during transport or the preparation of bulks during the manufacturing process. Reducing sugars (which contain free aldehyde or ketone groups), such as glucose and lactose, can glycate surface lysine and arginine residues. Therefore, they generally are not among preferred polyols for use in accordance with the invention. In addition, sugars that form such reactive species, such as sucrose, which is hydrolyzed to fructose and glucose under acidic conditions, and consequently engenders glycation, also is not among preferred amino acids of the invention in this regard. PEG is useful to stabilize proteins and as a cryoprotectant and can be used in the invention in this regard, such as it is in Recombinate®.

iv. Surfactants

Protein molecules are susceptible to adsorption on surfaces and to denaturation and consequent aggregation at air-liquid, solid-liquid, and liquid-liquid interfaces. These effects generally scale inversely with protein concentration. These deleterious interactions generally scale inversely with protein concentration and typically are exacerbated by physical agitation, such as that generated during the shipping and handling of a product.

Surfactants routinely are used to prevent, minimize, or reduce surface adsorption. Useful surfactants in the invention in this regard include polysorbate 20, polysorbate 80, other fatty acid esters of sorbitan polyethoxylates, and poloxamer 188.

Surfactants also are commonly used to control protein conformational stability. The use of surfactants in this regard is protein-specific since, any given surfactant typically will stabilize some proteins and destabilize others.

Polysorbates are susceptible to oxidative degradation and often, as supplied, contain sufficient quantities of peroxides to cause oxidation of protein residue side-chains, especially methionine, Consequently, polysorbates should be used carefully, and when used, should be employed at their lowest effective concentration. In this regard, polysorbates exemplify the general rule that excipients should be used in their lowest effective concentrations.

v. Antioxidants

A variety of processes can result in harmful oxidation of proteins in pharmaceutical formulations. To some extent deleterious oxidation of proteins can be prevented in pharmaceutical formulations by maintaining proper levels of ambient oxygen and temperature and by avoiding exposure to light, Antioxidant excipients can be used as well to prevent oxidative degradation of proteins. Among useful antioxidants in this regard are reducing agents, oxygen/free-radical scavengers, and chelating agents. Antioxidants for use in therapeutic protein formulations in accordance with the invention preferably are water-soluble and maintain their activity throughout the shelf life of a product. EDTA is a preferred antioxidant in accordance with the invention in this regard and can be used in the invention in much the same way it has been used in formulations of acidic fibroblast growth factor and in products such as Kineret® and Ontak®.

Antioxidants can damage proteins. For instance, reducing agents, such as glutathione in particular, can disrupt intramolecular disulfide linkages. Thus, antioxidants for use in the invention are selected to, among other things, eliminate or sufficiently reduce the possibility of themselves damaging proteins in the formulation.

vi. Metal Ions

Formulations in accordance with the invention may include metal ions that are protein co-factors and that are necessary to form protein coordination complexes, such as zinc necessary to form certain insulin suspensions. Metal ions also can inhibit some processes that degrade proteins. However, metal ions also catalyze physical and chemical processes that degrade proteins.

Magnesium ions (10-120 mM) can be used to inhibit isomerization of aspartic acid to isoaspartic acid. $Ca^{+2}$ ions (up to 100 mM) can increase the stability of human deoxyribonuclease (rhDNase, Pulmozyme®), $Mg^{+2}$, $Mn^{+2}$, and $Zn^{+2}$, however, can destabilize rhDNase. Similarly, $Ca^{+2}$ and $Sr^{+2}$ can stabilize Factor VIII, it can be destabilized by $Mg^{+2}$, $Mn^{+2}$ and $Zn^{+2}$, $Cu^{+2}$ and $Fe^{+2}$, and its aggregation can be increased by $Al^{+3}$ ions.

vii. Preservatives

Preservatives are necessary when developing multi-dose parenteral formulations that involve more than one extraction from the same container. Their primary function is to inhibit microbial growth and ensure product sterility throughout the shelf-life or term of use of the drug product. Commonly used preservatives include benzyl alcohol, phenol and m-cresol. Although preservatives have a long history of use with small-molecule parenterals, the development of protein formulations that includes preservatives can be challenging. Preservatives almost always have a destabilizing effect (aggregation) on proteins, and this has become a major factor in limiting their use in multi-dose protein formulations. To date, most protein drugs have been formulated for single-use only. However, when multi-dose formulations are possible, they have the added advantage of enabling patient convenience, and increased marketability. A good example is that of human growth hormone (hGH) where the development of preserved formulations has led to commercialization of more convenient, multi-use injection pen presentations. At least four such pen devices containing preserved formulations of hGE are currently available on the market. Norditropin® (liquid, Novo Nordisk), Nutropin AQ® (liquid, Genentech) & Genotropin (lyophilized—dual chamber cartridge, Pharmacia & Upjohn) contain phenol while Somatrope®(Eli Lilly) is formulated with m-cresol.

Several aspects need to be considered during the formulation and development of preserved dosage forms. The effective preservative concentration in the drug product must be optimized. This requires testing a given preservative in the dosage form with concentration ranges that confer anti-microbial effectiveness without compromising protein stability. For example, three preservatives were successfully screened in the development of a liquid formulation for interleukin-1 receptor (Type I) using differential scanning calorimetry (DSC). The preservatives were rank ordered based on their impact on stability at concentrations commonly used in marketed products.

As might be expected, development of liquid formulations containing preservatives are more challenging than lyophilized formulations. Freeze-dried products can be lyophilized without the preservative and reconstituted with a preservative containing diluent at the time of use. This shortens the time for which a preservative is in contact with the protein, significantly minimizing the associated stability risks. With liquid formulations, preservative effectiveness and stability have to be maintained over the entire product shelf-life (~18 to 24 months). An important point to note is that preservative effectiveness has to be demonstrated in the final formulation containing the active drug and all excipient components.

Self-buffering protein formulations in accordance with the invention, particularly self-buffering biopharmaceutical protein formulations, generally will be designed for specific routes and methods of administration, for specific administration dosages and frequencies of administration, for specific treatments of specific diseases, with ranges of bioavailability and persistence, among other things.

Formulations thus may be designed in accordance with the invention for delivery by any suitable route, including but not limited to orally, aurally, opthalmically, rectally, and vaginally, and by parenteral routes, including intravenous and intraarterial injection, intramuscular injection, and subcutaneous injection.

b. Formulations for Parenteral Administration

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents.

When parenteral administration is contemplated, the therapeutic compositions for use in this invention may be in the form of a pyrogen-free, parenterally acceptable aqueous solution comprising the desired protein in a pharmaceutically acceptable vehicle. A particularly suitable vehicle for parenteral injection is sterile pure water in which the protein is formulated as a sterile, isotonic self-buffering solution.

Such preparations may also involve the formulation of the desired protein in the form of, among other things, injectable microspheres, bio-erodible particles, polymeric compounds (polylactic acid, polyglycolic acid), beads, or liposomes, including those that provide for controlled or sustained release. Such formulations may be introduced by implantable drug delivery devices, among others.

Formulations for parenteral administration also may contain substances that adjust the viscosity, such as carboxymethyl cellulose, sorbitol, and dextran. Formulations may also contain ingredients that increase solubility of the desired protein or other ingredients and those that stabilize one or more such ingredients, including in some cases, the self-buffering protein.

c, Formulations for Pulmonary Administration

A pharmaceutical composition in accordance with certain embodiments of the invention may be suitable for inhalation. For pulmonary administration, the pharmaceutical composition may be administered in the form of an aerosol or with an inhaler including dry powder aerosol. For example, a binding agent may be formulated as a dry powder for inhalation. Inhalation solutions may also be formulated with a propellant for aerosol delivery. In yet another embodiment, solutions may be nebulized. Pulmonary administration is further described in PCI Application No. PCT/US94/001875, which describes pulmonary delivery of chemically modified proteins.

d. Formulations for Oral Administration

For oral administration, the pharmaceutical composition may be in the form of, for example, a tablet, capsule, suspension, or liquid. The pharmaceutical composition is preferably made in the form of a dosage unit containing a particular amount of the active ingredient. Examples of much dosage units are tablets or capsules. Formulations for oral administration in accordance with the invention in this regard can be made conventionally wherein buffering in the formulation is provided by the self-buffering protein as described elsewhere herein.

e. Controlled Release Form Formations

Among additional formulations that can be useful in the invention as herein described are sustained- and controlled-delivery formulations. Techniques for making such sustained- and controlled-delivery formulations that may be used in accordance with various aspects and preferred embodiments of the invention are well-known to those skilled in the art. Among these are delivery methods that use liposome carriers, bio-erodible microparticles, porous beads, and semi-permeable polymer matrices, such as those described in PCT/US93/00829; U.S. Pat. No. 3,773,919; EP 58,481; Sidman et al., *Biopolymers*, 22:547-556 (1983); Langer et al. *J. Biomed Mater. Res.*, 15:167-277, (1981); Langer et al., *Chem. Tech.*, 12:98-105 (1982); EP 133.988; Eppstein et al., *Proc. Natl. Acad. Sci. (USA)*, 82:3688-3692 (1985); EP 36,676; EP 88,046; and EP 143,949, each of which is hereby incorporated by reference in its entirety, particularly in parts pertinent to self-buffering sustained- and controlled-delivery pharmaceutical protein formulations in accordance with the invention herein described.

f. Sterilization

The pharmaceutical composition to be used for in vivo administration typically must be sterile. This may be accomplished by filtration through sterile filtration membranes. Where the composition is lyophilized, sterilization using this method may be conducted either prior to or following lyophilization and reconstitution. The composition for parenteral administration may be stored in lyophilized form or in solution. In addition, parenteral compositions generally are placed into a container having a sterile access port, for example, an intravenous solution bag or vial having a stopper pierceable by a hypodermic injection needle.

g. Storage

Once the pharmaceutical composition has been formulated, it may be stored in sterile vials as a solution, suspension, gel, emulsion, solid, or a dehydrated or lyophilized powder. Such formulations may be stored either in a ready-to-use form or in a form (e.g., lyophilized) requiring reconstitution prior to administration.

h. Additional Pharmaceutical Agents

Self-buffering protein compositions in accordance with the invention, particularly self-buffering pharmaceutical protein compositions, can comprise in addition to the self-buffering protein of the composition, one or more additional pharmaceutical agents. Such agents may be proteins as well, or they may be other types of agents. Included among such agents are those for prevention or treatment of any disorder or disease. Such agents include, for instance, antibiotics and antimycotics. They also include agents for treating human disorders, including but not limited to, agents for treating inflammatory diseases, cancers, metabolic disorders, neurological and renal disorders, to name just a few. Agents that may be used in the invention in this regard also include agents useful to augment the action of a self-buffering composition and or prevent, ameliorate, or treat any undesirable side effects of the administration thereof.

i. Methods for Making Self-Buffering Protein Formulations

Compositions in accordance with the invention may be produced using well-known, routine methods for making, formulating, and using proteins, particularly pharmaceutical proteins. In certain of the preferred embodiments of a number of aspects of the invention in this regard, methods for preparing the compositions comprise the use of counter ions to remove residual buffering agents. In this regard the term counter ion is any polar or charged constituent that acts to displace buffer from the composition during its preparation, Counter ions useful in this regard include, for instance, glycine, chloride, sulfate, and phosphate. The term counter ion in this regard is used to mean much the same thing as displacement ion.

Residual buffering agents can be removed using the counter ions in this regard, using a variety of well-known methods, including but not limited to, standard methods of dialysis and high performance membrane diffusion-based methods such as tangential flow diafiltration. Methods for residual buffer removal employing a counter ion in this regard can also, in some cases, be carried out using size exclusion chromatography.

In certain related preferred embodiments in this regard, compositions in accordance with the invention are prepared by a process that involves dialysis against a bufferless solution at a pH below that of the preparation containing the self-buffering protein. In particularly preferred embodiments of the invention in this regard, the bufferless solution comprises counter ions, particularly those that facilitate removal of residual buffer and do not adversely affect the self-buffering protein or the formulation thereof. In further particularly preferred embodiments of the invention in this regard, following dialysis the pH of the preparation is adjusted to the desired pH using dilute acid or dilute base.

In certain related particularly preferred embodiments in this regard, compositions in accordance with the invention are prepared by a process that involves tangential flow diafiltration against a bufferless solution at a pH below that of the preparation containing the self-buffering protein. In particularly preferred embodiments of the invention in this regard, the bufferless solution comprises counter ions, particularly those that facilitate removal of residual buffer and do not adversely affect the self-buffering protein or the formulation thereof. In further particularly preferred embodiments of the invention in this regard, following diafiltration the pH of the preparation is adjusted to the desired pH using dilute acid or dilute base.

5. Routes of Administration

Formulations in accordance with the invention, in various embodiments, may be administered by a variety of suitable routes, well-known to those skilled in the art of administering therapeutics to a subject. In embodiments of the invention in this regard, one or more formulations, as described elsewhere herein, are administered via the alimentary canal. In other embodiments one or more formulations as described elsewhere herein are administered parenterally. In various embodiments one or more formulations may be administered via the alimentary canal in conjunction with one or more other formulations administered parenterally.

Such routes in a variety of embodiments include but are not limited to administration of the compositions orally, ocularly, mucosally, topically, rectally, pulmonarily, such as by inhalation spray, and epicutaneously. The following parenteral routes of administration also are useful in various embodiments of the invention: administration by intravenous, intraarterial, intracardiac, intraspinal, intrathecal, intraosseous, intraarticular, intrasynovial, intracutaneous, intradermal, subcutaneous, peritoneal, and/or intramuscular injection. In some embodiments intravenous, intraarterial, intracutaneous, intradermal, subcutaneous and/or intramuscular injection are used. In some embodiments intravenous, intraarterial, intracutaneous, subcutaneous, and/or intramuscular injection are used.

In certain embodiments of the invention the compositions are administered locally, for instance by intraocular injection to treat ocular neovascularization, retinopathy, or age-related macular degeneration.

6. Doses

The amount of a self-buffering protein formulation administered and the dosage regimen for treating a disease condition with the formulation depends on a variety of factors, including the age, weight, sex, and medical condition of the subject, the type of disease, the severity of the disease, the route and frequency of administration, and the particular formulation employed. In particular the amount will depend on the protein therapeutic being administered and any other therapeutic agents being administered in conjunction therewith. Dosages can be determined for formulations in accordance with the invention using well-established routine pharmaceutical procedures for this purpose.

7. Dosing Regimens

Formulations of the invention can be administered in dosages and by techniques well-known to those skilled in the medical and veterinary arts taking into consideration such factors as the age, sex, weight, and condition of the particular patient, and the formulation that will be administered (e.g., solid vs. liquid). Doses for humans or other mammals can be determined without undue experimentation by the skilled artisan, from this disclosure, the documents cited herein, and the knowledge in the art.

In accordance with various embodiments, proper dosages and dosing plans will depend on numerous factors, and may vary in different circumstances. The parameters that will determine the optimal dosage plans to be administered typically will include some or all of the following: the disease being treated and its stage; the species of the subject, their health, gender, age, weight, and metabolic rate; other therapies being administered; and expected potential complications from the subject's history or genotype.

The optimal dosing plan in a given situation also will take into consideration the nature of the formulation, the way it is administered, the distribution route following administration, and the rate at which it will be cleared both from sites of action and from the subject's body. Finally, the determination of optimal dosing preferably will provide an effective dose that is neither below the threshold of maximal beneficial effect nor above the threshold where the deleterious effects associated with the dose of the active agents outweighs the advantages of the increased dose.

It will be appreciated that a "dose" may be delivered all at once, fractionally, or continuously over a period of time. The entire dose also may be delivered to a single location or spread fractionally over several locations. Furthermore, doses may remain the same over a treatment, or they may vary.

In various embodiments, formulations in accordance with the invention are administered in an initial dose, and thereafter maintained by further administrations. A formulation of the invention in some embodiments is administered by one method initially, and thereafter administered by the same method or by one or more different methods. The dosages of on-going administrations may be adjusted to maintain at certain values the levels of the active agents in the subject. In some embodiments the compositions are administered initially, and/or to maintain their level in the subject, by intravenous injection. In a variety of embodiments, other forms of administration are used.

Formulations of the invention may be administered in many frequencies over a wide range of times, including any suitable frequency and range of times that delivers a treatment-effective dose. Doses may be continuously delivered, administered every few hours, one or more times a day, every day, every other day or several times a week, or less frequently. In some embodiments they are administered over periods of one, two, three, four, five, six, seven, eight, nine, ten, eleven, twelve, thirteen, fourteen, or more days. In some embodiments they are administered over periods of one, two, three, four, five, six, seven, eight, nine, ten, eleven, twelve, or more months. In a variety of embodiments they are administered for a period of one, two, three, four, five, six, seven, eight, nine, ten, or more years. Suitable regimens for initial administration and further doses for sequential administrations may all be the same or may be variable. Appropriate regimens can be ascertained by the skilled artisan, from this disclosure, the documents cited herein, and the knowledge in the art. Generally lengths of treatment will be proportional to the length of the disease process, the effectiveness of the therapies being applied, and the condition and response of the subject being treated.

8. Diseases and Treatments

Self-buffering pharmaceutical protein compositions in accordance with the invention, in preferred embodiments, are useful to treat subjects suffering from a wide variety of disorders and diseases. As noted elsewhere herein, the invention provides, among others, self-buffering compositions of pharmaceutical antibodies, antibody-derived pharmaceutical proteins, and antibody-related pharmaceutical proteins, that can comprise Fc effector functions and binding domains specific for a wide variety of disease-related, targets and that are useful for treating disease. These proteins and self-buffering compositions thereof are described at length herein above, as well as their use in treating various disorders and diseases associated with their targets. Methods for using the compositions, including formulation methods, administration methods, doses, and dosing methods are all described illustratively above. The formulation and administration of any particular composition of the invention can be tailored to the treatment of a particular disease, using well-known and routine techniques in the arts for doing so, taken in light of the guidance provided by the present description of the invention. Among diseases usefully treated using self-buffering pharmaceutical protein formulations in accordance with various aspects and preferred embodiments of the invention are inflammatory diseases, cancers, metabolic disorders, neurological and renal disorders, to name just a few.

9, Packaging and Kits

The invention also provides kits comprising self-buffering protein formulations, particularly kits comprising in one more containers, a self-buffering pharmaceutical protein formulation and instructions regarding the use thereof, particularly such kits wherein the formulation is a pharmaceutically acceptable formulation for human use. Among preferred kits are those comprising one or more containers of a self-buffering protein formulation of the invention and one or more separate documents, information pertaining to the contents of the kit, and/or the use of its contents, particularly those wherein the protein is a biopharmaceutical protein, especially those wherein the protein is a biopharmaceutical protein formulated for the treatment of a disease in humans.

In certain aspects of the invention in this regard, preferred kits include kits as above further comprising one or more single or multi-chambered syringes (e.g., liquid syringes and lyosyringes) for administering one or more self-buffering protein formulations of the invention. In certain aspects of the invention in this regard, certain of the particularly preferred kits further comprise preloaded syringes. In further particularly preferred embodiments in this regard, the kits comprise a self-buffering pharmaceutical composition for parenteral administration, sealed in a vial under partial vacuum in a form ready for loading into a syringe and administration to a subject. In especially preferred embodiments in this regard, the composition is disposed therein under partial vacuum. In all of these regards and others, in certain further particularly preferred embodiments the kits contain one or more vials in accordance with any of the foregoing, wherein each vial contains a single unit dose for administration to a subject. In all these respects and others the invention further relates to kits comprising lyophilates, disposed as above, that upon reconstitution provide compositions in accordance therewith. In this regard, the invention further provides in certain of its preferred embodiments, kits that contain a lyophilate in accordance with the invention and a sterile diluent for reconstituting the lyophilate.

EXAMPLES

The present invention is additionally described by way of the following illustrative, non-limiting Examples.

Example 1

Acid Titrations and Buffer Capacities of Sodium Acetate Buffers in the Range pH 5.0 to 4.0

A stock solution of known concentration of acetic acid was prepared by diluting ultrapure glacial acetic acid in HPLC grade water and then titrating the pH up to the desired value with NaOH. Stocks were equilibrated to the air and to 21° C. Volumetric standards were prepared at a concentration of 1 N and diluted as necessary with HPLC water.

One mM, 2.5 mM, 5 mM, 7.5 mM, 10 mM, and 15 mM sodium acetate buffers were prepared by diluting the stock in HPLC water. The solutions were titrated with HCl. 0.2 N HCl was used for the 1, 2.5, and 5 DIM solutions, 0.4 N HCl was used for the 7.5 mM solution, and 0.8 N HCl was used for the 10 and 15 mM solutions. The titrations were performed using standard analytical laboratory techniques.

FIG. 1. Panel A shows the titration data and the least squares trend lines calculated from the data for each solution. The slope of the trend line calculated from each data set was taken as the buffer capacity of the corresponding acetate buffer. The linear dependence of buffer capacity on acetate buffer concentration is shown in FIG. 1, Panel B.

Example 2

Base Titrations and Buffer Capacities of Sodium Acetate Buffers in the Range pH 5.0 to 5.5

Acetate buffer stocks and solutions for titration were prepared as described in Example 1, The solutions were titrated as described in Example 1, except that the solutions were titrated from pH 5.0 to 5.5 and the titrations were done using NaOH instead of HCl. 0.2 N NaOH was used to titrate the 1, 2.5, and 5 mM solutions and 0.4 N NaOH was used for the 7.5, 10, and 15 mM solutions. The results of the titrations are shown in FIG. 2A. The linear dependence of buffer capacity on concentration of acetate buffer is displayed in FIG. 2B.

In addition to the items above, the following particular options are set forth;

1. A composition comprising a pharmaceutical protein, wherein at the pH of the composition, 21° C., one atmosphere, and equilibrium with ambient atmosphere, the protein has a buffer capacity per unit volume of at least that of approximately 4.0 mM sodium acetate buffer in pure water in the range of pH 5.0 to 4.0 or pH 5.0 to 5.5 under the same conditions, wherein further, exclusive of the buffer capacity of said protein, the buffer capacity per unit volume of the composition under the same conditions is no more than that of 2.0 mM sodium acetate buffer in pure water in the range of pH 5.0 to 4.0 or pH 5.0 to 5.5 under the same conditions, wherein the composition has been approved for pharmaceutical use by an authority legally empowered to grant such approval.

2. A composition comprising a pharmaceutical protein, wherein at the pH of the composition, 21° C., one atmosphere, and equilibrium with ambient atmosphere, the protein has a buffer capacity per unit volume of at least 1.50 mEq/liter-pH unit, wherein further, exclusive thereof, the buffer capacity per unit volume of the composition is less than 0.5 mEq/liter-pH unit, wherein the composition has been approved for pharmaceutical use by an authority legally empowered to grant such approval.

3. A composition according to option 1, wherein the protein provides at least 80% of the buffer capacity of the composition.

4. A composition according to option 3, wherein the concentration of the protein is between approximately 20 and 400 mg/ml.

5. A composition according to option 4, wherein the pH maintained by the buffering action of the protein is between approximately 3.5 and 8.0. 6. A composition according to option 5, wherein the pH maintained by the buffering action of the protein is between approximately 4 and 6.

7. A composition according to option 5, further comprising one or more pharmaceutically acceptable salts, wherein the total salt concentration is less than 150 mM.

8. A composition according to option 7, further comprising one or more pharmaceutically acceptable salts, wherein the total salt concentration is less than 100 mM, 9. A composition according to option 5, further comprising one or more pharmaceutically acceptable polyols.

10. A composition according to option 9, wherein the polyol is one or more of sorbitol, mannitol, sucrose, trehalose, or glycerol.

11. A composition according to option 5, further comprising one or more pharmaceutically acceptable surfactants.

12. A composition according to option 11, wherein the surfactant is one or more of polysorbate 20, polysorbate 80, other fatty acid esters of sorbitan, polyethoxylates, and poloxamer 188.

13. A composition according to option 9, further comprising one or more pharmaceutically acceptable surfactants.

14. A composition according to option 1, further comprising one or more pharmaceutically acceptable: osmotic balancing agents; anti-oxidants; antibiotics; antimycotics; bulking agents; lyoprotectants; anti-foaming agents; chelating agents; preservatives; colorants; analgesics; or additional pharmaceutical agents.

15. A composition according to option 5, further comprising one or more pharmaceutically acceptable: osmotic balancing agents; anti-oxidants; antibiotics; antimycotics; bulking agents; lyoprotectants; anti-foaming agents; chelating agents; preservatives; colorants; analgesics; or additional pharmaceutical agents.

16. A composition according to option 7, further comprising one or more pharmaceutically acceptable: osmotic balancing agents; anti-oxidants; antibiotics; antimycotics; bulking agents; lyoprotectants; anti-foaming agents; chelating agents; preservatives; colorants; analgesics; or additional pharmaceutical agents.

17. A composition according to any of options 1, 5, 7, 9, 11, 13, or 14, wherein the protein is or comprises: an antibody, Fab fragment, Fab2 fragment, Fab3 fragment, Fc fragment, scFv fragment, bis-scFv(s) fragment, minibody, diabody, triabody tetrabody, VhH domain, V-NAR domain, VH domain, VL domain, camel Ig, Ig NAR, receptibody, peptibody, or a variant or a derivative thereof or a protein related thereto, or a modification thereof.

18. A composition according to option 17, wherein the protein comprises an Fc fragment or a part thereof, or a variant or a derivative of an Fc fragment or a part thereof or a protein related to an Fc fragment or part thereof, or a modification of any thereof.

19. A composition according to option 18, wherein the protein further comprises a first binding moiety of a pair of cognate binding moieties.

20. A composition according to any of options 1, 5, 7, 9, 11, 13, or 14, wherein the protein is selected from the group consisting of proteins that bind specifically to one or more CD proteins, HER receptor family proteins, cell adhesion molecules, growth factors, nerve growth factors, fibroblast growth factors, transforming growth factors (TGF), insulin-like growth factors, osteoinductive factors, insulins and insulin-related proteins, coagulation and coagulation-related proteins, colony stimulating factors (CSFs), other blood and serum proteins blood group antigens; receptors, receptor-associated proteins, growth hormone receptors, T-cell receptors; neurotrophic factors, neurotrophins, relaxins, interferons, interleukins, viral antigens, lipoproteins, integrins, rheumatoid factors, immunotoxins, surface membrane proteins, transport proteins, homing receptors, addressins, regulatory proteins, and immunoadhesins, 21. A composition according to any of options 1, 5, 7, 9, 11, 13, or 14, wherein the protein is selected from the group consisting of: OPGL specific binding proteins, myostatin specific binding proteins, IL-4 receptor specific binding proteins, IL1-R1 specific binding proteins, Ang2 specific binding proteins, NGF-specific binding proteins, CD22 specific binding proteins, IGF-I receptor specific binding proteins, B7RP-1 specific binding proteins, IFN gamma specific binding proteins, TALL-I specific binding proteins, stem cell factors, Flt-3 ligands, and IL-17 receptors.

22. A composition according to any of options 1, 5, 7, 9, 11, 13 or 14, wherein the protein is selected from the group consisting of proteins that bind specifically to one or more of: CD3, CD4, CD8, CD19, CD20, CD34; HER2, HER3, HER4, the EGF receptor; LFA-I, MoI, p150,95,VLA-4, ICAM-I, VCAM, alpha v/beta 3 integrin; vascular endothelial growth factor ("VEGF"); growth hormone, thyroid stimulating hormone, follicle stimulating hormone, luteinizing hormone, growth hormone releasing factor, parathyroid hormone, mullerian-inhibiting substance, human macrophage inflammatory protein (MIP-I-alpha), erythropoietin (EPO), NGF-beta, platelet-derived growth factor (PDGF), aFGF, bFGF, epidermal growth factor (EGF), TGF-alpha, TGF-beta1, TGF-beta2, TGF-beta3, TGF-beta4, TGF-beta5, IGF-I, IGF-II, des(1-3)-IGF-I (brain IGF-I), insulin, insulin A-chain, insulin B-chain, proinsulin, insulin-like growth factor binding proteins;, such as, among others, factor VIII, tissue factor, von Willebrands factor, protein C, alpha-1-antitrypsin, plasminogen activators, such as urokinase and tissue plasminogen activator ("t-P A"), bombazine, thrombin, and thrombopoietin; M-CSF, GM-CSF, G-CSF, albumin, IgE, flk2/flt3 receptor, obesity (OB) receptor, bone-derived neurotrophic factor (BDNF), NT-3, NT-4, NT-5, NT-6); relaxin A-chain, relaxin B-chain, prorelaxin; interferon-alpha, -beta, and -gamma;IL-1 to IL-IO; AIDS envelope viral antigen; calcitonin, glucagon, atrial natriuretic factor, lung surfactant, tumor necrosis factor-alpha and -beta, enkephalinase, RANTES, mouse gonadotropin-associated peptide, Dnase, inhibin, and activin; protein A or D, bone morphogenetic protein (BMP), superoxide dismutase, decay accelerating factor (DAF).

23. A composition according to any of options 1, 5, 7, 9, 11, 13 or 14, wherein the protein is selected from the group consisting of: Actimmune (Interferon-gamma-Ib), Activase (Alteplase), Aldurazme (Laronidase), Amevive (Alefacept), Avonex (Interferon beta-Ia), BeneFIX(Nonacog alfa), Beromun (Tasonermin), Beatseron (Interferon-beta-1b), BEXXAR (Tositumomab), Tev-Tropin (Somatropin), Bioclate or RECOMBINATE (Recombinant), CEREZME (Imiglucerase), ENBREL (Etanercept), Eprex (epoetin alpha), EPOGEN/Procit (Epoetin alfa), FABRAZYME (Agalsidase beta), Fasturtec/Elitek ELITEK (Rasburicase), FORTEO (Teriparatide), GENOTROPIN (Somatropin), GlucaGen (Glucagon), Glucagon (Glucagon, rDNA origin), GONAL-F (follitropin alfa), KOGENATE FS (Octocog alfa), HERCEPTIN (Trastuzumab), HUMATROPE (SOMATROPIN), HUMIRA (Adalimumab), Insulin in Solution, INFERGEN (R) (Interferon alfacon-1), KINERET(R) (anakinra), Kogenate FS (Antihemophilic Factor), LEUKIN (SARGRAMOSTIM Recombinant human granulocyte-macrophage colony stimulating factor (rhuGM-CSF)), CAMPATH (Alemtuzumab), RITUXAN(R) (Rituximab), TNKase (Tenecteplase), MYLOTARG (gemtuzumab ozogamicin), NATRECOR(Nesiritide), ARANESP (darbepoetm alfa), NEULASTA (pegfilgrastim), NEUMEGA (oprelvekin), NEUPOGEN (Filgrastim), NORDITROPIN CARTRIDGES (Somatropin), NOVOSEVEN (Eptacog alfa), NUTROPIN AQ (somatropin), Oncaspar (pegaspargase), ONTAK (denileukin diftitox), ORTHOCLONE OKT (muromonab-CD3), OVIDREL (choriogonadotropin alfa), PEGASYS (peginterferon alfa-2a), PROLEUKIN (Aldesleukin), PULMOZYME (dornase alfa), Retavase (Reteplase), REBETRON Combination Therapy containing REBETOL(R) (Ribavirin) and INTRON(R) A (Interferon alfa-2b), REBIF (interferon beta-1a), REFACTO (Antihemophilic Factor), REFLUDAN (lepirudin), REMICADE (infliximab), REOPRO (abciximab)ROFERON(R)-A (Interferon alfa-2a), SIMULECT (baasiliximab), SOMAVERT (Pegivisomant), SYNAGIS(R) (palivizumab), Stemben (Ancestim, Stem cell factor), THYROGEN, INTRON(R) A (Interferon alfa-2b), PEG-INTRON(R) (Peginterferon alfa-2b), XIGRIS(R) (Drotrecogin alfa activated), XOLAIR(R) (Omalizumab), ZENAP AX(R) (daclizumab), and ZEVALIN(R) (Ibritumomab Tiuxetan).

24. A composition according to any of options 1, 5, 7, 9, 11, 13, or 14, wherein the protein is Ab-hOPGL or a fragment thereof, or a variant or derivative of Ab-hOPGL or of a fragment thereof, or an Ab-hOPGL related protein or fragment thereof, or a modification of any thereof, 25. A composition according to any of options 1, 5, 7, 9, 11, 13, or 14, wherein the protein is Ab-hOPGL.

26. A composition according to any of options 1, 5, 7, 9, 11, 13, or 14, wherein the protein is Ab-hIL4R or a fragment thereof, or a variant or derivative of Ab-hIL4R or of a fragment thereof, or an Ab-hIL4R related protein or fragment thereof, or a modification of any thereof.

27. A composition according to any of options 1, 5, 7, 9, 11, 13, or 14, wherein the protein is Ab-hIL4R.

28. A composition according to any of options 1, 5, 7, 9, 11, 13, or 14, wherein the protein is Ab-hB7RP1 or a fragment thereof, or a variant or derivative of Ab-hB7RP1 or of a fragment thereof, or an Ab-hB7RP1 related protein or fragment thereof, or a modification of any thereof.

29. A composition according to any of options 1, 5, 7, 9, 11, 13, or 14, wherein the protein is Ab-hB7RP 1.

30. A lyophilate which upon reconstitution provides a composition according to any of option 1, 5, 7, 9, 11, 13 or 14.

31. A kit comprising in one or more containers a composition according to any of option 1, 5, 7, 9, 11, 13 or 14 and instructions regarding the use thereof.

32. A kit comprising in one or more containers a lyophilate according to option 31, and instructions regarding the use thereof.

33. A method for treating a subject, comprising administering to a subject in an amount and by a route effective for treatment, a composition according to any of option 1, 5, 7, 9, 11, 13 or 14.

34. A process for preparing a composition according to any of option 1, 5, 7, 9, 11, 13 or 14, comprising removing residual buffer using a counter ion.

35. A process for preparing a composition according to option 34, comprising removing residual buffer using any one or more of the following in the presence of a counter ion: size exclusion chromatography, dialysis, and/or tangential flow filtration.

36. A process for preparing a composition according to option 35, comprising removing residual buffer using ion exchange chromatography.

37. A process for preparing a composition according to any of option 1, 5, 7, 9, 11, 13 or 14, comprising removing residual buffer by diafiltration against a bufferless solution having a pH below the desired pH.

38. A process for preparing a composition according to option 37, wherein following diafiltration the pH is adjusted to a desired pH by addition of dilute acid and/or dilute base.

39. A lyophilate which upon reconstitution provides a composition according to option 20.

40. A kit comprising in one or more containers a composition according to option 20 and instructions regarding the use thereof.

41. A kit comprising in one or more containers a lyophilate according to option 40, and instructions regarding the use thereof.

42. A method for treating a subject, comprising administering to a subject in an amount and by a route effective for treatment, a composition according to option 20.

43. A process for preparing a composition according to option 20, comprising removing residual buffer using a counter ion.

44. A process for preparing a composition according to option 43, comprising removing residual buffer using any one or more of the following in the presence of a counter ion: size exclusion chromatography, dialysis, and/or tangential flow filtration.

45. A process for preparing a composition according to option 43, comprising removing residual buffer using ion exchange chromatography.

46. A process for preparing a composition according to option 20, comprising removing residual buffer by diafiltration against a bufferless solution having a pH below the desired pH.

47. A process for preparing a composition according to option 46, wherein following diafiltration the pH is adjusted to a desired pH by addition of dilute acid and/or dilute base.

48. A lyophilate which upon reconstitution provides a composition according to option 21.

49. A kit comprising in one or more containers a composition according option 21 and instructions regarding the use thereof.

50. A kit comprising in one or more containers a lyophilate according to option 49, and instructions regarding the use thereof.

51. A method for treating a subject, comprising administering to a subject in an amount and by a route effective for treatment, a composition according to option 21.

52. A process for preparing a composition according to option 21, comprising removing residual buffer using a counter ion.

53. A process for preparing a composition according to option 52, comprising removing residual buffer using any one or more of the following in the presence of a counter ion: size exclusion chromatography, dialysis, and/or tangential flow filtration.

54. A process for preparing a composition according to option 52, comprising removing residual buffer using ion exchange chromatography.

55. A process for preparing a composition according to option 21, comprising removing residual buffer by diafiltration against a bufferless solution having a pH below the desired pH.

56. A process for preparing a composition according to option 55, wherein following diafiltration the pH is adjusted to a desired pH by addition of dilute acid and/or dilute base.

57. A lyophilate which upon reconstitution provides a composition according to option 23.

58. A kit comprising in one or more containers a composition according option 23 and instructions regarding the use thereof.

59. A kit comprising in one or more containers a lyophilate according to option 57, and instructions regarding the use thereof.

60. A method for treating a subject, comprising administering to a subject in an amount and by a route effective for treatment, a composition according to option 23.

61. A process for preparing a composition according to option 23, comprising removing residual buffer using a counter ion.

62. A process for preparing a composition according to option 61, comprising removing residual buffer using any one or more of the following in the presence of a counter ion: size exclusion chromatography, dialysis, and/or tangential flow filtration.

63. A process for preparing a composition according to option 61, comprising removing residual buffer using ion exchange chromatography.

64. A process for preparing a composition according to option 21, comprising removing residual buffer by diafiltration against a bufferless solution having a pH below the desired pH.

65. A process for preparing a composition according to option 62, wherein following diafiltration the pH is adjusted to a desired pH by addition of dilute acid and/or dilute base.

Example 3

Determination of Acetate by HPLC

Acetate was determined in acetate buffer samples using analytical SE-HPLC. A standard curve for peak areas as a function of acetate concentration was established by analysis of acetate in buffers of known acetate concentration. The amount of acetate in test samples was interpolated from the standard curve. A standard curve is shown in FIG. 3. Nominal and measured amount of acetate in test buffers are tabulated below the standard curve in the figure.

Example 4

Acid Titrations of Ab-hOPGL Formulations Over the Range of pH 5.0 to pH 4.0

Bulk Ab-hOPGL in 10 mM acetate (nominal value), 5% sorbitol, pH 5.0 was diafiltered against 5.25% sorbitol, pH 3.2 (adjusted with HCl) in a LABSCALE TFF® system (Millipore) with a multi-manifold cassette, using 3 Millipore Pellicon XL 50 regenerated cellulose ultra-filtration membranes. The diafiltration solution was exchanged 8 to 10 times over the course of the diafiltration for each formulation. Following diafiltration, the pH of the resulting buffer-free solution was measured and adjusted to pH 5.0, using 0.05 N HCl or 0.05 N NaOH.

One, 10, 30, 60, 90, and 110 mg/ml solutions were prepared for titration by dilution. The pH of each dilution was adjusted to pH 5.0 with NaOH or HCl as necessary. Titrations were carried out as described in the foregoing Examples, 0.2 N HCl was used to titrate the 1, 10, and 30 mg/ml solutions. 0.4 N HCl was used to titrate the 60 mg/ml solution. 0.8 N HCl was used to titrate the 90 and 110 solutions.

The results of the titrations are depicted in FIG. 4. The least squares regression line is shown for the dataset for each concentration. The buffer capacity was taken as the slope of the regression line for each concentration.

Example 5

Base Titrations of Ab-hOPGL Formulations Over the Range of pH 5.0 to 6.0

One, 10, 30, 60, 90, and 110 mg/ml solutions of Ab-hOPGL were prepared for titration as described in Example 4. Base titrations were carried out using NaOH as described in preceding Examples. 0.2 N NaOH was used for the 1, 10, 30, and 60 mg/ml solutions and 0.4 N NaOH was used for the 90 and 110 mg/ml solutions. Results of the titrations are depicted in the graph in FIG. 5. Linear regression lines are shown for the data for each concentration. The buffer capacity was taken as the slope of the regression line for each concentration.

Example 6

Residual Acetate Levels in Self-Buffering Ab-hOPGL Formulations

The amount of residual acetate was determined in Ab-hOPGL formulations using the methods described in Example 3. The results are depicted graphically in FIG. 6, which shows a standard curve relating HPLC measurements to acetate concentrations and, below the graph, a tabulation of the results of determinations made on Ab-hOPGL formulations at different concentrations, Ab-hOPGL concentrations are indicated on the left ("Nominal") and the measured concentration of acetate in each of the Ab-hOPGL concentration is indicated on the right.

Example 7

Buffer Capacity of Ab-hOPGL Formulations Plus or Minus Residual Acetate

In the Range of pH 5.0 to 1.0

Self-buffered. Ab-hOPGL formulations were prepared and titrated with HCl as described in foregoing Examples. In addition, data was adjusted by subtracting the contribution of residual acetate buffer based on the determination of acetate content by SE-HPLC as described in, for instance, Example 3. Buffer capacities were determined as described above. The same analysis was carried out on both sets of data. The results, depicted in FIG. 7, show the effect of residual acetate on the buffer capacity of the Ab-hOPGL preparations. The results make it clear that the buffer capacity of residual acetate is a minor factor in the buffer capacity of the self-buffering Ab-hOPGL formulations that were analyzed.

Example 8

Buffer Capacity of Ab-hOPGL Plus or Minus Residual Acetate in the Range of pH 5.0 to 6.0

Self-buffered Ab-hOPGL formulations were prepared and titrated with NaOH as described in foregoing Examples. In addition, data was adjusted by subtracting the contribution of residual acetate buffer based on the determination of acetate content by SE-HPLC as described in, for instance, Example 3. Buffer capacities were determined as described above. The same analysis was carried out on both sets of data. The results, depicted in FIG. 8, show the effect of residual acetate on the buffer capacity of the Ab-hOPGL preparations. The results make it clear that the buffer capacity of residual acetate is a minor factor in the buffer capacity of the self-buffering Ab-hOPGL formulations that were analyzed.

Example 9 pH and Ab-hOPGL Stability in Self-Buffered and Conventionally Buffered Formulations Self-buffering formulations of Ab-hOPGL were prepared as described in the foregoing Examples. In addition, formulations were made containing a conventional buffering agent, either acetate or glutamate. All formulations contained 60 mg/ml Ab-hOPGL. The stability of pH and Ab-hOPGL in the formulations was monitored for six months of storage at 4° C. Stability was monitored by determining monomeric Ab-hOPGL in the formulations over the time course of storage. The determination was made using SE-HPLC as described above. The results for all three formulations are shown in FIG. 9. Panel A shows the stability of Ab-hOPGL in the three formulations. Stability in the self-buffered formulation is as good as in the conventionally buffered formulations, Panel B shows the pH stability of the three formulations. Again, pH stability in the self-buffered formulation is as good as in the conventionally buffered formulations.

Example 10

Titration and Buffer Capacities of Ab-hB7RP1 pH 5.0 to 4.0

Self-buffering formulations of Ab-hB7RP1 were prepared in concentrations of 1, 10, 30, and 60 mg/ml, as described for Ab-hOPGL in the foregoing Examples. Titrations were carried out using HCl as described above. In addition, data was adjusted by subtracting the contribution of residual acetate buffer based on the determination of acetate content by SE-HPLC as described in, for instance, Example 3. FIG. 10, Panel A shows the titration results. FIG. 10, Panel B shows the dependence of buffer capacity on the concentration of Ab-hB7RP1 formulations before and after subtracting the contribution of residual acetate buffer. The results clearly show the self-buffering capacity of Ab-hB7RP1 in this pH range. At 40 mg/ml it provides approximately as much buffer capacity in this pH range as 10 mM sodium acetate buffer. At 60 mg/ml it provides approximately as much buffer capacity as 15 mM sodium acetate buffer.

Example 11

Titration and Buffer Capacities for Ab-hB7RP1—pH 5.0 to 6.0

Self-buffering formulations of Ab-hB7RP1 were prepared in concentrations of 1, 10, 30, and 60 mg/ml, as described for Ab-hOPGL in the foregoing Examples. Titrations were carried out using NaOH as described above. In addition, data was adjusted by subtracting the contribution of residual acetate buffer based on the determination of acetate content by SE-HPLC as described in, for instance, Example 3. FIG. 11, Panel A shows the titration results. FIG. 11, Panel B shows the dependence of buffer capacity on the concentration of Ab-hB7RP1 formulations before and after subtracting the contribution of residual acetate buffer. The results clearly show the self-buffering capacity of Ab-hB7RP1 in this pH range. At 60 mg/ml it provides approximately as much buffer capacity in this pH range as 10 mM sodium acetate buffer.

Example 12

Ab-hB7RP1 Stability in Self-Buffering and Conventionally Buffered Formulations at 4° C. and 29° C.

Ab-hB7RP1 was prepared as described in the foregoing Examples and formulated as described above, in self-buffering formulations and in formulations using a conventional buffering, agent, either acetate or glutamate. All formulations contained 60 mg/ml Ab-hB7RP1, The stability of the solution's pH and of the Ab-hB7RP1 in the solution was monitored for twenty-six weeks of storage at 4° C. or at 29°

C. Stability was monitored by determining monomeric Ab-hB7RP1 in the formulations over the time course of storage. The determination was made using SE-HPLC as described above. The results are shown in FIG. 12. Panel A shows the results for storage at 4° C. Panel B shows the results for storage at 29° C. Ab-hB7RP1 was at least as stable in the self-buffered formulation at 4° C. as the conventionally buffered formulations. At 29° C. the self-buffered formulation was at least as stable as the conventionally buffered formulations, and may have been slightly better from 10 weeks through the last time point.

Example 13 pH Stability of Self-Buffered Ab-hB7RP1 at 4° C. and 29° C.

Self-buffered Ab-hB7RP1 at 60 mg/ml was prepared as described in the foregoing Example. pH was monitored over the time course and at the same temperatures as described therein. The results are shown in FIG. 13.

Example 14

Buffer Capacity of Ab-hCD22 Formulations—pH 4.0 to 6.0

Self-buffering formulations of Ab-hCD22 were prepared and titrated over the range of pH 5.0 to 4.0 and the range of 5.0 to 6.0, as described for Ab-hOPGL and Ab-hB7RP1 in the foregoing Examples, Buffer capacities were calculated from the titration data, also as described above. Buffer capacity as a function of concentration is shown in FIG. 14 for both pH ranges. Panel A shows the buffer capacity of the Ab-hCD22 formulations over the range of pH 5.0 to 4.0. Buffer capacity is linearly dependent on concentration, and an approximately 21 mg/ml formulation of Ab-hCD22 has a buffer capacity equal to that of 10 mM sodium acetate buffer pH 5.0, measured in the same way. Panel B shows the buffer capacity as a function of concentration over the pH range 5.0 to 6.0. In this range of pH an approximately 30 mg/ml formulation of Ab-hCD22 has a buffer capacity equal to that of 10 in M sodium acetate buffer pH 5.0, measured in the same way.

Example 15

Titrations and Buffer Capacities of Ab-hIL4R Formulations—pH 5.0 to 4.0

Self-buffering formulations of Ab-hIL4R were prepared in concentrations of 1, 10, 25, and 90 mg/ml, as described for Ab-hOPGL, in the foregoing Examples. Titrations were carried out using HCl as described above. FIG. 15, Panel A shows the titration results. FIG. 15, Panel B shows the dependence of buffer capacity on the concentration of Ab-hIL4R. The results clearly show the self-buffering capacity of Ab-hIL4R in this pH range. At approximately 75 mg/ml it provides as much buffer capacity in this pH range as 10 DIM sodium acetate pH 5.0, measured in the same way.

Example 16

Titrations and Buffer Capacities of Ab-hIL4R Formulations—pH 5.0 to 6.0

Self-buffering formulations of Ab-hIL4R were prepared in concentrations of 1, 10, 25, and 90 mg/ml, as described for Ab-hOPGL in the foregoing Examples. Titrations were carried out using NaOH as described above. FIG. 16, Panel A shows the titration results. FIG. 16, Panel B shows the dependence of buffer capacity on the concentration of Ab-hIL4R in this pH range. The results clearly show the self-buffering capacity of Ab-hIL4R in this pH range. At approximately 90 mg/ml it provides as much buffer capacity in this pH range as 10 mM sodium acetate pH 5.0, measured in the same way.

Example 17

Ab-hIL4R and pH Stability in Acetate and Self-Buffered Ab-hIL4R Formulations at 37° C.

Self-buffered and acetate buffered formulations of Ab-hIL4R at pH 5.0 and 70 mg/ml were prepared as described above. pH and Ab-hIL4R stability were monitored in the formulations for 4 weeks at 37° C. Ab-hIL4R stability was monitored by SE-HPLC as described above. The results are shown in FIG. 17. Panel A shows that Ab-hIL4R is at least as stable in the self-buffered formulation as in the sodium acetate buffer formulation. Panel B shows that pH in the self-buffered formulation is as stable as in the sodium acetate buffer formulation.

Reference to Sequence Listing

The present application includes a Sequence Listing in electronic format. The Sequence Listing is provided as file entitled AMGN001C1SEQLIST,txt created and last modified on Oct. 25, 2018, which is 8,613 bytes in size, The information in the electronic format of the Sequence Listing is incorporated herein by reference in its entirety.

What is claimed:

1. A method for preparing an aqueous self-buffering formulation of a pharmaceutical antibody, comprising
using a technique selected from the group consisting of dialysis, ion exchange chromatography, and size exclusion chromatography to remove residual buffer from a first solution comprising said pharmaceutical antibody, a buffering agent other than said pharmaceutical antibody, and water, until said first solution is substantially free of any buffering agent other than said pharmaceutical antibody, thereby generating a second solution that (i) comprises said pharmaceutical antibody and water, and (ii) is substantially free of any buffering agent other than said pharmaceutical antibody, wherein said pharmaceutical antibody is adalimumab or an antibody to OPGL.

2. A method for preparing an aqueous self-buffering formulation of a pharmaceutical antibody, comprising
using a technique selected from the group consisting of dialysis, ion exchange chromatography, and size exclusion chromatography to remove residual buffer from a first solution comprising said pharmaceutical antibody, a buffering agent other than said pharmaceutical antibody, and water, until said pharmaceutical antibody is the only buffering agent in said first solution, thereby generating a second solution that comprises said pharmaceutical antibody and water, wherein said pharmaceutical antibody is the only buffering agent in said second solution, and wherein said pharmaceutical antibody is adalimumab or an antibody to OPGL.

3. A method for preparing an aqueous self-buffering formulation of a pharmaceutical antibody, comprising
using a technique selected from the group consisting of dialysis, ion exchange chromatography, and size exclusion chromatography to remove residual buffer from a first solution comprising said pharmaceutical antibody, a buffering agent other than said pharmaceutical antibody, and water, until said first solution is substantially free of any buffering agent other than said pharmaceutical antibody, thereby generating a second solution that (i) comprises said pharmaceutical antibody and water, and (ii) is substantially free of any buffering agent other than said pharmaceutical antibody, wherein said pharmaceutical antibody is an antibody to OPGL, hB7RP1, hCD22, hIL4R, or IGF-1 receptor.

4. The method of claim 3, wherein said pharmaceutical antibody is an antibody to hB7RP1.

5. The method of claim 3, wherein said pharmaceutical antibody is an antibody to hCD22.

6. The method of claim 3, wherein said pharmaceutical antibody is an antibody to hIL4R.

7. The method of claim 3, wherein said pharmaceutical antibody is an antibody to IGF-1 receptor.

8. A method for preparing an aqueous self-buffering formulation of a pharmaceutical antibody, comprising
using a technique selected from the group consisting of dialysis, ion exchange chromatography, and size exclusion chromatography to remove residual buffer from a first solution comprising said pharmaceutical antibody, a buffering agent other than said pharmaceutical antibody, and water, until said first solution is substantially free of any buffering agent other than said pharmaceutical antibody is the only buffering agent in said first solution, thereby generating a second solution that comprises said pharmaceutical antibody and water, wherein said pharmaceutical antibody is the only buffering agent in said second solution, and wherein said pharmaceutical antibody is an antibody to OPGL, hB7RP1, hCD22, hIL4R, or IGF-1 receptor.

9. A protein formulation comprising:
an antibody to OPGL, hB7RP1, hCD22, hIL4R, or IGF-1 receptor, or antibody 146B7 at a concentration between 20 and 200 mg/ml; and
water, wherein, apart from the antibody, there is no buffer in the formulation.

10. The protein formulation of claim 9, wherein the formulation, exclusive of the buffer capacity of the antibody, has a buffer capacity per unit volume of the solution at the pH of the solution, 21° C., one atmosphere of pressure, and equilibrium with ambient atmosphere of no more than that of 2.0 mM sodium acetate buffer in pure water in the range of pH 5.0 to 4.0 or pH 5.0 to 5.5 at 21° C., one atmosphere of pressure, and equilibrium with ambient atmosphere.

11. The protein formulation of claim 9, wherein the formulation further comprises a polyol.

12. The protein formulation of claim 11, wherein the polyol is selected from the group consisting of mannitol, sorbitol, and sucrose.

13. The protein formulation of claim 9, wherein the formulation further comprises a surfactant.

14. The protein formulation of claim 13, wherein the surfactant is selected from the group consisting of polysorbate 80 and polysorbate 20.

15. The protein formulation of claim 9, wherein a pH of the formulation is from 4 to 8.

16. The protein formulation of claim 9, wherein a pH of the formulation is from 4 to 6.

17. The protein formulation of claim 9, wherein a pH of the formulation is from 5 to 6.

18. The protein formulation of claim 9, wherein a pH of the formulation is 5.

19. The formulation of claim 9, wherein a pH of the formulation is between approximately 4 and 6.

20. The formulation of claim 9, further comprising one or more pharmaceutically acceptable salts, wherein the total salt concentration is less than 100 mM.

21. The formulation of claim 9, wherein the formulation further comprises a polyol.

22. The formulation of claim 21, wherein the polyol is one or more of sorbitol, mannitol, sucrose, trehalose, or glycerol.

23. The formulation of claim 13, wherein the surfactant is one or more of polysorbate 20, polysorbate 80, polyethoxylates, and poloxamer 188.

24. The formulation of claim 23, wherein the formulation further comprises a polyol, and wherein the polyol is one or more of sorbitol, mannitol, sucrose, trehalose, or glycerol.

25. The protein formulation of claim 9, wherein the antibody is the antibody to OPGL, hB7RP1, hCD22, or hIL4R.

26. The protein formulation of claim 9, wherein the antibody is the antibody to OPGL.

27. The protein formulation of claim 9, wherein the antibody is the antibody to hB7RP1.

28. The protein formulation of claim 9, wherein the antibody is the antibody to hCD22.

29. The protein formulation of claim 9, wherein the antibody is the antibody to hIL4R.

30. The protein formulation of claim 9, wherein the antibody is the antibody to IGF-1 receptor.

31. The protein formulation of claim 9, wherein the antibody is antibody 146B7.

32. The protein formulation of claim 9, wherein the antibody comprises a light chain complementarity determining region (CDR) CDR1 that is a CDR1 in SEQ ID NO: 1; a light chain CDR2 that is a CDR2 in SEQ ID NO: 1; a light chain CDR3 that is a CDR3 in SEQ ID NO: 1; a heavy chain CDR1 that is a CDR1 in SEQ ID NO: 2;
a heavy chain CDR2 that is a CDR2 in SEQ ID NO: 2; and
a heavy chain CDR3 that is a CDR3 in SEQ ID NO: 2.

33. The protein formulation of claim 9, wherein the antibody comprises a light chain variable region (LCVR) that is a LCVR in SEQ ID NO: 1;and a heavy chain variable region (HCVR) that is a LCVR in SEQ ID NO: 2.

34. The protein formulation of claim 9, wherein the antibody comprises a light chain comprising SEQ ID NO: 3 and a heavy chain comprising SEQ ID NO: 4.

35. The protein formulation of claim 9, wherein the antibody is Ab-hOPGL.

36. A protein formulation comprising:
an antibody to OPGL at a concentration between 20 and 200 mg/ml; and
water, wherein, apart from the antibody, there is no buffer in the formulation.

37. The protein formulation of claim 36, wherein the antibody comprises a light chain complementarity determining region (CDR) CDR1 that is a CDR1 in SEQ ID NO: 1; a light chain CDR2 that is a CDR2 in SEQ ID NO: 1; a light chain CDR3 that is a CDR3 in SEQ ID NO: 1; a heavy chain CDR1 that is a CDR1 in SEQ ID NO: 2;
a heavy chain CDR2 that is a CDR2 in SEQ ID NO: 2; and
a heavy chain CDR3 that is a CDR3 in SEQ ID NO: 2.

38. The protein formulation of claim 36, wherein the antibody comprises a light chain variable region (LCVR) that is a LCVR in SEQ ID NO: 1;and a heavy chain variable region (HCVR) that is a LCVR in SEQ ID NO: 2.

39. The protein formulation of claim 36, wherein the antibody comprises a light chain comprising SEQ ID NO: 3 and a heavy chain comprising SEQ ID NO: 4.

40. The protein formulation of claim 36, wherein the antibody is Ab-hOPGL.

41. An aqueous pharmaceutical formulation consisting of:
an antibody to OPGL, hB7RP1, hCD22, hIL4R, IGF-1 receptor, or antibody 146B7; and
water.

42. An aqueous pharmaceutical formulation comprising:
an antibody to OPGL, hB7RP1, hCD22, hIL4R, IGF-1 receptor, or antibody 146B7; and
water;
wherein the formulation does not comprise a buffering agent other than the antibody.

43. A protein formulation consisting of:
water; and
an antibody to OPGL, hB7RP1, hCD22, hIL4R, IGF-1 receptor, or antibody 146B7 at a concentration between 20 and 200 mg/ml.

44. A formulation consisting of:
water; and
an antibody to OPGL, hB7RP1, hCD22, hIL4R, IGF-1 receptor, or antibody 146B7 at a concentration between 20 and 200 mg/ml, wherein the formulation has a pH of 4 to 6.

45. The aqueous pharmaceutical formulation of claim 41, wherein the antibody is the antibody to OPGL, hB7RP1, hCD22, or hIL4R.

46. The aqueous pharmaceutical formulation of claim 41, wherein the antibody comprises a light chain complementarity determining region (CDR) CDR1 that is a CDR1 in SEQ ID NO: 1; a light chain CDR2 that is a CDR2 in SEQ ID NO: 1; a light chain CDR3 that is a CDR3 in SEQ ID NO: 1; a heavy chain CDR1 that is a CDR1 in SEQ ID NO: 2; a heavy chain CDR2 that is a CDR2 in SEQ ID NO: 2; and a heavy chain CDR3 that is a CDR3 in SEQ ID NO: 2.

47. The aqueous pharmaceutical formulation of claim 41, wherein the antibody comprises a light chain variable region (LCVR) that is a LCVR in SEQ ID NO: 1; and a heavy chain variable region (HCVR) that is a LCVR in SEQ ID NO: 2.

48. The aqueous pharmaceutical formulation of claim 41, wherein the antibody comprises a light chain comprising SEQ ID NO: 3 and a heavy chain comprising SEQ ID NO: 4.

49. The aqueous pharmaceutical formulation of claim 42, wherein the antibody is the antibody to OPGL, hB7RP1, hCD22, or hIL4R.

50. The aqueous pharmaceutical formulation of claim 42, wherein the antibody comprises a light chain complementarity determining region (CDR) CDR1 that is a CDR1 in SEQ ID NO: 1; a light chain CDR2 that is a CDR2 in SEQ ID NO: 1; a light chain CDR3 that is a CDR3 in SEQ ID NO: 1; a heavy chain CDR1 that is a CDR1 in SEQ ID NO: 2; a heavy chain CDR2 that is a CDR2 in SEQ ID NO: 2; and a heavy chain CDR3 that is a CDR3 in SEQ ID NO: 2.

51. The aqueous pharmaceutical formulation of claim 42, wherein the antibody comprises a light chain variable region (LCVR) that is a LCVR in SEQ ID NO: 1; and a heavy chain variable region (HCVR) that is a LCVR in SEQ ID NO: 2.

52. The aqueous pharmaceutical formulation of claim 42, wherein the antibody comprises a light chain comprising SEQ ID NO: 3 and a heavy chain comprising SEQ ID NO: 4.

53. The protein formulation of claim 43, wherein the antibody is the antibody to OPGL, hB7RP1, hCD22, or hIL4R.

54. The protein formulation of claim 43, wherein the antibody comprises a light chain complementarity determining region (CDR) CDR1 that is a CDR1 in SEQ ID NO: 1; a light chain CDR2 that is a CDR2 in SEQ ID NO: 1; a light chain CDR3 that is a CDR3 in SEQ ID NO: 1; a heavy chain CDR1 that is a CDR1 in SEQ ID NO: 2; a heavy chain CDR2 that is a CDR2 in SEQ ID NO: 2; and a heavy chain CDR3 that is a CDR3 in SEQ ID NO: 2.

55. The protein formulation of claim 43, wherein the antibody comprises a light chain variable region (LCVR) that is a LCVR in SEQ ID NO: 1; and a heavy chain variable region (HCVR) that is a LCVR in SEQ ID NO: 2.

56. The protein formulation of claim 43, wherein the antibody comprises a light chain comprising SEQ ID NO: 3 and a heavy chain comprising SEQ ID NO: 4.

57. The formulation of claim 44, wherein the antibody is the antibody to OPGL, hB7RP1, hCD22, or hIL4R.

58. The formulation of claim 44, wherein the antibody comprises a light chain complementarity determining region (CDR) CDR1 that is a CDR1 in SEQ ID NO: 1; a light chain CDR2 that is a CDR2 in SEQ ID NO: 1; a light chain CDR3 that is a CDR3 in SEQ ID NO: 1; a heavy chain CDR1 that is a CDR1 in SEQ ID NO: 2; a heavy chain CDR2 that is a CDR2 in SEQ ID NO: 2; and a heavy chain CDR3 that is a CDR3 in SEQ ID NO: 2.

59. The formulation of claim 44, wherein the antibody comprises a light chain variable region (LCVR) that is a LCVR in SEQ ID NO: 1; and a heavy chain variable region (HCVR) that is a LCVR in SEQ ID NO: 2.

60. The formulation of claim 44, wherein the antibody comprises a light chain comprising SEQ ID NO: 3 and a heavy chain comprising SEQ ID NO: 4.

61. A protein formulation comprising:
an antibody to OPGL at a concentration between 20 and 200 mg/ml, the antibody comprising:
a heavy chain comprising the amino acid sequence of:

```
E VQLLESGGGL VQPGGSLRLS CAASGFTFSS YAMSWVRQAP

GKGLEWVSGI TGSGGSTYYA DSVKGRFTIS RDNSKNTLYL

QMNSLRAEDT AVYYCAKDPG TTVIMSWFDP WGQGTLVTVS

SASTKGPSVF PLAPCSRSTS ESTAALGCLV KDYFPEPVTV

SWNSGALTSG VHTFPAVLQS SGLYSLSSVV TVPSSNFGTQ

TYTCNVDHKP SNTKVDKTVE RKCCVECPPC PAPPVAGPSV

FLFPPKPKDT LMISRTPEVT CVVVDVSHED PEVQFNWYVD

GVEVHNAKTK PREEQFNSTF RVVSVLTVVH QDWLNGKEYK

CKVSNKGLPA PIEKTISKTK GQPREPQVYT LPPSREEMTK

NQVSLTCLVK GFYPSDIAVE WESNGQPENN YKTTPPMLDS

DGSFFLYSKL TVDKSRWQQG NVFSCSVMHE ALHNHYTQKS

LSLSPGK
```

(residues 20 to 467 of SEQ ID NO: 2); and
a light chain comprising the amino acid sequence of:

```
EIVLTQSPGT LSLSPGERAT LSCRASQSVR GRYLAWYQQK

PGQAPRLLIY GASSRATGIP DRFSGSGSGT DFTLTISRLE

PEDFAVFYCQ QYGSSPRTFG QGTKVEIKRT VAAPSVFI FP

PSDEQLKSGT ASVVCLLNNF YPREAKVQWK VDNALQSGNS

QESVTEQDSK DSTYSLSSTL TLSKADYEKH KVYACEVTHQ

GLSSPVTKSF NRGEC
```

(residues 21 to 235 of SEQ ID NO: 1); and
water, wherein, apart from the antibody, there is no buffer in the formulation.

62. The protein formulation of claim 61, wherein the formulation, exclusive of the buffer capacity of the antibody, has a buffer capacity per unit volume of the solution at the pH of the solution, 21° C., one atmosphere of pressure, and equilibrium with ambient atmosphere of no more than that of 2.0 mM sodium acetate buffer in pure water in the range of pH 5.0 to 4.0 or pH 5.0 to 5.5 at 21° C., one atmosphere of pressure, and equilibrium with ambient atmosphere.

63. The protein formulation of claim 61, wherein, the formulation, exclusive of the buffer capacity of the antibody, has a buffer capacity per unit volume of the solution at the pH of the solution, 21° C., one atmosphere of pressure, and equilibrium with ambient atmosphere of no more than that of 2.0 mM sodium acetate buffer in pure water in the range of pH 5.0 to 4.0 or pH 5.0 to 5.5 at 21° C., one atmosphere of pressure, and equilibrium with ambient atmosphere, and wherein at the pH of the composition, 21° C., one atmosphere of pressure, and equilibrium with ambient atmosphere, the antibody has a buffer capacity per unit volume of at least that of 4.0 mM sodium acetate buffer in pure water in the range of pH 5.0 to 4.0 or pH 5.0 to 5.5 at 21° C., one atmosphere of pressure, and equilibrium with ambient atmosphere.

64. The protein formulation of claim 61, wherein the formulation further comprises a polyol.

65. The protein formulation of claim 64, wherein the polyol is selected from the group consisting of mannitol, sorbitol, and sucrose.

66. The protein formulation of claim 61, wherein the formulation further comprises a surfactant.

67. The protein formulation of claim 66, wherein the surfactant is selected from the group consisting of polysorbate 80 and polysorbate 20.

68. The protein formulation of claim 61, wherein a pH of the formulation is from 4 to 8.

69. The protein formulation of claim 61, wherein a pH of the formulation is from 4 to 6.

70. The protein formulation of claim 61, wherein a pH of the formulation is from 5 to 6.

71. The protein formulation of claim 61, wherein a pH of the formulation is 5.

72. An aqueous pharmaceutical formulation consisting of: an antibody to OPGL, the antibody comprising: a heavy chain comprising the amino acid sequence of:

```
E VQLLESGGGL VQPGGSLRLS CAASGFTFSS YAMSWVRQAP
GKGLEWVSGI TGSGGSTYYA DSVKGRFTIS RDNSKNTLYL
QMNSLRAEDT AVYYCAKDPG TTVIMSWFDP WGQGTLVTVS
SASTKGPSVF PLAPCSRSTS ESTAALGCLV KDYFPEPVTV
SWNSGALTSG VHTFPAVLQS SGLYSLSSVV TVPSSNFGTQ
TYTCNVDHKP SNTKVDKTVE RKCCVECPPC PAPPVAGPSV
FLFPPKPKDT LMISRTPEVT CVVVDVSHED PEVQFNWYVD
GVEVHNAKTK PREEQFNSTF RVVSVLTVVH QDWLNGKEYK
CKVSNKGLPA PIEKTISKTK GQPREPQVYT LPPSREEMTK
NQVSLTCLVK GFYPSDIAVE WESNGQPENN YKTTPPMLDS
DGSFFLYSKL TVDKSRWQQG NVFSCSVMHE ALHNHYTQKS
LSLSPGK
```

(residues 20 to 467 of SEQ ID NO: 2); and
a light chain comprising the amino acid sequence of:

```
EIVLTQSPGT LSLSPGERAT LSCRASQSVR GRYLAWYQQK
PGQAPRLLIY GASSRATGIP DRFSGSGSGT DFTLTISRLE
PEDFAVFYCQ QYGSSPRTFG QGTKVEIKRT VAAPSVFI FP
PSDEQLKSGT ASVVCLLNNF YPREAKVQWK VDNALQSGNS
QESVTEQDSK DSTYSLSSTL TLSKADYEKH KVYACEVTHQ
GLSSPVTKSF NRGEC
```

(residues 21 to 235 of SEQ ID NO: 1); and
water.

73. The aqueous pharmaceutical formulation of claim 72, wherein a pH of the formulation is from 5 to 6.

74. The aqueous pharmaceutical formulation of claim 72, wherein a pH of the formulation is from 4 to 8.

75. The aqueous pharmaceutical formulation of claim 72, wherein a pH of the formulation is from 4 to 6.

76. The aqueous pharmaceutical formulation of claim 72, wherein, the formulation, exclusive of the buffer capacity of the antibody, has a buffer capacity per unit volume of the solution at the pH of the solution, 21° C., one atmosphere of pressure, and equilibrium with ambient atmosphere of no more than that of 2.0 mM sodium acetate buffer in pure water in the range of pH 5.0 to 4.0 or pH 5.0 to 5.5 at 21° C., one atmosphere of pressure, and equilibrium with ambient atmosphere, and wherein at the pH of the composition, 21° C., one atmosphere of pressure, and equilibrium with ambient atmosphere, the antibody has a buffer capacity per unit volume of at least that of 4.0 mM sodium acetate buffer in pure water in the range of pH 5.0 to 4.0 or pH 5.0 to 5.5 at 21° C., one atmosphere of pressure, and equilibrium with ambient atmosphere.

77. An aqueous pharmaceutical formulation comprising: an antibody to OPGL, the antibody comprising: a heavy chain comprising the amino acid sequence of:

```
E VQLLESGGGL VQPGGSLRLS CAASGFTFSS YAMSWVRQAP
GKGLEWVSGI TGSGGSTYYA DSVKGRFTIS RDNSKNTLYL
QMNSLRAEDT AVYYCAKDPG TTVIMSWFDP WGQGTLVTVS
SASTKGPSVF PLAPCSRSTS ESTAALGCLV KDYFPEPVTV
SWNSGALTSG VHTFPAVLQS SGLYSLSSVV TVPSSNFGTQ
TYTCNVDHKP SNTKVDKTVE RKCCVECPPC PAPPVAGPSV
FLFPPKPKDT LMISRTPEVT CVVVDVSHED PEVQFNWYVD
GVEVHNAKTK PREEQFNSTF RVVSVLTVVH QDWLNGKEYK
CKVSNKGLPA PIEKTISKTK GQPREPQVYT LPPSREEMTK
NQVSLTCLVK GFYPSDIAVE WESNGQPENN YKTTPPMLDS
DGSFFLYSKL TVDKSRWQQG NVFSCSVMHE ALHNHYTQKS
LSLSPGK
```

(residues 20 to 467 of SEQ ID NO: 2); and
a light chain comprising the amino acid sequence of:

```
EIVLTQSPGT LSLSPGERAT LSCRASQSVR GRYLAWYQQK
PGQAPRLLIY GASSRATGIP DRFSGSGSGT DFTLTISRLE
PEDFAVFYCQ QYGSSPRTFG QGTKVEIKRT VAAPSVFI FP
PSDEQLKSGT ASVVCLLNNF YPREAKVQWK VDNALQSGNS
QESVTEQDSK DSTYSLSSTL TLSKADYEKH KVYACEVTHQ
GLSSPVTKSF NRGEC
```

(residues 21 to 235 of SEQ ID NO: 1); and
water;
wherein the formulation does not comprise a buffering agent other than the antibody.

78. The aqueous pharmaceutical formulation of claim 77, wherein the formulation further comprises a non-ionizable excipient.

79. The aqueous pharmaceutical formulation of claim 77, wherein the formulation further comprises a polyol.

80. The aqueous pharmaceutical formulation of claim 79, wherein the polyol is selected from the group consisting of mannitol, sorbitol, and sucrose.

81. The aqueous pharmaceutical formulation of claim 77, wherein the formulation further comprises a surfactant.

82. The aqueous pharmaceutical formulation of claim 81, wherein the surfactant is selected from the group consisting of polysorbate 80 and polysorbate 20.

83. The aqueous pharmaceutical formulation of claim 77, wherein the pH of the formulation is from 4 to 8.

84. The aqueous pharmaceutical formulation of claim 77, wherein the pH of the formulation is from 4 to 6.

85. The aqueous pharmaceutical formulation of claim 77, wherein the pH of the formulation is from 5 to 6.

86. The aqueous pharmaceutical formulation of claim 77, wherein the pH of the formulation is 5.

87. The aqueous pharmaceutical formulation of claim 77, wherein, the formulation, exclusive of the buffer capacity of the antibody, has a buffer capacity per unit volume of the solution at the pH of the solution, 21° C., one atmosphere of pressure, and equilibrium with ambient atmosphere of no more than that of 2.0 mM sodium acetate buffer in pure water in the range of pH 5.0 to 4.0 or pH 5.0 to 5.5 at 21° C., one atmosphere of pressure, and equilibrium with ambient atmosphere, and wherein at the pH of the composition, 21° C., one atmosphere of pressure, and equilibrium with ambient atmosphere, the antibody has a buffer capacity per unit volume of at least that of 4.0 mM sodium acetate buffer in pure water in the range of pH 5.0 to 4.0 or pH 5.0 to 5.5 at 21° C., one atmosphere of pressure, and equilibrium with ambient atmosphere.

88. A protein formulation consisting of:
water; and
an antibody to OPGL at a concentration between 20 and 200 mg/ml in the water, the antibody comprising:
a heavy chain comprising the amino acid sequence of:

```
E VQLLESGGGL VQPGGSLRLS CAASGFTFSS YAMSWVRQAP
GKGLEWVSGI TGSGGSTYYA DSVKGRFTIS RDNSKNTLYL
QMNSLRAEDT AVYYCAKDPG TTVIMSWFDP WGQGTLVTVS
SASTKGPSVF PLAPCSRSTS ESTAALGCLV KDYFPEPVTV
SWNSGALTSG VHTFPAVLQS SGLYSLSSVV TVPSSNFGTQ
TYTCNVDHKP SNTKVDKTVE RKCCVECPPC PAPPVAGPSV
FLFPPKPKDT LMISRTPEVT CVVVDVSHED PEVQFNWYVD
GVEVHNAKTK PREEQFNSTF RVVSVLTVVH QDWLNGKEYK
CKVSNKGLPA PIEKTISKTK GQPREPQVYT LPPSREEMTK
NQVSLTCLVK GFYPSDIAVE WESNGQPENN YKTTPPMLDS
DGSFFLYSKL TVDKSRWQQG NVFSCSVMHE ALHNHYTQKS
LSLSPGK
```

(residues 20 to 467 of SEQ ID NO: 2); and
a light chain comprising the amino acid sequence of:

```
EIVLTQSPGT LSLSPGERAT LSCRASQSVR GRYLAWYQQK
PGQAPRLLIY GASSRATGIP DRFSGSGSGT DFTLTISRLE
PEDFAVFYCQ QYGSSPRTFG QGTKVEIKRT VAAPSVFI FP
PSDEQLKSGT ASVVCLLNNF YPREAKVQWK VDNALQSGNS
QESVTEQDSK DSTYSLSSTL TLSKADYEKH KVYACEVTHQ
GLSSPVTKSF NRGEC
```

(residues 21 to 235 of SEQ ID NO: 1).

89. The protein formulation of claim 88, wherein the self-buffering formulation is a pharmaceutical formulation.

90. The protein formulation of claim 88, wherein the pH of the self-buffering formulation is from 4 to 8.

91. The protein formulation of claim 88, wherein the pH of the formulation is from 5 to 6.

92. The protein formulation of claim 88, wherein the pH of the formulation is from 4 to 6.

93. A formulation consisting of:
water; and
an antibody to OPGL at a concentration between 20 and 200 mg/ml, wherein the formulation has a pH of 4 to 6, the antibody comprising:
a heavy chain comprising the amino acid sequence of:

```
E VQLLESGGGL VQPGGSLRLS CAASGFTFSS YAMSWVRQAP
GKGLEWVSGI TGSGGSTYYA DSVKGRFTIS RDNSKNTLYL
QMNSLRAEDT AVYYCAKDPG TTVIMSWFDP WGQGTLVTVS
SASTKGPSVF PLAPCSRSTS ESTAALGCLV KDYFPEPVTV
SWNSGALTSG VHTFPAVLQS SGLYSLSSVV TVPSSNFGTQ
TYTCNVDHKP SNTKVDKTVE RKCCVECPPC PAPPVAGPSV
FLFPPKPKDT LMISRTPEVT CVVVDVSHED PEVQFNWYVD
GVEVHNAKTK PREEQFNSTF RVVSVLTVVH QDWLNGKEYK
CKVSNKGLPA PIEKTISKTK GQPREPQVYT LPPSREEMTK
NQVSLTCLVK GFYPSDIAVE WESNGQPENN YKTTPPMLDS
DGSFFLYSKL TVDKSRWQQG NVFSCSVMHE ALHNHYTQKS
LSLSPGK
```

(residues 20 to 467 of SEQ ID NO: 2); and
a light chain comprising the amino acid sequence of:

```
EIVLTQSPGT LSLSPGERAT LSCRASQSVR GRYLAWYQQK
PGQAPRLLIY GASSRATGIP DRFSGSGSGT DFTLTISRLE
PEDFAVFYCQ QYGSSPRTFG QGTKVEIKRT VAAPSVFI FP
PSDEQLKSGT ASVVCLLNNF YPREAKVQWK VDNALQSGNS
QESVTEQDSK DSTYSLSSTL TLSKADYEKH KVYACEVTHQ
GLSSPVTKSF NRGEC
```

(residues 21 to 235 of SEQ ID NO: 1).

94. The formulation of claim 93, wherein the pH of the formulation is from 5 to 6.

95. The method formulation of claim 1, wherein the second solution, exclusive of the buffer capacity of the antibody, has a buffer capacity per unit volume of the solution at the pH of the solution, 21° C., one atmosphere of pressure, and equilibrium with ambient atmosphere of no more than that of 2.0 mM sodium acetate buffer in pure water in the range of pH 5.0 to 4.0 or pH 5.0 to 5.5 at 21° C., one atmosphere of pressure, and equilibrium with ambient atmosphere.

96. The method formulation of claim 3, wherein the second solution, exclusive of the buffer capacity of the antibody, has a buffer capacity per unit volume of the solution at the pH of the solution, 21° C., one atmosphere of pressure, and equilibrium with ambient atmosphere of no more than that of 2.0 mM sodium acetate buffer in pure water in the range of pH 5.0 to 4.0 or pH 5.0 to 5.5 at 21° C., one atmosphere of pressure, and equilibrium with ambient atmosphere.

* * * * *

UNITED STATES PATENT AND TRADEMARK OFFICE
CERTIFICATE OF CORRECTION

| | | |
|---|---|---|
| PATENT NO. | : 11,607,451 B2 | Page 1 of 16 |
| APPLICATION NO. | : 13/797622 | |
| DATED | : March 21, 2023 | |
| INVENTOR(S) | : Yatin R. Gokarn | |

It is certified that error appears in the above-identified patent and that said Letters Patent is hereby corrected as shown below:

On the Title Page

Column 1, Lines 4-5, item [*], under Notice:, delete "This patent is subject to a terminal disclaimer".

Column 1, Line 4, under Related U.S. Application Data, delete "PCT/US2006/022509" and insert --PCT/US2006/022599--.

Column 2, Line 1, under Date of Patent:, delete "*".

On Page 3, 1st Column, Line 28, item [56], under Other Publications, after "(2002)", insert --)--.

On Page 4, 1st Column, Line 12, item [56], under Other Publications, delete "Etannercept" and insert --Etanercept--.

On Page 4, 1st Column, Line 13, item [56], under Other Publications, delete "Amm" and insert --Ann--.

On Page 4, 1st Column, Line 33, item [56], under Other Publications, delete "Pharmacuetial" and insert --Pharmaceutical--.

On Page 4, 1st Column, Line 39, item [56], under Other Publications, delete "Inyrtlrukin" and insert --Interleukin--.

On Page 4, 2nd Column, Line 12, item [56], under Other Publications, delete "Prethombin" and insert --Prothrombin--.

On Page 4, 2nd Column, Line 26, item [56], under Other Publications, delete "(etamercept)" and insert --(etanercept)--.

Signed and Sealed this
Sixteenth Day of September, 2025

Coke Morgan Stewart
*Acting Director of the United States Patent and Trademark Office*

On Page 4, 2nd Column, Line 27, item [56], under Other Publications, delete "(etamercept)" and insert --(etanercept)--.

On Page 4, 2nd Column, Line 37, item [56], under Other Publications, delete "Artifical" and insert --Artificial--.

On Page 4, 2nd Column, Line 59, item [56], under Other Publications, delete "Biotechology" and insert --Biotechnology--.

On Page 5, 1st Column, Line 65, item [56], under Other Publications, delete "Purfication" and insert --Purification--.

On Page 5, 1st Column, Line 65, item [56], under Other Publications, delete "Streptoccal" and insert --Streptococcal--.

On Page 5, 2nd Column, Line 37, item [56], under Other Publications, delete ""Immunobiologies" and insert --"Immunobiologics--.

On Page 5, 2nd Column, Line 46, item [56], under Other Publications, delete "Biologies" and insert --Biologics--.

On Page 5, 2nd Column, Line 56, item [56], under Other Publications, delete "13/188,329" and insert --13/797,622--.

On Page 5, 2nd Column, Line 59, item [56], under Other Publications, delete "UsingJnjectable Biologies." and insert --Using Injectable Biologics.--.

On Page 5, 2nd Column, Line 71, item [56], under Other Publications, delete "13/188,329" and insert --13/797,622--.

On Page 6, 1st Column, Line 14, item [56], under Other Publications, delete "13/188,329" and insert --13/797,622--.

On Page 6, 1st Column, Line 47, item [56], under Other Publications, delete "13/188,329" and insert --13/797,622--.

On Page 6, 1st Column, Line 67, item [56], under Other Publications, delete "13/188,329" and insert --13/797,622--.

On Page 6, 2nd Column, Line 3, item [56], under Other Publications, delete "13/188,329" and insert --13/797,622--.

On Page 6, 2nd Column, Line 42, item [56], under Other Publications, delete "13/188,329" and insert --13/797,622--.

On Page 6, 2nd Column, Line 47, item [56], under Other Publications, delete "13/188,329" and insert --13/797,622--.

On Page 6, 2nd Column, Line 52, item [56], under Other Publications, delete "13/188,329" and insert --13/797,622--.

On Page 6, 2nd Column, Line 56, item [56], under Other Publications, delete "13/188,329" and insert --13/797,622--.

On Page 6, 2nd Column, Line 60, item [56], under Other Publications, delete "13/188,329" and insert --13/797,622--.

On Page 6, 2nd Column, Line 63, item [56], under Other Publications, delete "13/188,329)" and insert --60/690,582)--.

On Page 6, 2nd Column, Line 64, item [56], under Other Publications, delete "13/188,329" and insert --13/797,622--.

On Page 6, 2nd Column, Line 68, item [56], under Other Publications, delete "13/188,329" and insert --13/797,622--.

On Page 6, 2nd Column, Line 71, item [56], under Other Publications, delete "13/188,329" and insert --13/797,622--.

On Page 7, 1st Column, Line 2, item [56], under Other Publications, delete "13/188,329" and insert --13/797,622--.

On Page 7, 1st Column, Line 5, item [56], delete "13/188,329" and insert --13/797,622--.

On Page 7, 1st Column, Line 8, item [56], delete "13/188,329" and insert --13/797,622--.

On Page 7, 1st Column, Line 11, item [56], delete "13/188,329" and insert --13/797,622--.

On Page 7, 1st Column, Line 33, item [56], delete "13/188,329" and insert --13/797,622--.

On Page 7, 1st Column, Line 36, item [56], under Other Publications, delete "13/188,329" and insert --13/797,622--.

On Page 7, 1st Column, Line 39, item [56], under Other Publications, delete "13/188,329" and insert --13/797,622--.

CERTIFICATE OF CORRECTION (continued)
U.S. Pat. No. 11,607,451 B2

On Page 7, 1st Column, Line 42, item [56], under Other Publications, delete "13/188,329" and insert --13/797,622--.

On Page 7, 1st Column, Line 44, item [56], under Other Publications, delete "Oppostion" and insert --Opposition--.

On Page 7, 1st Column, Line 46, item [56], under Other Publications, delete "13/188,329" and insert --13/797,622--.

On Page 7, 2nd Column, Line 32, item [56], under Other Publications, delete "NavlD" and insert --NavID--.

On Page 7, 2nd Column, Line 34, item [56], under Other Publications, delete "NavlD_301.htm" and insert --NavID_301.htm]--.

On Page 7, 2nd Column, Line 43, item [56], under Other Publications, delete "Diptheria," and insert --Diphtheria,--.

On Page 8, 1st Column, Line 5, item [56], under Other Publications, delete "cols." and insert --columns.--.

On Page 8, 1st Column, Line 33, item [56], under Other Publications, delete "Pharmacuetical." and insert --Pharmaceutical.--.

On Page 9, 1st Column, Line 14, item [56], under Other Publications, delete "13/188,329" and insert --13/797,622--.

On Page 9, 2nd Column, Line 39, item [56], under Other Publications, delete "Pulmozyne® (dronase" and insert --Pulmozyme® (dornase--.

On Page 9, 2nd Column, Line 42, item [56], under Other Publications, delete "lnterleukin-" and insert --Interleukin- --.

On Page 9, 2nd Column, Line 52, item [56], under Other Publications, delete "13/188,329" and insert --13/797,622--.

On Page 9, 2nd Column, Line 55, item [56], under Other Publications, delete "(inflizimab)" and insert --(infliximab)--.

On Page 9, 2nd Column, Line 56, item [56], under Other Publications, delete "(inflizimab)" and insert --(infliximab)--.

On Page 10, 2nd Column, Line 18, item [56], delete "soultions." and insert --solutions.--.

CERTIFICATE OF CORRECTION (continued)
U.S. Pat. No. 11,607,451 B2

On Page 10, 2nd Column, Line 56, item [56], delete "Mediciness.," and insert --Medicines.,--.

On Page 11, 1st Column, Line 49, item [56], delete "immunogluobulin" and insert --immunoglobulin--.

On Page 11, 1st Column, Line 52, item [56], delete "Immuniology," and insert --Immunology,--.

On Page 11, 1st Column, Line 66, item [56], under Other Publications, delete "Grit." and insert --Crit.--.

On Page 11, 2nd Column, Line 3, item [56], under Other Publications, delete "Organd" and insert --Organs--.

On Page 11, 2nd Column, Line 44, item [56], under Other Publications, delete "13/188,329" and insert --13/797,622--.

On Page 11, 2nd Column, Line 47, item [56], under Other Publications, delete "13/188,329" and insert --13/797,622--.

On Page 11, 2nd Column, Line 56, item [56], under Other Publications, delete "13/188,329" and insert --13/797,622--.

On Page 11, 2nd Column, Line 59, item [56], under Other Publications, delete "13/188,329" and insert --13/797,622--.

On Page 12, 2nd Column, Line 62, item [56], under Other Publications, delete "103976s5231lbi" and insert --103976s5231lbl--.

On Page 12, 2nd Column, Line 65, item [56], under Other Publications, delete "1250s1980156" and insert --125019s0156--.

On Page 13, 1st Column, Line 1, item [56], under Other Publications, delete "May 2, 20203]." and insert --May 23, 2020].--.

On Page 13, 2nd Column, Line 42, item [56], under Other Publications, delete ".eom" and insert --.com--.

On Page 13, 2nd Column, Line 52, item [56], under Other Publications, delete "hi B4"," and insert --h1B4",--.

On Page 14, 1st Column, Line 19, item [56], under Other Publications, after "Platform", insert --https://www.j-platpat.inpit.go.jp/;--.

CERTIFICATE OF CORRECTION (continued)

U.S. Pat. No. 11,607,451 B2

On Page 14, 2nd Column, Line 19, item [56], under Other Publications, delete "3-galactosidase"," and insert --β-galactosidase",--.

In the Specification

In Column 1, Line 60, delete "action, if" and insert --action. If--.

In Column 3, Line 49, delete "Drag" and insert --Drug--.

In Column 4, Line 2, delete "DEM" and insert --mM--.

In Column 4, Line 13, delete "1.0" and insert --1.0 mM,--.

In Column 4, Line 31, delete "6," and insert --6.--.

In Column 4, Line 39, delete "determined," and insert --determined--.

In Column 5, Line 20, delete "596" and insert --5%--.

In Column 5, Line 25, delete "sotbitan," and insert --sorbitan,--.

In Column 5, Line 49, delete "owing," and insert --following,--.

In Column 5, Line 59, delete "Fe" and insert --Fc--.

In Column 5, Line 65, delete "Fe" and insert --Fc--.

In Column 5, Line 66, delete "Fe" and insert --Fc--.

In Column 6, Line 26, delete "immunoadhesins," and insert --immunoadhesins.--.

In Column 6, Line 31, delete "proteins." and insert --proteins,--.

In Column 6, Line 41, delete "LEA" and insert --LFA--.

In Column 6, Line 43, delete "("VEGF")," and insert --("VEGF");--.

In Column 6, Line 49, delete "TGF-beta" and insert --TGF-beta1,--.

In Column 6, Line 53, delete "proteins:" and insert --proteins;--.

In Column 6, Line 54, delete "Willebrands" and insert --Willebrand--.

CERTIFICATE OF CORRECTION (continued)
U.S. Pat. No. 11,607,451 B2

In Column 6, Line 54, delete "-L-" and insert -- -1- --.

In Column 6, Line 55, after "such", insert --as--.

In Column 6, Line 56, delete ""t-PA")" insert --("t-PA")--.

In Column 6, Line 59, delete "NT-6);" and insert --NT-6;--.

In Column 6, Line 67, delete "(DAT)." and insert --(DAF).--.

In Column 7, Line 4, delete "Aldurazme" and insert --Aldurazyme--.

In Column 7, Line 6, delete "(Tasonermin)" and insert --(Tasonermin),--.

In Column 7, Line 6, delete "Beatseron" and insert --Betaseron--.

In Column 7, Line 8, delete "CEREZME" and insert --CEREZYME--.

In Column 7, Line 28, delete "NUTROPIIN" and insert --NUTROPIN--.

In Column 7, Lines 31-32, delete "(Aldesletikin)," and insert --(Aldesleukin),--.

In Column 7, Line 35, delete "REHIF" and insert --REBIF--.

In Column 7, Line 38, delete "SINIULECT" and insert --SIMULECT--.

In Column 7, Line 38, delete "(baasiliximab)," and insert --(basiliximab),--.

In Column 7, Lines 38-39, delete "(Pegivisomant)," and insert --(Pegvisomant),--.

In Column 7, Line 44, delete "Thixetan)." and insert --Tiuxetan).--.

In Column 7, Line 65, delete "in M" and insert --mM--.

In Column 8, Line 30, delete "preparation" and insert --preparation,--.

In Column 8, Line 44, after "Example", insert --1.--.

In Column 8, Line 53, delete "microequivlents" and insert --microequivalents--.

In Column 9, Line 3, delete "microequivlents" and insert --microequivalents--.

In Column 9, Line 40, delete "4.0," and insert --4.0.--.

CERTIFICATE OF CORRECTION (continued)

U.S. Pat. No. 11,607,451 B2

In Column 9, Line 44, after "ml" insert --of--.

In Column 9, Line 46, after "Ab-hOPGL" insert --in--.

In Column 9, Line 48, after "Example" insert --1--.

In Column 10, Line 5, after "depicts the" insert --pH--.

In Column 10, Line 12 (Approx.), after "of" insert --pH--.

In Column 10, Line 15 (Approx.), delete "nil" and insert --ml--.

In Column 10, Line 29 (Approx.), delete "ing/ml." and insert --mg/ml.--.

In Column 10, Line 49, delete "Shown" and insert --shown--.

In Column 10, Line 60, delete "Ab-hB7RP" and insert --Ab-hB7RP1,--.

In Column 10, Line 61, delete "Ab-hB7RP" and insert --Ab-hB7RP1--.

In Column 10, Line 62, delete "storage," and insert --storage--.

In Column 10, Line 65, delete "axis," and insert --axis.--.

In Column 11, Line 9, delete "11" and insert --14--.

In Column 11, Line 18, delete "nil" and insert --ml--.

In Column 11, Line 20, delete "signal." and insert --mg/ml.--.

In Column 11, Line 47, delete "data," and insert --data.--.

In Column 13, Line 40, delete "proteins," and insert --proteins.--.

In Column 13, Line 48, delete "0.1" and insert --J--.

In Column 14, Line 43, delete "Molarity" and insert --Molarity=--.

In Column 14, Line 61, delete "nova" and insert --novo--.

In Column 14, Line 67, delete "well know" and insert --well-known--.

In Column 15, Line 34, delete "mute" and insert --route--.

CERTIFICATE OF CORRECTION (continued)
U.S. Pat. No. 11,607,451 B2

In Column 16, Line 29, delete "(h)" and insert --(b)--.

In Column 17, Line 1, delete "hut" and insert --but--.

In Column 17, Line 28, delete "polypeptide," and insert --polypeptide.--.

In Column 17, Line 37, delete "as" and insert --as,--.

In Column 17, Line 41, delete "R," and insert --R.--.

In Column 18, Line 5, delete ""pharmaceutical,"" and insert --"pharmaceutical."--.

In Column 18, Line 52, delete "thereof" and insert --thereof,--.

In Column 19, Line 10 (Approx.), delete "neoplasm," and insert --neoplasm.--.

In Column 19, Line 23, delete "related," and insert --related--.

In Column 19, Line 57, delete "agents," and insert --agents.--.

In Column 19, Line 66, delete "in M." and insert --mM.--.

In Column 20, Line 9, delete "ich" and insert --which--.

In Column 20, Line 27, delete "thr" and insert --for--.

In Column 20, Line 37, delete "base," and insert --base.--.

In Column 20, Line 41, delete "amount," and insert --amount.--.

In Column 20, Line 52, delete "Hasselbaleh" and insert --Hasselbalch--.

In Column 21, Line 6 (Approx.), delete "in M," and insert --mM,--.

In Column 21, Line 19, delete "nanonmoles" and insert --nanomoles--.

In Column 21, Line 22, delete "thr" and insert --for--.

In Column 21, Line 22, delete "4.76," and insert --4.76.--.

In Column 22, Line 19, delete "t" and insert --the--.

In Column 22, Line 50, Before "of" insert --pH--.

CERTIFICATE OF CORRECTION (continued)
U.S. Pat. No. 11,607,451 B2

In Column 23, Line 9, delete "thr" and insert --for--.

In Column 24, Line 56, delete "REMINGTON;" and insert --REMINGTON:--.

In Column 25, Line 18, delete "forms," and insert --forms.--.

In Column 25, Line 20, delete "molts/mass" and insert --moles/mass--.

In Column 25, Line 21, delete "kg." and insert --kg).--.

In Column 25, Line 26, delete "described, above. And," and insert --described above. And--.

In Column 25, Line 27, delete "standard," and insert --standard--.

In Column 25, Line 31, delete "employed," and insert --employed--.

In Column 25, Line 50, delete "carried, out using:" and insert --carried out using--.

In Column 26, Line 2, delete "thr" and insert --for--.

In Column 27, Line 23, after "generally" insert --a--.

In Column 27, Line 27, delete "in" and insert --(in--.

In Column 28, Line 61, delete "herein," and insert --herein.--.

In Column 29, Line 28, delete "hi-specific" and insert --bi-specific--.

In Column 29, Line 53, delete "by" and insert --(by--.

In Column 30, Line 28, delete "(LH)$_7$" and insert --(LH)$_2$--.

In Column 30, Line 64, delete "antibodies," and insert --antibodies.--.

In Column 31, Line 2, delete ""("scFv(s)")," and insert --("scFv(s)").--.

In Column 31, Line 14 (Approx.), delete "Bis-say(s)" and insert --Bis-scFv(s)--.

In Column 31, Line 17 (Approx.), delete "hi-," and insert --bi-,--.

In Column 31, Line 42, delete "L," and insert --L.--.

In Column 31, Line 44, delete "Antibodies."" and insert --Antibodies,"--.

In Column 32, Line 20, delete "LEA-1," and insert --LFA-1,--.

In Column 32, Lines 44-45, delete "Willebrands" and insert --Willebrand--.

In Column 32, Line 63, delete "(Ws)," and insert --(ILs),--.

In Column 32, Line 64, delete "(xiiv)" and insert --(xiv)--.

In Column 33, Line 5, delete "integin," and insert --integrin,--.

In Column 33, Line 50, delete "cool" and insert --con1--.

In Column 33, Line 51, after "TN8-19" insert --con2;--.

In Column 33, Line 60, delete "PCT/US2004/03742;" and insert --PCT/US2004/03742,--.

In Column 33, Line 62, after "to" insert --IL-4--.

In Column 33, Line 65, delete "L1M 1;" and insert --L1H11;--.

In Column 34, Line 44, delete "NOF" and insert --NGF--.

In Column 34, Line 50, delete "4D10" and insert --14D10--.

In Column 34, Line 54, delete "CD" and insert --CD22--.

In Column 34, Line 54, delete "related," and insert --related--.

In Column 34, Line 58, delete "humanized," and insert --humanized--.

In Column 35, Line 2, delete "described," and insert --described--.

In Column 35, Line 14, delete "L18F18," and insert --L18H18,--.

In Column 35, Line 29, delete "Inhibit" and insert --inhibit--.

In Column 35, Line 50, delete "related," and insert --related--.

In Column 36, Line 1, delete "and," and insert --and--.

In Column 36, Line 10, delete "described," and insert --described--.

In Column 36, Line 20, delete "Aldurazme" and insert --Aldurazyme--.

In Column 36, Line 22, delete "Beatseron" and insert --Betaseron--.

In Column 36, Line 24, delete "CEREZME" and insert --CEREZYME--.

In Column 36, Line 43, delete "NUTROPIIN" and insert --NUTROPIN--.

In Column 36, Line 45, delete "OVIDREL," and insert --OVIDREL--.

In Column 36, Line 47, delete "alfa)." and insert --alfa),--.

In Column 36, Line 51, delete "REFUTDAN" and insert --REFLUDAN--.

In Column 36, Line 53, delete "(baasiliximab)," and insert --(basiliximab),--.

In Column 36, Lines 53-54, delete "(Pegivisomant)," and insert --(Pegvisomant),--.

In Column 37, Line 13, delete "PASTA," and insert --FASTA,--.

In Column 37, Line 20, delete "comparisons" and insert --comparisons:--.

In Column 37, Line 64, delete "others," and insert --others.--.

In Column 38, Line 5, after "Tool,"", delete "or".

In Column 38, Lines 14-15, delete "Ed, T. E, Creighton, IRL," and insert --Ed. T. E. Creighton, IRL--.

In Column 38, Line 16, delete "databases."" and insert --databases,"--.

In Column 38, Line 18, delete "Blosci" and insert --Biosci--.

In Column 39, Line 36, delete "vane" and insert --variety--.

In Column 39, Line 62, delete "agents," and insert --agents.--.

In Column 40, Line 23, delete "1.00" and insert --100--.

In Column 40, Line 23, delete "00" and insert --200--.

In Column 40, Line 34, delete "L5" and insert --1.5--.

In Column 40, Line 36, delete "determined," and insert --determined--.

In Column 41, Line 5, Before "wherein" insert --A,--.

CERTIFICATE OF CORRECTION (continued)
U.S. Pat. No. 11,607,451 B2

In Column 41, Line 6, Before "and 300," insert --20--.

In Column 41, Line 51, delete "1.88," and insert --188,--.

In Column 42, Line 3, delete "0.0296" and insert --0.02%--.

In Column 42, Line 37, delete "285'91" and insert --285-91--.

In Column 42, Line 42, delete "et" and insert --et al.,--.

In Column 42, Line 43, delete "interactions,"Pharm" and insert --interactions," Pharm--.

In Column 43, Line 57, delete "chaotropic," and insert --chaotropic.--.

In Column 43, Line 58, delete "e.g.," and insert --(e.g.,--.

In Column 44, Line 40 (Approx.), delete "mEq/L:" and insert --mEq/L--.

In Column 44, Line 66, delete "Enbreil®" and insert --Enbrel®--.

In Column 45, Line 13, delete "Enbreil®" and insert --Enbrel®--.

In Column 45, Line 51, delete "methionine," and insert --methionine.--.

In Column 45, Line 62, delete "light," and insert --light.--.

In Column 46, Line 51, delete "hGE" and insert --hGH--.

In Column 46, Line 55, delete "Somatrope®(Eli" and insert --Somatrope® (Eli--.

In Column 47, Line 58, delete "c," and insert --c.--.

In Column 48, Line 1, delete "PCI" and insert --PCT--.

In Column 48, Line 10, delete "much" and insert --such--.

In Column 48, Line 15, delete "Form Formations" and insert --Formulations--.

In Column 48, Line 27, delete "al." and insert --al.,--.

In Column 48, Line 28, delete "133.988;" and insert --133,988;--.

In Column 49, Lines 14-15, delete "preparation," and insert --preparation.--.

In Column 51, Line 40, delete "disease-related," and insert --disease-related--.

In Column 51, Line 58, delete "9," and insert --9.--.

In Column 52, Line 49, delete "DIM" and insert --mM--.

In Column 52, Line 53, delete "1." and insert --1,--.

In Column 52, Line 66, delete "1," and insert --1.--.

Column 53, Line 8, to Column 58, Line 7, delete the text beginning "In addition to the items above," and ending "and/or dilute base." and insert the same after Column 52, Line 28, and above the heading, EXAMPLES.

In Column 53, Line 9 (Approx.), delete "forth;" and insert --forth:--.

In Column 53, Line 46, delete "7.A" and insert --7. A--.

In Column 53, Line 51, delete "mM," and insert --mM.--.

In Column 53, Line 54, delete "10.A" and insert --10. A--.

In Column 53, Line 57, delete "11.A" and insert --11. A--.

In Column 53, Line 59, delete "12.A" and insert --12. A--.

In Column 54, Line 24, delete "18.A" and insert --18. A--.

In Column 54, Line 24, delete "17,wherein" and insert --17, wherein--.

In Column 54, Line 29, delete "18,wherein" and insert --18, wherein--.

In Column 54, Line 47, delete "immunoadhesins," and insert --immunoadhesins.--.

In Column 54, Line 60, delete "ormore" and insert --or more--.

In Column 54, Line 62, delete "p150,95,VLA-4," and insert --p150, 95, VLA-4,--.

In Column 55, Line 8, delete "Willebrands" and insert --Willebrand--.

In Column 55, Line 15, delete "-gamma;IL-1" and insert -- -gamma; IL-1--.

In Column 55, Line 24, delete "gamma- Ib)," and insert --gamma-Ib),--.

CERTIFICATE OF CORRECTION (continued)
U.S. Pat. No. 11,607,451 B2

In Column 55, Line 25, delete "Aldurazme" and insert --Aldurazyme--.

In Column 55, Line 27, delete "Beatseron" and insert --Betaseron--.

In Column 55, Line 29, delete "CEREZME" and insert --CEREZYME--.

In Column 55, Line 44, delete "(darbepoetm" and insert --(darbepoetin--.

In Column 55, Line 58, delete "(baasiliximab)," and insert --(basiliximab),--.

In Column 55, Line 59, delete "(Pegivisomant)," and insert --(Pegvisomant),--.

In Column 56, Line 2, delete "thereof," and insert --thereof.--.

In Column 58, Line 43, delete "Examples," and insert --Examples.--.

In Column 59, Line 12, delete "concentrations," and insert --concentrations.--.

In Column 59, Line 22, delete "In" and insert --in--.

In Column 59, Line 22, delete "In the Range of pH 5.0 to 1.0" and insert the same on, Column 59, Line 20, as continuation of the same heading.

In Column 59, Line 22, delete "1.0" and insert --4.0--.

In Column 59, Line 23, delete "Self-buffered." and insert --Self-buffered--.

In Column 60, Line 7, delete "formulations," and insert --formulations.--.

In Column 60, Line 64, delete "buffering," and insert --buffering--.

In Column 60, Line 65, delete "Ab-hB7RP1," and insert --Ab-hB7RP1.--.

In Column 61, Line 30 (Approx.), delete "Examples," and insert --Examples.--.

In Column 61, Line 35 (Approx.), delete "linearally" and insert --linearly--.

In Column 61, Line 42 (Approx.), delete "in M" and insert --mM--.

In Column 62, Line 1, delete "Ab-hOPGL," and insert --Ab-hOPGL--.

In Column 62, Line 8, delete "DIM" and insert --mM--.

CERTIFICATE OF CORRECTION (continued)
U.S. Pat. No. 11,607,451 B2

In the Claims

In Column 67, Claim 1, Line 39, after "aqueous", delete "self-buffering".

In Column 67, Claim 1, Line 51, after "antibody,", insert --wherein a buffer capacity of the second solution is provided substantially by the pharmaceutical antibody, and--.

In Column 67, Claim 1, Line 52, after "is", delete "adalimumab or".

In Column 67, Claim 2, Line 54, after "aqueous", delete "self-buffering".

In Column 67, Claim 2, Line 67, after "is", delete "adalimumab or".

In Column 68, Claim 3, Line 38, after "aqueous", delete "self-buffering".

In Column 68, Claim 3, Line 50, after "antibody,", insert --wherein a buffer capacity of the second solution is provided substantially by the pharmaceutical antibody, and--.

In Column 68, Claim 8, Line 61, after "aqueous", delete "self-buffering".

In Column 69, Claim 8, Lines 1-2, after "said", delete "first solution is substantially free of any buffering agent other than said".

In Column 70, Claim 33, Line 15, delete "1;and" and insert --1; and--.

In Column 70, Claim 38, Line 37, delete "1;and" and insert --1; and--.

In Column 76, Claim 95, Line 59, after "method", delete "formulation".

In Column 77, Claim 96, Line 1, after "method", delete "formulation".

SEQUENCE LISTING

<160> NUMBER OF SEQ ID NOS: 4

<210> SEQ ID NO 1
<211> LENGTH: 235
<212> TYPE: PRT
<213> ORGANISM: Mus musculus

<400> SEQUENCE: 1

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

```
Leu Ser Pro Gly Glu Arg Ala Thr Leu Ser Cys Arg Ala Ser Gln Ser
            35                  40                  45

Val Arg Gly Arg Tyr Leu Ala Trp Tyr Gln Gln Lys Pro Gly Gln Ala
 50                  55                  60

Pro Arg Leu Leu Ile Tyr Gly Ala Ser Ser Arg Ala Thr Gly Ile Pro
 65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Phe Tyr Cys Gln Gln Tyr
            100                 105                 110

Gly Ser Ser Pro Arg Thr Phe Gly Gln Gly Thr Lys Val Glu Ile Lys
            115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
            195                 200                 205

Lys His Lys Val Tyr Ala Cys Glu Val Thr His Gln Gly Leu Ser Ser
        210                 215                 220

Pro Val Thr Lys Ser Phe Asn Arg Gly Glu Cys
225                 230                 235

<210> SEQ ID NO 2
<211> LENGTH: 467
<212> TYPE: PRT
<213> ORGANISM: Mus musculus

<400> SEQUENCE: 2

Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
            35                  40                  45

Ser Ser Tyr Ala Met Ser Trp Val Arg Gln Ala Pro Gly Lys Gly Leu
 50                  55                  60

Glu Trp Val Ser Gly Ile Thr Gly Ser Gly Gly Ser Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Asp Pro Gly Thr Thr Val Ile Met Ser Trp Phe
            115                 120                 125

Asp Pro Trp Gly Gln Gly Thr Leu Val Thr Val Ser Ser Ala Ser Thr
130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
```

-continued

```
                165                 170                 175
Pro Val Thr Val Ser Trp Asn Ser Gly Ala Leu Thr Ser Gly Val His
            180                 185                 190
Thr Phe Pro Ala Val Leu Gln Ser Ser Gly Leu Tyr Ser Leu Ser Ser
            195                 200                 205
Val Val Thr Val Pro Ser Ser Asn Phe Gly Thr Gln Thr Tyr Thr Cys
210                 215                 220
Asn Val Asp His Lys Pro Ser Asn Thr Lys Val Asp Lys Thr Val Glu
225                 230                 235                 240
Arg Lys Cys Cys Val Glu Cys Pro Pro Cys Pro Ala Pro Pro Val Ala
                245                 250                 255
Gly Pro Ser Val Phe Leu Phe Pro Pro Lys Pro Lys Asp Thr Leu Met
            260                 265                 270
Ile Ser Arg Thr Pro Glu Val Thr Cys Val Val Val Asp Val Ser His
        275                 280                 285
Glu Asp Pro Glu Val Gln Phe Asn Trp Tyr Val Asp Gly Val Glu Val
    290                 295                 300
His Asn Ala Lys Thr Lys Pro Arg Glu Glu Gln Phe Asn Ser Thr Phe
305                 310                 315                 320
Arg Val Val Ser Val Leu Thr Val Val His Gln Asp Trp Leu Asn Gly
                325                 330                 335
Lys Glu Tyr Lys Cys Lys Val Ser Asn Lys Gly Leu Pro Ala Pro Ile
            340                 345                 350
Glu Lys Thr Ile Ser Lys Thr Lys Gly Gln Pro Arg Glu Pro Gln Val
        355                 360                 365
Tyr Thr Leu Pro Pro Ser Arg Glu Glu Met Thr Lys Asn Gln Val Ser
    370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Met Leu Asp Ser Asp Gly Ser Phe Phe Leu Tyr Ser Lys Leu Thr Val
            420                 425                 430
Asp Lys Ser Arg Trp Gln Gln Gly Asn Val Phe Ser Cys Ser Val Met
        435                 440                 445
His Glu Ala Leu His Asn His Tyr Thr Gln Lys Ser Leu Ser Leu Ser
    450                 455                 460
Pro Gly Lys
465

<210> SEQ ID NO 3
<211> LENGTH: 108
<212> TYPE: PRT
<213> ORGANISM: Mus musculus

<400> SEQUENCE: 3

Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Arg Gly Arg
            20                  25                  30
Tyr Leu Ala Trp Tyr Gln Gln Lys Pro Gly Gln Ala Pro Arg Leu Leu
        35                  40                  45
Ile Tyr Gly Ala Ser Ser Arg Ala Thr Gly Ile Pro Asp Arg Phe Ser
    50                  55                  60
```

```
Gly Ser Gly Ser Gly Thr Asp Phe Thr Leu Thr Ile Ser Arg Leu Glu
65                  70                  75                  80

Pro Glu Asp Phe Ala Val Phe Tyr Cys Gln Gln Tyr Gly Ser Ser Pro
                85                  90                  95

Arg Thr Phe Gly Gln Gly Thr Lys Val Glu Ile Lys
            100                 105

<210> SEQ ID NO 4
<211> LENGTH: 122
<212> TYPE: PRT
<213> ORGANISM: Mus musculus

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Gly Ile Thr Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Asp Pro Gly Thr Thr Val Ile Met Ser Trp Phe Asp Pro Trp
            100                 105                 110

Gly Gln Gly Thr Leu Val Thr Val Ser Ser
            115                 120
```